United States Patent
Aponte et al.

(10) Patent No.: US 10,392,630 B2
(45) Date of Patent: Aug. 27, 2019

(54) PLANTS HAVING INCREASED TOLERANCE TO HERBICIDES

(71) Applicant: BASF AGRO B.V., EA Arnheim (NL)

(72) Inventors: Raphael Aponte, Mannheim (DE); Stefan Tresch, Kirchheim (DE); Matthias Witschel, Bad Duerkheim (DE); Jens Lerchl, Golm (DE); Dario Massa, Mannheim (DE); Tobias Seiser, Mannheim (DE); Thomas Mietzner, Annweiler (DE); Jill Marie Paulik, Cary, NC (US); Chad Brommer, Raleigh, NC (US)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 14/911,814

(22) PCT Filed: Aug. 12, 2014

(86) PCT No.: PCT/IB2014/063877
§ 371 (c)(1),
(2) Date: Feb. 12, 2016

(87) PCT Pub. No.: WO2015/022640
PCT Pub. Date: Feb. 19, 2015

(65) Prior Publication Data
US 2016/0201078 A1    Jul. 14, 2016

Related U.S. Application Data

(60) Provisional application No. 61/866,067, filed on Aug. 15, 2013, provisional application No. 61/864,671, filed on Aug. 12, 2013, provisional application No. 61/864,672, filed on Aug. 12, 2013.

(51) Int. Cl.
| | | |
|---|---|---|
| *C12N 15/82* | (2006.01) |
| *A01N 37/48* | (2006.01) |
| *A01N 43/54* | (2006.01) |
| *A01N 43/653* | (2006.01) |
| *A01N 43/84* | (2006.01) |
| *A01N 57/16* | (2006.01) |
| *C12N 9/02* | (2006.01) |

(52) U.S. Cl.
CPC ......... *C12N 15/8274* (2013.01); *A01N 37/48* (2013.01); *A01N 43/54* (2013.01); *A01N 43/653* (2013.01); *A01N 43/84* (2013.01); *A01N 57/16* (2013.01); *C12N 9/001* (2013.01); *C12N 9/0071* (2013.01); *C12Y 103/03004* (2013.01)

(58) Field of Classification Search
None
See application file for complete search history.

(56) References Cited

U.S. PATENT DOCUMENTS

| | | |
|---|---|---|
| 5,169,770 A | 12/1992 | Chee et al. |
| 5,198,013 A | 3/1993 | Hirai et al. |
| 5,322,783 A | 6/1994 | Tomes et al. |
| 5,366,892 A | 11/1994 | Foncerrada et al. |
| 5,376,543 A | 12/1994 | Chee et al. |
| 5,380,831 A | 1/1995 | Adang et al. |
| 5,436,391 A | 7/1995 | Fujimoto et al. |
| 5,485,192 A | 1/1996 | Nagahata et al. |
| 5,593,881 A | 1/1997 | Thompson et al. |
| 5,723,756 A | 3/1998 | Peferoen et al. |
| 5,737,514 A | 4/1998 | Stiffler |
| 5,747,450 A | 5/1998 | Ohba et al. |
| 5,767,373 A | 6/1998 | Ward et al. |
| 5,773,702 A | 6/1998 | Penner et al. |
| 5,859,348 A | 1/1999 | Penner et al. |
| 5,939,360 A | 8/1999 | Adachi et al. |
| 5,939,602 A | 8/1999 | Volrath et al. |
| 5,948,917 A | 9/1999 | Adachi et al. |
| 5,990,387 A | 11/1999 | Tomes et al. |
| 6,018,105 A | 1/2000 | Johnson et al. |
| 6,027,945 A | 2/2000 | Smith et al. |
| 6,084,155 A | 7/2000 | Volrath et al. |
| 6,160,206 A | 12/2000 | Sato et al. |
| 6,308,458 B1 | 10/2001 | Volrath et al. |
| 6,368,800 B1 | 4/2002 | Smith et al. |
| 6,653,529 B2 | 11/2003 | Peng et al. |

(Continued)

FOREIGN PATENT DOCUMENTS

| | | |
|---|---|---|
| CA | 2382090 A1 | 2/2001 |
| CA | 2807035 A1 | 2/2012 |

(Continued)

OTHER PUBLICATIONS

Maniatis et al., 1982, Molecular Cloning: A Laboratory Manual, Cold Spring Harbor Laboratory, pp. 324-343 and 387-389.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Brachypodium distachyon protoporphyrinogen oxidase with UniProt accession No. I1IZ42, published on Jun. 13, 2012.*
Koch et al., 2004, EMBO J. 23: 1720-1728.*

(Continued)

*Primary Examiner* — Bratislav Stankovic
(74) *Attorney, Agent, or Firm* — Marshall, Gerstein & Borun LLP

(57) ABSTRACT

The invention refers to plants comprising wild-type or mutated *Alopecurus* PPO enzymes, and methods of obtaining such plants. The present invention further refers to a method for controlling weeds at a plant cultivation site, the method comprising the steps of providing, at said site, a plant that comprises at least one nucleic acid comprising a nucleotide sequence encoding a wild-type or a mutated *Alopecurus* PPO enzyme which is resistant or tolerant to a PPO-inhibiting herbicide by applying to said site an effective amount of said herbicide.

7 Claims, 6 Drawing Sheets

Specification includes a Sequence Listing.

(56) References Cited

U.S. PATENT DOCUMENTS

| | | |
|---|---|---|
| 6,905,852 B1 | 6/2005 | Horikoshi et al. |
| 7,671,254 B2 | 3/2010 | Tranel et al. |
| 7,705,200 B2 | 4/2010 | Dam et al. |
| 7,745,699 B2 | 6/2010 | Nakajima et al. |
| 7,842,856 B2 | 11/2010 | Tranel et al. |
| 8,097,774 B2 | 1/2012 | Hawkes et al. |
| 8,129,589 B2 | 3/2012 | Tanaka et al. |
| 8,338,337 B2 | 12/2012 | Song et al. |
| 2003/0236208 A1 | 12/2003 | Kmiec et al. |
| 2004/0082770 A1 | 4/2004 | Castle et al. |
| 2005/0084859 A1 | 4/2005 | Nakajima et al. |
| 2007/0039067 A1* | 2/2007 | Feldmann .......... C07K 14/415 800/278 |
| 2007/0050863 A1 | 3/2007 | Tranel et al. |
| 2007/0214515 A1 | 9/2007 | Dam et al. |
| 2009/0049567 A1 | 2/2009 | Olhoft et al. |
| 2010/0100988 A1 | 4/2010 | Tranel et al. |
| 2011/0201501 A1 | 8/2011 | Song et al. |
| 2012/0122223 A1 | 5/2012 | Gocal et al. |
| 2013/0184155 A1 | 7/2013 | Newton et al. |
| 2014/0123340 A1 | 5/2014 | Aponte et al. |
| 2014/0189906 A1 | 7/2014 | Gocal et al. |
| 2015/0299725 A1 | 10/2015 | Lerchl et al. |
| 2016/0194654 A1 | 7/2016 | Aponte et al. |
| 2016/0201078 A1 | 7/2016 | Aponte et al. |

FOREIGN PATENT DOCUMENTS

| | | |
|---|---|---|
| CN | 1150820 A | 5/1997 |
| CN | 1036571 C | 12/1997 |
| CN | 1212724 A | 3/1999 |
| CN | 1175107 C | 11/2004 |
| CN | 1894408 A | 1/2007 |
| CN | 101215289 A | 7/2008 |
| CN | 101437844 A | 5/2009 |
| CN | 101998988 A | 3/2011 |
| DE | 19505995 A1 | 8/1996 |
| EP | 0397687 A1 | 11/1990 |
| EP | 0424047 A1 | 4/1991 |
| EP | 0900795 A1 | 3/1999 |
| WO | WO-93/07256 A1 | 4/1993 |
| WO | WO-95/34659 A1 | 12/1995 |
| WO | WO-96/26202 A1 | 8/1996 |
| WO | WO-1997/004088 A1 | 2/1997 |
| WO | WO-1997/032011 A1 | 9/1997 |
| WO | WO-97/41116 A1 | 11/1997 |
| WO | WO-97/41117 A1 | 11/1997 |
| WO | WO-97/41118 A1 | 11/1997 |
| WO | WO-1998/029554 A1 | 7/1998 |
| WO | WO-1998/033927 A1 | 8/1998 |
| WO | WO-2001/012815 A1 | 2/2001 |
| WO | WO-2001/068826 A2 | 9/2001 |
| WO | WO-01/83459 A2 | 11/2001 |
| WO | WO-02/068607 A2 | 9/2002 |
| WO | WO-2005/107437 A2 | 11/2005 |
| WO | WO-2006/024820 A1 | 3/2006 |
| WO | WO-2006/037945 A1 | 4/2006 |
| WO | WO-2007/024739 A2 | 3/2007 |
| WO | WO-2007/071900 A1 | 6/2007 |
| WO | WO-2007/096576 A1 | 8/2007 |
| WO | WO-2008/124495 A2 | 10/2008 |
| WO | WO-2008/141154 A2 | 11/2008 |
| WO | WO-2010/049269 A1 | 5/2010 |
| WO | WO-2010/049270 A1 | 5/2010 |
| WO | WO-2010/145992 A1 | 12/2010 |
| WO | WO-2011/018486 A2 | 2/2011 |
| WO | WO 2012/018862 A2 * | 2/2012 |
| WO | WO-2012/018862 A2 | 2/2012 |
| WO | WO-2012/041789 A1 | 4/2012 |
| WO | WO-2012/080975 A1 | 6/2012 |
| WO | WO 2012/080975 A1 * | 6/2012 |
| WO | WO-2013/189984 A2 | 12/2013 |
| WO | WO-2015/022636 A2 | 2/2015 |
| WO | WO-2015/022639 A2 | 2/2015 |
| WO | WO-2015/092706 A1 | 6/2015 |

OTHER PUBLICATIONS

Arnould et al., The domain structure of protoporphyrinogen oxidase, the molecular target of diphenyl ether-type herbicides. *Proc. Natl. Acad. Sci. USA*, 95: 10553-8 (1998).

Che et al., Molecular characterization and subcellular localization of protoporphyrinogen oxidase in spinach chloroplasts. *Plant Physiol.* 124: 59-70 (2000).

Choi et al., Generation of resistance to the diphenyl ether herbicide, oxyfluorfen, via expression of the *Bacillus subtilis* protoporphyrinogen oxidase gene in transgenic tobacco plants. *Biosci. Biotechnol. Biochem.* 62(3): 558-60 (1998).

Corradi et al., Crystal structure of protoporphyrinogen oxidase from *Myxococcus xanthus* and it complex with the inhibitor acifluorfen. *J Biol Chem.* 281(50): 38625-33 (2006).

Dayan et al., Phytotoxicity of Protoporphyrinogen Oxidase Inhibitors: Phenomenology, Mode of Action and Mechanisms of Resistance, *Herbicide Activity: Toxicology, Biochemistry and Molecular Biology*, eds. Roe et al., pp. 11-35 (1997).

Extended European Search Report, issued in co-assigned application No. 11848519.2, dated Apr. 23, 2014.

GenBank Accession No. AX084732, submitted on Mar. 9, 2001.

Ha et al., The plastidic *Arabidopsis* protoporphyrinogen IX oxidase gene, with or without the transit sequence, confers resistance to the diphenyl ether herbicide in rice. *Plant Cell Environ.* 27: 79-88 (2003).

Hanin et al., Gene targeting in *Arabidopsis. Plant J.* 28: 671-7 (2001).

Hao et al., Protoporphyrinogen oxidase inhibitor: An ideal target for herbicide discovery. *Chimia*, 65(12): 961-9 (2011).

Heinemann et al., Functional definition of the tobacco protoporphyrinogen IX oxidase substrate-binding site. *Biochem. J.* 402: 575-80 (2007).

Holmberg, A fine line: New herbicide-tolerant crops blur the fine line between weed control and crop injury. *Successful Farm.* 98(5): 25-7 (2000).

Huang et al., Synthesis and herbicidal activity of isoindoline-1,3-dione substituted benzoxazinone derivatives containing a carboxylic ester group. *J. Agric. Food Chem.* 57: 9585-92 (2009).

International Preliminary Report on Patentability, issued in PCT/IB2011/055701, dated Jun. 27, 2013.

International Search Report, corresponding International Application No. PCT/EP2013/062744, dated Dec. 10, 2014.

International Search Report, issued in PCT/IB2011/055701, dated May 3, 2012.

Jung et al., Dual targeting of *Myxococcus xanthus* protoporphyrinogen oxidase into chloroplasts and mitochondria and high level oxyfluorfen resistance. *Plant Cell Environ.* 27: 1436-46 (2004).

Jung et al., Resistance mechanisms in protoporphyrinogen oxidase (PROTOX) inhibitor-resistant transgenic rice. *J. Plant Biol.* 50(3): 586-94 (2007).

Koch et al., Crystal structure of protoporphyrinogen IX oxidase: A key enzyme in Haem and chlorophyll biosynthesis. *EMBO J.* 23: 1720-8 (2004).

Layer et al., Structure and function of enzymes in Heme biosynthesis. *Protein Sci.* 19: 1137-61 (2010).

Lee et al., Expression of human protoporphyrinogen oxidase in transgenic rice induces both a photodynamic response and oxyfluorfen resistance. *Pesticide Biochem. Physiol.* 80: 65-74 (2004).

Lee et al., Transgenic rice plants expressing a *Bacillus subtilis* protoporphyrinogen oxidase gene are resistant to diphenyl ether herbicide oxyfluorfen. *Plant Cell Physiol.* 41(6): 743-9 (2000).

Lermontova et al., Cloning and characterization of a plastidal and a mitochondria' isoform of tobacco protoporphyrinogen IX oxidase. *Proc. Natl. Acad. Sci. USA*, 94: 8895-900 (1997).

Lermontova et al., Overexpression of plastidic protoporphyrinogen IX oxidase leads to resistance to the diphenyl-ether herbicide acifluorfen. *Plant Physiol.* 122: 75-83 (2000).

(56) References Cited

OTHER PUBLICATIONS

Li et al., Development of protoporphyrinogen oxidase as an efficient selection marker for *Agrobacterium* tumefaciens-mediated transformation of maize. Plant Physiol. 133: 736-47 (2003).
Lyga et al., Structural replacements for the benzoxazinone protox inhibitors. *Pesticide Sci.* 55: 281-7 (1999).
Macias et al., Optimization of benzoxazinones as natural herbicide models by lipophilicity enhancement. *J. Acric. Food Chem.* 54: 9357-65 (2006).
Mulwa et al., Biotechnology approaches to developing herbicide tolerance/selectivity in crops. *Afr. J. Biotechnol.* 5(5): 396-404 (2006).
Rousonelos, S., Master's Thesis, University of Illinois, published Aug. 2010.
Watanabe et al., Molecular characterization of photomixotrophic tobacco cells resistant to protoporphyrinogen oxidase-inhibiting herbicides. *Plant Physiol.* 118: 751-8 (1998).
Supplemental Partial European Search Report, European patent application No. EP 14836899, dated Mar. 20, 2017.
Extended European Search Report, issued in application No. EP 14836729.5, dated Jun. 6, 2017.
EBI Accession No. GSP:BBB23069, Amaranthus tuberculatus PPO variant R128A/T208S/F420V #1 (Feb. 13, 2014).
Extended European Search Report, European Patent Application No. 14836899.6, dated Jun. 30, 2017 (4 pp.).
Che et al., Localization of target-site of the protoporphyrinogen oxidase-inhibiting herbicide, S-23142, in *Spinacia oleracea* L., Z. Naturforsch, 48e:350-5 (1992).
Cole-Strauss et al., Targeted gene repair directed by the chimeric RNA/DNA oligonucleotide in a mammalian cell-free extract, Nucleic Acids Res., 27(5):1323-30 (1999).
Dailey et al., Expression of a cloned protoporphyrinogen oxidase, J. Biol. Chem., 289(2):813-15 (1994).
Dayan et al., Biochemical and structural consequences of a glycine deletion in the alpha-8 helix of protoporphyrinogen oxidase, Biochim. Biophys. Acta, 1804(7):1548-56 (2010).
Duke et al., Protoporphyrinogen oxidase-inhibiting herbicides, Weed Sci., 39:465-73 (1991).
Geiser et al., The hypervariable region in the genes coding for entomopathogenic crystal proteins of Bacillus thuringiensis: nucleotide sequence of the kurhd1 gene of subsp. kurstaki HD1, Gene, 48(1):109-18 (1986).
GenBank Accession No. ACF78832, unknown [*Zea mays*], Jul. 30, 2008.
GenBank Accession No. DQ386114, Amaranthus tuberculatus biotype herbicide-susceptible WC mitochrondrial protoporphyrinogen oxidase (PPX2L) mRNA, complete cds; nuclear gene for mitochrondrial product, Aug. 18, 2006.
GenBank Accession No. XP_004976030.1, Predicted: protoporhyrinogen oxidase, mitochondrial [Setaria italica] (Nov. 30, 2015).
GenBank Accession No. XM_004975973, Predicted: Setaria italica protoporphyrinogen oxidase, mitochondrial (LOC101781148), mRNA (Nov. 30, 2015).
International Preliminary Report on Patentability, International Application No. PCT/IB2014/063877, dated Feb. 16, 2016.
International Search Report and Written Opinion, International Application No. PCT/IB2014/063877, dated Feb. 10, 2015.

Jacobs et al., Assay for enzymatic protoporphyrinogen oxidation, a late step in heme synthesis, Enzyme, 28)2-3):206-19 (1982).
Kataoka et al., Isolation and partial characterization of mutant Chlamydomonas reinhardtii resistant to herbicide S-23142, J. Pesticide Sci., 15:449-51 (1990).
Lee et al., Cellular localization of protoporphyrinogen-oxidizing activities of etiolated barley (*Hordeum vulgare* L.) leaves, Plant Physiol., 102:881-9 (1993).
Lewis et al., Interactions between redox partners in various cytochrome P450 systems: functional and structural aspects, Biochim. Biophys. Acta, 1460(2-3):353-74 (2000).
Li et al., Development of PPO inhibitor-resistant cultures and crops, Pest Management Science, 61(3):277-85 (2005).
Loppes, A new class of arginine-requiring mutants in Chlamydomonas reinhardi, Mol. Gen. Genet., 104(2):172-7 (1969).
Matringe et al., Protoporphyrinogen oxidase as a molecular target for diphenyl ether herbicides, Biochem. J., 260(1):231-5 (1989).
Matringe et al., Protoporphyrinogen oxidase inhibition by three peroxidizing herbicides: oxadiazon, LS 82-556 and M&B 39279, FEBS Lett., 245(1-20:35-8 (1989).
Murray et al., Codon usage in plant genes, Nucleic Acids Res., 17(2):477-98 (1989).
Nandihalli et al., Quantative structure-activity relationships of protoporphyrinogen oxidase-inhibiting diphenyl ether herbicides, Pesticide Biochem Physiol., 43:193-211 (1992).
Oshio et al., Isolation and characterization of a Chlamydomonas reinhardtii mutant resistant to photobleaching herbicides, Z. Naturforsch, 48c:339-44 (1993).
Patzoldt et al., A codon deletion confers resistance to herbicides inhibiting protoporphyrinogen oxidase, Proc. Natl. Acad. Sci. USA, 103(33):12329-34 (2006).
Randolph-Anderson et al., Isolation and characterization of a mutant protoporphyrinogen oxidase gene from Chlamydomonas reinhardtii conferring resistance to porphyric herbicides, Plant Mol. Biol., 38(5):839-59 (1998).
Sasarman et al., Mapping of a new hem gene in *Escherichia coli* K12, J. Gen. Microbiol., 113(2):297-303 (1979).
Sasarman et al., Nucleotide sequence of the hemG gene involved in the protoporphyrinogen oxidase activity of *Escherichia coli* K12, Can. J. Microbiol., 39(12):1155-61 (1993).
Shibata et al., Isolation and characterization of a Chlamydomonas reinhardtii mutant resistant to an experimental herbicide S-23142, which inhibits chlorophyll synthesis, in: Murata (ed.), Research in Photosynthesis, vol. III, pp. 567-570 (1992).
Su et al., The development of protoporphyrinogen oxidase inhibiting herbicides, Agrochemicals Research & Application, 15(1):1-5 (2011).
Yanase et al., Porphyrin synthesis involvement in diphenyl ether-like mode of action of TNPP-ethyl, a novel phenylpyrazole herbicide, Pesticide Biochemistry and Physiology, 35:70-80 (1989).
Partial Supplementary European Search Report, European patent application No. 14836729.5, dated Mar. 28, 2017.
NCBI Reference Sequence XM_004975973.1, Predicted: Setaria italica protoporphyrinogen oxidase, chloroplastic/mitochrondrial-like (LOC101781148), mRNA, Jun. 26, 2013.
U.S. Appl. No. 14/408,439, filed Dec. 16, 2014.
U.S. Appl. No. 13/918,212, filed Jun. 14, 2013.
U.S. Appl. No. 13/994,374, filed Oct. 9, 2013.

* cited by examiner

```
AMARE_WC_herb_sus     MVIQSITHLSPNLALPSPLSVSTKNYP---VAVMGN--------ISEREEPTSAKRVAVVG
AMARE_AC_herb_sus     MVIQSITHLSPNLALPSPLSVSTKNYP---VAVMGN--------ISEREEPTSAKRVAVVG
AMARE_AC_herb_resis   MVIQSITHLSPNLALPSPLSVSTKNYP---VAVMGN--------ISEREEPTSAKRVAVVG
AMARE_CC_herb_resis   MVIQSITHLSPNLALPSPLSVSTKNYP---VAVMGN--------ISEREEPTSAKRVAVVG
SEQ_ID_NO_002_ALOMY   MLTSATTPSSSSASSRASTRFASSSRPRRTAYARGRRLRPVLAMAASDDPR-ARSVAVVG AMARE_WC_herb_sus     AGVSGLAAAYKLKSHGLSVTLFEADSRAGGKLKTVKKDGFIWDEGANTMTESEAEVSSLI
AMARE_AC_herb_sus     AGVSGLAAAYKLKSHGLSVTLFEADSRAGGKLKTVKKDGFIWDEGANTMTESEAEVSSLI
AMARE_AC_herb_resis   AGVSGLAAAYKLKSHGLSVTLFEADSRAGGKLKTVKKDGFIWDEGANTMTESEAEVSSLI
AMARE_CC_herb_resis   AGVSGLAAAYKLKSHGLSVTLFEANSRAGGKLKTVKKDGFIWDEGANTMTESEAEVSSLI
SEQ_ID_NO_002_ALOMY   AGISGLVAAYRLSKSGVRVTVFEADDRAGGKIRTNSDSGFLWDEGANTMTESALEASRLI AMARE_WC_herb_sus     DDLGLREKQQLPISQNKRYIARDGLPVLLPSNPAALLTSNILSAKSKLQIMLEPFLWRKH
AMARE_AC_herb_sus     DDLGLREKQQLPISQNKRYIARAGLPVLLPSNPAALLTSNILSAKSKLQIMLEPFLWRKH
AMARE_AC_herb_resis   DDLGLREKQQLPISQNKRYIARDGLPVLLPSNPAALLTSNILSAKSKLQIMLEPFLWRKH
AMARE_CC_herb_resis   DDLGLREKQQLPISQNKRYIARDGLPVLLPSNPAALLTSNILSAKSKLQIMLEPFLWRKH
SEQ_ID_NO_002_ALOMY   DDLGLEDRLQYPNSQHKRYTVKDGAPALIPSDPIALMKSSLLSTKSKFKLFLEPFLYDKS AMARE_WC_herb_sus     N----ATELSDEHVQESVGEFFERHFGKEFVDYVIDPFVAGTCGGDPQSLSMHHTFPEVWN
AMARE_AC_herb_sus     N----ATELSDEHVQESVGEFFERHFGKEFVDYVIDPFVAGTCGGDPQSLSMHHTFPEVWN
AMARE_AC_herb_resis   N----ATELSDEHVQESVGEFFERHFGKEFVDYVIDPFVAGTCG-DPQSLSMHHTFPEVWN
AMARE_CC_herb_resis   N----ATELSDEHVQESVGEFFERHFGKEFVDYVIDPFVAGTCG-DPQSLSMYHTFPEVWN
SEQ_ID_NO_002_ALOMY   STKSSKKVSDEHISESVGSFFERHFGKEVVDYLIDPFVAGTSAGDPESLSIRHAFPGLWN AMARE_WC_herb_sus     IEKRFGSVFAGLIQSTLLSKKEKGGENASIKKPRVRGSFSFQGGMQTLVDTMCKQLGEDE
AMARE_AC_herb_sus     IEKRFGSVFAGLIQSTLLSKKEKGGENASIKKPRVRGSFSFQGGMQTLVDTMCKQLGEDE
AMARE_AC_herb_resis   IEKRFGSVFAGLIQSTLLSKKEKGGENASIKKPRVRGSFSFQGGMQTLVDTMCKQLGEDE
AMARE_CC_herb_resis   IEKRFGSVFAGLIQSTLLSKKEKGGENASIKKPRVRGSFSFQGGMQTLVDTMCKQLGEDE
SEQ_ID_NO_002_ALOMY   LEKKYGSIIVGAIMSKLTAKGDKKGSAVSGKGRNKRASFSFHGGMQTLVDALHKEVGDGN AMARE_WC_herb_sus     LKLQCEVLSLSYNQKGIPSLGNWSVSSMSNNTS-----EDQSYDAVVVTAPIRNVKEMKI
AMARE_AC_herb_sus     LKLQCEVLSLSYNQKGIPSLGNWSVSSMSNNTS-----EDQSYDAVVVTAPIRNVKEMKI
AMARE_AC_herb_resis   LKLQCEVLSLSYNQKGIPSLGNWSVSSMSNNTS-----EDQSYDAVVVTAPIRNVKEMKI
AMARE_CC_herb_resis   LKLQCEVLSLSYNQKGIPSLGNWSVSSMSNNTS-----EDQSYDAVVVTAPIRNVKEMKI
SEQ_ID_NO_002_ALOMY   VKLGAQVLSLACICDGLSASDGWSISVDSKDASNKELTKNHSFDAVIMTAPLSNVQRMKF AMARE_WC_herb_sus     MKFGNPFSLDFIPEVTYVPLSVMITAFKKDKVKRPLEGFGVLIPSKEQ-HNGLKTLGTLF
AMARE_AC_herb_sus     MKFGNPFSLDFIPEVTYVPLSVMITAFKKDKVKRPLEGFGVLIPSKEQ-HNGLKTLGTLF
AMARE_AC_herb_resis   MKFGNPFSLDFIPEVTYVPLSVMITAFKKDKVKRPLEGFGVLIPSKEQ-HNGLKTLGTLF
AMARE_CC_herb_resis   MKFGNPFSLDFIPEVTYVPLSVMITAFKKDKVKRPLEGFGVLIPSKEQ-HNGLKTLGTLF
SEQ_ID_NO_002_ALOMY   TKGGAPFVLDFLPKVDYLPLSLMVTAFKKEDVKRPLEGFGVLIPYKEQQKHGLKTLGTLF AMARE_WC_herb_sus     SSMMFPDRAPSDMCLFTTFVGGSRNRKLANASTDELKQIVSSDLQQLLGTEDEPSFVNHL
AMARE_AC_herb_sus     SSMMFPDRAPSDMCLFTTFVGGSRNRKLANASTDELKQIVSSDLQQLLGTEDEPSFVNHL
AMARE_AC_herb_resis   SSMMFPDRAPSDMCLFTTFVGGSRNRKLANASTDELKQIVSSDLQQLLGTEDEPSFVNHL
AMARE_CC_herb_resis   SSMMFPDRAPSDMCLFTTFVGGSRNRKLANASTDELKQIVSSDLQQLLGTEDEPSFVNHL
SEQ_ID_NO_002_ALOMY   SSMMFPDRAPNDQHLFTTFVGGSHNRDLAGAPTSILKQLVTSDLGKLLGVEGQPTFVKHI AMARE_WC_herb_sus     FWSNAFPLYGHNYDSVLRAIDKMEKDLPGFFYAGNHKGGLSVGKAMASGCKAAELVISYL
AMARE_AC_herb_sus     FWSNAFPLYGHNYDSVLRAIDKMEKDLPGFFYAGNHKGGLSVGKAMASGCKAAELVISYL
AMARE_AC_herb_resis   FWSNAFPLYGHNYDCVLRAIDKMEKDLPGFFYAGNHKGGLSVGKAMASGCKAAELVISYL
AMARE_CC_herb_resis   FWSNAFPLYGHNYDSVLRAIDKMEKDLPGFFYAGNHKGGLSVGKAMASGCKAAELVISYL
SEQ_ID_NO_002_ALOMY   HWRNAFPLYGHDYDSALEAIGKMESDLPGFFYAGNNKDGLAVGNVIASGSKTADLVISYL AMARE_WC_herb_sus     DSHIYVKMDEKTA
AMARE_AC_herb_sus     DSHIYVKMDEKTA
AMARE_AC_herb_resis   DSHIYVKMDEKTA
AMARE_CC_herb_resis   DSHIYVKMDEKTA
SEQ_ID_NO_002_ALOMY   ESG--IKQDN---
```

Figure 1a

```
PPO1_ALOMY    ----MVGATMAIATVTAALPLRVRVPGRSRR----GQAR------CAVASDATEAPAAPS
PPO1_AMARE    MSAMALSSSILQCPPHSDISFRFFAHTRTQPPIFFGRPRKLSYIHCSTSSSSTANYQNTI

PPO1_ALOMY    ARLS------ADCVIVGGGISGLCTAQALATKYGVS--DLLVTEARARPGGNITTVERPDE
PPO1_AMARE    TSQGEGDKVLDCVIVGAGISGLCIAQALSTKHIQSNLNFIVTEAKHRVGGNITTME--SD

PPO1_ALOMY    GYLWEEGPNSFQPSDPVLTMAVDSGLKDELVFGDPNAPRFVLWEGKLRPVPSKPGDLPFF
PPO1_AMARE    GYIWEEGPNSFQPSDPVLTMAVDSGLKDDLVLGDPNAPRFVLWNGKLRPVPSKPTDLPFF

PPO1_ALOMY    DLMSIPGKLRAGLGALGIRPPPPGREESVEEFVRRNLGAEVFERLIEPFCSGVYAGDPSK
PPO1_AMARE    DLMSFPGKIRAGLGALGLRPPPPSYEESVEEFVRRNLGDEVFERLIEPFCSGVYAGDPAK

PPO1_ALOMY    LSMRAAFGKVWRLEENGGSIIGGTIKAIQDKGKNPKPPRDPRLPAPKGQTVASFRKGLAM
PPO1_AMARE    LSMKAAFGKVWTLEQKGGSIIAGTLKTIQERKNNPPPPRDPRLPKPKGQTVGSFRKGLIM

PPO1_ALOMY    LPNAIASRLGSKVKLSWKLTSITKSENQGYVLGYETPEGVVSVQAKSVIMTIPSYIASDI
PPO1_AMARE    LPTAIAARLGSKVKLSWTLSNIDKSLNGEYNLTYQTPDGPVSVRTKAVVMTVPSYIASSL

PPO1_ALOMY    LRPLSSDAADGLSKFYYPPVAAVTVSYPKEAIRKECLIDGELQGFGQLHPRSQGVETLGT
PPO1_AMARE    LRPLSDVAADSLSKFYYPPVAAVSLSYPKEAIRPECLIDGELKGFGQLHPRSQGVETLGT

PPO1_ALOMY    IYSSSLFPNRAPAGRVLLLNYIGGATNTGIVSKTESDLVEAVDRDLRKMLINPRAADPLA
PPO1_AMARE    IYSSSLFPGRAPPGRTLILSYIGGATNLGILQKSEDELAETVDKDLRKILINPNAKGSRV

PPO1_ALOMY    LGVRVWPQAIPQFLIGHLDRLDAAKSALVRSGCSGLFLGGNYVAGVALGRCIEGAYDSAS
PPO1_AMARE    LGVRVWPKAIPQFLVGHFDVLDAAKAGLANAGQKGLFLGGNYVSGVALGRCIEGAYDSAS

PPO1_ALOMY    EVSDFLNKYAYK
PPO1_AMARE    EVVDFLSQYKDK
```

Figure 1b

SEQUENCE LISTING

```
<160> NUMBER OF SEQ ID NOS: 31

<210> SEQ ID NO 1
<211> LENGTH: 1644
<212> TYPE: DNA
<213> ORGANISM: Alopecurus myosuroides

<400> SEQUENCE: 1
atgctcactt ccgccaccac cccctcctcc tcctccgctt cgtcccgcgc gtccacccgc      60
ttcgcctcct cgtcccgtcc tcgtcgcacc gcctacgcgc gcgggcgccg gcttcgcccc     120
gtgctcgcca tggccgcctc cgacgaccca cgcgccaggt cggtcgccgt tgtaggcgcc     180
ggcatcagtg ggctcgtggc ggcgtacaga ctgagcaaga gcgcgtgcg ggtcacggtg      240 ttcgaggcgg acgaccgggc aggagggaag atacggacca actccgacag cggattcctc     300
tgggacgaag gagccaacac catgacagaa agtgcgctgg aggcgagtag actaatcgat     360
gatcttggtc ttgaggacag gctgcagtat cctaactccc agcacaagcg gtacactgtt     420
aaagatggag cgccagcact gatccctca gatcccattg cgctgatgaa aagcagtctt     480
ctttctacga aatcaaagtt caagttattt ttggaaccat ttctctacga caagtctagc     540
acaaagagct ccaagaaagt gtctgatgag catataagtg agagtgttgg gagcttcttt     600
gaacgccact ttggaaaaga agttgttgac tatcttattg atccatttgt agctggaaca     660
agtgcaggag atcccgagtc attatctatc cgtcatgcat ttccagggtt atggaattta     720
gaaaagaagt atggttctat cattgttggt gccatcatgt ctaaactaac agctaaaggt     780
gataagaaag gaagcgctgt atcaggaaaa ggaaggaata agcgggcgtc attttcattt     840
catggtggta tgcagacact agtagatgca cttcacaaag aagttggaga tggtaatgtg     900
aaacttggag cacaagtgtt gtcattggca tgtatctgtg atgggctctc tgcatcagat     960
gggtggtcaa tttctgttga ttcaaaagat gctagtaaca aggagctaac aaagaaccat    1020
tcctttgatg ctgttatcat gacagctcca ctgtctaatg tccagaggat gaagtttaca    1080
aaaggtggag ctccatttgt gctagacttt cttcctaagg tggattatct gccgttgtcc    1140
ctcatggtaa cagcttttaa gaaggaagat gtcaaaagac tctggaagg atttgggtg     1200 ttgatccct acaaggaaca gcaaaagcat ggtctgaaaa cccttggaac tctcttctcc    1260
tctatgatgt ttccagatcg agctcctaat gaccaacact tatttacaac attcgttggg    1320
ggaagccaca acagggatct tgctggagct ccaacgtcta tcttaaaaca acttgtgacc    1380
tctgaccttg gaaagctcct gggtgtagag ggacagccaa cttttgtgaa acatatacat    1440
```

```
tggagaaatg cttttccttt atatggccat gattatgatt cggcattgga agctatagga    1500
aagatggaga gtgatcttcc agggttcttc tatgcaggaa ataacaagga cgggttggct    1560
gttggaaatg ttatagcttc aggaagtaag actgctgatc tggtgatctc gtatcttgag    1620
tcaggcatca agcaagataa ttaa                                           1644
```

<210> SEQ ID NO 2
<211> LENGTH: 547
<212> TYPE: PRT
<213> ORGANISM: Alopecurus myosuroides

<400> SEQUENCE: 2

```
Met Leu Thr Ser Ala Thr Thr Pro Ser Ser Ser Ala Ser Ser Arg
1               5                   10                  15

Ala Ser Thr Arg Phe Ala Ser Ser Arg Pro Arg Arg Thr Ala Tyr
                20                  25                  30

Ala Arg Gly Arg Arg Leu Arg Pro Val Leu Ala Met Ala Ala Ser Asp
                35                  40                  45

Asp Pro Arg Ala Arg Ser Val Ala Val Gly Ala Gly Ile Ser Gly
    50                  55                  60

Leu Val Ala Ala Tyr Arg Leu Ser Lys Ser Gly Val Arg Val Thr Val
65                  70                  75                  80

Phe Glu Ala Asp Asp Arg Ala Gly Gly Lys Ile Arg Thr Asn Ser Asp
                85                  90                  95

Ser Gly Phe Leu Trp Asp Glu Gly Ala Asn Thr Met Thr Glu Ser Ala
                100                 105                 110

Leu Glu Ala Ser Arg Leu Ile Asp Asp Leu Gly Leu Glu Asp Arg Leu
                115                 120                 125

Gln Tyr Pro Asn Ser Gln His Lys Arg Tyr Thr Val Lys Asp Gly Ala
    130                 135                 140

Pro Ala Leu Ile Pro Ser Asp Pro Ile Ala Leu Met Lys Ser Ser Leu
145                 150                 155                 160

Leu Ser Thr Lys Ser Lys Phe Lys Leu Phe Leu Glu Pro Phe Leu Tyr
                165                 170                 175

Asp Lys Ser Ser Thr Lys Ser Ser Lys Lys Val Ser Asp Glu His Ile
                180                 185                 190

Ser Glu Ser Val Gly Ser Phe Phe Glu Arg His Phe Gly Lys Glu Val
                195                 200                 205

Val Asp Tyr Leu Ile Asp Pro Phe Val Ala Gly Thr Ser Ala Gly Asp
    210                 215                 220

Pro Glu Ser Leu Ser Ile Arg His Ala Phe Pro Gly Leu Trp Asn Leu
225                 230                 235                 240

Glu Lys Lys Tyr Gly Ser Ile Ile Val Gly Ala Ile Met Ser Lys Leu
                245                 250                 255

Thr Ala Lys Gly Asp Lys Lys Gly Ser Ala Val Ser Gly Lys Gly Arg
                260                 265                 270

Asn Lys Arg Ala Ser Phe Ser Phe His Gly Gly Met Gln Thr Leu Val
                275                 280                 285

Asp Ala Leu His Lys Glu Val Gly Asp Gly Asn Val Lys Leu Gly Ala
    290                 295                 300

Gln Val Leu Ser Leu Ala Cys Ile Cys Asp Gly Leu Ser Ala Ser Asp
305                 310                 315                 320

Gly Trp Ser Ile Ser Val Asp Ser Lys Asp Ala Ser Asn Lys Glu Leu
                325                 330                 335
```

```
Thr Lys Asn His Ser Phe Asp Ala Val Ile Met Thr Ala Pro Leu Ser
            340                 345                 350

Asn Val Gln Arg Met Lys Phe Thr Lys Gly Gly Ala Pro Phe Val Leu
        355                 360                 365

Asp Phe Leu Pro Lys Val Asp Tyr Leu Pro Leu Ser Leu Met Val Thr
370                 375                 380

Ala Phe Lys Lys Glu Asp Val Lys Arg Pro Leu Glu Gly Phe Gly Val
385                 390                 395                 400

Leu Ile Pro Tyr Lys Glu Gln Gln Lys His Gly Leu Lys Thr Leu Gly
                405                 410                 415

Thr Leu Phe Ser Ser Met Met Phe Pro Asp Arg Ala Pro Asn Asp Gln
            420                 425                 430

His Leu Phe Thr Thr Phe Val Gly Gly Ser His Asn Arg Asp Leu Ala
        435                 440                 445

Gly Ala Pro Thr Ser Ile Leu Lys Gln Leu Val Thr Ser Asp Leu Gly
    450                 455                 460

Lys Leu Leu Gly Val Glu Gly Gln Pro Thr Phe Val Lys His Ile His
465                 470                 475                 480

Trp Arg Asn Ala Phe Pro Leu Tyr Gly His Asp Tyr Asp Ser Ala Leu
                485                 490                 495

Glu Ala Ile Gly Lys Met Glu Ser Asp Leu Pro Gly Phe Phe Tyr Ala
            500                 505                 510

Gly Asn Asn Lys Asp Gly Leu Ala Val Gly Asn Val Ile Ala Ser Gly
        515                 520                 525

Ser Lys Thr Ala Asp Leu Val Ile Ser Tyr Leu Glu Ser Gly Ile Lys
    530                 535                 540

Gln Asp Asn
545
```

<210> SEQ ID NO 3
<211> LENGTH: 1596
<212> TYPE: DNA
<213> ORGANISM: Alopecurus myosuroides

<400> SEQUENCE: 3

| | | | | | |
|---|---|---|---|---|---|
| atggtcggcg | caaccatggc | catcgctacc | gtcacggcgg | cgctaccgct | ccgcgttcgg | 60 |
| gtccccggtc | gctcccgccg | cggccaggcg | cgctgcgcgg | tcgccagcga | cgccactgag | 120 |
| gccccggctg | cgcccagcgc | acggctgtcc | gcggactgcg | tgatcgtcgg | aggcggcatc | 180 |
| agcggcctct | gcactgcaca | agcgctggcc | accaagtacg | tgtcagcga | cttgctcgtc | 240 |
| acagaggctc | gcgcccgccc | aggcggcaac | atcaccaccg | tcgagcgccc | cgacgagggg | 300 |
| tacctctggg | aggagggacc | caacagcttc | cagccctctg | accccgtcct | cacaatggcc | 360 |
| gtagacagcg | ggctcaagga | tgaattggtg | ttcggggacc | ctaacgcgcc | gcggttcgtc | 420 |
| ctgtgggagg | aaagctaag | gccggtgccg | tccaagccag | cgacctgcc | tttcttcgac | 480 |
| ctcatgagca | ttcctgggaa | gctcagggcg | ggccttggcg | cgctgggcat | cgccctcct | 540 |
| cctccagggc | gtgaggagtc | ggtggaggag | tttgtacgcc | gcaacctcgg | cgccgaggtc | 600 |
| tttgagcgcc | tcattgagcc | tttctgttca | ggtgtgtatg | cgggtgatcc | ttcgaagctc | 660 |
| agtatgaggg | ctgcgtttgg | gaaggtgtgg | agactggagg | agaatggagg | tagtattatt | 720 |
| ggtggaacca | tcaaggcaat | tcaggataaa | gggaaaaacc | ccaaaccgcc | aagggatccc | 780 |
| cgacttccgg | caccaagggg | gcagacggtg | gcatctttca | ggaagggtct | agccatgctc | 840 |
| ccaaatgcta | tcgcctctag | gttgggtagt | aaagtcaaac | tgtcatggaa | gctcacgagt | 900 |

```
attacaaagt cagaaaacca gggatatgtg ttagggtatg aaacaccgga aggagttgtt    960
tcagtgcagg ctaaaagtgt tatcatgacc attccatcat atattgctag tgatatcttg   1020
cgcccactct cgagtgatgc agcagatggt ctttcaaaat tctattatcc accagttgct   1080
gctgtaactg tttcatatcc aaaagaagct attaggaaag aatgcttaat tgatggggag   1140
ctccagggtt tcggccagtt gcatccacgt agccaaggag ttgagacttt agggacaata   1200
tatagctctt ctctctttcc gaatcgtgct cctgctggaa gagtgttact gctgaactac   1260
atcggggtg ctacaaatac agggatcgtc tccaagactg agagcgactt agtagaagca   1320
gttgatcgtg acctcagaaa aatgttgata aatcctagag cagcagaccc tttagccttg   1380
ggtgtccgag tgtggccaca agccatacca cagttttga ttgggcacct tgatcgcctt   1440
gatgcggcaa atctgccct ggtcagaagc ggctgcagtg ggttgttcct aggaggtaac   1500
tatgtagcag gagttgcctt gggccgatgc attgagggtg cgtacgacag tgcctcagaa   1560
gtatcggact tcttgaacaa gtatgcctac aagtga                             1596
```

<210> SEQ ID NO 4
<211> LENGTH: 531
<212> TYPE: PRT
<213> ORGANISM: Alopecurus myosuroides

<400> SEQUENCE: 4

```
Met Val Gly Ala Thr Met Ala Ile Ala Thr Val Thr Ala Ala Leu Pro
1               5                   10                  15

Leu Arg Val Arg Val Pro Gly Arg Ser Arg Arg Gly Gln Ala Arg Cys
            20                  25                  30

Ala Val Ala Ser Asp Ala Thr Glu Ala Pro Ala Ala Pro Ser Ala Arg
        35                  40                  45

Leu Ser Ala Asp Cys Val Ile Val Gly Gly Gly Ile Ser Gly Leu Cys
    50                  55                  60

Thr Ala Gln Ala Leu Ala Thr Lys Tyr Gly Val Ser Asp Leu Leu Val
65                  70                  75                  80

Thr Glu Ala Arg Ala Arg Pro Gly Gly Asn Ile Thr Thr Val Glu Arg
                85                  90                  95

Pro Asp Glu Gly Tyr Leu Trp Glu Glu Gly Pro Asn Ser Phe Gln Pro
            100                 105                 110

Ser Asp Pro Val Leu Thr Met Ala Val Asp Ser Gly Leu Lys Asp Glu
        115                 120                 125

Leu Val Phe Gly Asp Pro Asn Ala Pro Arg Phe Val Leu Trp Glu Gly
    130                 135                 140

Lys Leu Arg Pro Val Pro Ser Lys Pro Gly Asp Leu Pro Phe Phe Asp
145                 150                 155                 160

Leu Met Ser Ile Pro Gly Lys Leu Arg Ala Gly Leu Gly Ala Leu Gly
                165                 170                 175

Ile Arg Pro Pro Pro Gly Arg Glu Glu Ser Val Glu Glu Phe Val
            180                 185                 190

Arg Arg Asn Leu Gly Ala Glu Val Phe Glu Arg Leu Ile Glu Pro Phe
        195                 200                 205

Cys Ser Gly Val Tyr Ala Gly Asp Pro Ser Lys Leu Ser Met Arg Ala
    210                 215                 220

Ala Phe Gly Lys Val Trp Arg Leu Glu Glu Asn Gly Gly Ser Ile Ile
225                 230                 235                 240

Gly Gly Thr Ile Lys Ala Ile Gln Asp Lys Gly Lys Asn Pro Lys Pro
```

```
                        245                 250                 255
Pro Arg Asp Pro Arg Leu Pro Ala Pro Lys Gly Gln Thr Val Ala Ser
            260                 265                 270

Phe Arg Lys Gly Leu Ala Met Leu Pro Asn Ala Ile Ala Ser Arg Leu
        275                 280                 285

Gly Ser Lys Val Lys Leu Ser Trp Lys Leu Thr Ser Ile Thr Lys Ser
    290                 295                 300

Glu Asn Gln Gly Tyr Val Leu Gly Tyr Glu Thr Pro Glu Gly Val Val
305                 310                 315                 320

Ser Val Gln Ala Lys Ser Val Ile Met Thr Ile Pro Ser Tyr Ile Ala
                325                 330                 335

Ser Asp Ile Leu Arg Pro Leu Ser Ser Asp Ala Ala Asp Gly Leu Ser
            340                 345                 350

Lys Phe Tyr Tyr Pro Pro Val Ala Ala Val Thr Val Ser Tyr Pro Lys
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Leu Asn Tyr Ile Gly Gly Ala Thr Asn Thr Gly Ile Val Ser Lys
            420                 425                 430

Thr Glu Ser Asp Leu Val Glu Ala Val Asp Arg Asp Leu Arg Lys Met
        435                 440                 445

Leu Ile Asn Pro Arg Ala Ala Asp Pro Leu Ala Leu Gly Val Arg Val
    450                 455                 460

Trp Pro Gln Ala Ile Pro Gln Phe Leu Ile Gly His Leu Asp Arg Leu
465                 470                 475                 480

Asp Ala Ala Lys Ser Ala Leu Val Arg Ser Gly Cys Ser Gly Leu Phe
                485                 490                 495

Leu Gly Gly Asn Tyr Val Ala Gly Val Ala Leu Gly Arg Cys Ile Glu
            500                 505                 510

Gly Ala Tyr Asp Ser Ala Ser Glu Val Ser Asp Phe Leu Asn Lys Tyr
        515                 520                 525

Ala Tyr Lys
    530

<210> SEQ ID NO 5
<211> LENGTH: 54
<212> TYPE: PRT
<213> ORGANISM: Alopecurus

<400> SEQUENCE: 5

Met Leu Thr Ser Ala Thr Thr Pro Ser Ser Ser Ala Ser Ser Arg
1               5                   10                  15

Ala Ser Thr Arg Phe Ala Ser Ser Arg Pro Arg Arg Thr Ala Tyr
                20                  25                  30

Ala Arg Gly Arg Arg Leu Arg Pro Val Leu Ala Met Ala Ala Ser Asp
        35                  40                  45

Asp Pro Arg Ala Arg Ser
    50

<210> SEQ ID NO 6
<211> LENGTH: 1644
```

<212> TYPE: DNA
<213> ORGANISM: Alpecurus

<400> SEQUENCE: 6

```
atgcttactt cagctacaac tccttctagt tcttctgctt cttctagggc ttctaccagg      60
ttcgcttctt catcaaggcc tagaaggacc gcttatgcta gaggaagaag gctcagacct     120
gttctcgcta tggctgcttc tgatgatcct agggctagat ctgttgctgt tgtgggagct     180
ggaatctctg gacttgttgc tgcttacagg ctctctaagt ctggtgtgag agtgactgtg     240
ttcgaggctg atgataggge tggtggaaag atcaggacca actctgattc tggattcctc     300
tgggatgagg gtgctaacac tatgactgag tctgctctcg aggcttctag gcttatcgat     360
gatcttggac tcgaggatag gctccagtac cctaactctc agcacaagag atacaccgtg     420
aaggatggtg ctcctgctct cattccttct gatcctatcg ctcttatgaa gtcatcactc     480
ctcagtacca agtctaagtt caagttgttc ctcgagccat tcctctacga taagtcatct     540
accaagagtt ctaagaaagt gtctgatgag cacatctctg agtctgtggg atcattcttc     600
gagaggcact tcggaaaaga agtggtggat tacctcatcg atcctttcgt ggctggaacc     660
tctgctggtg atcctgagtc tttgtctatc aggcatgctt tccctggact ttggaacctc     720
gagaagaagt acggatctat catcgtggga gctatcatgt ctaagctcac cgctaagggt     780
gataagaagg gatctgctgt ttctggaaag ggtaggaaca gagggcttc tttctctttc      840
cacggtggaa tgcagactct cgtggatgct ctccacaaag aggttggaga tgaaacgtt      900
aagctcggtg ctcaggttct ctctctcgct tgtatctgtg atggactctc tgcttcagat     960
ggatggtcta tctctgtgga ttctaaggat gcttctaaca aagagcttac caagaaccac    1020
tctttcgatg ctgtgatcat gaccgctcca ctctcaaacg tgcagaggat gaagtttacc    1080
aagggtggtg caccttcgt gctcgatttc ttgcctaaag ttgattacct cccactctct    1140
ctcatggtga ccgcttcaa gaaagaggat gttaagaggc cactcgaggg attcggagtt    1200
ctcatccctt acaaagagca gcagaagcac ggactcaaga ctctcggaac tctcttctct    1260
tctatgatgt tcccagatag ggctcctaac gatcagcacc tcttcactac tttcgtggga    1320
ggatctcaca caggggatct tgctggtgct ccaaccagta tccttaagca gctcgtgact    1380
tctgatctcg gaaagcttct tggagttgag ggacagccta ccttcgtgaa gcacatccat    1440
tggagaaacg ctttccctct ctacggacac gattacgatt ctgctttgga ggctatcgga    1500
aagatggaat ctgatctccc tggattcttc tacgctggaa caacaagga tggactcgct    1560
gtgggtaacg tgatcgcttc tggatctaag accgctgatc tcgtgatctc ttacctcgag    1620
tctggaatca agcaggataa ctga                                           1644
```

<210> SEQ ID NO 7
<211> LENGTH: 1596
<212> TYPE: DNA
<213> ORGANISM: Alopecurus

<400> SEQUENCE: 7

```
atggttggag ctactatggc tattgctact gtgactgctg ctttgcctct cagagttaga      60
gtgcctggaa ggtctagaag aggacaggct agatgtgctg tggcttctga tgctactgaa     120
gctcctgctg ctccttctgc tagactctct gctgattgcg ttatcgtggg aggtggaatc     180
tctggattgt gtactgctca ggctctcgct actaagtacg tgtttctga tctcctcgtg      240
accgaggcta gagctagacc tggtggaaac atcactactg ttgagaggcc tgatgaggga    300
```

```
tacctttggg aagaaggacc taactctttc cagccttctg atcctgtgct caccatggct    360
gttgattctg gactcaagga tgagcttgtg ttcggagatc ctaacgctcc tagattcgtt    420
ctctgggagg gaaagcttag gcctgttcct tctaagcctg gtgatctccc tttcttcgat    480
ctcatgtcta tccctggaaa gctcagggct ggacttggtg ctcttggaat tagacctcct    540
ccacctggaa gagaagagtc tgttgaagag ttcgtgagaa gaaacctcgg agctgaggtt    600
ttcgagagac tcatcgagcc tttctgctct ggtgtttacg ctggtgatcc ttcaaagctc    660
tctatgaggg ctgcttccgg aaaggtttgg aggcttgaag agaacggtgg atctatcatc    720
ggaggaacca tcaaggctat ccaggataag ggaaagaacc ctaagcctcc tagagatcct    780
agactcccag ctcctaaggg acagactgtt gcttctttca gaaagggact cgctatgctc    840
cctaacgcta tcgcttctag actcggatct aaggtgaagc tctcttggaa gctcacctct    900
atcaccaagt ctgagaacca gggatacgtg ctcggatatg agactcctga gggtgttgtt    960
tctgtgcagg ctaagtctgt gatcatgacc atccctagtt acattgcttc tgatatcctc   1020
aggccactct cttcagatgc tgctgatgga ctctctaagt tctactaccc tcctgtggct   1080
gctgtgactg tgtcttatcc taaagaggct atcagaaaag aatgcctcat cgatggtgag   1140
ttgcaggat tcggacagct ccatcctaga tctcaaggtg ttgagactct cggaacaatc   1200
tactcttctt cactttttcc aaacagggct ccagctggta gagttcttct cctcaactac   1260
atcgaggtg ctaccaacac tggaatcgtg tctaagaccg agtctgatct cgttgaggct   1320
gtggataggg atctcagaaa gatgctcatc aaccctaggg ctgctgatcc tcttgctctc   1380
ggtgttagag tttggcctca agctatccca cagttcctca tcggacatct cgatagactc   1440
gatgctgcta agtcagctct cgtgagatct ggttgctctg acttttcct cggtggaaac   1500
tatgttgctg gtgtggctct cggaagatgt atcgagggag cttacgattc tgcttctgag   1560
gtgtcagatt tcctcaacaa gtacgcttac aagtga                             1596

<210> SEQ ID NO 8
<211> LENGTH: 44
<212> TYPE: PRT
<213> ORGANISM: Zea mays

<400> SEQUENCE: 8

Met Leu Ala Leu Thr Ala Ser Ala Ser Ser Ser His Pro Tyr
1               5                   10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro
            35                  40

<210> SEQ ID NO 9
<211> LENGTH: 44
<212> TYPE: PRT
<213> ORGANISM: Sorghum bicolor

<400> SEQUENCE: 9

Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
                20                  25                  30

Ala Met Ala Gly Ser Asp Asp Ser Arg Ala Ala Pro
            35                  40
```

```
<210> SEQ ID NO 10
<211> LENGTH: 540
<212> TYPE: PRT
<213> ORGANISM: Artificial
<220> FEATURE:
<223> OTHER INFORMATION: chimeric construct tp-ZeamaPPO2::AlomyPPO2

<400> SEQUENCE: 10

Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
            35                  40                  45

Ala Val Val Gly Ala Gly Val Ser Gly Leu Val Ala Ala Tyr Arg Leu
        50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
        115                 120                 125

Lys Arg Tyr Thr Val Lys Asp Gly Ala Pro Ala Leu Ile Pro Ser Asp
130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Ser Thr Lys Ser
                165                 170                 175

Ser Lys Lys Val Ser Asp Glu His Ile Ser Glu Ser Val Gly Ser Phe
            180                 185                 190

Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
    210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
        275                 280                 285

Gly Asp Gly Asn Val Lys Leu Gly Ala Gln Val Leu Ser Leu Ala Cys
    290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
```

```
            370                 375                 380
Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Phe Val
            420                 425                 430

Gly Gly Ser His Asn Arg Asp Leu Ala Gly Ala Pro Thr Ser Ile Leu
                435                 440                 445

Lys Gln Leu Val Thr Ser Asp Leu Gly Lys Leu Leu Gly Val Glu Gly
            450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
                500                 505                 510

Ala Val Gly Asn Val Ile Ala Ser Gly Ser Lys Thr Ala Asp Leu Val
                515                 520                 525

Ile Ser Tyr Leu Glu Ser Gly Ile Lys Gln Asp Asn
                530                 535                 540

<210> SEQ ID NO 11
<211> LENGTH: 540
<212> TYPE: PRT
<213> ORGANISM: Artificial
<220> FEATURE:
<223> OTHER INFORMATION: chimeric construct
      tp-ZeamaPPO2::AlomyPPO2_R130A

<400> SEQUENCE: 11

Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
            35                  40                  45

Ala Val Val Gly Ala Gly Val Ser Gly Leu Val Ala Ala Tyr Arg Leu
        50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
                100                 105                 110

Asp Asp Leu Gly Leu Glu Asp Arg Leu Gln Tyr Pro Asn Ser Gln His
            115                 120                 125

Lys Ala Tyr Thr Val Lys Asp Gly Ala Pro Ala Leu Ile Pro Ser Asp
            130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Ser Thr Lys Ser
                165                 170                 175

Ser Lys Lys Val Ser Asp Glu His Ile Ser Glu Ser Val Gly Ser Phe
            180                 185                 190
```

-continued

```
Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
    210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
        275                 280                 285

Gly Asp Gly Asn Val Lys Leu Gly Ala Gln Val Leu Ser Leu Ala Cys
    290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
    370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Phe Val
            420                 425                 430

Gly Gly Ser His Asn Arg Asp Leu Ala Gly Ala Pro Thr Ser Ile Leu
        435                 440                 445

Lys Gln Leu Val Thr Ser Asp Leu Gly Lys Leu Leu Gly Val Glu Gly
    450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
    530                 535                 540

<210> SEQ ID NO 12
<211> LENGTH: 540
<212> TYPE: PRT
<213> ORGANISM: Artificial
<220> FEATURE:
<223> OTHER INFORMATION: chimeric construct
      tp-ZeamaPPO2::AlomyPPO2_F431V

<400> SEQUENCE: 12

Met Leu Ala Leu Thr Ala Ser Ala Ser Ser Ala Ser Ser His Pro Tyr
1               5                   10                  15
```

```
Arg His Ala Ser Ala His Thr Arg Arg Pro Arg Leu Arg Ala Val Leu
            20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Val Ala Ala Tyr Arg Leu
    50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
            115                 120                 125

Lys Arg Tyr Thr Val Lys Asp Gly Ala Pro Ala Leu Ile Pro Ser Asp
130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Thr Lys Ser
                165                 170                 175

Ser Lys Lys Val Ser Asp Glu His Ile Ser Glu Ser Val Gly Ser Phe
            180                 185                 190

Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
    210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
        275                 280                 285

Gly Asp Gly Asn Val Lys Leu Gly Ala Gln Val Leu Ser Leu Ala Cys
    290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
    370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Val Val
            420                 425                 430
```

```
Gly Gly Ser His Asn Arg Asp Leu Ala Gly Ala Pro Thr Ser Ile Leu
            435                 440                 445

Lys Gln Leu Val Thr Ser Asp Leu Gly Lys Leu Leu Gly Val Glu Gly
450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Lys Asp Gly Leu
            500                 505                 510

Ala Val Gly Asn Val Ile Ala Ser Gly Ser Lys Thr Ala Asp Leu Val
            515                 520                 525

Ile Ser Tyr Leu Glu Ser Gly Ile Lys Gln Asp Asn
530                 535                 540

<210> SEQ ID NO 13
<211> LENGTH: 540
<212> TYPE: PRT
<213> ORGANISM: Artificial
<220> FEATURE:
<223> OTHER INFORMATION: chimeric construct
      tp-ZeamaPPO2::AlomyPPO2_R130A_F431V

<400> SEQUENCE: 13

Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
            35                  40                  45

Ala Val Val Gly Ala Gly Val Ser Gly Leu Val Ala Ala Tyr Arg Leu
        50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
        115                 120                 125

Lys Ala Tyr Thr Val Lys Asp Gly Ala Pro Ala Leu Ile Pro Ser Asp
130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Ser Thr Lys Ser
                165                 170                 175

Ser Lys Lys Val Ser Asp Glu His Ile Ser Glu Ser Val Gly Ser Phe
            180                 185                 190

Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255
```

```
Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
        275                 280                 285

Gly Asp Gly Asn Val Lys Leu Gly Ala Gln Val Leu Ser Leu Ala Cys
    290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
                340                 345                 350

Thr Lys Gly Gly Ala Pro Phe Val Leu Asp Phe Leu Pro Lys Val Asp
            355                 360                 365

Tyr Leu Pro Leu Ser Leu Met Val Thr Ala Phe Lys Lys Glu Asp Val
    370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Val Val
                420                 425                 430

Gly Gly Ser His Asn Arg Asp Leu Ala Gly Ala Pro Thr Ser Ile Leu
            435                 440                 445

Lys Gln Leu Val Thr Ser Asp Leu Gly Lys Leu Leu Gly Val Glu Gly
        450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
    530                 535                 540
```

<210> SEQ ID NO 14
<211> LENGTH: 540
<212> TYPE: PRT
<213> ORGANISM: Artificial
<220> FEATURE:
<223> OTHER INFORMATION: tp-ZeamaPPO2::c-AlomyPPO2_R130L

<400> SEQUENCE: 14

```
Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
            35                  40                  45

Ala Val Val Gly Ala Gly Val Ser Gly Leu Val Ala Ala Tyr Arg Leu
        50                  55                  60

Ser Lys Ser Gly Val Arg Val Thr Val Phe Glu Ala Asp Asp Arg Ala
65                  70                  75                  80
```

-continued

```
Gly Gly Lys Ile Arg Thr Asn Ser Asp Ser Gly Phe Leu Trp Asp Glu
                85                  90                  95
Gly Ala Asn Thr Met Thr Glu Ser Ala Leu Glu Ala Ser Arg Leu Ile
            100                 105                 110
Asp Asp Leu Gly Leu Glu Asp Arg Leu Gln Tyr Pro Asn Ser Gln His
        115                 120                 125
Lys Leu Tyr Thr Val Lys Asp Gly Ala Pro Leu Ile Pro Ser Asp
    130                 135                 140
Pro Ile Ala Leu Met Lys Ser Ser Leu Leu Ser Thr Lys Ser Lys Phe
145                 150                 155                 160
Lys Leu Phe Leu Glu Pro Phe Leu Tyr Asp Lys Ser Thr Lys Ser
                165                 170                 175
Ser Lys Lys Val Ser Asp Glu His Ile Ser Glu Ser Val Gly Ser Phe
            180                 185                 190
Phe Glu Arg His Phe Gly Lys Glu Val Val Asp Tyr Leu Ile Asp Pro
        195                 200                 205
Phe Val Ala Gly Thr Ser Ala Gly Asp Pro Glu Ser Leu Ser Ile Arg
    210                 215                 220
His Ala Phe Pro Gly Leu Trp Asn Leu Glu Lys Lys Tyr Gly Ser Ile
225                 230                 235                 240
Ile Val Gly Ala Ile Met Ser Lys Leu Thr Ala Lys Gly Asp Lys Lys
                245                 250                 255
Gly Ser Ala Val Ser Gly Lys Gly Arg Asn Lys Arg Ala Ser Phe Ser
            260                 265                 270
Phe His Gly Gly Met Gln Thr Leu Val Asp Ala Leu His Lys Glu Val
        275                 280                 285
Gly Asp Gly Asn Val Lys Leu Gly Ala Gln Val Leu Ser Leu Ala Cys
    290                 295                 300
Ile Cys Asp Gly Leu Ser Ala Ser Asp Gly Trp Ser Ile Ser Val Asp
305                 310                 315                 320
Ser Lys Asp Ala Ser Asn Lys Glu Leu Thr Lys Asn His Ser Phe Asp
                325                 330                 335
Ala Val Ile Met Thr Ala Pro Leu Ser Asn Val Gln Arg Met Lys Phe
            340                 345                 350
Thr Lys Gly Gly Ala Pro Phe Val Leu Asp Phe Leu Pro Lys Val Asp
        355                 360                 365
Tyr Leu Pro Leu Ser Leu Met Val Thr Ala Phe Lys Lys Glu Asp Val
    370                 375                 380
Lys Arg Pro Leu Glu Gly Phe Gly Val Leu Ile Pro Tyr Lys Glu Gln
385                 390                 395                 400
Gln Lys His Gly Leu Lys Thr Leu Gly Thr Leu Phe Ser Ser Met Met
                405                 410                 415
Phe Pro Asp Arg Ala Pro Asn Asp Gln His Leu Phe Thr Thr Phe Val
            420                 425                 430
Gly Gly Ser His Asn Arg Asp Leu Ala Gly Ala Pro Thr Ser Ile Leu
        435                 440                 445
Lys Gln Leu Val Thr Ser Asp Leu Gly Lys Leu Leu Gly Val Glu Gly
    450                 455                 460
Gln Pro Thr Phe Val Lys His Ile His Trp Arg Asn Ala Phe Pro Leu
465                 470                 475                 480
Tyr Gly His Asp Tyr Asp Ser Ala Leu Glu Ala Ile Gly Lys Met Glu
                485                 490                 495
```

```
Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
        530                 535                 540

<210> SEQ ID NO 15
<211> LENGTH: 540
<212> TYPE: PRT
<213> ORGANISM: Artificial
<220> FEATURE:
<223> OTHER INFORMATION: tp-ZeamaPPO2::c-AlomyPPO2_R130A_F431M

<400> SEQUENCE: 15

Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
            20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Val Ala Ala Tyr Arg Leu
    50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
        115                 120                 125

Lys Ala Tyr Thr Val Lys Asp Gly Ala Pro Ala Leu Ile Pro Ser Asp
    130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Thr Lys Ser
                165                 170                 175

Ser Lys Lys Val Ser Asp Glu His Ile Ser Glu Ser Val Gly Ser Phe
            180                 185                 190

Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
    210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
        275                 280                 285

Gly Asp Gly Asn Val Lys Leu Gly Ala Gln Val Leu Ser Leu Ala Cys
    290                 295                 300

Ile Cys Asp Gly Leu Ser Ala Ser Asp Gly Trp Ser Ile Ser Val Asp
305                 310                 315                 320
```

-continued

Ser Lys Asp Ala Ser Asn Lys Glu Leu Thr Lys Asn His Ser Phe Asp
            325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
    370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
            405                 410                 415

Phe Pro Asp Arg Ala Pro Asn Asp Gln His Leu Phe Thr Thr Met Val
            420                 425                 430

Gly Gly Ser His Asn Arg Asp Leu Ala Gly Ala Pro Thr Ser Ile Leu
        435                 440                 445

Lys Gln Leu Val Thr Ser Asp Leu Gly Lys Leu Leu Gly Val Glu Gly
    450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
            485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
    530                 535                 540

<210> SEQ ID NO 16
<211> LENGTH: 540
<212> TYPE: PRT
<213> ORGANISM: Artificial
<220> FEATURE:
<223> OTHER INFORMATION: tp-ZeamaPPO2::c-AlomyPPO2_R130L_F431V

<400> SEQUENCE: 16

Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
            20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Val Ala Ala Tyr Arg Leu
    50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
            85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
        115                 120                 125

Lys Leu Tyr Thr Val Lys Asp Gly Ala Pro Ala Leu Ile Pro Ser Asp
    130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Ser Thr Lys Ser
            165                 170                 175

Ser Lys Lys Val Ser Asp Glu His Ile Ser Glu Ser Val Gly Ser Phe
        180                 185                 190

Phe Glu Arg His Phe Gly Lys Glu Val Val Asp Tyr Leu Ile Asp Pro
    195                 200                 205

Phe Val Ala Gly Thr Ser Ala Gly Asp Pro Glu Ser Leu Ser Ile Arg
210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
    275                 280                 285

Gly Asp Gly Asn Val Lys Leu Gly Ala Gln Val Leu Ser Leu Ala Cys
290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Val Val
            420                 425                 430

Gly Gly Ser His Asn Arg Asp Leu Ala Gly Ala Pro Thr Ser Ile Leu
        435                 440                 445

Lys Gln Leu Val Thr Ser Asp Leu Gly Lys Leu Leu Gly Val Glu Gly
450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
530                 535                 540

<210> SEQ ID NO 17
<211> LENGTH: 540
<212> TYPE: PRT

<213> ORGANISM: Artificial
<220> FEATURE:
<223> OTHER INFORMATION: tp-ZeamaPPO2::c-AlomyPPO2_R130L_F431M

<400> SEQUENCE: 17

```
Met Leu Ala Leu Thr Ala Ser Ala Ser Ala Ser Ser His Pro Tyr
1               5                   10                  15

Arg His Ala Ser Ala His Thr Arg Arg Pro Arg Leu Arg Ala Val Leu
                20                  25                  30

Ala

```
                385                 390                 395                 400
Gln Lys His Gly Leu Lys Thr Leu Gly Thr Leu Phe Ser Ser Met Met
                    405                 410                 415
Phe Pro Asp Arg Ala Pro Asn Asp Gln His Leu Phe Thr Thr Met Val
                420                 425                 430
Gly Gly Ser His Asn Arg Asp Leu Ala Gly Ala Pro Thr Ser Ile Leu
                435                 440                 445
Lys Gln Leu Val Thr Ser Asp Leu Gly Lys Leu Leu Gly Val Glu Gly
            450                 455                 460
Gln Pro Thr Phe Val Lys His Ile His Trp Arg Asn Ala Phe Pro Leu
465                 470                 475                 480
Tyr Gly His Asp Tyr Asp Ser Ala Leu Glu Ala Ile Gly Lys Met Glu
                        485                 490                 495
Ser Asp Leu Pro Gly Phe Phe Tyr Ala Gly Asn Asn Lys Asp Gly Leu
                500                 505                 510
Ala Val Gly Asn Val Ile Ala Ser Gly Ser Lys Thr Ala Asp Leu Val
                515                 520                 525
Ile Ser Tyr Leu Glu Ser Gly Ile Lys Gln Asp Asn
                530                 535                 540

<210> SEQ ID NO 18
<211> LENGTH: 540
<212> TYPE: PRT
<213> ORGANISM: Artificial
<220> FEATURE:
<223> OTHER INFORMATION: tp-ZeamaPPO2::c-AlomyPPO2_R130M_F431V

<400> SEQUENCE: 18

Met Leu Ala Leu Thr Ala Ser Ala Ser Ser Ala Ser Ser His Pro Tyr
1               5                   10                  15
Arg His Ala Ser Ala His Thr Arg Arg Pro Arg Leu Arg Ala Val Leu
                20                  25                  30
Ala Met Ala Gly Ser Asp Asp Pro Arg Ala Ala Pro Ala Arg Ser Val
            35                  40                  45
Ala Val Val Gly Ala Gly Val Ser Gly Leu Val Ala Ala Tyr Arg Leu
        50                  55                  60
Ser Lys Ser Gly Val Arg Val Thr Val Ph

```
            210                 215                 220
His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
                260                 265                 270

Phe His Gly Gly Met Gln Thr Leu Val Asp Ala Leu His Lys Glu Val
            275                 280                 285

Gly Asp Gly Asn Val Lys Leu Gly Ala Gln Val Leu Ser Leu Ala Cys
        290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
    370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Val Val
            420                 425                 430

Gly Gly Ser His Asn Arg Asp Leu Ala Gly Ala Pro Thr Ser Ile Leu
        435                 440                 445

Lys Gln Leu Val Thr Ser Asp Leu Gly Lys Leu Leu Gly Val Glu Gly
    450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
    530                 535                 540

<210> SEQ ID NO 19
<211> LENGTH: 540
<212> TYPE: PRT
<213> ORGANISM: Artificial
<220> FEATURE:
<223> OTHER INFORMATION: tp-ZeamaPPO2::c-AlomyPPO2_R130M_F431M

<400> SEQUENCE: 19

Met Leu Ala Leu Thr Ala Ser Ala Ser Ser Ala Ser His Pro Tyr
1               5                   10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
```

```
            35                  40                  45
Ala Val Val Gly Ala Gly Val Ser Gly Leu Val Ala Ala Tyr Arg Leu
 50                  55                  60
Ser Lys Ser Gly Val Arg Val Thr Val Phe Glu Ala Asp Arg Ala
 65                  70                  75                  80
Gly Gly Lys Ile Arg Thr Asn Ser Asp Ser Gly Phe Leu Trp Asp Glu
                     85                  90                  95
Gly Ala Asn Thr Met Thr Glu Ser Ala Leu Glu Ala Ser Arg Leu Ile
                    100                 105                 110
Asp Asp Leu Gly Leu Glu Asp Arg Leu Gln Tyr Pro Asn Ser Gln His
                    115                 120                 125
Lys Met Tyr Thr Val Lys Asp Gly Ala Pro Ala Leu Ile Pro Ser Asp
                    130                 135                 140
Pro Ile Ala Leu Met Lys Ser Ser Leu Leu Ser Thr Lys Ser Lys Phe
145                 150                 155                 160
Lys Leu Phe Leu Glu Pro Phe Leu Tyr Asp Lys Ser Ser Thr Lys Ser
                    165                 170                 175
Ser Lys Lys Val Ser Asp Glu His Ile Ser Glu Ser Val Gly Ser Phe
                    180                 185                 190
Phe Glu Arg His Phe Gly Lys Glu Val Val Asp Tyr Leu Ile Asp Pro
                    195                 200                 205
Phe Val Ala Gly Thr Ser Ala Gly Asp Pro Glu Ser Leu Ser Ile Arg
210                 215                 220
His Ala Phe Pro Gly Leu Trp Asn Leu Glu Lys Lys Tyr Gly Ser Ile
225                 230                 235                 240
Ile Val Gly Ala Ile Met Ser Lys Leu Thr Ala Lys Gly Asp Lys Lys
                    245                 250                 255
Gly Ser Ala Val Ser Gly Lys Gly Arg Asn Lys Arg Ala Ser Phe Ser
                    260                 265                 270
Phe His Gly Gly Met Gln Thr Leu Val Asp Ala Leu His Lys Glu Val
                    275                 280                 285
Gly Asp Gly Asn Val Lys Leu Gly Ala Gln Val Leu Ser Leu Ala Cys
                    290                 295                 300
Ile Cys Asp Gly Leu Ser Ala Ser Asp Gly Trp Ser Ile Ser Val Asp
305                 310                 315                 320
Ser Lys Asp Ala Ser Asn Lys Glu Leu Thr Lys Asn His Ser Phe Asp
                    325                 330                 335
Ala Val Ile Met Thr Ala Pro Leu Ser Asn Val Gln Arg Met Lys Phe
                    340                 345                 350
Thr Lys Gly Gly Ala Pro Phe Val Leu Asp Phe Leu Pro Lys Val Asp
                    355                 360                 365
Tyr Leu Pro Leu Ser Leu Met Val Thr Ala Phe Lys Lys Glu Asp Val
                    370                 375                 380
Lys Arg Pro Leu Glu Gly Phe Gly Val Leu Ile Pro Tyr Lys Glu Gln
385                 390                 395                 400
Gln Lys His Gly Leu Lys Thr Leu Gly Thr Leu Phe Ser Ser Met Met
                    405                 410                 415
Phe Pro Asp Arg Ala Pro Asn Asp Gln His Leu Phe Thr Thr Met Val
                    420                 425                 430
Gly Gly Ser His Asn Arg Asp Leu Ala Gly Ala Pro Thr Ser Ile Leu
                    435                 440                 445
Lys Gln Leu Val Thr Ser Asp Leu Gly Lys Leu Leu Gly Val Glu Gly
                    450                 455                 460
```

```
Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
    530                 535                 540
```

<210> SEQ ID NO 20
<211> LENGTH: 540
<212> TYPE: PRT
<213> ORGANISM: Artificial
<220> FEATURE:
<223> OTHER INFORMATION: tp-SorbiPPO2::c-AlomyPPO2_R130A_F431M

<400> SEQUENCE: 20

```
Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
            20                  25                  30

Ala Met Ala Gly Ser Asp Asp Ser Arg Ala Ala Pro Ala Arg Ser Val
        35                  40                  45

Ala Val Val Gly Ala Gly Val Ser Gly Leu Val Ala Ala Tyr Arg Leu
    50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
        115                 120                 125

Lys Ala Tyr Thr Val Lys Asp Gly Ala Pro Ala Leu Ile Pro Ser Asp
    130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Ser Thr Lys Ser
                165                 170                 175

Ser Lys Lys Val Ser Asp Glu His Ile Ser Glu Ser Val Gly Ser Phe
            180                 185                 190

Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
    210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
        275                 280                 285
```

-continued

Gly Asp Gly Asn Val Lys Leu Gly Ala Gln Val Leu Ser Leu Ala Cys
        290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Met Val
            420                 425                 430

Gly Gly Ser His Asn Arg Asp Leu Ala Gly Ala Pro Thr Ser Ile Leu
        435                 440                 445

Lys Gln Leu Val Thr Ser Asp Leu Gly Lys Leu Leu Gly Val Glu Gly
450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
530                 535                 540

<210> SEQ ID NO 21
<211> LENGTH: 540
<212> TYPE: PRT
<213> ORGANISM: Artificial
<220> FEATURE:
<223> OTHER INFORMATION: tp-SorbiPPO2::c-AlomyPPO2_R130L_F431V

<400> SEQUENCE: 21

Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
            20                  25                  30

Ala Met Ala Gly Ser Asp Asp Ser Arg Ala Ala Pro Ala Arg Ser Val
        35                  40                  45

Ala Val Val Gly Ala Gly Val Ser Gly Leu Val Ala Ala Tyr Arg Leu
    50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
            100                 105                 110

```
Asp Asp Leu Gly Leu Glu Asp Arg Leu Gln Tyr Pro Asn Ser Gln His
        115                 120                 125

Lys Leu Tyr Thr Val Lys Asp Gly Ala Pro Ala Leu Ile Pro Ser Asp
        130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Ser Thr Lys Ser
                165                 170                 175

Ser Lys Lys Val Ser Asp Glu His Ile Ser Glu Ser Val Gly Ser Phe
                180                 185                 190

Phe Glu Arg His Phe Gly Lys Val Val Asp Tyr Leu Ile Asp Pro
        195                 200                 205

Phe Val Ala Gly Thr Ser Ala Gly Asp Pro Glu Ser Leu Ser Ile Arg
        210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
        260                 265                 270

Phe His Gly Gly Met Gln Thr Leu Val Asp Ala Leu His Lys Glu Val
        275                 280                 285

Gly Asp Gly Asn Val Lys Leu Gly Ala Gln Val Leu Ser Leu Ala Cys
        290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
                340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
        370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Val Val
                420                 425                 430

Gly Gly Ser His Asn Arg Asp Leu Ala Gly Ala Pro Thr Ser Ile Leu
        435                 440                 445

Lys Gln Leu Val Thr Ser Asp Leu Gly Lys Leu Leu Gly Val Glu Gly
        450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
                500                 505                 510

Ala Val Gly Asn Val Ile Ala Ser Gly Ser Lys Thr Ala Asp Leu Val
        515                 520                 525
```

```
Ile Ser Tyr Leu Glu Ser Gly Ile Lys Gln Asp Asn
    530                 535                 540

<210> SEQ ID NO 22
<211> LENGTH: 540
<212> TYPE: PRT
<213> ORGANISM: Artificial
<220> FEATURE:
<223> OTHER INFORMATION: tp-SorbiPPO2::c-AlomyPPO2_R130L_F431M

<400> SEQUENCE: 22

Met Leu Ala Arg Thr Ala Thr Val Ser Ser Thr Ser His Ser His
1               5                   10                  15

Pro Tyr Arg Pro Thr Ser Ala Arg Ser Leu Arg Leu Pro Val Leu
                20                  25                  30

Ala Met Ala Gly Ser Asp Asp Ser Arg Ala Ala Pro Ala Arg Ser Val
            35                  40                  45

Ala Val Val Gly Ala Gly Val Ser Gly Leu Val Ala Ala Tyr Arg Leu
        50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
        115                 120                 125

Lys Leu Tyr Thr Val Lys Asp Gly Ala Pro Ala Leu Ile Pro Ser Asp
    130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Ser Thr Lys Ser
                165                 170                 175

Ser Lys Lys Val Ser Asp Glu His Ile Ser Glu Ser Val Gly Ser Phe
            180                 185                 190

Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
    210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
        275                 280                 285

Gly Asp Gly Asn Val Lys Leu Gly Ala Gln Val Leu Ser Leu Ala Cys
    290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350
```

```
Thr Lys Gly Gly Ala Pro Phe Val Leu Asp Phe Leu Pro Lys Val Asp
            355                 360                 365

Tyr Leu Pro Leu Ser Leu Met Val Thr Ala Phe Lys Lys Glu Asp Val
    370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
            405                 410                 415

Phe Pro Asp Arg Ala Pro Asn Asp Gln His Leu Phe Thr Thr Met Val
            420                 425                 430

Gly Gly Ser His Asn Arg Asp Leu Ala Gly Ala Pro Thr Ser Ile Leu
            435                 440                 445

Lys Gln Leu Val Thr Ser Asp Leu Gly Lys Leu Leu Gly Val Glu Gly
        450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
            485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
            515                 520                 525

Ile Ser Tyr Leu Glu Ser Gly Ile Lys Gln Asp Asn
            530                 535                 540

<210> SEQ ID NO 23
<211> LENGTH: 540
<212> TYPE: PRT
<213> ORGANISM: Artificial
<220> FEATURE:
<223> OTHER INFORMATION: tp-SorbiPPO2::AlomyPPO2

<400> SEQUENCE: 23

Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
            20                  25                  30

Ala Met Ala Gly Ser Asp Asp Ser Arg Ala Ala Pro Ala Arg Ser Val
        35                  40                  45

Ala Val Val Gly Ala Gly Val Ser Gly Leu Val Ala Ala Tyr Arg Leu
    50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
            85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
        115                 120                 125

Lys Arg Tyr Thr Val Lys Asp Gly Ala Pro Ala Leu Ile Pro Ser Asp
130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Thr Lys Ser
            165                 170                 175
```

```
Ser Lys Lys Val Ser Asp Glu His Ile Ser Glu Ser Val Gly Ser Phe
            180                 185                 190

Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
    210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                245                 250                 255

Gly Ser Ala Val Ser Gly Lys Gly Arg Asn Lys Arg Ala Ser Phe Ser
            260                 265                 270

Phe His Gly Gly Met Gln Thr Leu Val Asp Ala Leu His Lys Glu Val
        275                 280                 285

Gly Asp Gly Asn Val Lys Leu Gly Ala Gln Val Leu Ser Leu Ala Cys
    290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
    370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Phe Val
            420                 425                 430

Gly Gly Ser His Asn Arg Asp Leu Ala Gly Ala Pro Thr Ser Ile Leu
        435                 440                 445

Lys Gln Leu Val Thr Ser Asp Leu Gly Lys Leu Leu Gly Val Glu Gly
    450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
    530                 535                 540

<210> SEQ ID NO 24
<211> LENGTH: 540
<212> TYPE: PRT
<213> ORGANISM: Artificial
<220> FEATURE:
<223> OTHER INFORMATION: tp-SorbiPPO2::AlomyPPO2_R130A

<400> SEQUENCE: 24
```

```
Met Leu Ala Arg Thr Ala Thr Val Ser Ser Thr Ser His Ser His
 1               5                  10                 15

Pro Tyr Arg Pro Thr Ser Ala Arg Ser Leu Arg Leu Arg Pro Val Leu
             20                  25                  30

Ala Met Ala Gly Ser Asp Asp Ser Arg Ala Ala Pro Ala Arg Ser Val
         35                  40                  45

Ala Val Val Gly Ala Gly Val Ser Gly Leu Val Ala Ala Tyr Arg Leu
     50                  55                  60

Ser Lys Ser Gly Val Arg Val Thr Val Phe Glu Ala Asp Asp Arg Ala
 65                  70                  75                  80

Gly Gly Lys Ile Arg Thr Asn Ser Asp Ser Gly Phe Leu Trp Asp Glu
                 85                  90                  95

Gly Ala Asn Thr Met Thr Glu Ser Ala Leu Glu Ala Ser Arg Leu Ile
             100                 105                 110

Asp Asp Leu Gly Leu Glu Asp Arg Leu Gln Tyr Pro Asn Ser Gln His
         115                 120                 125

Lys Ala Tyr Thr Val Lys Asp Gly Ala Pro Ala Leu Ile Pro Ser Asp
     130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Ser Thr Lys Ser
                 165                 170                 175

Ser Lys Lys Val Ser Asp Glu His Ile Ser Glu Ser Val Gly Ser Phe
             180                 185                 190

Phe Glu Arg His Phe Gly Lys Glu Val Val Asp Tyr Leu Ile Asp Pro
         195                 200                 205

Phe Val Ala Gly Thr Ser Ala Gly Asp Pro Glu Ser Leu Ser Ile Arg
     210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                 245                 250                 255

Gly Ser Ala Val Ser Gly Lys Gly Arg Asn Lys Arg Ala Ser Phe Ser
             260                 265                 270

Phe His Gly Gly Met Gln Thr Leu Val Asp Ala Leu His Lys Glu Val
         275                 280                 285

Gly Asp Gly Asn Val Lys Leu Gly Ala Gln Val Leu Ser Leu Ala Cys
     290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                 325                 330                 335

Ala Val Ile Met Thr Ala Pro Leu Ser Asn Val Gln Arg Met Lys Phe
             340                 345                 350

Thr Lys Gly Gly Ala Pro Phe Val Leu Asp Phe Leu Pro Lys Val Asp
         355                 360                 365

Tyr Leu Pro Leu Ser Leu Met Val Thr Ala Phe Lys Lys Glu Asp Val
     370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                 405                 410                 415

Phe Pro Asp Arg Ala Pro Asn Asp Gln His Leu Phe Thr Thr Phe Val
```

```
                420             425             430
Gly Gly Ser His Asn Arg Asp Leu Ala Gly Ala Pro Thr Ser Ile Leu
            435             440             445

Lys Gln Leu Val Thr Ser Asp Leu Gly Lys Leu Leu Gly Val Glu Gly
    450             455             460

Gln Pro Thr Phe Val Lys His Ile His Trp Arg Asn Ala Phe Pro Leu
465             470             475             480

Tyr Gly His Asp Tyr Asp Ser Ala Leu Glu Ala Ile Gly Lys Met Glu
                485             490             495

Ser Asp Leu Pro Gly Phe Phe Tyr Ala Gly Asn Asn Lys Asp Gly Leu
            500             505             510

Ala Val Gly Asn Val Ile Ala Ser Gly Ser Lys Thr Ala Asp Leu Val
        515             520             525

Ile Ser Tyr Leu Glu Ser Gly Ile Lys Gln Asp Asn
    530             535             540

<210> SEQ ID NO 25
<211> LENGTH: 540
<212> TYPE: PRT
<213> ORGANISM: Artificial
<220> FEATURE:
<223> OTHER INFORMATION: tp-SorbiPPO2::AlomyPPO2_F431V

<400> SEQUENCE: 25

Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
            20                  25                  30

Ala Met Ala Gly Ser Asp Asp Ser Arg Ala Ala Pro Ala Arg Ser Val
        35                  40                  45

Ala Val Val Gly Ala Gly Val Ser Gly Leu Val Ala Ala Tyr Arg Leu
    50                  55                  60

Ser Lys Ser Gly Val Arg Val Thr Val Phe Glu Ala Asp Asp Arg Ala
65                  70                  75                  80

Gly Gly Lys Ile Arg Thr Asn Ser Asp Ser Gly Phe Leu Trp Asp Glu
                85                  90                  95

Gly Ala Asn Thr Met Thr Glu Ser Ala Leu Glu Ala Ser Arg Leu Ile
            100                 105                 110

Asp Asp Leu Gly Leu Glu Asp Arg Leu Gln Tyr Pro Asn Ser Gln His
        115                 120                 125

Lys Arg Tyr Thr Val Lys Asp Gly Ala Pro Ala Leu Ile Pro Ser Asp
    130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Thr Lys Ser
                165                 170                 175

Ser Lys Lys Val Ser Asp Glu His Ile Ser Glu Ser Val Gly Ser Phe
            180                 185                 190

Phe Glu Arg His Phe Gly Lys Glu Val Val Asp Tyr Leu Ile Asp Pro
        195                 200                 205

Phe Val Ala Gly Thr Ser Ala Gly Asp Pro Glu Ser Leu Ser Ile Arg
    210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
```

```
                    245                 250                 255
Gly Ser Ala Val Ser Lys Gly Arg Asn Lys Arg Ala Ser Phe Ser
                260                 265                 270

Phe His Gly Gly Met Gln Thr Leu Val Asp Ala Leu His Lys Glu Val
            275                 280                 285

Gly Asp Gly Asn Val Lys Leu Gly Ala Gln Val Leu Ser Leu Ala Cys
        290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                325                 330                 335

Ala Val Ile Met Thr Ala Pro Leu Ser Asn Val Gln Arg Met Lys Phe
            340                 345                 350

Thr Lys Gly Gly Ala Pro Phe Val Leu Asp Phe Leu Pro Lys Val Asp
        355                 360                 365

Tyr Leu Pro Leu Ser Leu Met Val Thr Ala Phe Lys Lys Glu Asp Val
    370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asn Asp Gln His Leu Phe Thr Thr Val Val
            420                 425                 430

Gly Gly Ser His Asn Arg Asp Leu Ala Gly Ala Pro Thr Ser Ile Leu
        435                 440                 445

Lys Gln Leu Val Thr Ser Asp Leu Gly Lys Leu Leu Gly Val Glu Gly
    450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                485                 490                 495

Ser Asp Leu Pro Gly Phe Phe Tyr Ala Gly Asn Asn Lys Asp Gly Leu
            500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
    530                 535                 540

<210> SEQ ID NO 26
<211> LENGTH: 540
<212> TYPE: PRT
<213> ORGANISM: Artificial
<220> FEATURE:
<223> OTHER INFORMATION: tp-SorbiPPO2::AlomyPPO2_R130A_F431V

<400> SEQUENCE: 26

Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
            20                  25                  30

Ala Met Ala Gly Ser Asp Asp Ser Arg Ala Ala Pro Ala Arg Ser Val
        35                  40                  45

Ala Val Val Gly Ala Gly Val Ser Gly Leu Val Ala Ala Tyr Arg Leu
    50                  55                  60

Ser Lys Ser Gly Val Arg Val Thr Val Phe Glu Ala Asp Asp Arg Ala
```

```
            65                  70                  75                  80
Gly Gly Lys Ile Arg Thr Asn Ser Asp Ser Gly Phe Leu Trp Asp Glu
                    85                  90                  95

Gly Ala Asn Thr Met Thr Glu Ser Ala Leu Glu Ala Ser Arg Leu Ile
                100                 105                 110

Asp Asp Leu Gly Leu Glu Asp Arg Leu Gln Tyr Pro Asn Ser Gln His
                115                 120                 125

Lys Ala Tyr Thr Val Lys Asp Gly Ala Pro Ala Leu Ile Pro Ser Asp
                130                 135                 140

Pro Ile Ala Leu Met Lys Ser Ser Leu Leu Ser Thr Lys Ser Lys Phe
145                 150                 155                 160

Lys Leu Phe Leu Glu Pro Phe Leu Tyr Asp Lys Ser Thr Lys Ser
                    165                 170                 175

Ser Lys Lys Val Ser Asp Glu His Ile Ser Glu Ser Val Gly Ser Phe
                180                 185                 190

Phe Glu Arg His Phe Gly Lys Glu Val Val Asp Tyr Leu Ile Asp Pro
                    195                 200                 205

Phe Val Ala Gly Thr Ser Ala Gly Asp Pro Glu Ser Leu Ser Ile Arg
                210                 215                 220

His Ala Phe Pro Gly Leu Trp Asn Leu Glu Lys Lys Tyr Gly Ser Ile
225                 230                 235                 240

Ile Val Gly Ala Ile Met Ser Lys Leu Thr Ala Lys Gly Asp Lys Lys
                    245                 250                 255

Gly Ser Ala Val Ser Gly Lys Gly Arg Asn Lys Arg Ala Ser Phe Ser
                260                 265                 270

Phe His Gly Gly Met Gln Thr Leu Val Asp Ala Leu His Lys Glu Val
                    275                 280                 285

Gly Asp Gly Asn Val Lys Leu Gly Ala Gln Val Leu Ser Leu Ala Cys
                290                 295                 300

Ile Cys Asp Gly Leu Ser Ala Ser Asp Gly Trp Ser Ile Ser Val Asp
305                 310                 315                 320

Ser Lys Asp Ala Ser Asn Lys Glu Leu Thr Lys Asn His Ser Phe Asp
                    325                 330                 335

Ala Val Ile Met Thr Ala Pro Leu Ser Asn Val Gln Arg Met Lys Phe
                340                 345                 350

Thr Lys Gly Gly Ala Pro Phe Val Leu Asp Phe Leu Pro Lys Val Asp
                    355                 360                 365

Tyr Leu Pro Leu Ser Leu Met Val Thr Ala Phe Lys Lys Glu Asp Val
                370                 375                 380

Lys Arg Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                    405                 410                 415

Phe Pro Asp Arg Ala Pro Asn Asp Gln His Leu Phe Thr Thr Val Val
                420                 425                 430

Gly Gly Ser His Asn Arg Asp Leu Ala Gly Ala Pro Thr Ser Ile Leu
                    435                 440                 445

Lys Gln Leu Val Thr Ser Asp Leu Gly Lys Leu Leu Gly Val Glu Gly
                450                 455                 460

Gln Pro Thr Phe Val Lys His Ile His Trp Arg Asn Ala Phe Pro Leu
465                 470                 475                 480

Tyr Gly His Asp Tyr Asp Ser Ala Leu Glu Ala Ile Gly Lys Met Glu
                    485                 490                 495
```

```
Ser Asp Leu Pro Gly Phe Phe Tyr Ala Gly Asn Asn Lys Asp Gly Leu
        500                 505                 510

Ala Val Gly Asn Val Ile Ala Ser Gly Ser Lys Thr Ala Asp Leu Val
        515                 520                 525

Ile Ser Tyr Leu Glu Ser Gly Ile Lys Gln Asp Asn
        530                 535                 540

<210> SEQ ID NO 27
<211> LENGTH: 534
<212> TYPE: PRT
<213> ORGANISM: Amaranthus

<400> SEQUENCE: 27

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
        260                 265                 270

Gln Thr Leu Val Asp Thr Met Cys Lys Gln Leu Gly Glu Asp Glu Leu
    275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
```

```
                     325                 330                 335
Val Lys Glu Met Lys Ile Met Lys Phe Gly Asn Pro Phe Ser Leu Asp
                340                 345                 350
Phe Ile Pro Glu Val Thr Tyr Val Pro Leu Ser Val Met Ile Thr Ala
                355                 360                 365
Phe Lys Asp Lys Val Lys Arg Pro Leu Glu Gly Phe Gly Val Leu
                370                 375                 380
Ile Pro Ser Lys Glu Gln His Asn Gly Leu Lys Thr Leu Gly Thr Leu
385                 390                 395                 400
Phe Ser Ser Met Met Phe Pro Asp Arg Ala Pro Ser Asp Met Cys Leu
                405                 410                 415
Phe Thr Thr Phe Val Gly Gly Ser Arg Asn Arg Lys Leu Ala Asn Ala
                420                 425                 430
Ser Thr Asp Glu Leu Lys Gln Ile Val Ser Ser Asp Leu Gln Gln Leu
                435                 440                 445
Leu Gly Thr Glu Asp Glu Pro Ser Phe Val Asn His Leu Phe Trp Ser
                450                 455                 460
Asn Ala Phe Pro Leu Tyr Gly His Asn Tyr Asp Ser Val Leu Arg Ala
465                 470                 475                 480
Ile Asp Lys Met Glu Lys Asp Leu Pro Gly Phe Phe Tyr Ala Gly Asn
                485                 490                 495
His Lys Gly Gly Leu Ser Val Gly Lys Ala Met Ala Ser Gly Cys Lys
                500                 505                 510
Ala Ala Glu Leu Val Ile Ser Tyr Leu Asp Ser His Ile Tyr Val Lys
                515                 520                 525
Met Asp Glu Lys Thr Ala
                530

<210> SEQ ID NO 28
<211> LENGTH: 534
<212> TYPE: PRT
<213> ORGANISM: Amaranthus

<400> SEQUENCE: 28

Met Val Ile Gln Ser Ile Thr His Leu Ser Pro Asn Leu Ala Leu Pro
1               5                   10                  15
Ser Pro Leu Ser Val Ser Thr Lys Asn Tyr Pro Val Ala Val Met Gly
                20                  25                  30
Asn Ile Ser Glu Arg Glu Glu Pro Thr Ser Ala Lys Arg Val Ala Val
                35                  40                  45
Val Gly Ala Gly Val Ser Gly Leu Ala Ala Ala Tyr Lys Leu Lys Ser
                50                  55                  60
His Gly Leu Ser Val Thr Leu Phe Glu Ala Asp Ser Arg Ala Gly Gly
65                  70                  75                  80
Lys Leu Lys Thr Val Lys Lys Asp Gly Phe Ile Trp Asp Glu Gly Ala
                85                  90                  95
Asn Thr Met Thr Glu Ser Glu Ala Glu Val Ser Ser Leu Ile Asp Asp
                100                 105                 110
Leu Gly Leu Arg Glu Lys Gln Gln Leu Pro Ile Ser Gln Asn Lys Arg
                115                 120                 125
Tyr Ile Ala Arg Ala Gly Leu Pro Val Leu Pro Ser Asn Pro Ala
                130                 135                 140
Ala Leu Leu Thr Ser Asn Ile Leu Ser Ala Lys Ser Lys Leu Gln Ile
145                 150                 155                 160
```

-continued

Met Leu Glu Pro Phe Leu Trp Arg Lys His Asn Ala Thr Glu Leu Ser
            165                 170                 175

Asp Glu His Val Gln Glu Ser Val Gly Glu Phe Phe Arg His Phe
        180                 185                 190

Gly Lys Glu Phe Val Asp Tyr Val Ile Asp Pro Phe Val Ala Gly Thr
            195                 200                 205

Cys Gly Gly Asp Pro Gln Ser Leu Ser Met His His Thr Phe Pro Glu
210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530

<210> SEQ ID NO 29
<211> LENGTH: 533
<212> TYPE: PRT
<213> ORGANISM: Amaranthus

<400> SEQUENCE: 29

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asn Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
            115                 120                 125

Tyr Ile Ala Arg Asp Gly Leu Pro Val Leu Leu Pro Ser Asn Pro Ala
        130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
            195                 200                 205

Cys Gly Asp Pro Gln Ser Leu Ser Met Tyr His Thr Phe Pro Glu Val
            210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Gln Gly Gly Met Gln
            260                 265                 270

Thr Leu Val Asp Thr Met Cys Lys Gln Leu Gly Glu Asp Glu Leu Lys
            275                 280                 285

Leu Gln Cys Glu Val Leu Ser Leu Ser Tyr Asn Gln Lys Gly Ile Pro
        290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
            325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
            355                 360                 365

Lys Lys Asp Lys Val Lys Arg Pro Leu Glu Gly Phe Gly Val Leu Ile
            370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415
```

```
Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
            435                 440                 445

Gly Thr Glu Asp Glu Pro Ser Phe Val Asn His Leu Phe Trp Ser Asn
450                 455                 460

Ala Phe Pro Leu Tyr Gly His Asn Tyr Asp Ser Val Leu Arg Ala Ile
465                 470                 475                 480

Asp Lys Met Glu Lys Asp Leu Pro Gly Phe Phe Tyr Ala Gly Asn His
            485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
            515                 520                 525

Asp Glu Lys Thr Ala
            530

<210> SEQ ID NO 30
<211> LENGTH: 533
<212> TYPE: PRT
<213> ORGANISM: Amaranthus

<400> SEQUENCE: 30

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
            35                  40                  45

Val Gly Ala Gly Val Ser Gly Leu Ala Ala Ala Tyr Lys Leu Lys Ser
        50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
            115                 120                 125

Tyr Ile Ala Arg Asp Gly Leu Pro Val Leu Leu Pro Ser Asn Pro Ala
        130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met His His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255
```

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Met Ser Asn Asn Thr Ser Glu
305                 310                 315                 320

Asp Gln Ser Tyr Asp Ala Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
            355                 360                 365

Lys Lys Asp Lys Val Lys Arg Pro Leu Glu Gly Phe Gly Val Leu Ile
            370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
        435                 440                 445

Gly Thr Glu Asp Glu Pro Ser Phe Val Asn His Leu Phe Trp Ser Asn
    450                 455                 460

Ala Phe Pro Leu Tyr Gly His Asn Tyr Asp Cys Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
        515                 520                 525

Asp Glu Lys Thr Ala
    530

<210> SEQ ID NO 31
<211> LENGTH: 550
<212> TYPE: PRT
<213> ORGANISM: Amaranthus

<400> SEQUENCE: 31

Met Ser Ala Met Ala Leu Ser Ser Ile Leu Gln Cys Pro Pro His
1               5                   10                  15

Ser Asp Ile Ser Phe Arg Phe Phe Ala His Thr Arg Thr Gln Pro Pro
            20                  25                  30

Ile Phe Phe Gly Arg Pro Arg Lys Leu Ser Tyr Ile His Cys Ser Thr
        35                  40                  45

Ser Ser Ser Ser Thr Ala Asn Tyr Gln Asn Thr Ile Thr Ser Gln Gly
    50                  55                  60

Glu Gly Asp Lys Val Leu Asp Cys Val Ile Val Gly Ala Gly Ile Ser
65                  70                  75                  80

Gly Leu Cys Ile Ala Gln Ala Leu Ser Thr Lys His Ile Gln Ser Asn

```
                         85                  90                      95
Leu Asn Phe Ile Val Thr Glu Ala Lys His Arg Val Gly Gly Asn Ile
                100                 105                 110
Thr Thr Met Glu Ser Asp Gly Tyr Ile Trp Glu Gly Pro Asn Ser
                115                 120                 125
Phe Gln Pro Ser Asp Pro Val Leu Thr Met Ala Val Asp Ser Gly Leu
            130                 135                 140
Lys Asp Asp Leu Val Leu Gly Asp Pro Asn Ala Pro Arg Phe Val Leu
145                 150                 155                 160
Trp Asn Gly Lys Leu Arg Pro Val Pro Ser Lys Pro Thr Asp Leu Pro
                165                 170                 175
Phe Phe Asp Leu Met Ser Phe Pro Gly Lys Ile Arg Ala Gly Leu Gly
            180                 185                 190
Ala Leu Gly Leu Arg Pro Pro Pro Ser Tyr Glu Glu Ser Val Glu
            195                 200                 205
Glu Phe Val Arg Arg Asn Leu Gly Asp Glu Val Phe Glu Arg Leu Ile
        210                 215                 220
Glu Pro Phe Cys Ser Gly Val Tyr Ala Gly Asp Pro Ala Lys Leu Ser
225                 230                 235                 240
Met Lys Ala Ala Phe Gly Lys Val Trp Thr Leu Glu Gln Lys Gly Gly
                245                 250                 255
Ser Ile Ile Ala Gly Thr Leu Lys Thr Ile Gln Glu Arg Lys Asn Asn
                260                 265                 270
Pro Pro Pro Pro Arg Asp Pro Arg Leu Pro Lys Pro Lys Gly Gln Thr
                275                 280                 285
Val Gly Ser Phe Arg Lys Gly Leu Ile Met Leu Pro Thr Ala Ile Ala
                290                 295                 300
Ala Arg Leu Gly Ser Lys Val Lys Leu Ser Trp Thr Leu Ser Asn Ile
305                 310                 315                 320
Asp Lys Ser Leu Asn Gly Glu Tyr Asn Leu Thr Tyr Gln Thr Pro Asp
                325                 330                 335
Gly Pro Val Ser Val Arg Thr Lys Ala Val Val Met Thr Val Pro Ser
                340                 345                 350
Tyr Ile Ala Ser Ser Leu Leu Arg Pro Leu Ser Asp Val Ala Ala Asp
                355                 360                 365
Ser Leu Ser Lys Phe Tyr Tyr Pro Pro Val Ala Ala Val Ser Leu Ser
                370                 375                 380
Tyr Pro Lys Glu Ala Ile Arg Pro Glu Cys Leu Ile Asp Gly Glu Leu
385                 390                 395                 400
Lys Gly Phe Gly Gln Leu His Pro Arg Ser Gln Gly Val Glu Thr Leu
                405                 410                 415
Gly Thr Ile Tyr Ser Ser Leu Phe Pro Gly Arg Ala Pro Pro Gly
                420                 425                 430
Arg Thr Leu Ile Leu Ser Tyr Ile Gly Gly Ala Thr Asn Leu Gly Ile
                435                 440                 445
Leu Gln Lys Ser Glu Asp Glu Leu Ala Glu Thr Val Asp Lys Asp Leu
                450                 455                 460
Arg Lys Ile Leu Ile Asn Pro Asn Ala Lys Gly Ser Arg Val Leu Gly
465                 470                 475                 480
Val Arg Val Trp Pro Lys Ala Ile Pro Gln Phe Leu Val Gly His Phe
                485                 490                 495
Asp Val Leu Asp Ala Ala Lys Ala Gly Leu Ala Asn Ala Gly Gln Lys
                500                 505                 510
```

```
Gly Leu Phe Leu Gly Gly Asn Tyr Val Ser Gly Val Ala Leu Gly Arg
        515                 520                 525

Cys Ile Glu Gly Ala Tyr Asp Ser Ala Ser Glu Val Val Asp Phe Leu
    530                 535                 540

Ser Gln Tyr Lys Asp Lys
545             550
```

PLANTS HAVING INCREASED TOLERANCE TO HERBICIDES

This application is a National Stage application of International Application No. PCT/IB2014/063877, filed Aug. 12, 2014, which claims the benefit of U.S. Provisional Application No. 61/864,671, filed Aug. 12, 2013, U.S. Provisional Application No. 61/864,672 filed Aug. 12, 2013, and U.S. Provisional Application No. 61/866,067, filed Aug. 15, 2013; the entire contents of which are hereby incorporated herein by reference in their its entirety.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "77455_Seqlisting.txt" created on Feb. 8, 2016, and is 123,357 bytes in size. The sequence listing contained in this .txt file is part of the specification and is hereby incorporated by reference herein in its entirety.

FIELD OF THE INVENTION

The present invention relates in general to methods for conferring on plants agricultural level tolerance to a herbicide. Particularly, the invention refers to plants having an increased tolerance to PPO-inhibiting herbicides. More specifically, the present invention relates to methods and plants obtained by mutagenesis and cross-breeding and transformation that have an increased tolerance to PPO-inhibiting herbicides.

BACKGROUND OF THE INVENTION

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis which is the oxidation of protoporphyrinogen IX to protoporphyrin IX. (Matringe et al. 1989. Biochem. 1. 260: 231). PPO-inhibiting herbicides include many different structural classes of molecules (Duke et al. 1991. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70). These herbicidal compounds include the diphenylethers {e.g. lactofen, (+−)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobenzoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs. Many of these compounds competitively inhibit the normal reaction catalyzed by the enzyme, apparently acting as substrate analogs.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102: 881).

Not all PPO enzymes are sensitive to herbicides which inhibit plant PPO enzymes. Both the *Escherichia coli* and *Bacillus subtilis* PPO enzymes (Sasarmen et al. 1993. Can. J. Microbiol. 39: 1155; Dailey et al. 1994. J. Biol. Chem. 269: 813) are resistant to these herbicidal inhibitors.

Mutants of the unicellular alga *Chlamydomonas reinhardtii* resistant to the phenylimide herbicide S-23142 have been reported (Kataoka et al. 1990. J. Pesticide Sci. 15: 449; Shibata et al. 1992. In Research in Photosynthesis, Vol. III, N. Murata, ed. Kluwer:Netherlands. pp. 567-70). At least one of these mutants appears to have an altered PPO activity that is resistant not only to the herbicidal inhibitor on which the mutant was selected, but also to other classes of protox inhibitors (Oshio et al. 1993. Z. Naturforsch. 48c: 339; Sato et al. 1994. In ACS Symposium on Porphyric Pesticides, S. Duke, ed. ACS Press: Washington, D.C.). A mutant tobacco cell line has also been reported that is resistant to the inhibitor S-21432 (Che et al. 1993. Z. Naturforsch. 48c: 350). Auxotrophic *E. coli* mutants have been used to confirm the herbicide resistance of cloned plant PPO-inhibiting herbicides.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to PPO inhibitors (see e.g. U.S. Pat. No. 5,767,373 or 5,939,602, and patent family members thereof.). In addition, US 2010/0100988 and WO 2007/024739 discloses nucleotide sequences encoding amino acid sequences having enzymatic activity such that the amino acid sequences are resistant to PPO inhibitor herbicidal chemicals, in particular 3-phenyluracil inhibitor specific PPO mutants.

WO 2012/080975 discloses plants the tolerance of which to a PPO-inhibiting herbicide named "benzoxazinone-derivative" herbicide (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione; "BAS 850H") had been increased by transforming said plants with nucleic acids encoding mutated PPO (mutated PPO) enzymes. In particular, WO 2012/080975 discloses that the introduction of nucleic acids which code for a mutated PPO of an *Amaranthus* type II PPO in which the Arginine at position 128 had been replaced by a leucine, alanine, or valine, and the phenylalanine at position 420 had been replaced by a methionine, cysteine, isoleucine, leucine, or threonine, confers increased tolerance/resistance to a benzoxazinone-derivative herbicide. The inventors of the present invention have now surprisingly found that those types of double-mutants in the type II or type I PPO of *Alopecurus myosuroides*, and, furthermore, novel substitutions which are not disclosed in WO 2012/080975 confer increased tolerance/resistance to a wide variety of PPO inhibitors. In addition, the inventors of the present invention have surprisingly found, that the wildtype sequence of type II PPO of *Alopecurus myosuroides* as well as single mutations introduced therein confers increased tolerance/resistance to a wide variety of PPO inhibitors. Thus, to date, the prior art has not described PPO-inhibiting herbicide tolerant plants containing a PPO nucleic acid according to the present invention, which are tolerant/resistant to a broad spectrum of PPO inhibitors. Therefore, what is needed in the art are crop plants and crop plants having increased tolerance to herbicides such as PPO-inhibiting herbicide and containing at least one wildtype and/or mutated PPO nucleic acid according to the present invention. Also needed are methods for controlling weed growth in the vicinity of such crop plants or crop plants. These compositions and methods would allow for the use of spray over techniques when applying herbicides to areas containing crop plants or crop plants.

SUMMARY OF THE INVENTION

Accordingly, in one embodiment, the present invention provides a method for producing a plant having an increased herbicide tolerance or resistance as compared to a corresponding wild type plant whereby the method comprises at least the following step: increasing or generating in a plant the activity of a transgenic wildtype or mutant *Alopecurus myosuroides* PPO polypeptide, or a homolog thereof.

Accordingly, the invention provides a transgenic plant that over-expresses an isolated PPO polynucleotide as defined herein, or a homolog thereof, in the sub-cellular compartment and tissue as indicated herein. The transgenic plant of the invention demonstrates an improved or increased herbicide tolerance or resistance as compared to a wild type variety of the plant.

Accordingly, the invention provides a method for producing a plant with increased herbicide tolerance or resistance as compared to a corresponding wild type plant comprising at least one of the steps selected from the group consisting of: (i) increasing or generating the activity of a PPO polypeptide comprising the sequence of SEQ ID NO: 2 or 4, or a homolog thereof; or (ii) increasing or generating the activity of an expression product of one or more isolated polynucleotide(s) comprising one or more polynucleotide(s) comprising the sequence of SEQ ID NO: 1 or 3, or a homolog thereof.

The invention further provides an isolated and/or recombinant and/or synthetic nucleic acid molecule comprising a nucleic acid molecule selected from the group consisting of:
(a) a nucleic acid molecule encoding the PPO polypeptide comprising the sequence of SEQ ID NO: 2 or 4, or a homolog thereof;
(b) a nucleic acid molecule comprising the sequence of SEQ ID NO: 1 or 3, or a homolog thereof,
(c) a nucleic acid molecule, which, as a result of the degeneracy of the genetic code, can be derived from a PPO polypeptide sequence of SEQ ID NO: 2 or 4, or a homolog thereof, and confers increased herbicide tolerance or resistance, as compared to a corresponding, e.g. non-transformed, wild type plant cell, a plant or a part thereof;
(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of SEQ ID NO: 1 or 3, or a homolog thereof, and confers increased herbicide tolerance or resistance, as compared to a corresponding, e.g. non-transformed, wild type plant cell, a plant or a part thereof;
(e) a nucleic acid molecule encoding a polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the PPO polypeptide sequence of SEQ ID NO: 2 or 4, and confers increased herbicide tolerance or resistance, as compared to a corresponding, e.g. non-transformed, wild type plant cell, a plant or a part thereof;
(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;

The invention further provides a method for increasing herbicide tolerance or resistance of a crop plant, the method comprising the following steps: (i) increasing or generating of the expression of at least one polynucleotide; and/or (ii) increasing or generating the expression of an expression product encoded by at least one polynucleotide; and/or (iii) increasing or generating one or more activities of an expression product encoded by at least one polynucleotide, wherein the polynucleotide is selected from the group consisting of:
(a) an isolated polynucleotide encoding the PPO polypeptide comprising the sequence of SEQ ID NO: 2 or 4, or a homolog thereof;
(b) an isolated polynucleotide comprising the sequence of SEQ ID NO: 1 or 3, or a homolog thereof;
(c) an isolated polynucleotide, which, as a result of the degeneracy of the genetic code, can be derived from a PPO polypeptide comprising the sequence of SEQ ID NO: 2 or 4, or a homolog thereof and confers an increased herbicide tolerance or resistance as compared to a corresponding, e.g. non-transformed, wild type plant cell, a transgenic plant or a part thereof;
(d) an isolated polynucleotide having 30% or more identity, for example 50%, 60%, 70%, 80%, 85%, 90%, 95%, 97%, 98%, or 99% (percent) or more identity with the sequence of a polynucleotide comprising the sequence of SEQ ID NO: 1 or 3, or a homolog thereof and conferring an increased herbicide tolerance or resistance as compared to a corresponding, e.g. non-transformed, wild type plant cell, a transgenic plant or a part thereof;
(e) an isolated polynucleotide encoding a polypeptide having 30% or more identity, for example 50%, 60%, 70%, 80%, 85%, 90%, 95%, 97%, 98%, or 99% or more identity with the amino acid sequence of the polypeptide encoded by the isolated polynucleotide of (a) to (c) and conferring an increased herbicide tolerance or resistance as compared to a corresponding, e.g. non-transformed, wild type plant cell, a transgenic plant or a part thereof;
(f) an isolated polynucleotide which hybridizes with an isolated polynucleotide of (a) to (c) under stringent hybridization conditions and confers an increased herbicide tolerance or resistance as compared to a corresponding, e.g. non-transformed, wild type plant cell, a transgenic plant or a part thereof;

Furthermore, the invention relates to a method for producing a transgenic plant with increased herbicide tolerance or resistance as compared to a corresponding, e.g. non-transformed, wild type plant, comprising transforming a plant cell or a plant cell nucleus or a plant tissue to produce such a plant, with an isolated polynucleotide selected from the group consisting of:

(a) an isolated polynucleotide encoding the PPO polypeptide comprising the sequence of SEQ ID NO: 2 or 4, or a homolog thereof;
(b) an isolated polynucleotide comprising the sequence of SEQ ID NO: 1 or 3, or a homolog thereof;
(c) an isolated polynucleotide, which, as a result of the degeneracy of the genetic code, can be derived from a PPO polypeptide comprising the sequence of SEQ ID NO: 2 or 4, or a homolog thereof and confers an increased herbicide tolerance or resistance as compared to a corresponding, e.g. non-transformed, wild type plant cell, a transgenic plant or a part thereof;
(d) an isolated polynucleotide having 30 or more, for example 50%, 60%, 70%, 80%, 85%, 90%, 95%, 97%, 98%, or 99% (percent) or more identity with the sequence of a polynucleotide comprising the sequence of SEQ ID NO: 1 or 3, or a homolog thereof and conferring an increased herbicide tolerance or resistance as compared to a corresponding, e.g. non-transformed, wild type plant cell, a transgenic plant or a part thereof;
(e) an isolated polynucleotide encoding a polypeptide having 30 or more, for example 50%, 60%, 70%, 80%, 85%, 90%, 95%, 97%, 98%, or 99% or more identity with the amino acid sequence of the PPO polypeptide encoded by the isolated polynucleotide of (a) to (c) and conferring an increased herbicide tolerance or resistance as compared to a corresponding, e.g. non-transformed, wild type plant cell, a transgenic plant or a part thereof;
(f) an isolated polynucleotide which hybridizes with an isolated polynucleotide of (a) to (c) under stringent hybridization conditions and confers an increased herbicide tolerance or resistance as compared to a corresponding, e.g. non-transformed, wild type plant cell, a transgenic plant or a part thereof;

Furthermore, the invention relates to a method for controlling undesired vegetation at a plant cultivation site, the method comprising the steps of:
a) providing, at said site, a plant that comprises at least one nucleic acid comprising a nucleotide sequence encoding a PPO polypeptide comprising the sequence of SEQ ID NO: 2 or 4, or a homolog thereof, which is resistant or tolerant to a PPO-inhibiting herbicide and/or
b) applying to said site an effective amount of said herbicide.

In another embodiment, the invention refers to a method for growing the plant according to the present invention while controlling weeds in the vicinity of said plant, said method comprising the steps of:
a) growing said plant; and
b) applying a herbicide composition comprising a PPO-inhibiting herbicide to the plant and weeds, wherein the herbicide normally inhibits protoporphyrinogen oxidase, at a level of the herbicide that would inhibit the growth of a corresponding wild-type plant.

In another embodiment, the invention relates to a combination useful for weed control, comprising (a) a polynucleotide encoding a wildtype or mutated PPO polypeptide according to the present invention, which polynucleotide is capable of being expressed in a plant to thereby provide to that plant tolerance to a PPO inhibiting herbicide; and (b) a PPO inhibiting herbicide.

In another embodiment, the invention relates to a process for preparing a combination useful for weed control comprising (a) providing a polynucleotide encoding a wildtype or mutated PPO polypeptide according to the present invention, which polynucleotide is capable of being expressed in a plant to thereby provide to that plant tolerance to a PPO inhibiting herbicide; and (b) providing a PPO inhibiting herbicide.

In a preferred embodiment, said step of providing a polynucleotide comprises providing a plant containing the polynucleotide.

In another preferred embodiment, said step of providing a polynucleotide comprises providing a seed containing the polynucleotide.

In another preferred embodiment, said process further comprises a step of applying the PPO inhibiting herbicide to the seed.

In another embodiment, the invention relates to the use of a combination useful for weed control, comprising (a) a polynucleotide encoding a wildtype or mutated PPO polypeptide according to the present invention, which polynucleotide is capable of being expressed in a plant to thereby provide to that plant tolerance to a PPO inhibiting herbicide; and (b) a PPO inhibiting herbicide, to control weeds at a plant cultivation site.

BRIEF DESCRIPTION OF THE DRAWINGS

FIG. 1 shows an amino acid sequence alignment of *Amaranthus tuberculatus* (*A. tuberculatus*) PPO sequences with *Alopecurus myosuroides* sequence of the present invention. FIG. 1*a*: AMARE_WC_herb_sus (SEQ ID NO: 27); AMARE_AC_herb_sus (SEQ ID NO: 28); AMARE_AC_herb_resis (SEQ ID NO: 30); AMARE_CC_herb_resis (SEQ ID NO: 29); and SEQ_ID_NO_002_ALOMY (SEQ ID NO: 2). FIG. 1*b*: PPO1_ALOMY (SEQ ID NO: 4); and PPO1_AMARE (SEQ ID NO: 31).

KEY TO SEQUENCE LISTING

TABLE 1

Figure 2:
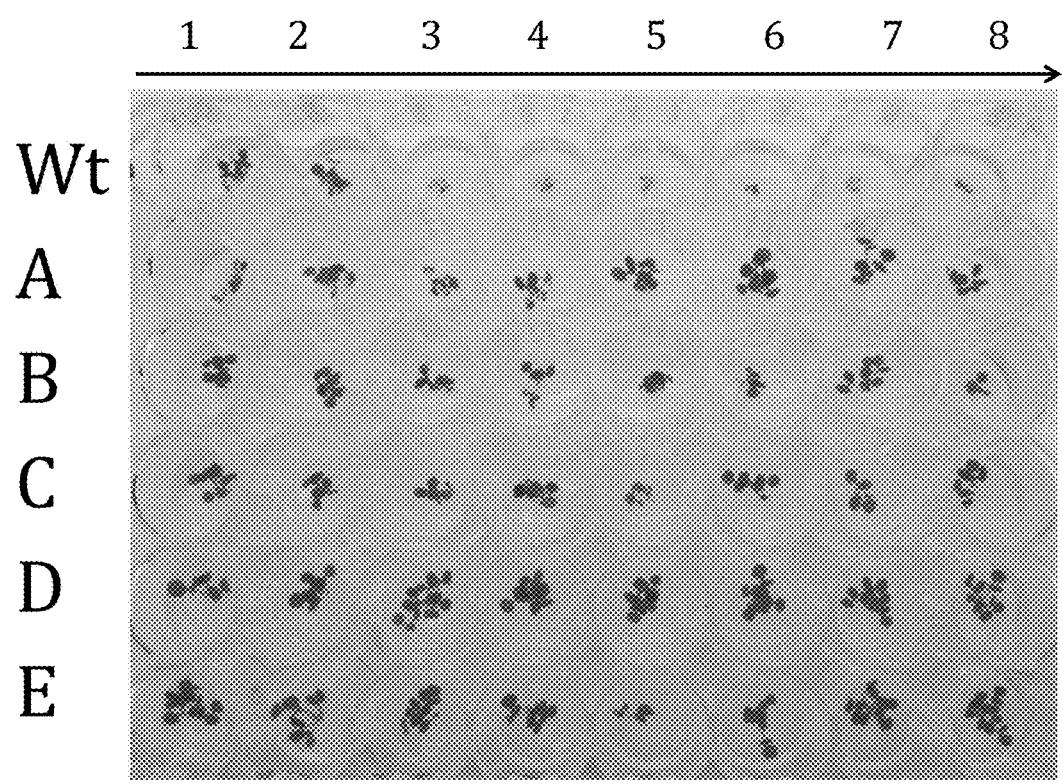
FIG. 2 shows transgenic *Arabidopsis* plants transformed with nucleic acids encoding mutated *Alopecurus* (ALOMY) PPO2 comprising a double mutation Am_PPO2_R137M_F438V, treated with various concentrations of BAS 850H (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione); A, B, C, D, E, represent different events; 2-8 represents different treatment concentrations. 1 represents mock treated control. 1=DMSO, 2=1.00E-09M; 3=6.00E-09M; 4=1.00E-08M; 5=2.50E-08M; 6=5.00E-08M; 7=1.00E-07M; 8=3.00E-07M.

| SEQ. ID NO: | Description | Organism | Gene | Accession No: |
|---|---|---|---|---|
| 1 | PPO nucleic acid | *Alopecurus myosuroides* | PPO2 | |
| 2 | PPO amino acid | *Alopecurus myosuroides* | PPO2 | |
| 3 | PPO nucleic acid | *Alopecurus myosuroides* | PPO1 | |
| 4 | PPO amino acid | *Alopecurus myosuroides* | PPO1 | |
| 5 | PPO amino acid | *Alopecurus myosuroides* | PPO transit peptide | |
| 6 | PPO nucleic acid | *Alopecurus myosuroides* | PPO2 codon-optimized | |
| 7 | PPO nucleic acid | *Alopecurus myosuroides* | PPO1 codon-optimized | |
| 8 | PPO amino acid | *Zea mays* | PPO2 transit peptide | |
| 9 | PPO amino acid | *Sorghum bicolor* | PPO2 transit peptide | |
| 27 | PPO amino acid | *Amaranthus* | PPO2 | WC_HS |
| 28 | PPO amino acid | *Amaranthus* | PPO2 | AC_HS |
| 29 | PPO amino acid | *Amaranthus* | PPO2 | CC_HR |
| 30 | PPO amino acid | *Amaranthus* | PPO2 | AC_HR |
| 31 | PPO amino acid | *Amaranthus* | PPO1 | |

DETAILED DESCRIPTION

An "herbicide tolerance or resistance-increasing activity" according to the invention refers to an activity of a PPO from *Alopecurus myosuroides* comprising the sequence of SEQ ID NO: 2 or 4, or a homolog thereof. A polypeptide conferring a herbicide tolerance or resistance-increasing activity can be encoded by a nucleic acid sequence comprising the sequence of SEQ ID NO: 1 or 3, or a homolog thereof, and/or comprises or consists of a polypeptide comprising the sequence of SEQ ID NO: 2 or 4, or a homolog thereof.

A "transgenic plant", as used herein, refers to a plant which contains a foreign nucleotide sequence inserted into either its nuclear genome or organelle genome. It encompasses further the offspring generations i.e. the T1-, T2- and consecutively generations or BC1-, BC2- and consecutively generation as well as crossbreeds thereof with non-transgenic or other transgenic plants.

A modification, i.e. an increase, can be caused by endogenous or exogenous factors. For example, an increase in activity in an organism or a part thereof can be caused by adding a gene product or a precursor or an activator or an agonist to the media or nutrition or can be caused by introducing said subjects into a organism, transient or stable. Furthermore such an increase can be reached by the introduction of the inventive nucleic acid sequence or the encoded protein in the correct cell compartment for example into the nucleus or cytoplasmic respectively or into plastids either by transformation and/or targeting.

For the purposes of the description of the present invention, the terms "cytoplasmic" and "non-targeted" shall indicate, that the nucleic acid of the invention is expressed without the addition of a non-natural transit peptide encoding sequence. A non-natural transit peptide encoding sequence is a sequence which is not a natural part of a nucleic acid of the invention, e.g. of the nucleic acids depicted in SEQ ID NO: 1 or 3, or a homolog thereof, but is rather added by molecular manipulation steps which are well known to the person skilled in the art or as for example described hereinafter. Therefore the terms "cytoplasmic" and "non-targeted" shall not exclude a targeted localization to any cell compartment for the products of the inventive nucleic acid sequences by their naturally occurring sequence properties within the background of the transgenic organism. The sub-cellular location of the mature polypeptide derived from the enclosed sequences can be predicted by a skilled person for the organism (plant) by using software tools like TargetP (Emanuelsson et al., (2000), Predicting sub-cellular localization of proteins based on their N-terminal amino acid sequence. J. Mol. Biol. 300, 1005-1016), ChloroP (Emanuelsson et al. (1999), ChloroP, a neural network-based method for predicting chloroplast transit peptides and their cleavage sites. Protein Science, 8: 978-984) or other predictive software tools (Emanuelsson et al. (2007), locating proteins in the cell using TargetP, SignalP, and related tools (Nature Protocols 2, 953-971).

The term "organelle" according to the invention shall mean for example "mitochondria", "plastid" or endoplasmic reticulum (ER). The term "plastid" according to the invention is intended to include various forms of plastids including proplastids, chloroplasts, chromoplasts, gerontoplasts, leucoplasts, amyloplasts, elaioplasts and etioplasts, preferably chloroplasts. They all have as a common ancestor the aforementioned proplasts.

The term "introduced" in the context of this specification shall mean the insertion of a nucleic acid sequence into the organism by means of a "transfection", "transduction" or preferably by "transformation".

A plastid, such as a chloroplast, has been "transformed" by an exogenous (preferably foreign) nucleic acid sequence if nucleic acid sequence has been introduced into the plastid that means that this sequence has crossed the membrane or the membranes of the plastid. The foreign DNA may be integrated (covalently linked) into plastid DNA making up the genome of the plastid, or it may remain not integrated (e.g., by including a chloroplast origin of replication). "Stably" integrated DNA sequences are those, which are inherited through plastid replication, thereby transferring new plastids, with the features of the integrated DNA sequence to the progeny.

As used herein, "plant" is meant to include not only a whole plant but also a part thereof i.e., one or more cells, and tissues, including for example, leaves, stems, shoots, roots, flowers, fruits and seeds.

The term "herbicide tolerance or resistance" as used herein it is intended that a plant that is tolerant or resistant to at least one herbicide at a level that would normally kill, or inhibit the growth of, a normal or wild-type plant.

Any increase in herbicide tolerance or resistance is an improved herbicide tolerance or resistance in accordance with the invention. For example, the improvement in herbicide tolerance or resistance can comprise a 1.5×, 2×, 2.5×, 3×, 5×, 10×, 20×, 30×, 40×, 50×, 75×, 100×, 150×, 200× or greater increase in any measurable parameter.

Unless otherwise specified, the terms "polynucleotides", "nucleic acid" and "nucleic acid molecule" are interchangeably in the present context. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or deoxyribonucleotides. The terms "gene(s)", "polynucleotide", "nucleic acid sequence", "nucleotide sequence", or "nucleic acid molecule(s)" as used herein include known types of modifications, for example, methylation, "caps", substitutions of one or more of the naturally occurring nucleotides with an analogue. Preferably, the DNA or RNA sequence comprises a coding sequence encoding the herein defined polypeptide.

As also used herein, the terms "nucleic acid" and "nucleic acid molecule" are intended to include DNA molecules (e.g. cDNA or genomic DNA) and RNA molecules (e.g. mRNA) and analogs of the DNA or RNA generated using nucleotide analogs. The nucleic acid molecule can be single-stranded or double-stranded.

An "isolated" nucleic acid molecule is one that is substantially separated from other nucleic acid molecules, which are present in the natural source of the nucleic acid. That means other nucleic acid molecules are present in an amount less than 5% based on weight of the amount of the desired nucleic acid, preferably less than 2% by weight, more preferably less than 1% by weight, most preferably less than 0.5% by weight. Preferably, an "isolated" nucleic acid is free of some of the sequences that naturally flank the nucleic acid (i.e., sequences located at the 5' and 3' ends of the nucleic acid) in the genomic DNA of the organism from which the nucleic acid is derived. For example, in various embodiments, the isolated herbicide resistance and/or tolerance related protein encoding nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A "coding sequence" is a nucleotide sequence, which is transcribed into an RNA, e.g. a regulatory RNA, such as a miRNA, a ta-sRNA, co-suppression molecule, an RNAi, a ribozyme, etc. or into a mRNA which is translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, recombinant nucleotide sequences or genomic DNA, while introns may be present as well under certain circumstances.

As used in the present context a nucleic acid molecule may also encompass the untranslated sequence located at the 3' and at the 5' end of the coding gene region, for example 2000, preferably less, e.g. 500, preferably 200, especially preferable 100, nucleotides of the sequence upstream of the 5' end of the coding region and for example 300, preferably less, e.g. 100, preferably 50, especially preferable 20, nucleotides of the sequence downstream of the 3' end of the coding gene region.

"Polypeptide" refers to a polymer of amino acid (amino acid sequence) and does not refer to a specific length of the molecule. Thus, peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. An "isolated" polynucleotide or nucleic acid molecule is separated from other polynucleotides or nucleic acid molecules, which are present in the natural source of the nucleic acid molecule. An isolated nucleic acid molecule may be a chromosomal fragment of several kb, or preferably, a molecule only comprising the coding region of the gene. Accordingly, an isolated nucleic acid molecule of the invention may comprise chromosomal regions, which are adjacent 5' and 3' or further adjacent chromosomal regions, but preferably comprises no such sequences which naturally flank the nucleic acid molecule sequence in the genomic or chromosomal context in the organism from which the nucleic acid molecule originates (for example sequences which are adjacent to the regions encoding the 5'- and 3'-UTRs of the nucleic acid molecule). An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of a protein in which the polypeptide is separated from some of the cellular components of the cells in which it is naturally or recombinantly produced.

The terms "comprise" or "comprising" and grammatical variations thereof when used in this specification are to be taken to specify the presence of stated features, integers, steps or components or groups thereof, but not to preclude the presence or addition of one or more other features, integers, steps, components or groups thereof.

In accordance with the invention, a protein or polypeptide has the "activity of a PPO protein if its de novo activity, or its increased expression directly or indirectly leads to and confers increased herbicide tolerance or resistance, as compared to a corresponding, e.g. non-transformed, wild type plant and the protein has the above mentioned activity of a PPO.

Throughout the specification the activity or preferably the biological activity of such a protein or polypeptide or an nucleic acid molecule or sequence encoding such protein or polypeptide is identical or similar if it still has the biological or enzymatic activity of a protein comprising the sequence of SEQ ID NO: 2 or 4, or a homolog thereof, or which has 10% or more of the original enzymatic activity, preferably 20%, 30%, 40%, 50%, particularly preferably 60%, 70%, 80% most particularly preferably 90%, 95%, 98%, 99% or more in comparison to a protein comprising the sequence of SEQ ID NO: 2 or 4, or a homolog thereof.

In another embodiment the biological or enzymatic activity of a protein comprising the sequence of SEQ ID NO: 2 or 4, or a homolog thereof, has 100% or more of the original enzymatic activity, preferably 110%, 120%, 130%, 150%, particularly preferably 150%, 200%, 300% or more in comparison to a protein comprising the sequence of SEQ ID NO: 2 or 4, or a homolog thereof.

The terms "increased", "raised", "extended", "enhanced", "improved" or "amplified" relate to a corresponding change of a property in a plant, an organism, a part of an organism such as a tissue, seed, root, leave, flower etc. or in a cell and are interchangeable. Preferably, the overall activity in the volume is increased or enhanced in cases if the increase or enhancement is related to the increase or enhancement of an activity of a gene product, independent whether the amount of gene product or the specific activity of the gene product or both is increased or enhanced or whether the amount, stability or translation efficacy of the nucleic acid sequence or gene encoding for the gene product is increased or enhanced.

The terms "increase" include the change of said property in only parts of the subject of the present invention, for example, the modification can be found in compartment of a cell, like a organelle, or in a part of a plant, like tissue, seed, root, leave, flower etc. but is not detectable if the overall subject, i.e. complete cell or plant, is tested. Accordingly, the term "increase" means that the specific activity of an enzyme as well as the amount of a compound or metabolite, e.g. of a polypeptide, a nucleic acid molecule of the invention or an encoding mRNA or DNA, can be increased in a volume. The term "increase" includes, that a compound or an activity, especially an activity, is introduced into a cell, the cytoplasm or a sub-cellular compartment or organelle de novo or that the compound or the activity, especially an activity, has not been detected before, in other words it is "generated". Accordingly, in the following, the term "increasing" also comprises the term "generating" or "stimulating". The increased activity manifests itself in increased herbicide tolerance or resistance, as compared to a corresponding, e.g. non-transformed, wild type plant cell, plant or part thereof.

Under "change of a property" it is understood that the activity, expression level or amount of a gene product or the metabolite content is changed in a specific volume relative to a corresponding volume of a control, reference or wild type, including the de novo creation of the activity or expression.

"Amount of protein or mRNA" is understood as meaning the molecule number of polypeptides or mRNA molecules in an organism, especially a plant, a tissue, a cell or a cell compartment. "Increase" in the amount of a protein means the quantitative increase of the molecule number of said protein in an organism, especially a plant, a tissue, a cell or a cell compartment such as an organelle like a plastid or mitochondria or part thereof—for example by one of the methods described herein below—in comparison to a wild type, control or reference.

The increase in molecule number amounts preferably to 1% or more, preferably to 10% or more, more preferably to 30% or more, especially preferably to 50%, 70% or more, very especially preferably to 100%, most preferably to 500% or more. However, a de novo expression is also regarded as subject of the present invention.

The terms "wild type", "control" or "reference" are exchangeable and can be a cell or a part of organisms such as an organelle like a chloroplast or a tissue, or an organism, in particular a plant, which was not modified or treated according to the herein described process according to the invention. Accordingly, the cell or a part of organisms such as an organelle like a chloroplast or a tissue, or an organism, in particular a plant used as wild type, control or reference corresponds to the cell, organism, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property.

Preferably, any comparison is carried out under analogous conditions. The term "analogous conditions" means that all conditions such as, for example, culture or growing conditions, soil, nutrient, water content of the soil, temperature, humidity or surrounding air or soil, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, an organism, in particular a plant, which was not modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-" -organelle, -cell, -tissue or -organism, in particular plant, relates to an organelle, cell, tissue or organism, in particular plant, which is nearly genetically identical to the organelle, cell, tissue or organism, in particular plant, of the present invention or a part thereof preferably 90% or more, e.g. 95%, more preferred are 98%, even more preferred are 99.00%, in particular 99.10%, 99.30%, 99.50%, 99.70%, 99.90%, 99.99%, 99.999% or more. Most preferable the "reference", "control", or "wild type" is a subject, e.g. an organelle, a cell, a tissue, an organism, in particular a plant, which is genetically identical to the organism, in particular plant, cell, a tissue or organelle used according to the process of the invention except that the responsible or activity conferring nucleic acid molecules or the gene product encoded by them are amended, manipulated, exchanged or introduced according to the inventive process. In case, a control, reference or wild type differing from the subject of the present invention only by not being subject of the process of the invention can not be provided, a control, reference or wild type can be an organism in which the cause for the modulation of an activity conferring the enhanced tolerance or resistance to herbicides as compared to a corresponding, e.g. non-transformed, wild type plant cell, plant or part thereof or expression of the nucleic acid molecule of the invention as described herein has been switched back or off, e.g. by knocking out the expression of responsible gene product, e.g. by antisense or RNAi or miRNA inhibition, by inactivation of an activator or agonist, by activation of an inhibitor or antagonist, by inhibition through adding inhibitory antibodies, by adding active compounds as e.g. hormones, by introducing negative dominant mutants, etc. A gene production can for example be knocked out by introducing inactivating point mutations, which lead to an enzymatic activity inhibition or a destabilization or an inhibition of the ability to bind to cofactors etc. Accordingly, preferred reference subject is the starting subject of the present process of the invention. Preferably, the reference and the subject matter of the invention are compared after standardization and normalization, e.g. to the amount of total RNA, DNA, or protein or activity or expression of reference genes, like housekeeping genes, such as ubiquitin, actin or ribosomal proteins.

The term "expression" refers to the transcription and/or translation of a codogenic gene segment or gene. As a rule, the resulting product is an mRNA or a protein.

The increase or modulation according to this invention can be constitutive, e.g. due to a stable permanent transgenic expression or to a stable mutation in the corresponding endogenous gene encoding the nucleic acid molecule of the invention or to a modulation of the expression or of the behavior of a gene conferring the expression of the polypeptide of the invention, or transient, e.g. due to an transient transformation or temporary addition of a modulator such as a agonist or antagonist or inducible, e.g. after transformation with a inducible construct carrying the nucleic acid molecule of the invention under control of a inducible promoter and adding the inducer, e.g. tetracycline or as described herein below.

Less influence on the regulation of a gene or its gene product is understood as meaning a reduced regulation of the enzymatic activity leading to an increased specific or cellular activity of the gene or its product. An increase of the enzymatic activity is understood as meaning an enzymatic activity, which is increased by 10% or more, advantageously 20%, 30% or 40% or more, especially advantageously by 50%, 60% or 70% or more in comparison with the starting organism. This leads to increased herbicide tolerance or resistance, as compared to a corresponding, e.g. non-transformed, wild type plant or part thereof.

The increase in activity of the polypeptide amounts in a cell, a tissue, an organelle, an organ or an organism, preferably a plant, or a part thereof preferably to 5% or more, preferably to 20% or to 50%, especially preferably to 70%, 80%, 90% or more, very especially preferably are to 100%, 150% or 200%, most preferably are to 250% or more in comparison to the control, reference or wild type. In one embodiment the term increase means the increase in amount in relation to the weight of the organism or part thereof (w/w).

By "vectors" is meant with the exception of plasmids all other vectors known to those skilled in the art such as by way of example phages, viruses such as SV40, CMV, baculovirus, adenovirus, transposons, IS elements, phasmids, phagemids, cosmids, linear or circular DNA. These vectors can be replicated autonomously in the host organism or be chromosomally replicated, chromosomal replication being preferred. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) are integrated into the genome of a host cell or a organelle upon introduction into the host cell, and thereby are replicated along with the host or organelle genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

As used herein, "operatively linked" is intended to mean that the nucleotide sequence of interest is linked to the regulatory sequence(s) in a manner which allows for expression of the nucleotide sequence (e.g. in an in vitro transcription/translation system or in a host cell when the vector is introduced into the host cell). The term "regulatory sequence" is intended to include promoters, enhancers, and other expression control elements (e.g. polyadenylation signals).

Such regulatory sequences are described, for example, in Goeddel, Gene Expression Technology: Methods in Enzymology 185, Academic Press, San Diego, Calif. (1990), and Gruber and Crosby, in: Methods in Plant Molecular Biology and Biotechnology, eds. Glick and Thompson, Chapter 7, 89-108, CRC Press; Boca Raton, Fla., including the references therein. Regulatory sequences include those that direct constitutive expression of a nucleotide sequence in many types of host cells and those that direct expression of the nucleotide sequence only in certain host cells or under certain conditions.

"Transformation" is defined herein as a process for introducing heterologous DNA into a plant cell, plant tissue, or plant. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time. Transformed plant cells, plant tissue, or plants are understood to encompass not only the end product of a transformation process, but also transgenic progeny thereof.

The terms "transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extra-chromosomal molecule. Such an extra-chromosomal molecule can be auto-replicating. Transformed cells, tissues, or plants are understood to encompass not only the end product of a transformation process, but also transgenic progeny thereof. A "non-transformed", "non-transgenic" or "non-recombinant" host refers to a wild-type organism, e.g. a bacterium or plant, which does not contain the heterologous nucleic acid molecule.

The terms "host organism", "host cell", "recombinant (host) organism" and "transgenic (host) cell" are used here interchangeably. Of course these terms relate not only to the particular host organism or the particular target cell but also to the descendants or potential descendants of these organisms or cells. Since, due to mutation or environmental effects certain modifications may arise in successive generations, these descendants need not necessarily be identical with the parental cell but nevertheless are still encompassed by the term as used here.

For the purposes of the invention "transgenic" or "recombinant" means with regard for example to a nucleic acid sequence, an expression cassette (=gene construct, nucleic acid construct) or a vector containing the nucleic acid sequence according to the invention or an organism transformed by said nucleic acid sequences, expression cassette or vector according to the invention all those constructions produced by genetic engineering methods in which either
(a) the nucleic acid sequence comprising the sequence of SEQ ID NO: 1 or 3, or a homolog thereof, or its derivatives or parts thereof; or
(b) a genetic control sequence functionally linked to the nucleic acid sequence described under (a), for example a 3'- and/or 5'-genetic control sequence such as a promoter or terminator, or
(c) (a) and (b);
are not found in their natural, genetic environment or have been modified by genetic engineering methods, wherein the modification may by way of example be a substitution, addition, deletion, inversion or insertion of one or more nucleotide residues.

"Natural genetic environment" means the natural genomic or chromosomal locus in the organism of origin or inside the host organism or presence in a genomic library. In the case of a genomic library the natural genetic environment of the nucleic acid sequence is preferably retained at least in part. The environment borders the nucleic acid sequence at least on one side and has a sequence length of at least 50 bp, preferably at least 500 bp, particularly preferably at least 1,000 bp, most particularly preferably at least 5,000 bp. A naturally occurring expression cassette— for example the naturally occurring combination of the natural promoter of the nucleic acid sequence according to the invention with the corresponding gene—turns into a transgenic expression cassette when the latter is modified by unnatural, synthetic ("artificial") methods such as by way of example a mutagenation. Appropriate methods are described by way of example in U.S. Pat. No. 5,565,350 or WO 00/15815.

The term "transgenic plants" used in accordance with the invention also refers to the progeny of a transgenic plant, for example the $T_1$, $T_2$, $T_3$ and subsequent plant generations or the $BC_1$, $BC_2$, $BC_3$ and subsequent plant generations. Thus, the transgenic plants according to the invention can be raised and selfed or crossed with other individuals in order to obtain further transgenic plants according to the invention. Transgenic plants may also be obtained by propagating transgenic plant cells vegetatively. The present invention also relates to transgenic plant material, which can be derived from a transgenic plant population according to the invention. Such material includes plant cells and certain tissues, organs and parts of plants in all their manifestations, such as seeds, leaves, anthers, fibers, tubers, roots, root hairs, stems, embryo, calli, cotelydons, petioles, harvested material, plant tissue, reproductive tissue and cell cultures, which are derived from the actual transgenic plant and/or can be used for bringing about the transgenic plant. Any transformed plant obtained according to the invention can be used in a conventional breeding scheme or in in vitro plant propagation to produce more transformed plants with the same characteristics and/or can be used to introduce the same characteristic in other varieties of the same or related species. Such plants are also part of the invention. Seeds obtained from the transformed plants genetically also contain the same characteristic and are part of the invention. As mentioned before, the present invention is in principle applicable to any plant and crop that can be transformed with any of the transformation method known to those skilled in the art.

The term "homology" means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations. These mutations may occur naturally or may be obtained by mutagenesis techniques. The allelic variations may be naturally occurring allelic variants as well as synthetically produced or genetically engineered variants. Structurally equivalents can, for example, be identified by testing the binding of said polypeptide to antibodies or computer based predictions. Structurally equivalent have the similar immunological characteristic, e.g. comprise similar epitopes.

As used herein, the terms "gene" and "recombinant gene" refer to nucleic acid molecules comprising an open reading frame encoding the polypeptide of the invention or comprising the nucleic acid molecule of the invention or encoding the polypeptide used in the process of the present invention. Such natural variations can typically result in 1 to 5% variance in the nucleotide sequence of the gene. Any and all such nucleotide variations and resulting amino acid polymorphisms in genes encoding a polypeptide of the invention or comprising a the nucleic acid molecule of the invention that are the result of natural variation and that do not alter the functional activity as described are intended to be within the scope of the invention.

Specific Embodiments

Accordingly, this invention provides measures and methods to produce plants with increased herbicide tolerance or resistance.

Accordingly, the present invention provides transgenic plants showing increased tolerance or resistance to one or more herbicides as compared to the corresponding origin or the wild type plant and methods for producing such transgenic plants with increased herbicide tolerance or resistance. One or more enhanced herbicide tolerance-related phenotypes are increased in accordance with the invention by increasing or generating the activity of a PPO enzyme from *Alopecurus myosuroides*.

The nucleic acid molecule of the present invention or used in accordance with the present invention, encodes a protein conferring an activity of a PPO enzyme from *Alopecurus myosuroides*.

Accordingly, in one embodiment, the present invention relates to a nucleic acid molecule that encodes a polypeptide with an herbicide tolerance or resistance-increasing activity which is encoded by a nucleic acid sequence comprising the sequence of SEQ ID NO: 1 or 3, or a homolog thereof, and/or which is a protein comprising or consisting of a polypeptide comprising the sequence of SEQ ID NO: 2 or 4, or a homolog thereof.

In a preferred embodiment, the homolog refers to a mutated PPO enzyme from *Alopecurus myosuroides* comprising the sequence of SEQ ID NO: 2 or 4, in which the wildtype amino acid at or corresponding to position 137 of SEQ ID NO: 2 and/or the wildtype amino acid at or corresponding to position 415 of SEQ ID NO: 2, and/or the wildtype amino acid at or corresponding to position 438 of SEQ ID NO: 2 is substituted by another amino acid, as described in greater detail hereinafter.

The increase or generation of said "activity" is for example conferred by the increase of activity or of amount in a cell or a part thereof of one or more expression products of said nucleic acid molecule, e.g. proteins, or by de novo expression, i.e. by the generation of said "activity" in the plant.

In one embodiment, said herbicide tolerance or resistance-increasing activity is increased by increasing the amount and/or the specific activity of a PPO protein comprising the sequence of SEQ ID NO: 2 or 4, or a homolog thereof.

Accordingly, in one embodiment, an increased herbicide tolerance or resistance as compared to a correspondingly non-modified, e.g. a non-transformed, wild type plant is conferred according to method of the invention, by increasing or generating the activity of a polypeptide comprising the sequence of SEQ ID NO: 2 or 4, or a homolog thereof, or encoded by the nucleic acid molecule (or gene) the sequence of SEQ ID NO: 1 or 3, or a homolog of said nucleic acid molecule or polypeptide.

Thus, in one embodiment, the present invention provides a method for producing a plant showing increased or improved herbicide resistance or tolerance as compared to the corresponding origin or wild type plant, by increasing or generating the activity of an PPO enzyme, e.g. which is conferred by one or more polynucleotide(s) comprising the sequence of SEQ ID NO: 1 or 3, or a homolog thereof, or by one or more protein(s), each comprising a polypeptide encoded by one or more nucleic acid sequence(s) comprising the sequence of SEQ ID NO: 1 or 3, or a homolog thereof, or by one or more protein(s) each comprising a polypeptide comprising the sequence of SEQ ID NO: 2 or 4, or a homolog thereof, and (b) optionally, growing the plant cell, plant or part thereof under conditions which permit the development of the plant cell, the plant or the part thereof, and (c) regenerating a plant with increased herbicide tolerance or resistance, as compared to a corresponding, e.g. non-transformed, wild type plant or a part thereof.

Accordingly, in one further embodiment, the said method for producing a plant or a part thereof for the regeneration of said plant, the plant showing an increased herbicide tolerance or resistance, said method comprises (i) growing the plant or part thereof together with a, e.g. non-transformed, wild type plant under conditions of herbicide treatment; and (ii) selecting a plant with increased herbicide tolerance or resistance as compared to a corresponding, e.g. non-transformed, wild type plant, for example after the, e.g. non-transformed, wild type plant shows visual symptoms of deficiency and/or death.

Further, the present invention relates to a method for producing a plant with increased herbicide tolerance or resistance as compared to a corresponding origin or wild type plant, e.g. a transgenic plant, which comprises: (a) increasing or generating, in a plant cell nucleus, a plant cell, a plant or a part thereof, the activity of an PPO polypeptide of the present invention, e.g. by the methods mentioned herein; and (b) cultivating or growing the plant cell, the plant or the part thereof under conditions which permit the development of the plant cell, the plant or the part thereof; and (c) recovering a plant from said plant cell nucleus, said plant cell, or said plant part, which shows increased herbicide tolerance or resistance as compared to a corresponding, e.g. non-transformed, origin or wild type plant; and (d) optionally, selecting the plant or a part thereof, showing increased herbicide tolerance or resistance, as compared to a corresponding, e.g. non-transformed, wild type plant cell, e.g. which shows visual symptoms of deficiency and/or death.

Furthermore, the present invention also relates to a method for the identification of a plant with an increased herbicide tolerance or resistance comprising screening a population of one or more plant cell nuclei, plant cells, plant tissues or plants or parts thereof for said "activity", comparing the level of activity with the activity level in a reference; identifying one or more plant cell nuclei, plant cells, plant tissues or plants or parts thereof with the activity increased compared to the reference, optionally producing a plant from the identified plant cell nuclei, cell or tissue.

In one further embodiment, the present invention also relates to a method for the identification of a plant with an increased herbicide tolerance or resistance comprising screening a population of one or more plant cell nuclei, plant cells, plant tissues or plants or parts thereof for the expression level of an nucleic acid coding for an polypeptide conferring said activity, comparing the level of expression with a reference; identifying one or more plant cell nuclei, plant cells, plant tissues or plants or parts thereof with the expression level increased compared to the reference, optionally producing a plant from the identified plant cell nuclei, cell or tissue.

Accordingly, in a preferred embodiment, the present invention provides a method for producing a transgenic cell for the regeneration or production of a plant with increased herbicide tolerance or resistance, as compared to a corresponding, e.g. non-transformed, wild type cell by increasing or generating the activity of a PPO polypeptide of the present invention. The cell can be for example a host cell, e.g. a transgenic host cell. A host cell can be for example a microorganism, e.g. derived from fungi or bacteria, or a plant cell particular useful for transformation.

Thus, the present invention fulfills the need to identify new, unique genes capable of conferring increased herbicide tolerance or resistance to plants, upon expression or overexpression of exogenous genes. Accordingly, the present invention provides novel PPO enzymes comprising the sequence of SEQ ID NO: 2 or 4, or a homolog thereof.

In one embodiment the increase in activity of the polypeptide amounts in an organelle such as a plastid. In another embodiment the increase in activity of the polypeptide amounts in the cytoplasm.

The specific activity of a polypeptide encoded by a nucleic acid molecule of the present invention or of the polypeptide of the present invention can be tested as described in the examples. In particular, the expression of a protein in question in a cell, e.g. a plant cell in comparison to a control is an easy test and can be performed as described in the state of the art.

Accordingly, in one embodiment, the process of the present invention for producing a plant with increased herbicide tolerance or resistance comprises increasing or generating the activity of a gene product conferring the activity of a PPO enzyme from *Alopecurus myosuroides* or its functional equivalent or its homolog, e.g. the increase of (a) a gene product of a gene comprising the nucleic acid molecule comprising the sequence of SEQ ID NO: 1 or 3, or a functional equivalent or a homologue thereof; or
(b) a polypeptide comprising a polypeptide, a consensus sequence or a polypeptide motif comprising the sequence of SEQ ID NO: 2 or 4 or a functional equivalent or a homologue thereof.

Accordingly, an activity of a PPO polypeptide from *Alopecurus myosuroides* is increased in one or more specific compartment(s) or organelle(s) of a cell or plant and confers said increased herbicide tolerance or resistance. For example, said activity can be increased in plastids or mitochondria of a plant cell, thus conferring increase of herbicide tolerance or resistance in a corresponding plant.

In one embodiment, an activity conferred by an expression of a gene described herein or its expression product; i.e. by a PPO polypeptide of the present invention is increased or generated in the plastid.

In one embodiment, an activity conferred by the expression of a gene described herein or its expression product; i.e. by a PPO polypeptide of the present invention is increased or generated in the mitochondria.

In one embodiment, an activity conferred by the expression of a gene described herein or its expression product; i.e. by a PPO polypeptide of the present invention is increased or generated in the cytoplasm.

In one embodiment, an activity conferred by the expression of a gene described herein or its expression product; i.e. by a PPO polypeptide of the present invention is increased or generated in the endoplasmic reticulum.

As the terms "cytoplasmic" and "non-targeted" shall not exclude a targeted localisation to any cell compartment for the products of the inventive nucleic acid sequences by their naturally occurring sequence properties within the background of the transgenic organism, in one embodiment, an activity as disclosed herein as being conferred by a polypeptide shown in SEQ ID NO: 2 or 4, or a homolog thereof is increase or generated non-targeted. For the purposes of the description of the present invention, the term "cytoplasmic" shall indicate, that the nucleic acid of the invention is expressed without the addition of a non-natural transit peptide encoding sequence. A non-natural transient peptide encoding sequence is a sequence which is not a natural part of a nucleic acid of the invention but is rather added by molecular manipulation steps which are well-known to the person skilled in the art. Therefore the term "cytoplasmic" shall not exclude a targeted localisation to any cell compartment for the products of the inventive nucleic acid sequences by their naturally occurring sequence properties.

In another embodiment the present invention is related to a method for producing a, e.g. transgenic, plant with increased herbicide tolerance or resistance, or a part thereof, as compared to a corresponding, e.g. non-transformed, wild type plant, which comprises (a1) increasing or generating the activity of an PPO polypeptide, e.g. the activity of said gene or the gene product gene, in an organelle of a plant cell, or
(a2) increasing or generating the activity of a protein comprising the sequence of SEQ ID NO: 2 or 4, or a homolog thereof or as encoded by the nucleic acid sequences comprising the sequence of SEQ ID NO: 1 or 3, or a homolog thereof, and which is joined to a nucleic acid sequence encoding a transit peptide in the plant cell; or
(a3) increasing or generating the activity of a protein comprising the sequence of SEQ ID NO: 2 or 4, or a homolog thereof or as encoded by the nucleic acid sequences comprising the sequence of SEQ ID NO: 1 or 3, or a homolog thereof, and which is joined to a nucleic acid sequence encoding an organelle localization sequence, especially a chloroplast localization sequence, in a plant cell,
(a4) increasing or generating the activity of a protein comprising the sequence of SEQ ID NO: 2 or 4, or a homolog thereof or as encoded by the nucleic acid sequences comprising the sequence of SEQ ID NO: 1 or 3, or a homolog thereof, and which is joined to a nucleic acid sequence encoding an mitochondrion localization sequence in a plant cell,
and
(b) regenerating a plant from said plant cell;
(c) growing the plant under conditions which permit the development of a plant with increased herbicide tolerance or resistance as compared to a corresponding, e.g. non-transformed, wild type plant.

The skilled worker is able to link transit peptide nucleic acid sequences to the nucleic acid sequences comprising the sequence of SEQ ID NO: 1 or 3, or a homolog thereof.

Any transit peptide may be used in accordance with the various embodiments of the present invention. For example, specific nucleic acid sequences are encoding transit peptides are disclosed by von Heijne et al. (Plant Molecular Biology Reporter, 9 (2), 104, (1991)) or other transit peptides are disclosed by Schmidt et al. (J. Biol. Chem. 268 (36), 27447 (1993)), Della-Cioppa et al. (Plant. Physiol. 84, 965 (1987)), de Castro Silva Filho et al. (Plant Mol. Biol. 30, 769 (1996)), Zhao et al. (J. Biol. Chem. 270 (11), 6081(1995)), Römer et al. (Biochem. Biophys. Res. Commun. 196 (3), 1414 (1993)), Keegstra et al. (Annu. Rev. Plant Physiol. Plant Mol. Biol. 40, 471(1989)), Lubben et al. (Photosynthesis Res. 17, 173 (1988)) and Lawrence et al. (J. Biol. Chem. 272 (33), 20357 (1997)), which are hereby incorporated by reference. A general review about targeting is disclosed by Kermode Allison R. in Critical Reviews in Plant Science 15 (4), 285 (1996) under the title "Mechanisms of Intracellular Protein Transport and Targeting in Plant Cells".

Additional nucleic acid sequences encoding a transit peptide can be isolated from any organism such as microorganisms, algae or plants containing plastids, preferably containing chloroplasts. A "transit peptide" is an amino acid sequence, whose encoding nucleic acid sequence is translated together with the corresponding structural gene. That means the transit peptide is an integral part of the translated protein and forms an amino terminal extension of the protein. Both are translated as so called "pre-protein". In general the transit peptide is cleaved off from the pre-protein during or just after import of the protein into the correct cell organelle such as a plastid to yield the mature protein. The transit peptide ensures correct localization of the mature protein by facilitating the transport of proteins through intracellular membranes.

For example, such transit peptides, which are beneficially used in the inventive process, are derived from the nucleic acid sequence encoding a protein selected from the group consisting of ribulose bisphosphate carboxylase/oxygenase, 5-enolpyruvyl-shikimate-3-phosphate synthase, acetolactate synthase, chloroplast ribosomal protein CS17, Cs protein, ferredoxin, plastocyanin, ribulose bisphosphate carboxylase activase, tryptophan synthase, acyl carrier protein, plastid chaperonin-60, cytochrome c552, 22-kDA heat shock protein, 33-kDa Oxygen-evolving enhancer protein 1, ATP synthase γ subunit, ATP synthase δ subunit, chlorophyll-a/b-binding proteinII-1, Oxygen-evolving enhancer protein 2, Oxygen-evolving enhancer protein 3, photosystem I: P21, photosystem I: P28, photosystem I: P30, photosystem I: P35, photosystem I: P37, glycerol-3-phosphate acyltransferases, chlorophyll a/b binding protein, CAB2 protein, hydroxymethyl-bilane synthase, pyruvate-orthophosphate dikinase, CAB3 protein, plastid ferritin, ferritin, early light-inducible protein, glutamate-1-semialdehyde aminotransferase, protochlorophyllide reductase, starch-granule-bound amylase synthase, light-harvesting chlorophyll a/b-binding protein of photosystem II, major pollen allergen Lol p 5a, plastid ClpB ATP-dependent protease, superoxide dismutase, ferredoxin NADP oxidoreductase, 28-kDa ribonucleoprotein, 31-kDa ribonucleoprotein, 33-kDa ribonucleoprotein, acetolactate synthase, ATP synthase $CF_0$ subunit 1, ATP synthase $CF_0$ subunit 2, ATP synthase $CF_0$ subunit 3, ATP synthase $CF_0$ subunit 4, cytochrome f, ADP-glucose pyrophosphorylase, glutamine synthase, glutamine synthase 2, carbonic anhydrase, GapA protein, heat-shock-protein hsp21, phosphate translocator, plastid ClpA ATP-dependent protease, plastid ribosomal protein CL24, plastid ribosomal protein CL9, plastid ribosomal protein PsCL18, plastid ribosomal protein PsCL25, DAHP synthase, starch phosphorylase, root acyl carrier protein II, betaine-aldehyde dehydrogenase, GapB protein, glutamine synthetase 2, phosphoribulokinase, nitrite reductase, ribosomal protein L12, ribosomal protein L13, ribosomal protein L21, ribosomal protein L35, ribosomal protein L40, triose phosphate-3-phosphoglyerate-phosphate translocator, ferredoxin-dependent glutamate synthase, glyceraldehyde-3-phosphate dehydrogenase, NADP-dependent malic enzyme and NADP-malate dehydrogenase, chloroplast 30S ribosomal protein PSrp-1, and the like.

In a preferred embodiment, the targeting sequence comprises a nucleotide sequence that encodes a transit peptide comprising the amino acid sequence of SEQ ID NO: 5, 8, or 9. Preferably, the transit peptide encoding nucleic acid is operably linked such that the transit peptide is fused to the valine at position 55 in SEQ ID NO: 2 or to the alanine at position 47 in SEQ ID NO: 4.

In a particularly preferred embodiment, the nucleic acid sequences of the present invention are linked to a nucleic acid encoding a so-called "signal sequence peptide". For the purposes of the present invention, "signal sequence peptide" refers to amino acid sequences of about 15 to about 50 amino acids in length which are known in the art to be generally located at the amino terminus of proteins and which are capable of targeting said proteins to the endoplasmic reticulum. The core of the signal peptide contains a long stretch of hydrophobic amino acids that has a tendency to form a single alpha-helix. In addition, many signal peptides begin with a short positively charged stretch of amino acids, which may help to enforce proper topology of the polypeptide during translocation by what is known as the positive-inside rule. At the end of the signal peptide there is typically a stretch of amino acids that is recognized and cleaved by signal peptidase. However this cleavage site is absent from transmembrane-domains that serve as signal peptides, which are sometimes referred to as signal anchor sequences. Signal peptidase may cleave during, or after completion of, translocation to generate a free signal peptide and a mature protein. The free signal peptides are then digested by specific proteases. Those skilled in the art would readily appreciate that many signal sequence peptides are known (van Heijne, G., J. Mol. Biol. 184: 99-105 (1985)) and that these peptide sequences or analogues thereof can be easily substituted as long as they fulfill the requirements for a signal peptide as described above.

The skilled worker will recognize that various other nucleic acid sequences encoding transit or signal sequence peptides can easily isolated from plastid-localized, mitochondria-localized or endoplasmic reticulum-localized proteins, which are expressed from nuclear genes as precursors and are then targeted to plastids, mitochondria or endoplasmic reticulum. Nucleic acid sequences encoding a transit or signal sequence peptide can be isolated from organelle-targeted proteins from any organism. Preferably, the transit or signal sequence peptide is isolated from an organism selected from the group consisting of the genera *Acetabularia, Arabidopsis, Brassica, Capsicum, Chlamydomonas, Cururbita, Dunaliella, Euglena, Flaveria, Glycine, Helianthus, Hordeum, Lemna, Lolium, Lycopersion, Malus, Medicago, Mesembryanthemum, Nicotiana, Oenotherea, Oryza, Petunia, Phaseolus, Physcomitrella, Pinus, Pisum, Raphanus, Silene, Sinapis, Solanum, Spinacea, Stevia, Synechococcus, Synechocystis, Triticum* and *Zea*. More preferably, the nucleic acid sequence encoding the transit or signal sequence peptide is isolated from an organism selected from the group consisting of the species *Acetabularia mediterranea, Arabidopsis thaliana, Brassica campestris, Brassica napus, Capsicum annuum, Chlamydomonas reinhardtii, Cururbita moschata, Dunaliella salina, Dunaliella tertiolecta, Euglena gracilis, Flaveria trinervia, Glycine max, Helianthus annuus, Hordeum vulgare, Lemna gibba, Lolium perenne, Lycopersion esculentum, Malus domestica, Medicago falcata, Medicago sativa, Mesembryanthemum crystallinum, Nicotiana plumbaginifolia, Nicotiana sylvestris, Nicotiana tabacum, Oenotherea hookeri, Oryza sativa, Petunia hybrida, Phaseolus vulgaris, Physcomitrella patens, Pinus tunbergii, Pisum sativum, Raphanus sativus, Silene pratensis, Sinapis alba, Solanum tuberosum, Spinacea oleracea, Stevia rebaudiana, Synechococcus, Synechocystis, Triticum aestivum* and *Zea mays*. Alternatively, nucleic acid sequences coding for transit or signal sequence peptides may be chemically synthesized either in part or wholly according to structure of transit peptide sequences disclosed in the prior art.

Such transit or signal sequence peptides encoding sequences can be used for the construction of other expression constructs. The transit or signal sequence peptides advantageously used in the inventive process and which are part of the inventive nucleic acid sequences and proteins are typically 20 to 120 amino acids, preferably 25 to 110, 30 to 100 or 35 to 90 amino acids, more preferably 40 to 85 amino acids and most preferably 45 to 80 amino acids as for transit peptides, or about 15 to about 50 amino acids as for signal sequence peptides in length and functions post-translational to direct the protein to the plastid, preferably to the chloroplast, the mitochondrion or endoplasmic reticulum. The nucleic acid sequences encoding such transit or signal sequence peptides are localized upstream of nucleic acid sequence encoding the mature protein. For the correct molecular joining of the transit or signal sequence peptide encoding nucleic acid and the nucleic acid encoding the protein to be targeted it is sometimes necessary to introduce additional base pairs at the joining position, which forms restriction enzyme recognition sequences useful for the molecular joining of the different nucleic acid molecules. This procedure might lead to very few additional amino acids at the N-terminal of the mature imported protein, which usually and preferably do not interfere with the protein function. In any case, the additional base pairs at the joining position which forms restriction enzyme recognition sequences have to be chosen with care, in order to avoid the formation of stop codons or codons which encode amino acids with a strong influence on protein folding, like e.g. proline. It is preferred that such additional codons encode small structural flexible amino acids such as glycine or alanine.

As mentioned above, the nucleic acid sequence coding for a protein comprising the sequence of SEQ ID NO: 2 or 4, or a homolog thereof, can be joined to a nucleic acid sequence encoding a transit or a signal sequence peptide. The nucleic acid sequence of the gene to be expressed and the nucleic acid sequence encoding the transit or signal sequence peptide are operably linked. Therefore the transit or signal sequence peptide is fused in frame to the nucleic acid sequence coding for a protein comprising the sequence of SEQ ID NO: 2 or 4, or a homolog thereof.

The proteins translated from said inventive nucleic acid sequences are a kind of fusion proteins that means the nucleic acid sequences encoding the transit or signal sequence peptide, are joint to a gene, e.g. the nucleic acid sequences comprising the sequence of SEQ ID NO: 1 or 3, or a homolog thereof.

In a preferred embodiment, said fusion proteins refer to mutated PPO polypeptides comprising the sequence of SEQ ID NO: 10, 11, 12, 13, 14, 15, 16, 17, 18, 19, 20, 21, 22, 23, 24, 25, or 26. It will be acknowledged by the person skilled in the art that by replacing the natural transit peptide of an *Alopecurus* PPO2 comprising the sequence of SEQ ID NO: 2, against a heterologous transit peptide from *Zea mays* (SEQ ID NO: 8) or *Sorghum bicolor* (SEQ ID NO: 9), the native N-terminal end of SEQ ID NO: 2 is shortened by 7 amino acids. Therefore, preferred mutational sites at or corresponding to positions R137 or F438 on SEQ ID NO: 2, as described hereinafter in greater detail, are identical to positions R130 or F431 in said fusion proteins.

The person skilled in the art is able to join said sequences in a functional manner. Advantageously the transit or signal sequence peptide part is cleaved off from the protein part during the transport preferably into the endoplasmic reticulum or plastids. The skilled worker knows that other short sequences are also useful in the expression of the PPO genes of the present invention. Furthermore the skilled worker is aware of the fact that there is not a need for such short sequences in the expression of the genes.

Alternatively to the targeting of the gene, e.g. proteins having the sequences comprising the sequence of SEQ ID NO: 2 or 4, or a homolog thereof, the nucleic acids of the invention can directly be introduced into the plastidic genome.

By transforming the plastids the intraspecies specific transgene flow is blocked, because a lot of species such as corn, cotton and rice have a strict maternal inheritance of plastids. By placing the gene e.g. the genes comprising the sequence of SEQ ID NO: 1 or 3, or a homolog thereof, or active fragments thereof in the plastids of plants, these genes will not be present in the pollen of said plants.

In another embodiment of the invention the gene, e.g. the nucleic acid molecules comprising the sequence of SEQ ID NO: 1 or 3, or a homolog thereof, used in the inventive process are transformed into mitochondria, which are metabolic active.

For a good expression in the plastids the gene, e.g. the nucleic acid sequences comprising the sequence of SEQ ID NO: 1 or 3, or a homolog thereof, are introduced into an expression cassette using a preferably a promoter and terminator, which are active in plastids, preferably a chloroplast promoter. Examples of such promoters include the psbA promoter from the gene from spinach or pea, the rbcL promoter, and the atpB promoter from corn.

In one embodiment, the process of the present invention comprises one or more of the following steps:
(a) stabilizing a protein conferring the increased expression of a protein encoded by the nucleic acid molecule of the invention or of the polypeptide of the invention having the herein-mentioned activity of an PPO and conferring increased herbicide tolerance or resistance, as compared to a corresponding, e.g. non-transformed, wild type plant cell, plant or part thereof;
(b) stabilizing an mRNA conferring the increased expression of a polynucleotide encoding a polypeptide as mentioned in (a);
(c) increasing the specific activity of a protein conferring the increased expression of a polypeptide as mentioned in (a);
(d) generating or increasing the expression of an endogenous or artificial transcription factor mediating the expression of a protein conferring the increased expression of a polypeptide as mentioned in (a);
(e) stimulating activity of a protein conferring the increased expression of a polypeptide as mentioned in (a), by adding one or more exogenous inducing factors to the organism or parts thereof;
(f) expressing a transgenic gene encoding a protein conferring the increased expression of a polypeptide as mentioned in (a); and/or
(g) increasing the copy number of a gene conferring the increased expression of a nucleic acid molecule encoding a polypeptide as mentioned in (a);
(h) increasing the expression of the endogenous gene encoding a polypeptide as mentioned in (a) by adding positive expression or removing negative expression elements, e.g. homologous recombination can be used to either introduce positive regulatory elements like for plants the 35S enhancer into the promoter or to remove repressor elements form regulatory regions. Further gene conversion methods can be used to disrupt repressor elements or to enhance to activity of positive elements-positive elements can be randomly introduced in plants by T-DNA or transposon mutagenesis and lines can be identified in which the positive elements have been integrated near to a gene of the invention, the expression of which is thereby enhanced; and/or
(i) modulating growth conditions of the plant in such a manner, that the expression or activity of the gene encoding a polypeptide as mentioned in (a), or the protein itself is enhanced;
(j) selecting of organisms with especially high activity of a polypeptide as mentioned in (a) from natural or from mutagenized resources and breeding them into the target organisms, e.g. the elite crops.

Preferably, said mRNA is encoded by the nucleic acid molecule of the present invention and/or the protein conferring the increased expression of a protein encoded by the nucleic acid molecule of the present invention alone or linked to a transit nucleic acid sequence or transit peptide encoding nucleic acid sequence or the polypeptide having the herein mentioned activity, e.g. conferring with increased herbicide tolerance or resistance, as compared to a corresponding, e.g. non-transformed, wild type plant cell, plant or part thereof after increasing the expression or activity of the encoded polypeptide or having the activity of a polypeptide having an activity as the protein comprising the sequence of SEQ ID NO: 2 or 4, or a homolog thereof In general, the amount of mRNA or polypeptide in a cell or a compartment of an organism correlates with the amount of encoded protein and thus with the overall activity of the encoded protein in said volume. Said correlation is not always linear, the activity in the volume is dependent on the stability of the molecules or the presence of activating or inhibiting cofactors. The activity of the abovementioned proteins and/or polypeptides encoded by the nucleic acid molecule of the present invention can be increased in various ways. For example, the activity in an organism or in a part thereof, like a cell, is increased via increasing the gene product number, e.g. by increasing the expression rate, like introducing a stronger promoter, or by increasing the stability of the mRNA expressed, thus increasing the translation rate, and/or increasing the stability of the gene product, thus reducing the proteins decayed. Further, the activity or turnover of enzymes can be influenced in such a way that a reduction or increase of the reaction rate or a modification (reduction or increase) of the affinity to the substrate results, is reached. A mutation in the catalytic centre of an polypeptide of the invention, e.g. as enzyme, can modulate the turn over rate of the enzyme, e.g. a knock out of an essential amino acid can lead to a reduced or completely knock out activity of the enzyme, or the deletion or mutation of regulator binding sites can reduce a negative regulation like a feedback inhibition (or a substrate inhibition, if the substrate level is also increased). The specific activity of an enzyme of the present invention can be increased such that the turn over rate is increased or the binding of a co-factor is improved. Improving the stability of the encoding mRNA or the protein can also increase the activity of a gene product. The stimulation of the activity is also under the scope of the term "increased activity".

Moreover, the regulation of the abovementioned nucleic acid sequences may be modified so that gene expression is increased. This can be achieved advantageously by means of heterologous regulatory sequences or by modifying, for example mutating, the natural regulatory sequences which are present. The advantageous methods may also be combined with each other.

In general, an activity of a gene product in an organism or part thereof, in particular in a plant cell or organelle of a plant cell, a plant, or a plant tissue or a part thereof or in a microorganism can be increased by increasing the amount of the specific encoding mRNA or the corresponding protein in said organism or part thereof.

A modification, i.e. an increase, can be caused by endogenous or exogenous factors. For example, an increase in activity in an organism or a part thereof can be caused by adding a gene product or a precursor or an activator or an agonist to the media or nutrition or can be caused by introducing said subjects into a organism, transient or stable. Furthermore such an increase can be reached by the introduction of the inventive nucleic acid sequence or the encoded protein in the correct cell compartment for example into the nucleus or cytoplasm respectively or into plastids either by transformation and/or targeting.

In one further embodiment of the process according to the invention, organisms are used in which one of the abovementioned genes, or one of the abovementioned nucleic acids, is mutated in a way that the activity of the encoded gene products is less influenced by cellular factors, or not at all, in comparison with the not mutated proteins. For example, well known regulation mechanisms of enzyme activity are substrate inhibition or feed back regulation mechanisms. Ways and techniques for the introduction of substitution, deletions and additions of one or more bases, nucleotides or amino acids of a corresponding sequence are described herein below in the corresponding paragraphs and the references listed there, e.g. in Sambrook et al., Molecular Cloning, Cold Spring Harbour, N Y, 1989. The person skilled in the art will be able to identify regulation domains and binding sites of regulators by comparing the sequence of the nucleic acid molecule of the present invention or the expression product thereof with the state of the art by computer software means which comprise algorithms for the identifying of binding sites and regulation domains or by introducing into a nucleic acid molecule or in a protein systematically mutations and assaying for those mutations which will lead to an increased specific activity or an increased activity per volume, in particular per cell.

The mutation is introduced in such a way that increased herbicide tolerance or resistance, is not adversely affected.

It can therefore be advantageous to express in an organism a nucleic acid molecule of the invention or a polypeptide of the invention derived from a evolutionary distantly related organism, as e.g. using a prokaryotic gene in a eukaryotic host, as in these cases the regulation mechanism of the host cell may not weaken the activity (cellular or specific) of the gene or its expression product.

The invention is not limited to specific nucleic acids, specific polypeptides, specific cell types, specific host cells, specific conditions or specific methods etc. as such, but may vary and numerous modifications and variations therein will be apparent to those skilled in the art. It is also to be understood that the terminology used herein is for the purpose of describing specific embodiments only and is not intended to be limiting.

Further, "proteins are generally composed of one or more functional regions, commonly termed domains. Different combinations of domains give rise to the diverse range of proteins found in nature. The identification of domains that occur within proteins can therefore provide insights into their function. Pfam-A entries are high quality, manually curated families. The Pfam database is a large collection of protein families, each represented by multiple sequence alignments and hidden Markov models (HMMs)." (see: The Pfam protein families database: R. D. Finn, et al., Nucleic Acids Research (2010), Database Issue 38:D211-222). The Pfam protein family database is a large collection of more than ten thousand protein families and is available at pfam.sanger.ac.uk/. Profile Hidden Markov Models (HMMs) are flexible, probabilistic models that can be used to describe the consensus patterns shared by sets of homologous protein/domain sequences. HMMs in the Pfam database are constructed from an alignment of a representative set of sequences for each protein domain, called a seed alignment.

Accordingly, the present invention relates to a nucleic acid molecule encoding a polypeptide which is 50% or more, preferably 60%, 70%, or 75%, more preferably 80%, 85%, 90%, or 95%, even more preferred 96%, 97%, 98%, 99% or more and most preferred 100% identical to the polypeptide of SEQ ID NO: 2 or 4, and conferring the increase of the herbicide tolerance or resistance of a plant as described herein. The invention also relates to the polypeptide encoded by said polynucleotide.

The present invention also relates to isolated nucleic acids comprising a nucleic acid molecule selected from the group consisting of:

(a) a nucleic acid molecule encoding the polypeptide comprising the sequence of SEQ ID NO: 2 or 4, or a homolog thereof;

(b) a nucleic acid molecule comprising the sequence of SEQ ID NO: 1 or 3, or a homolog thereof, (c) a nucleic acid molecule, which, as a result of the degeneracy of the genetic code, can be derived from a polypeptide sequence of SEQ ID NO: 2 or 4, or a homolog thereof, and confers increased herbicide tolerance or resistance, as compared to a corresponding, e.g. non-transformed, wild type plant cell, a plant or a part thereof;
(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of SEQ ID NO: 1 or 3, or a homolog thereof, and confers increased herbicide tolerance or resistance, as compared to a corresponding, e.g. non-transformed, wild type plant cell, a plant or a part thereof;
(e) a nucleic acid molecule encoding a polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the polypeptide encoded by the nucleic acid molecule of (a), (b), (c) or (d) and having the activity represented by a nucleic acid molecule comprising a polynucleotide of SEQ ID NO: 1 or 3, or a homolog thereof, and confers increased herbicide tolerance or resistance as compared to a corresponding, e.g. non-transformed, wild type plant cell, a plant or a part thereof;
(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;
(g) a nucleic acid molecule encoding a polypeptide which can be isolated with the aid of monoclonal or polyclonal antibodies made against a polypeptide encoded by one of the nucleic acid molecules of (a), (b), (c), (d), (e) or (f) and having the activity represented by the nucleic acid molecule comprising a polynucleotide as depicted in SEQ ID NO: 1 or 3, or a homolog thereof;
(h) a nucleic acid molecule which is obtainable by screening a suitable nucleic acid library, especially a cDNA library and/or a genomic library, under stringent hybridization conditions with a probe comprising a complementary sequence of a nucleic acid molecule of (a) or (b) or with a fragment thereof, having 15 nt, preferably 20 nt, 30 nt, 50 nt, 100 nt, 200 nt, 500 nt, 750 nt or 1000 nt or more of a nucleic acid molecule complementary to a nucleic acid molecule sequence characterized in (a) to (e) and encoding a polypeptide having the activity represented by a protein comprising a polypeptide as depicted SEQ ID NO: 2 or 4, or a homolog thereof.

In one embodiment the invention relates to homologs of the aforementioned sequences, which can be isolated advantageously from yeast, fungi, viruses, algae, bacteria, such as *Acetobacter* (subgen. *Acetobacter*) *aceti*; *Acidithiobacillus ferrooxidans*; *Acinetobacter* sp.; *Actinobacillus* sp; *Aeromonas salmonicida*; *Agrobacterium tumefaciens*; *Aquifex aeolicus*; *Arcanobacterium pyogenes*; *Aster yellows phytoplasma*; *Bacillus* sp.; *Bifidobacterium* sp.; *Borrelia burgdorferi*; *Brevibacterium linens*; *Brucella melitensis*; *Buchnera* sp.; *Butyrivibrio fibrisolvens*; *Campylobacter jejuni*; *Caulobacter crescentus*; *Chlamydia* sp.; *Chlamydophila* sp.; *Chlorobium limicola*; *Citrobacter rodentium*; *Clostridium* sp.; *Comamonas testosteroni*; *Corynebacterium* sp.; *Coxiella burnetii*; *Deinococcus radiodurans*; *Dichelobacter nodosus*; *Edwardsiella ictaluri*; *Enterobacter* sp.; *Erysipelothrix rhusiopathiae*; *E. coli*; *Flavobacterium* sp.; *Francisella tularensis*; *Frankia* sp. Cpl 1; *Fusobacterium nucleatum*; *Geobacillus stearothermophilus*; *Gluconobacter oxydans*; *Haemophilus* sp.; *Helicobacter pylori*; *Klebsiella pneumoniae*; *Lactobacillus* sp.; *Lactococcus lactis*; *Listeria* sp.; *Mannheimia haemolytica*; *Mesorhizobium loti*; *Methylophaga thalassica*; *Microcystis aeruginosa*; *Microscilla* sp. PRE1; *Moraxella* sp. TA 144; *Mycobacterium* sp.; *Mycoplasma* sp.; *Neisseria* sp.; *Nitrosomonas* sp.; *Nostoc* sp. PCC 7120; *Novosphingobium aromaticivorans*; *Oenococcus oeni*; *Pantoea citrea*; *Pasteurella multocida*; *Pediococcus pentosaceus*; *Phormidium foveolarum*; *Phytoplasma* sp.; *Plectonema boryanum*; *Prevotella ruminicola*; *Propionibacterium* sp.; *Proteus vulgaris*; *Pseudomonas* sp.; *Ralstonia* sp.; *Rhizobium* sp.; *Rhodococcus equi*; *Rhodothermus marinus*; *Rickettsia* sp.; *Riemerella anatipestifer*; *Ruminococcus flavefaciens*; *Salmonella* sp.; *Selenomonas ruminantium*; *Serratia entomophila*; *Shigella* sp.; *Sinorhizobium meliloti*; *Staphylococcus* sp.; *Streptococcus* sp.; *Streptomyces* sp.; *Synechococcus* sp.; *Synechocystis* sp. PCC 6803; *Thermotoga maritima*; *Treponema* sp.; *Ureaplasma urealyticum*; *Vibrio cholerae*; *Vibrio parahaemolyticus*; *Xylella fastidiosa*; *Yersinia* sp.; *Zymomonas mobilis*, preferably *Salmonella* sp. or *E. coli* or plants, preferably from yeasts such as from the genera *Saccharomyces, Pichia, Candida, Hansenula, Torulopsis* or *Schizosaccharomyces* or plants such as *A. thaliana*, maize, wheat, rye, oat, triticale, rice, barley, soybean, peanut, cotton, borage, sunflower, linseed, primrose, rapeseed, canola and turnip rape, *manihot*, pepper, sunflower, *tagetes*, solanaceous plant such as potato, tobacco, eggplant and tomato, *Vicia* species, pea, alfalfa, bushy plants such as coffee, cacao, tea, *Salix* species, trees such as oil palm, coconut, perennial grass, such as ryegrass and fescue, and forage crops, such as alfalfa and clover and from spruce, pine or fir for example.

The proteins of the present invention are preferably produced by recombinant DNA techniques. For example, a nucleic acid molecule encoding the protein is cloned into an expression vector, for example in to a binary vector, the expression vector is introduced into a host cell, for example the *A. thaliana* wild type NASC N906 or any other plant cell as described in the examples see below, and the protein is expressed in said host cell. Examples for binary vectors are pBIN19, pBI101, pBinAR (Hofgen and Willmitzer, Plant Science 66, 221 (1990)), pGPTV, pCAM BIA, pBIB-HYG, pBecks, pGreen or pPZP (Hajukiewicz, P. et al., Plant Mol. Biol. 25, 989 (1994), and Hellens et al, Trends in Plant Science 5, 446 (2000)).

In one embodiment as described in more detail SUPRA, the protein of the present invention is preferably targeted to a compartment of the cell, e.g. to the endoplasmic reticulum or in the plastids. Ways of introducing nucleic acids into the endoplasmic reticulum or plastids and producing proteins in this compartment are known to the person skilled in the art have been also described in this application. In one embodiment, the polypeptide of the invention is a protein localized after expression e.g. non-targeted, mitochondrial or plastidic, for example it is fused to a transit or signal sequence peptide as described above for plastidic or endoplasmic reticulum localisation. In another embodiment the protein of the present invention is produced without further targeting signal (e.g. as mentioned herein), e.g. in the cytoplasm of the cell. Ways of producing proteins in the cytoplasm are known to the person skilled in the art. Ways of producing proteins without artificial targeting are known to the person skilled in the art.

Advantageously, the nucleic acid sequences according to the invention or the gene construct together with at least one reporter gene are cloned into an expression cassette, which is introduced into the organism via a vector or directly into the genome. This reporter gene should allow easy detection via a growth, fluorescence, chemical, bioluminescence or tolerance assay or via a photometric measurement. Examples of reporter genes which may be mentioned are antibiotic- or herbicide-tolerance genes, hydrolase genes, fluorescence protein genes, bioluminescence genes, sugar or nucleotide metabolic genes or biosynthesis genes such as the Ura3 gene, the Ilv2 gene, the luciferase gene, the β-galactosidase gene, the gfp gene, the 2-desoxyglucose-6-phosphate phosphatase gene, the β-glucuronidase gene, β-lactamase gene, the neomycin phosphotransferase gene, the hygromycin phosphotransferase gene, a mutated acetohydroxyacid synthase (AHAS) gene (also known as acetolactate synthase (ALS) gene), a gene for a D-amino acid metabolizing enzyme or the BASTA (=gluphosinate-tolerance) gene. These genes permit easy measurement and quantification of the transcription activity and hence of the expression of the genes. In this way genome positions may be identified which exhibit differing productivity. For expression a person skilled in the art is familiar with different methods to introduce the nucleic acid sequences into different organelles such as the preferred plastids. Such methods are for example disclosed by Maiga P. (Annu. Rev. Plant Biol. 55, 289 (2004)), Evans T. (WO 2004/040973), McBride K. E. et al. (U.S. Pat. No. 5,455,818), Daniell H. et al. (U.S. Pat. Nos. 5,932,479 and 5,693,507) and Straub J. M. et al. (U.S. Pat. No. 6,781,033). A preferred method is the transformation of microspore-derived hypocotyl or cotyledonary tissue (which are green and thus contain numerous plastids) leaf tissue and afterwards the regeneration of shoots from said transformed plant material on selective medium. As methods for the transformation bombarding of the plant material or the use of independently replicating shuttle vectors are well known by the skilled worker. But also a PEG-mediated transformation of the plastids or *Agrobacterium* transformation with binary vectors is possible. Useful markers for the transformation of plastids are positive selection markers for example the chloramphenicol-, streptomycin-, kanamycin-, neomycin-, amikamycin-, spectinomycin-, triazine- and/or lincomycin-tolerance genes. As additional markers named in the literature often as secondary markers, genes coding for the tolerance against herbicides such as phosphinothricin (=glufosinate, BASTA™, Liberty™, encoded by the bar gene), glyphosate (=N-(phosphonomethyl)glycine, Roundup™, encoded by the 5-enolpyruvylshikimate-3-phosphate synthase gene=epsps), sulfonylureas (like Staple™, encoded by the acetolactate synthase (ALS) gene), imidazolinones [=IMI, like imazethapyr, imazamox, Clearfield™, encoded by the acetohydroxyacid synthase (AHAS) gene, also known as acetolactate synthase (ALS) gene] or bromoxynil (=Buctril™, encoded by the oxy gene) or genes coding for antibiotics such as hygromycin or G418 are useful for further selection. Such secondary markers are useful in the case when most genome copies are transformed. In addition negative selection markers such as the bacterial cytosine deaminase (encoded by the codA gene) are also useful for the transformation of plastids.

To increase the possibility of identification of transformants it is also desirable to use reporter genes other then the aforementioned tolerance genes or in addition to said genes. Reporter genes are for example β-galactosidase-, β-glucuronidase-(GUS), alkaline phosphatase- and/or green-fluorescent protein-genes (GFP).

In a preferred embodiment a nucleic acid construct, for example an expression cassette, comprises upstream, i.e. at the 5' end of the encoding sequence, a promoter and downstream, i.e. at the 3' end, a polyadenylation signal and optionally other regulatory elements which are operably linked to the intervening encoding sequence with one of the nucleic acids of SEQ ID NO: 1 or 3, or a homolog thereof. By an operable linkage is meant the sequential arrangement of promoter, encoding sequence, terminator and optionally other regulatory elements in such a way that each of the regulatory elements can fulfill its function in the expression of the encoding sequence in due manner. In one embodiment the sequences preferred for operable linkage are targeting sequences for ensuring subcellular localization in plastids. However, targeting sequences for ensuring subcellular localization in the mitochondrium, in the endoplasmic reticulum (=ER), in the nucleus, in oil corpuscles or other compartments may also be employed as well as translation promoters such as the 5' lead sequence in tobacco mosaic virus (Gallie et al., Nucl. Acids Res. 15 8693 (1987).

A nucleic acid construct, for example an expression cassette may, for example, contain a constitutive promoter or a tissue-specific promoter (preferably the USP or napin promoter) the gene to be expressed and the ER retention signal. For the ER retention signal the KDEL amino acid sequence (lysine, aspartic acid, glutamic acid, leucine) or the KKX amino acid sequence (lysine-lysine-X-stop, wherein X means every other known amino acid) is preferably employed.

For expression in a host organism, for example a plant, the expression cassette is advantageously inserted into a vector such as by way of example a plasmid, a phage or other DNA which allows optimal expression of the genes in the host organism. Examples of suitable plasmids are: in *E. coli* pLG338, pACYC184, pBR series such as e.g. pBR322, pUC series such as pUC18 or pUC19, M113mp series, pKC30, pRep4, pHS1, pHS2, pPLc236, pMBL24, pLG200, pUR290, pIN-III113-B1, Δgt11 or pBdCl; in *Streptomyces* pIJ101, pIJ364, pIJ702 or pIJ361; in *Bacillus* pUB110, pC194 or pBD214; in *Corynebacterium* pSA77 or pAJ667; in fungi pALS1, pIL2 or pBB116; other advantageous fungal vectors are described by Romanos M. A. et al., Yeast 8, 423 (1992) and by van den Hondel, C. A. M. J. J. et al. [(1991) "Heterologous gene expression in filamentous fungi"] as well as in "More Gene Manipulations" in "Fungi" in Bennet J. W. & Lasure L. L., eds., pp. 396-428, Academic Press, San Diego, and in "Gene transfer systems and vector development for filamentous fungi" [van den Hondel, C. A. M. J. J. & Punt, P. J. (1991) in: Applied Molecular Genetics of Fungi, Peberdy, J. F. et al., eds., pp. 1-28, Cambridge University Press: Cambridge]. Examples of advantageous yeast promoters are 2 µM, pAG-1, YEp6, YEp13 or pEMBLYe23. Examples of algal or plant promoters are pLGV23, pGHlac+, pBIN19, pAK2004, pVKH or pDH51 (see Schmidt, R. and Willmitzer, L., Plant Cell Rep. 7, 583 (1988)). The vectors identified above or derivatives of the vectors identified above are a small selection of the possible plasmids. Further plasmids are well known to those skilled in the art and may be found, for example, in "Cloning Vectors" (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press, Ch. 6/7, pp. 71-119). Advantageous vectors are known as shuttle vectors or binary vectors which replicate in *E. coli* and *Agrobacterium*.

In a further embodiment of the vector the expression cassette according to the invention may also advantageously be introduced into the organisms in the form of a linear DNA and be integrated into the genome of the host organism by way of heterologous or homologous recombination. This linear DNA may be composed of a linearized plasmid or only of the expression cassette as vector or the nucleic acid sequences according to the invention.

A nucleic acid sequence can also be introduced into an organism on its own.

If in addition to the nucleic acid sequence according to the invention further genes are to be introduced into the organism, all together with a reporter gene in a single vector or each single gene with a reporter gene in a vector in each case can be introduced into the organism, whereby the different vectors can be introduced simultaneously or successively.

The vector advantageously contains at least one copy of the nucleic acid sequences according to the invention and/or the expression cassette (=gene construct) according to the invention.

The invention further provides an isolated recombinant expression vector comprising a nucleic acid encoding a polypeptide comprising the sequence of SEQ ID NO: 2 or 4, or a homolog thereof, wherein expression of the vector in a host cell results in increased herbicide tolerance or resistance, as compared to a wild type variety of the host cell.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein.

The recombinant expression vectors of the invention can be designed for expression of the polypeptide of the invention in plant cells. For example, nucleic acid molecules of the present invention can be expressed in plant cells (see Schmidt R., and Willmitzer L., Plant Cell Rep. 7 (1988); Plant Molecular Biology and Biotechnology, C Press, Boca Raton, Fla., Chapter 6/7, p. 71-119 (1993); White F. F., Jenes B. et al., Techniques for Gene Transfer, in: Transgenic Plants, Vol. 1, Engineering and Utilization, eds. Kung and Wu R., 128-43, Academic Press: 1993; Potrykus, Annu. Rev. Plant Physiol. Plant Molec. Biol. 42, 205 (1991) and references cited therein). Suitable host cells are discussed further in Goeddel, Gene Expression Technology: Methods in Enzymology 185, Academic Press: San Diego, Calif. (1990). By way of example the plant expression cassette can be installed in the pRT transformation vector ((a) Toepfer et al., Methods Enzymol. 217, 66 (1993), (b) Toepfer et al., Nucl. Acids. Res. 15, 5890 (1987)). Alternatively, a recombinant vector (=expression vector) can also be transcribed and translated in vitro, e.g. by using the T7 promoter and the T7 RNA polymerase.

In an further embodiment of the present invention, the nucleic acid molecules of the invention are expressed in plants and plants cells such as unicellular plant cells (e.g. algae) (see Falciatore et al., Marine Biotechnology 1 (3), 239 (1999) and references therein) and plant cells from higher plants (e.g., the spermatophytes, such as crop plants), for example to regenerate plants from the plant cells. A nucleic acid molecule depicted in SEQ ID NO: 1 or 3, or a homolog thereof may be "introduced" into a plant cell by any means, including transfection, transformation or transduction, electroporation, particle bombardment, agroinfection, and the like. One transformation method known to those of skill in the art is the dipping of a flowering plant into an Agrobacteria solution, wherein the Agrobacteria contains the nucleic acid of the invention, followed by breeding of the transformed gametes. Other suitable methods for transforming or transfecting host cells including plant cells can be found in Sambrook et al., supra, and other laboratory manuals such as Methods in Molecular Biology, 1995, Vol. 44, *Agrobacterium* protocols, ed: Gartland and Davey, Humana Press, Totowa, N.J.

In one embodiment of the present invention, transfection of a nucleic acid molecule coding for a polypeptide comprising the sequence of SEQ ID NO: 2 or 4, or a homolog thereof into a plant is achieved by *Agrobacterium* mediated gene transfer. *Agrobacterium* mediated plant transformation can be performed using for example the GV3101(pM P90) (Koncz and Schell, Mol. Gen. Genet. 204, 383 (1986)) or LBA4404 (Clontech) *Agrobacterium tumefaciens* strain. Transformation can be performed by standard transformation and regeneration techniques (Deblaere et al., Nucl. Acids Res. 13, 4777 (1994), Gelvin, Stanton B. and Schilperoort Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick Bernard R., Thompson John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., Plant Cell Report 8, 238 (1989); De Block et al., Plant Physiol. 91, 694 (1989)). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., Plant Cell Report 13, 282 (1994). Additionally, transformation of soybean can be performed using for example a technique described in European Patent No. 424 047, U.S. Pat. No. 5,322,783, European Patent No. 397 687, U.S. Pat. No. 5,376,543 or 5,169,770. Transformation of maize can be achieved by particle bombardment, polyethylene glycol mediated DNA uptake or via the silicon carbide fiber technique. (see, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced nucleic acid molecule coding for a polypeptides depicted in SEQ ID NO: 2 or 4, or homologs thereof, may be maintained in the plant cell stably if it is incorporated into a non-chromosomal autonomous replicon or integrated into the plant chromosomes or organelle genome. Alternatively, the introduced nucleic acid molecule may be present on an extra-chromosomal non-replicating vector and be transiently expressed or transiently active.

In one embodiment, a homologous recombinant microorganism can be created wherein the nucleic acid molecule is integrated into a chromosome, a vector is prepared which contains at least a portion of a nucleic acid molecule coding for a protein depicted in SEQ ID NO: 2 or 4, or a homolog thereof into which a deletion, addition, or substitution has been introduced to thereby alter, e.g., functionally disrupt, the gene. For example, the gene is a yeast gene, like a gene of *S. cerevisiae*, or of *Synechocystis*, or a bacterial gene, like an *E. coli* gene, but it can be a homolog from a related plant or even from a mammalian or insect source. The vector can be designed such that, upon homologous recombination, the endogenous nucleic acid molecule coding for a protein depicted in SEQ ID NO: 2 or 4, or a homolog thereof is mutated or otherwise altered but still encodes a functional polypeptide (e.g., the upstream regulatory region can be altered to thereby alter the expression of the endogenous nucleic acid molecule). In a preferred embodiment the biological activity of the protein of the invention is increased upon homologous recombination. To create a point mutation via homologous recombination, DNA-RNA hybrids can be used in a technique known as chimeraplasty (Cole-Strauss et al., Nucleic Acids Research 27 (5), 1323 (1999) and Kmiec, Gene Therapy American Scientist. 87 (3), 240 (1999)). Homologous recombination procedures in *Physcomitrella patens* are also well known in the art and are contemplated for use herein.

Whereas in the homologous recombination vector, the altered portion of the nucleic acid molecule coding for a protein depicted in SEQ ID NO: 2 or 4, or a homolog thereof is flanked at its 5' and 3' ends by an additional nucleic acid molecule of the gene to allow for homologous recombination to occur between the exogenous gene carried by the vector and an endogenous gene, in a microorganism or plant. The additional flanking nucleic acid molecule is of sufficient length for successful homologous recombination with the endogenous gene. Typically, several hundreds of base pairs up to kilobases of flanking DNA (both at the 5' and 3' ends) are included in the vector. See, e.g., Thomas K. R., and Capecchi M. R., Cell 51, 503 (1987) for a description of homologous recombination vectors or Strepp et al., PNAS, 95 (8), 4368 (1998) for cDNA based recombination in *Physcomitrella patens*. The vector is introduced into a microorganism or plant cell (e.g. via polyethylene glycol mediated DNA), and cells in which the introduced gene has homologously recombined with the endogenous gene are selected using art-known techniques.

Whether present in an extra-chromosomal non-replicating vector or a vector that is integrated into a chromosome, the nucleic acid molecule coding for amino acid molecules depicted in SEQ ID NO: 2 or 4, or a homolog thereof preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., EMBO J. 3, 835 (1984)) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., Nucl. Acids Research 15, 8693 (1987)). Examples of plant expression vectors include those detailed in: Becker D. et al., Plant Mol. Biol. 20, 1195 (1992); and Bevan M. W., Nucl. Acid. Res. 12, 8711 (1984); and "Vectors for Gene Transfer in Higher Plants" in: Transgenic Plants, Vol. 1, Engineering and Utilization, eds. Kung and Wu R., Academic Press, 1993, S. 15-38.

The host organism (=transgenic organism) advantageously contains at least one copy of the nucleic acid according to the invention and/or of the nucleic acid construct according to the invention.

In principle all plants can be used as host organism. Preferred transgenic plants are, for example, selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, lridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants such as plants advantageously selected from the group of the genus peanut, oilseed rape, canola, sunflower, safflower, olive, sesame, hazelnut, almond, avocado, bay, pumpkin/squash, linseed, soya, pistachio, borage, maize, wheat, rye, oats, sorghum and millet, triticale, rice, barley, cassava, potato, sugarbeet, egg plant, alfalfa, and perennial grasses and forage plants, oil palm, vegetables (brassicas, root vegetables, tuber vegetables, pod vegetables, fruiting vegetables, onion vegetables, leafy vegetables and stem vegetables), buckwheat, Jerusalem artichoke, broad bean, vetches, lentil, dwarf bean, lupin, clover and Lucerne for mentioning only some of them.

In one embodiment of the invention transgenic plants are selected from the group comprising cereals, soybean, rapeseed (including oil seed rape, especially canola and winter oil seed rape), cotton, sugarcane, sugar beet and potato, especially corn, soy, rapeseed (including oil seed rape, especially canola and winter oil seed rape), cotton, wheat and rice.

In another embodiment of the invention the transgenic plant is a gymnosperm plant, especially a spruce, pine or fir.

In one embodiment, the host plant is selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, lridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants and in particular plants mentioned herein above as host plants such as the families and genera mentioned above for example preferred the species *Anacardium occidentale, Calendula officinalis, Carthamus tinctorius, Cichorium intybus, Cynara scolymus, Helianthus annus, Tagetes lucida, Tagetes erecta, Tagetes tenuifolia; Daucus carota; Corylus avellana, Corylus colurna, Borago officinalis; Brassica napus, Brassica rapa* ssp., *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis, Brassica oleracea, Arabidopsis thaliana, Anana comosus, Ananas ananas, Bromelia comosa, Carica papaya, Cannabis sative, Ipomoea batatus, Ipomoea pandurata, Convolvulus batatas, Convolvulus tiliaceus, Ipomoea fastigiata, Ipomoea tiliacea, Ipomoea triloba, Convolvulus panduratus, Beta vulgaris, Beta vulgaris* var. *altissima, Beta vulgaris* var. *vulgaris, Beta maritima, Beta vulgaris* var. *perennis, Beta vulgaris* var. *conditiva, Beta*

*vulgaris* var. *esculenta, Cucurbita maxima, Cucurbita mbda, Cucurbita pepo, Cucurbita moschata, Olea europaea, Manihot utilissima, Janipha manihot, Jatropha manihot, Manihot aipil, Manihot dulcis, Manihot manihot, Manihot melanobasis, Manihot esculenta, Ricinus communis, Pisum sativum, Pisum arvense, Pisum humile, Medicago sativa, Medicago falcata, Medicago varia, Glycine max Dolichos soja, Glycine gracilis, Glycine hispida, Phaseolus max, Soja hispida, Soja max, Cocos nucifera, Pelargonium grossularioides, Oleum cocoas, Laurus nobilis, Persea americana, Arachis hypogaea, Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense, Linum trigynum, Punica granatum, Gossypium hirsutum, Gossypium arboreum, Gossypium barbadense, Gossypium herbaceum, Gossypium thurberi, Musa nana, Musa acuminata, Musa paradisiaca, Musa* spp., *Elaeis guineensis, Papaver orientate, Papaver rhoeas, Papaver dubium, Sesamum indicum, Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata, Hordeum vulgare, Hordeum jubatum, Hordeum murinum, Hordeum secalinum, Hordeum distichon Hordeum aegiceras, Hordeum hexastichon., Hordeum hexastichum, Hordeum irregulare, Hordeum sativum, Hordeum secalinum, Avena sativa, Avena fatua, Avena byzantina, Avena fatua* var. *sativa, Avena hybrida, Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum, Zea mays, Triticum aestivum, Triticum durum, Triticum turgidum, Triticum hybernum, Triticum macha, Triticum sativum* or *Triticum vulgare, Coffea* spp., *Coffea arabica, Coffea canephora, Coffea liberica, Capsicum annuum, Capsicum annuum* var. *glabriusculum, Capsicum frutescens, Capsicum annuum, Nicotiana tabacum, Solanum tuberosum, Solanum melongena, Lycopersicon esculentum, Lycopersicon lycopersicum, Lycopersicon pyriforme, Solanum integrifolium, Solanum lycopersicum Theobroma cacao* or *Camellia sinensis.*

Anacardiaceae such as the genera *Pistacia, Mangifera, Anacardium* e.g. the species *Pistacia vera* [pistachios, Pistazie], *Mangifer indica* [Mango] or *Anacardium occidentale* [Cashew]; Asteraceae such as the genera *Calendula, Carthamus, Centaurea, Cichorium, Cynara, Helianthus, Lactuca, Locusta, Tagetes, Valeriana* e.g. the species *Calendula officinalis* [Marigold], *Carthamus tinctorius* [safflower], *Centaurea cyanus* [cornflower], *Cichorium intybus* [blue daisy], *Cynara scolymus* [Artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [lettuce], *Tagetes lucida, Tagetes erecta* or *Tagetes tenuifolia* [Marigold]; Apiaceae such as the genera *Daucus* e.g. the species *Daucus carota* [carrot]; Betulaceae such as the genera *Corylus* e.g. the species *Corylus avellana* or *Corylus colurna* [hazelnut]; Boraginaceae such as the genera *Borago* e.g. the species *Borago officinalis* [borage];

Brassicaceae such as the genera *Brassica, Melanosinapis, Sinapis, Arabidopsis* e.g. the species *Brassica napus, Brassica rapa* ssp. [canola, oilseed rape, turnip rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*; Bromeliaceae such as the genera *Anana, Bromelia* e.g. the species *Anana comosus, Ananas ananas* or *Bromelia comosa* [pineapple]; Caricaceae such as the genera *Carica* e.g. the species *Carica papaya* [papaya]; Cannabaceae such as the genera *Cannabis* e.g. the species *Cannabis sative* [hemp], Convolvulaceae such as the genera *Ipomea, Convolvulus* e.g. the species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, Man of the Earth, wild potato], Chenopodiaceae such as the genera *Beta*, i.e. the species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugar beet]; Cucurbitaceae such as the genera *Cucurbita* e.g. the species *Cucurbita maxima, Cucurbita mixta, Cucurbita pepo* or *Cucurbita moschata* [pumpkin, squash]; Elaeagnaceae such as the genera *Elaeagnus* e.g. the species *Olea europaea* [olive]; Ericaceae such as the genera *Kalmia* e.g. the species *Kalmia latifolia, Kalmia angustifolia, Kalmia microphylla, Kalmia polifolia, Kalmia occidentalis, Cistus chamaerhodendros* or *Kalmia lucida* [American laurel, broad-leafed laurel, calico bush, spoon wood, sheep laurel, alpine laurel, bog laurel, western bog-laurel, swamp-laurel]; Euphorbiaceae such as the genera *Manihot, Janipha, Jatropha, Ricinus* e.g. the species *Manihot utilissima, Janipha manihot, Jatropha manihot, Manihot aipil, Manihot dulcis, Manihot manihot, Manihot melanobasis, Manihot esculenta* [manihot, arrowroot, tapioca, cassava] or *Ricinus communis* [castor bean, Castor Oil Bush, Castor Oil Plant, Palma Christi, Wonder Tree]; Fabaceae such as the genera *Pisum, Albizia, Cathormion, Feuillea, Inga, Pithecolobium, Acacia, Mimosa, Medicajo, Glycine, Dolichos, Phaseolus, Soja* e.g. the species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [bastard logwood, silk tree, East Indian Walnut], *Medicago sativa, Medicago falcata, Medicago varia* [alfalfa] *Glycine max Dolichos soja, Glycine gracilis, Glycine hispida, Phaseolus max, Soja hispida* or *Soja max* [soybean]; Geraniaceae such as the genera *Pelargonium, Cocos, Oleum* e.g. the species *Cocos nucifera, Pelargonium grossularioides* or *Oleum cocois* [coconut]; Gramineae such as the genera *Saccharum* e.g. the species *Saccharum officinarum*; Juglandaceae such as the genera *Juglans, Wallia* e.g. the species *Juglans regia, Juglans ailanthifolia, Juglans sieboldiana, Juglans cinerea, Wallia cinerea, Juglans bixbyi, Juglans califomica, Juglans hindsii, Juglans intermedia, Juglans jamaicensis, Juglans major, Juglans microcarpa, Juglans nigra* or *Wallia nigra* [walnut, black walnut, common walnut, persian walnut, white walnut, butternut, black walnut]; Lauraceae such as the genera *Persea, Laurus* e.g. the species laurel *Laurus nobilis* [bay, laurel, bay laurel, sweet bay], *Persea americana Persea americana, Persea gratissima* or *Persea persea* [avocado]; Leguminosae such as the genera *Arachis* e.g. the species *Arachis hypogaea* [peanut]; Linaceae such as the genera *Linum, Adenolinum* e.g. the species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [flax, linseed]; Lythrarieae such as the genera *Punica* e.g. the species Pun/ca granatum [pomegranate]; Malvaceae such as the genera *Gossypium* e.g. the species *Gossypium hirsutum, Gossypium arboreum, Gossypium barbadense, Gossypium herbaceum* or *Gossypium thurberi* [cotton]; Musaceae such as the genera *Musa* e.g. the species *Musa nana, Musa acuminata, Musa paradisiaca, Musa* spp. [banana]; Onagraceae such as the genera *Camissonia, Oenothera* e.g. the species *Oenothera biennis* or *Camissonia brevipes* [primrose, evening primrose]; Palmae such as the genera *Elacis* e.g. the species *Elacis guineensis* [oil plam]; Papaveraceae such as the genera *Papaver* e.g. the species *Papaver orientale, Papaver rhoeas, Papaver dubium* [poppy, oriental poppy, corn poppy, field poppy, shirley poppies, field poppy, long-headed poppy, long-pod poppy]; Pedaliaceae such as the genera *Sesamum* e.g. the species *Sesamum indicum* [sesame]; Piperaceae such as the genera *Piper, Artanthe, Peperomia, Steffensia* e.g. the species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata.* [Cayenne pepper, wild pepper]; Poaceae such as the genera *Hordeum, Secale, Avena, Sorghum, Andropogon, Holcus, Panicum, Oryza, Zea, Triticum* e.g. the species *Hordeum vulgare, Hordeum jubatum, Hordeum murinum, Hordeum secalinum, Hordeum distichon Hordeum aegiceras, Hordeum hexastichon., Hordeum hexastichum, Hordeum irregulare, Hordeum sativum, Hordeum secalinum* [barley, pearl barley, foxtail barley, wall barley, meadow barley], *Secale cereale* [rye], *Avena sativa, Avena fatua, Avena byzantina, Avena fatua* var. *sativa, Avena hybrida* [oat], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum* [*Sorghum*, millet], *Oryza sativa, Oryza latifolia* [rice], *Zea mays* [corn, maize] *Triticum aestivum, Triticum durum, Triticum turgidum, Triticum hybernum, Triticum macha, Triticum sativum* or *Triticum vulgare* [wheat, bread wheat, common wheat], Proteaceae such as the genera *Macadamia* e.g. the species *Macadamia intergrifolia* [macadamia]; Rubiaceae such as the genera *Coffea* e.g. the species *Coffea* spp., *Coffea arabica, Coffea canephora* or *Coffea liberica* [coffee]; Scrophulariaceae such as the genera *Verbascum* e.g. the species *Verbascum blattaria, Verbascum chabdi, Verbascum densiflorum, Verbascum lagurus, Verbascum longifolium, Verbascum lychnitis, Verbascum nigrum, Verbascum olympicum, Verbascum phiomoides, Verbascum phoenicum, Verbascum pulverulentum* or *Verbascum thapsus* [mullein, white moth mullein, nettle-leaved mullein, dense-flowered mullein, silver mullein, long-leaved mullein, white mullein, dark mullein, greek mullein, orange mullein, purple mullein, hoary mullein, great mullein]; Solanaceae such as the genera *Capsicum, Nicotiana, Solanum, Lycopersicon* e.g. the species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [egg-plant] (*Lycopersicon esculentum, Lycopersicon lycopersicum., Lycopersicon pyriforme, Solanum integrifolium* or *Solanum lycopersicum* [tomato]; Sterculiaceae such as the genera *Theobroma* e.g. the species *Theobroma cacao* [cacao]; Theaceae such as the genera *Camellia* e.g. the species *Camellia sinensis*) [tea].

The introduction of the nucleic acids according to the invention, the expression cassette or the vector into organisms, plants for example, can in principle be done by all of the methods known to those skilled in the art. The introduction of the nucleic acid sequences gives rise to recombinant or transgenic organisms.

The transfer of foreign genes into the genome of a plant is called transformation. In doing this the methods described for the transformation and regeneration of plants from plant tissues or plant cells are utilized for transient or stable transformation. Suitable methods are protoplast transformation by poly(ethylene glycol)-induced DNA uptake, the "biolistic" method using the gene cannon—referred to as the particle bombardment method, electroporation, the incubation of dry embryos in DNA solution, microinjection and gene transfer mediated by *Agrobacterium*. Said methods are described by way of example in Jenes B. et al., Techniques for Gene Transfer, in: Transgenic Plants, Vol. 1, Engineering and Utilization, eds. Kung S. D and Wu R., Academic Press (1993) 128-143 and in Potrykus, Annu. Rev. Plant Physiol. Plant Molec. Biol. 42, 205 (1991). The nucleic acids or the construct to be expressed is preferably cloned into a vector which is suitable for transforming *Agrobacterium tumefaciens*, for example pBin19 (Bevan et al., Nucl. Acids Res. 12, 8711 (1984)). Agrobacteria transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. 16, 9877 (1988) or is known inter alia from White F. F., Vectors for Gene Transfer in Higher Plants; in Transgenic Plants, Vol. 1, Engineering and Utilization, eds. Kung S. D. and Wu R., Academic Press, 1993, pp. 15-38.

Agrobacteria transformed by an expression vector according to the invention may likewise be used in known manner for the transformation of plants such as test plants like *Arabidopsis* or crop plants such as cereal crops, corn, oats, rye, barley, wheat, soybean, rice, cotton, sugar beet, canola, sunflower, flax, hemp, potatoes, tobacco, tomatoes, carrots, paprika, oilseed rape, tapioca, cassava, arrowroot, *tagetes*, alfalfa, lettuce and the various tree, nut and vine species, in particular oil-containing crop plants such as soybean, peanut, castor oil plant, sunflower, corn, cotton, flax, oilseed rape, coconut, oil palm, safflower (*Carthamus tinctorius*) or cocoa bean, or in particular corn, wheat, soybean, rice, cotton and canola, e.g. by bathing bruised leaves or chopped leaves in an agrobacterial solution and then culturing them in suitable media.

The genetically modified plant cells may be regenerated by all of the methods known to those skilled in the art. Appropriate methods can be found in the publications referred to above by Kung S. D. and Wu R., Potrykus or Hofgen and Willmitzer.

Accordingly, a further aspect of the invention relates to transgenic organisms transformed by at least one nucleic acid sequence, expression cassette or vector according to the invention as well as cells, cell cultures, tissue, parts—such as, for example, leaves, roots, etc. in the case of plant organisms—or reproductive material derived from such organisms.

In one embodiment of the invention host plants for the nucleic acid, expression cassette or vector according to the invention are selected from the group comprising corn, soy, oil seed rape (including canola and winter oil seed rape), cotton, wheat and rice.

A further embodiment of the invention relates to the use of a nucleic acid construct, e.g. an expression cassette, containing one or more DNA sequences encoding one or more polypeptides shown in SEQ ID NO: 2 or 4, or a homolog thereof or comprising one or more nucleic acid molecules as depicted in SEQ ID NO: 1 or 3, or a homolog thereof or encoding or DNA sequences hybridizing therewith for the transformation of plant cells, tissues or parts of plants.

In doing so, depending on the choice of promoter, the nucleic acid molecules of the present invention can be expressed specifically in the leaves, in the seeds, the nodules, in roots, in the stem or other parts of the plant. Those transgenic plants overproducing sequences, e.g. as depicted in SEQ ID NO: 1 or 3, or a homolog thereof, the reproductive material thereof, together with the plant cells, tissues or parts thereof are a further object of the present invention.

The expression cassette or the nucleic acid sequences or construct according to the invention containing nucleic acid molecules or sequences as depicted in SEQ ID NO: 1 or 3, or a homolog thereof can, moreover, also be employed for the transformation of the organisms identified by way of example above such as bacteria, yeasts, filamentous fungi and plants.

Within the framework of the present invention, increased herbicide tolerance or resistance, relates to, for example, the artificially acquired trait of increased herbicide tolerance or resistance, by comparison with the non-genetically modified initial plants e.g. the trait acquired by genetic modification of the target organism, and due to functional over-expression of one or more polypeptide (sequences) of SEQ ID NO: 2 or 4, or a homolog thereof, e.g. encoded by the corresponding nucleic acid molecules as depicted in SEQ ID NO: 1 or 3, and/or homologs, in the organisms according to the invention, advantageously in the transgenic plant according to the invention or produced according to the method of the invention, at least for the duration of at least one plant generation.

A constitutive expression of the polypeptide sequences of SEQ ID NO: 2 or 4, or a homolog thereof, encoded by the corresponding nucleic acid molecule as depicted in SEQ ID NO: 1 or 3, or a homolog thereof is, moreover, advantageous. On the other hand, however, an inducible expression may also appear desirable. Expression of the polypeptide sequences of the invention can be either direct to the cytoplasm or the organelles, preferably the plastids of the host cells, preferably the plant cells.

The activity of the protein encoded by the sequences of SEQ ID NO: 2 or 4, or a homolog thereof, encoded by the corresponding nucleic acid molecule as depicted in SEQ ID NO: 1 or 3, or a homolog thereof can be determined, for example, in vitro as described in the Examples. In addition, a functional expression of the sequences of SEQ ID NO: 2 or 4, or a homolog thereof, encoded by the corresponding nucleic acid molecule as depicted in SEQ ID NO: 1 or 3, and/or homologs modified in nature and level and its effect on herbicide tolerance or resistance, but also on the metabolic pathways performance can be tested on test plants in greenhouse trials (see EXAMPLES).

An additional object of the invention comprises transgenic organisms such as transgenic plants transformed by an expression cassette containing sequences of as depicted in SEQ ID NO: 1 or 3, or a homolog thereof according to the invention or DNA sequences hybridizing therewith, as well as transgenic cells, tissue, parts and reproduction material of such plants. Particular preference is given in this case to transgenic crop plants such as by way of example barley, wheat, rye, oats, corn, soybean, rice, cotton, sugar beet, oilseed rape and canola, sunflower, flax, hemp, thistle, potatoes, tobacco, tomatoes, tapioca, cassava, arrowroot, alfalfa, lettuce and the various tree, nut and vine species.

In one embodiment of the invention transgenic plants transformed by an expression cassette containing or comprising nucleic acid molecules or sequences as depicted in SEQ ID NO: 1 or 3, or a homolog thereof, according to the invention or DNA sequences hybridizing therewith are selected from the group comprising corn, soy, oil seed rape (including canola and winter oil seed rape), cotton, wheat and rice.

For the purposes of the invention plants are mono- and dicotyledonous plants, mosses or algae, especially plants, for example in one embodiment monocotyledonous plants, or for example in another embodiment dicotyledonous plants. A further refinement according to the invention are transgenic plants as described above which contain a nucleic acid sequence or construct according to the invention or a expression cassette according to the invention.

However, transgenic also means that the nucleic acids according to the invention are located at their natural position in the genome of an organism, but that the sequence, e.g. the coding sequence or a regulatory sequence, for example the promoter sequence, has been modified in comparison with the natural sequence. Preferably, transgenic/recombinant is to be understood as meaning the transcription of one or more nucleic acids or molecules of the invention and being shown in SEQ ID NO: 1 or 3, or a homolog thereof, occurs at a non-natural position in the genome. In one embodiment, the expression of the nucleic acids or molecules is homologous. In another embodiment, the expression of the nucleic acids or molecules is heterologous. This expression can be transiently or of a sequence integrated stably into the genome. Advantageous inducible plant promoters are by way of example the PRP1 promoter (Ward et al., Plant. Mol. Biol. 22361 (1993)), a promoter inducible by benzenesulfonamide (EP 388 186), a promoter inducible by tetracycline (Gatz et al., Plant J. 2, 397 (1992)), a promoter inducible by salicylic acid (WO 95/19443), a promoter inducible by abscisic acid (EP 335 528) and a promoter inducible by ethanol or cyclohexanone (WO 93/21334). Other examples of plant promoters which can advantageously be used are the promoter of cytoplasmic FBPase from potato, the ST-LSI promoter from potato (Stockhaus et al., EMBO J. 8, 2445 (1989)), the promoter of phosphoribosyl pyrophosphate amidotransferase from *Glycine max* (see also gene bank accession number U87999) or a nodiene-specific promoter as described in EP 249 676.

Such promoters are known to the person skilled in the art or can be isolated from genes which are induced under the conditions mentioned above. In one embodiment, seed-specific promoters may be used for monocotylodonous or dicotylodonous plants.

In principle all natural promoters with their regulation sequences can be used like those named above for the expression cassette according to the invention and the method according to the invention. Over and above this, synthetic promoters may also advantageously be used. In the preparation of an expression cassette various DNA fragments can be manipulated in order to obtain a nucleotide sequence, which usefully reads in the correct direction and is equipped with a correct reading frame. To connect the DNA fragments (=nucleic acids according to the invention) to one another adaptors or linkers may be attached to the fragments. The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be both native or homologous as well as foreign or heterologous to the host organism, for example to the host plant. In the 5'-3' transcription direction the expression cassette contains the promoter, a DNA sequence which shown in SEQ ID NO: 1 or 3, or a homolog thereof and a region for transcription termination. Different termination regions can be exchanged for one another in any desired fashion.

A nucleic acid molecule of the present invention, e.g., a nucleic acid molecule encoding a polypeptide which confers increased herbicide tolerance or resistance, in plants, can be isolated using standard molecular biological techniques and the sequence information provided herein. For example, a microbial polypeptide encoding cDNA according to present invention can be isolated from a microbial c-DNA library using all or portion of one of the sequences shown in SEQ ID NO: 1 or 3, or a homolog thereof. Moreover, a nucleic acid molecule encompassing all or a portion of one of the sequences of SEQ ID NO: 1 or 3, or a homolog thereof can be isolated by the polymerase chain reaction using oligonucleotide primers designed based upon this sequence. For example, mRNA can be isolated from plant cells (e.g., by the guanidinium-thiocyanate extraction procedure of Chirgwin et al., Biochemistry 18, 5294 (1979)) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO: 1 or 3, or a homolog thereof. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, the genes employed in the present invention can be prepared by standard synthetic techniques, e.g., using a commercially available automated DNA synthesizer.

In a embodiment, an isolated nucleic acid molecule of the invention comprises one of the nucleotide sequences or molecules as shown in SEQ ID NO: 1 or 3, or a homolog thereof. Moreover, the nucleic acid molecule of the invention can comprise only a portion of the coding region of one of the sequences or molecules of a nucleic acid as shown in SEQ ID NO: 1 or 3, or a homolog thereof, for example, a fragment which can be used as a probe or primer or a fragment encoding a biologically active portion of a polypeptide-according to invention.

Portions of proteins encoded by the polypeptide according to the invention or a polypeptide encoding nucleic acid molecules of the invention are preferably biologically active portions described herein. As used herein, the term "biologically active portion of" a polypeptide is intended to include a portion, e.g. a domain/motif, of increased herbicide tolerance or resistance, in a plant. To determine whether a polypeptide according to the invention, or a biologically active portion thereof, results in an increased herbicide tolerance or resistance, an analysis of a plant comprising the polypeptide may be performed. Such analysis methods are well known to those skilled in the art, as detailed in the Examples. More specifically, nucleic acid fragments encoding biologically active portions of a polypeptide can be prepared by isolating a portion of one of the sequences of the nucleic acid molecules listed in SEQ ID NO: 1 or 3, or a homolog thereof expressing the encoded portion of the polypeptide or peptide thereof (e.g., by recombinant expression in vitro) and assessing the activity of the encoded portion.

Biologically active portions of the polypeptide according to the invention are encompassed by the present invention and include peptides comprising amino acid sequences derived from the amino acid sequence of the polypeptide encoding gene, or the amino acid sequence of a protein homologous to the polypeptide according to the invention, which include fewer amino acids than a full length polypeptide according to the invention or the full length protein which is homologous to the polypeptide according to the invention, and exhibits at least some enzymatic or biological activity of the polypeptide according to the invention. Typically, biologically active portions (e.g., peptides which are, for example, 5, 10, 15, 20, 30, 35, 36, 37, 38, 39, 40, 50, 100 or more amino acids in length) comprise a domain or motif with at least one activity of the polypeptide according to the invention. Moreover, other biologically active portions in which other regions of the protein are deleted can be prepared by recombinant techniques and evaluated for one or more of the activities described herein. Preferably, the biologically active portions of the polypeptide according to the invention include one or more selected domains/motifs or portions thereof having biological activity.

The term "biological active portion" or "biological activity" means a polypeptide as depicted in SEQ ID NO: 2 or 4, or a homolog thereof or a portion of said polypeptide which still has at least 10% or 20%, preferably 30%, 40%, 50% or 60%, especially preferably 70%, 75%, 80%, 90% or 95% of the enzymatic or biological activity of the natural or starting enzyme or protein.

In the process according to the invention nucleic acid sequences or molecules can be used, which, if appropriate, contain synthetic, non-natural or modified nucleotide bases, which can be incorporated into DNA or RNA. Said synthetic, non-natural or modified bases can for example increase the stability of the nucleic acid molecule outside or inside a cell. The nucleic acid molecules of the invention can contain the same modifications as aforementioned.

As used in the present context the term "nucleic acid molecule" may also encompass the untranslated sequence or molecule located at the 3' and at the 5' end of the coding gene region, for example at least 500, preferably 200, especially preferably 100, nucleotides of the sequence upstream of the 5' end of the coding region and at least 100, preferably 50, especially preferably 20, nucleotides of the sequence downstream of the 3' end of the coding gene region. It is often advantageous only to choose the coding region for cloning and expression purposes.

Preferably, the nucleic acid molecule used in the process according to the invention or the nucleic acid molecule of the invention is an isolated nucleic acid molecule. In one embodiment, the nucleic acid molecule of the invention is the nucleic acid molecule used in the process of the invention.

In various embodiments, the isolated nucleic acid molecule used in the process according to the invention may, for example comprise less than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid molecule originates.

The nucleic acid molecules used in the process, for example the polynucleotide of the invention or of a part thereof can be isolated using molecular-biological standard techniques and the sequence information provided herein. Also, for example a homologous sequence or homologous, conserved sequence regions at the DNA or amino acid level can be identified with the aid of comparison algorithms. The former can be used as hybridization probes under standard hybridization techniques (for example those described in Sambrook et al., supra) for isolating further nucleic acid sequences useful in this process.

A nucleic acid molecule encompassing a complete sequence of the nucleic acid molecules used in the process, for example the polynucleotide of the invention, or a part thereof may additionally be isolated by polymerase chain reaction, oligonucleotide primers based on this sequence or on parts thereof being used. For example, a nucleic acid molecule comprising the complete sequence or part thereof can be isolated by polymerase chain reaction using oligonucleotide primers which have been generated on the basis of this very sequence. For example, mRNA can be isolated from cells (for example by means of the guanidinium thiocyanate extraction method of Chirgwin et al., Biochemistry 18, 5294(1979)) and cDNA can be generated by means of reverse transcriptase (for example Moloney, MLV reverse transcriptase, available from Gibco/BRL, Bethesda, Md., or AMV reverse transcriptase, obtainable from Seikagaku America, Inc., St. Petersburg, Fla.).

Synthetic oligonucleotide primers for the amplification by means of polymerase chain reaction can be generated on the basis of a sequence shown herein, using known methods.

Moreover, it is possible to identify a conserved protein by carrying out protein sequence alignments with the polypeptide encoded by the nucleic acid molecules of the present invention, in particular with the sequences encoded by the nucleic acid molecule shown in SEQ ID NO: 1 or 3, or a homolog thereof, from which conserved regions, and in turn, degenerate primers can be derived. Conserved regions are those, which show a very little variation in the amino acid in one particular position of several homologs from different origin. Moreover, it is possible to identify conserved regions from various organisms by carrying out protein sequence alignments with the polypeptide encoded by the nucleic acid of the present invention, in particular with the sequences of the polypeptide molecule shown in SEQ ID NO: 2 or 4, or a homolog thereof, from which conserved regions, and in turn, degenerate primers can be derived.

Conserved domains can be identified from all sequences and are described using a subset of the standard Prosite notation, e.g. the pattern Y-x(21,23)-[FW] means that a conserved tyrosine is separated by minimum 21 and maximum 23 amino acid residues from either a phenylalanine or tryptophane. Patterns can match at least 80% of the investigated proteins. Conserved patterns can be identified with the software tool MEME version 3.5.1 or manually. MEME is described by Timothy L. Bailey and Charles Elkan (Proceedings of the Second International Conference on Intelligent Systems for Molecular Biology, pp. 28-36, AAAI Press, Menlo Park, Calif., 1994). The source code for the stand-alone program is publicly available from the San Diego Supercomputer centre. The Prosite patterns of the conserved domains can be used to search for protein sequences matching this pattern. Various established Bioinformatic centres provide public internet portals for using those patterns in database searches (e.g. PIR (Protein Information Resource, located at Georgetown University Medical Center) or ExPASy (Expert Protein Analysis System)). Alternatively, stand-alone software is available, like the program Fuzzpro, which is part of the EMBOSS software package. For example, the program Fuzzpro not only allows searching for an exact pattern-protein match but also allows setting various ambiguities in the performed search.

Degenerate primers can then be utilized by PCR for the amplification of fragments of novel proteins having above-mentioned activity, e.g. conferring increased herbicide tolerance or resistance, as compared to a corresponding, e.g. non-transformed, wild type plant cell, plant or part thereof after increasing the expression or activity or having the activity of a protein as shown in SEQ ID NO: 2 or 4, or a homolog thereof or further functional homologs of the polypeptide of the invention from other organisms.

These fragments can then be utilized as hybridization probe for isolating the complete gene sequence. As an alternative, the missing 5' and 3' sequences can be isolated by means of RACE-PCR. A nucleic acid molecule according to the invention can be amplified using cDNA or, as an alternative, genomic DNA as template and suitable oligonucleotide primers, following standard PCR amplification techniques. The nucleic acid molecule amplified thus can be cloned into a suitable vector and characterized by means of DNA sequence analysis. Oligonucleotides, which correspond to one of the nucleic acid molecules used in the process can be generated by standard synthesis methods, for example using an automatic DNA synthesizer.

Nucleic acid molecules which are advantageously for the process according to the invention can be isolated based on their homology to the nucleic acid molecules disclosed herein using the sequences or part thereof as or for the generation of a hybridization probe and following standard hybridization techniques under stringent hybridization conditions. In this context, it is possible to use, for example, isolated one or more nucleic acid molecules of at least 15, 20, 25, 30, 35, 40, 50, 60 or more nucleotides, preferably of at least 15, 20 or 25 nucleotides in length which hybridize under stringent conditions with the above-described nucleic acid molecules, in particular with those which encompass a nucleotide sequence of the nucleic acid molecule used in the process of the invention or encoding a protein used in the invention or of the nucleic acid molecule of the invention. Nucleic acid molecules with 30, 50, 100, 250 or more nucleotides may also be used.

By "hybridizing" it is meant that such nucleic acid molecules hybridize under conventional hybridization conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)) or in Current Protocols in Molecular Biology, John Wiley & Sons, N.Y. (1989), 6.3.1-6.3.6.

According to the invention, DNA as well as RNA molecules of the nucleic acid of the invention can be used as probes. Further, as template for the identification of functional homologues Northern blot assays as well as Southern blot assays can be performed. The Northern blot assay advantageously provides further information about the expressed gene product: e.g. expression pattern, occurrence of processing steps, like splicing and capping, etc. The Southern blot assay provides additional information about the chromosomal localization and organization of the gene encoding the nucleic acid molecule of the invention.

A preferred, non-limiting example of stringent hybridization conditions are hybridizations in 6× sodium chloride/sodium citrate (=SSC) at approximately 45° C., followed by one or more wash steps in 0.2×SSC, 0.1% SDS at 50 to 65° C., for example at 50° C., 55° C. or 60° C. The skilled worker knows that these hybridization conditions differ as a function of the type of the nucleic acid and, for example when organic solvents are present, with regard to the temperature and concentration of the buffer. The temperature under "standard hybridization conditions" differs for example as a function of the type of the nucleic acid between 42° C. and 58° C., preferably between 45° C. and 50° C. in an aqueous buffer with a concentration of 0.1×, 0.5×, 1×, 2×, 3×, 4× or 5×SSC (pH 7.2). If organic solvent(s) is/are present in the abovementioned buffer, for example 50% formamide, the temperature under standard conditions is approximately 40° C., 42° C. or 45° C. The hybridization conditions for DNA:DNA hybrids are preferably for example 0.1×SSC and 20° C., 25° C., 30° C., 35° C., 40° C. or 45° C., preferably between 30° C. and 45° C. The hybridization conditions for DNA:RNA hybrids are preferably for example 0.1×SSC and 30° C., 35° C., 40° C., 45° C., 50° C. or 55° C., preferably between 45° C. and 55° C. The abovementioned hybridization temperatures are determined for example for a nucleic acid approximately 100 bp (=base pairs) in length and a G+C content of 50% in the absence of formamide. The skilled worker knows to determine the hybridization conditions required with the aid of textbooks, for example the ones mentioned above, or from the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

A further example of one such stringent hybridization condition is hybridization at 4×SSC at 65° C., followed by a washing in 0.1×SSC at 65° C. for one hour. Alternatively, an exemplary stringent hybridization condition is in 50% formamide, 4×SSC at 42° C. Further, the conditions during the wash step can be selected from the range of conditions delimited by low-stringency conditions (approximately 2×SSC at 50° C.) and high-stringency conditions (approximately 0.2×SSC at 50° C., preferably at 65° C.) (20×SSC: 0.3 M sodium citrate, 3 M NaCl, pH 7.0). In addition, the temperature during the wash step can be raised from low-stringency conditions at room temperature, approximately 22° C., to higher-stringency conditions at approximately 65° C. Both of the parameters salt concentration and temperature can be varied simultaneously, or else one of the two parameters can be kept constant while only the other is varied. Denaturants, for example formamide or SDS, may also be employed during the hybridization. In the presence of 50% formamide, hybridization is preferably effected at 42° C. Relevant factors like 1) length of treatment, 2) salt conditions, 3) detergent conditions, 4) competitor DNAs, 5) temperature and 6) probe selection can be combined case by case so that not all possibilities can be mentioned herein.

Thus, in a preferred embodiment, Northern blots are prehybridized with Rothi-Hybri-Quick buffer (Roth, Karlsruhe) at 68° C. for 2 h. Hybridization with radioactive labelled probe is done overnight at 68° C. Subsequent washing steps are performed at 68° C. with 1×SSC. For Southern blot assays the membrane is prehybridized with Rothi-Hybri-Quick buffer (Roth, Karlsruhe) at 68° C. for 2 h. The hybridization with radioactive labelled probe is conducted over night at 68° C. Subsequently the hybridization buffer is discarded and the filter shortly washed using 2×SSC; 0.1% SDS. After discarding the washing buffer new 2×SSC; 0.1% SDS buffer is added and incubated at 68° C. for 15 minutes. This washing step is performed twice followed by an additional washing step using 1×SSC; 0.1% SDS at 68° C. for 10 min.

Some examples of conditions for DNA hybridization (Southern blot assays) and wash step are shown herein below:

(1) Hybridization conditions can be selected, for example, from the following conditions:
   (a) 4×SSC at 65° C.,
   (b) 6×SSC at 45° C.,
   (c) 6×SSC, 100 mg/ml denatured fragmented fish sperm DNA at 68° C.,
   (d) 6×SSC, 0.5% SDS, 100 mg/ml denatured salmon sperm DNA at 68° C.,
   (e) 6×SSC, 0.5% SDS, 100 mg/ml denatured fragmented salmon sperm DNA, 50% formamide at 42° C.,
   (f) 50% formamide, 4×SSC at 42° C.,
   (g) 50% (v/v) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
   (h) 2× or 4×SSC at 50° C. (low-stringency condition), or
   (i) 30 to 40% formamide, 2× or 4×SSC at 42° C. (low-stringency condition).
(2) Wash steps can be selected, for example, from the following conditions:
   (a) 0.015 M NaCl/0.0015 M sodium citrate/0.1% SDS at 50° C.
   (b) 0.1×SSC at 65° C.
   (c) 0.1×SSC, 0.5% SDS at 68° C.
   (d) 0.1×SSC, 0.5% SDS, 50% formamide at 42° C.
   (e) 0.2×SSC, 0.1% SDS at 42° C.
   (f) 2×SSC at 65° C. (low-stringency condition).

Polypeptides having above-mentioned activity, i.e. conferring increased herbicide tolerance or resistance, as compared to a corresponding, e.g. non-transformed, wild type plant cell, plant or part thereof, derived from other organisms, can be encoded by other DNA sequences which hybridize to the sequences shown in SEQ ID NO: 1 or 3, or a homolog thereof, under relaxed hybridization conditions and which code on expression for peptides conferring the increased herbicide tolerance or resistance, as compared to a corresponding, e.g. non-transformed, wild type plant cell, plant or part thereof.

Further, some applications have to be performed at low stringency hybridization conditions, without any consequences for the specificity of the hybridization. For example, a Southern blot analysis of total DNA could be probed with a nucleic acid molecule of the present invention and washed at low stringency (55° C. in 2×SSPE, 0.1% SDS). The hybridization analysis could reveal a simple pattern of only genes encoding polypeptides of the present invention or used in the process of the invention, e.g. having the herein-mentioned activity of enhancing the increased herbicide tolerance or resistance, as compared to a corresponding, e.g. non-transformed, wild type plant cell, plant or part thereof. A further example of such low-stringent hybridization conditions is 4×SSC at 50° C. or hybridization with 30 to 40% formamide at 42° C. Such molecules comprise those which are fragments, analogues or derivatives of the polypeptide of the invention or used in the process of the invention and differ, for example, by way of amino acid and/or nucleotide deletion(s), insertion(s), substitution (s), addition(s) and/or recombination (s) or any other modification(s) known in the art either alone or in combination from the above-described amino acid sequences or their underlying nucleotide sequence(s). However, it is preferred to use high stringency hybridization conditions.

Hybridization should advantageously be carried out with fragments of at least 5, 10, 15, 20, 25, 30, 35 or 40 bp, advantageously at least 50, 60, 70 or 80 bp, preferably at least 90, 100 or 110 bp. Most preferably are fragments of at least 15, 20, 25 or 30 bp. Preferably are also hybridizations with at least 100 bp or 200, very especially preferably at least 400 bp in length. In an especially preferred embodiment, the hybridization should be carried out with the entire nucleic acid sequence with conditions described above.

The terms "fragment", "fragment of a sequence" or "part of a sequence" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence or molecule referred to or hybridizing with the nucleic acid molecule of the invention or used in the process of the invention under stringent conditions, while the maximum size is not critical. In some applications, the maximum size usually is not substantially greater than that required to provide the desired activity and/or function(s) of the original sequence.

Typically, the truncated amino acid sequence or molecule will range from about 5 to about 310 amino acids in length. More typically, however, the sequence will be a maximum of about 250 amino acids in length, preferably a maximum of about 200 or 100 amino acids. It is usually desirable to select sequences of at least about 10, 12 or 15 amino acids, up to a maximum of about 20 or 25 amino acids.

The term "epitope" relates to specific immunoreactive sites within an antigen, also known as antigenic determinates. These epitopes can be a linear array of monomers in a polymeric composition—such as amino acids in a protein—or consist of or comprise a more complex secondary or tertiary structure. Those of skill will recognize that immunogens (i.e., substances capable of eliciting an immune response) are antigens; however, some antigen, such as haptens, are not immunogens but may be made immunogenic by coupling to a carrier molecule. The term "antigen" includes references to a substance to which an antibody can be generated and/or to which the antibody is specifically immunoreactive.

In one embodiment the present invention relates to a epitope of the polypeptide of the present invention or used in the process of the present invention and confers an increased herbicide tolerance or resistance as compared to a corresponding, e.g. non-transformed, wild type plant cell, plant or part thereof.

The term "one or several amino acids" relates to at least one amino acid but not more than that number of amino acids, which would result in a homology of below 50% identity. Preferably, the identity is more than 70% or 80%, more preferred are 85%, 90%, 91%, 92%, 93%, 94% or 95%, even more preferred are 96%, 97%, 98%, or 99% identity.

Further, the nucleic acid molecule of the invention comprises a nucleic acid molecule, which is a complement of one of the nucleotide sequences of above mentioned nucleic acid molecules or a portion thereof. A nucleic acid molecule or its sequence which is complementary to one of the nucleotide molecules or sequences shown in SEQ ID NO: 1 or 3, or a homolog thereof, is one which is sufficiently complementary to one of the nucleotide molecules or sequences shown in SEQ ID NO: 1 or 3, or a homolog thereof such that it can hybridize to one of the nucleotide sequences shown in SEQ ID NO: 1 or 3, or a homolog thereof, thereby forming a stable duplex. Preferably, the hybridization is performed under stringent hybridization conditions. However, a complement of one of the herein disclosed sequences is preferably a sequence complement thereto according to the base pairing of nucleic acid molecules well known to the skilled person. For example, the bases A and G undergo base pairing with the bases T and U or C, resp. and visa versa. Modifications of the bases can influence the base-pairing partner.

The nucleic acid molecule of the invention comprises a nucleotide sequence which is at least about 30%, 35%, 40% or 45%, preferably at least about 50%, 55%, 60% or 65%, more preferably at least about 70%, 80%, or 90%, and even more preferably at least about 95%, 97%, 98%, 99% or more homologous to a nucleotide sequence shown in SEQ ID NO: 1 or 3, or a homolog thereof, or a portion thereof and preferably has above mentioned activity, in particular having a herbicide tolerance or resistance increasing activity after increasing the activity or an activity of a gene as shown in SEQ ID NO: 1 or 3, or a homolog thereof or of a gene product, by for example expression either in the cytosol or cytoplasm or in an organelle such as a plastid or mitochondria or both, preferably in plastids.

In one embodiment, the nucleic acid molecules comprising the sequence of SEQ ID NO: 1 or 3, or a homolog thereof or gene products encoded by said nucleic acid molecules are expressed in combination with a targeting signal as described herein.

The nucleic acid molecule of the invention comprises a nucleotide sequence or molecule which hybridizes, preferably hybridizes under stringent conditions as defined herein, to one of the nucleotide sequences or molecule shown in SEQ ID NO: 1 or 3, or a homolog thereof, or a portion thereof and encodes a protein having above-mentioned activity, e.g. conferring an increased herbicide tolerance or resistance, as compared to a corresponding, e.g. non-transformed, wild type plant cell, plant or part thereof by for example expression either in the cytosol or in an organelle such as a plastid or mitochondria or both, preferably in plastids, and optionally, having the activity of an PPO enzyme.

Moreover, the nucleic acid molecule of the invention can comprise only a portion of the coding region of one of the sequences shown in SEQ ID NO: 1 or 3, or a homolog thereof, for example a fragment which can be used as a probe or primer or a fragment encoding a biologically active portion of the polypeptide of the present invention or of a polypeptide used in the process of the present invention, i.e. having above-mentioned activity, e.g. conferring an increased herbicide tolerance or resistance, as compared to a corresponding, e.g. non-transformed, wild type plant cell, plant or part thereof f its activity is increased by for example expression either in the cytosol or in an organelle such as a plastid or mitochondria or both, preferably in plastids. The nucleotide sequences determined from the cloning of the present protein-according-to-the-invention-encoding gene allows for the generation of probes and primers designed for use in identifying and/or cloning its homologues in other cell types and organisms. The probe/primer typically comprises substantially purified oligonucleotide. The oligonucleotide typically comprises a region of nucleotide sequence that hybridizes under stringent conditions to at least about 12, 15 preferably about 20 or 25, more preferably about 40, 50 or 75 consecutive nucleotides of a sense strand of one of the sequences set forth, e.g., in SEQ ID NO: 1 or 3, or a homolog thereof, an anti-sense sequence of one of the sequences, e.g., set forth in SEQ ID NO: 1 or 3, or a homolog thereof, or naturally occurring mutants thereof. Primers based on a nucleotide of invention can be used in PCR reactions to clone homologues of the polypeptide of the invention or of the polypeptide used in the process of the invention, e.g. as the primers described in the examples of the present invention, e.g. as shown in the examples. A PCR with primers based on SEQ ID NO: 1 or 3 will result in a fragment of the gene product as shown SEQ ID NO: 2 or 4, or a homolog thereof.

Primer sets are interchangeable. The person skilled in the art knows to combine said primers to result in the desired product, e.g. in a full length clone or a partial sequence. Probes based on the sequences of the nucleic acid molecule of the invention or used in the process of the present invention can be used to detect transcripts or genomic sequences encoding the same or homologous proteins. The probe can further comprise a label group attached thereto, e.g. the label group can be a radioisotope, a fluorescent compound, an enzyme, or an enzyme co-factor. Such probes can be used as a part of a genomic marker test kit for identifying cells which express an polypeptide of the invention or used in the process of the present invention, such as by measuring a level of an encoding nucleic acid molecule in a sample of cells, e.g., detecting mRNA levels or determining, whether a genomic gene comprising the sequence of the polynucleotide of the invention or used in the processes of the present invention has been mutated or deleted.

The nucleic acid molecule of the invention encodes a polypeptide or portion thereof which includes an amino acid sequence which is sufficiently homologous to the amino acid sequence shown in SEQ ID NO: 2 or 4, or a homolog thereof such that the protein or portion thereof maintains the ability to participate in increasing herbicide tolerance or resistance, as compared to a corresponding, e.g. non-transformed, wild type plant cell, plant or part thereof, in particular increasing the activity as mentioned above or as described in the examples in plants is comprised.

As used herein, the language "sufficiently homologous" refers to proteins or portions thereof which have amino acid sequences which include a minimum number of identical or equivalent amino acid residues (e.g., an amino acid residue which has a similar side chain as an amino acid residue in one of the sequences of the polypeptide of the present invention) to an amino acid sequence shown in SEQ ID NO: 2 or 4, or a homolog thereof such that the protein or portion thereof is able to participate in increasing herbicide tolerance or resistance, as compared to a corresponding, e.g. non-transformed, wild type plant cell, plant or part thereof.

In one embodiment, the nucleic acid molecule of the present invention comprises a nucleic acid that encodes a portion of the protein of the present invention. The protein is at least about 30%, 35%, 40%, 45% or 50%, preferably at least about 55%, 60%, 65% or 70%, and more preferably at least about 75%, 80%, 85%, 90%, 91%, 92%, 93% or 94% and most preferably at least about 95%, 97%, 98%, 99% or more homologous to an entire amino acid sequence SEQ ID NO: 2 or 4, and having above-mentioned activity, e.g. conferring an increased herbicide tolerance or resistance, as compared to a corresponding, e.g. non-transformed, wild type plant cell, plant or part thereof by for example expression either in the cytosol or in an organelle such as a plastid or mitochondria or both, preferably in plastids.

Portions of proteins encoded by the nucleic acid molecule of the invention are preferably biologically active, preferably having above-mentioned annotated activity, e.g. conferring an increased herbicide tolerance or resistance, as compared to a corresponding, e.g. non-transformed, wild type plant cell, plant or part thereof after increase of activity.

As mentioned herein, the term "biologically active portion" is intended to include a portion, e.g., a domain/motif, that confers an increased herbicide tolerance or resistance, e.g. an increased herbicide tolerance or resistance-related trait, as compared to a corresponding, e.g. non-transformed, wild type plant cell, plant or part thereof or has an immunological activity such that it is binds to an antibody binding specifically to the polypeptide of the present invention or a polypeptide used in the process of the present invention for increasing herbicide tolerance or resistance, as compared to a corresponding, e.g. non-transformed, wild type plant cell, plant or part thereof.

The invention further relates to nucleic acid molecules that differ from one of the nucleotide sequences shown in SEQ ID NO: 1 or 3, or a homolog thereof (and portions thereof) due to degeneracy of the genetic code and thus encode a polypeptide of the present invention, in particular a polypeptide having above mentioned activity, e.g. as that polypeptides depicted by the sequence shown in SEQ ID NO: 2 or 4, or the functional homologues. Advantageously, the nucleic acid molecule of the invention comprises, or in an other embodiment has, a nucleotide sequence encoding a protein comprising, or in an other embodiment having, an amino acid sequence shown in SEQ ID NO: 2 or 4, or the functional homologues. In a still further embodiment, the nucleic acid molecule of the invention encodes a full length protein which is substantially homologous to an amino acid sequence shown in SEQ ID NO: 2 or 4, or the functional homologues.

In addition, it will be appreciated by those skilled in the art that DNA sequence polymorphisms that lead to changes in the amino acid sequences may exist within a population. Such genetic polymorphism in the gene encoding the polypeptide of the invention or comprising the nucleic acid molecule of the invention may exist among individuals within a population due to natural variation.

Nucleic acid molecules corresponding to natural variants homologues of a nucleic acid molecule of the invention, which can also be a cDNA, can be isolated based on their homology to the nucleic acid molecules disclosed herein using the nucleic acid molecule of the invention, or a portion thereof, as a hybridization probe according to standard hybridization techniques under stringent hybridization conditions.

Accordingly, in another embodiment, a nucleic acid molecule of the invention is at least 15, 20, 25 or 30 nucleotides in length. Preferably, it hybridizes under stringent conditions to a nucleic acid molecule comprising a nucleotide sequence of the nucleic acid molecule of the present invention or used in the process of the present invention, e.g. comprising the sequence shown in SEQ ID NO: 1 or 3, or a homolog thereof. The nucleic acid molecule is preferably at least 20, 30, 50, 100, 250 or more nucleotides in length.

The term "hybridizes under stringent conditions" is defined above. In one embodiment, the term "hybridizes under stringent conditions" is intended to describe conditions for hybridization and washing under which nucleotide sequences at least 30%, 40%, 50% or 65% identical to each other typically remain hybridized to each other. Preferably, the conditions are such that sequences at least about 70%, more preferably at least about 75% or 80%, and even more preferably at least about 85%, 90% or 95% or more identical to each other typically remain hybridized to each other.

Preferably, nucleic acid molecule of the invention that hybridizes under stringent conditions to a sequence shown in SEQ ID NO: 1 or 3, or a homolog thereof corresponds to a naturally-occurring nucleic acid molecule of the invention. As used herein, a "naturally-occurring" nucleic acid molecule refers to an RNA or DNA molecule having a nucleotide sequence that occurs in nature (e.g., encodes a natural protein). Preferably, the nucleic acid molecule encodes a natural protein having above-mentioned activity, e.g. conferring increasing herbicide tolerance or resistance, after increasing the expression or activity thereof or the activity of a protein of the invention or used in the process of the invention by for example expression the nucleic acid sequence of the gene product in the cytosol and/or in an organelle such as a plastid or mitochondria, preferably in plastids.

In addition to naturally-occurring variants of the sequences of the polypeptide or nucleic acid molecule of the invention as well as of the polypeptide or nucleic acid molecule used in the process of the invention that may exist in the population, the skilled artisan will further appreciate that changes can be introduced by mutation into a nucleotide sequence of the nucleic acid molecule encoding the polypeptide of the invention or used in the process of the present invention, thereby leading to changes in the amino acid sequence of the encoded said polypeptide, without altering the functional ability of the polypeptide, preferably not decreasing said activity.

For example, nucleotide substitutions leading to amino acid substitutions at "non-essential" amino acid residues can be made in a sequence of the nucleic acid molecule of the invention or used in the process of the invention, e.g. shown in SEQ ID NO: 1 or 3, or a homolog thereof.

A "non-essential" amino acid residue is a residue that can be altered from the wild-type sequence of one without altering the activity of said polypeptide, whereas an "essential" amino acid residue is required for an activity as mentioned above, e.g. leading to increasing herbicide tolerance or resistance, as compared to a corresponding, e.g. non-transformed, wild type plant cell, plant or part thereof in an organism after an increase of activity of the polypeptide. Other amino acid residues, however, (e.g., those that are not conserved or only semi-conserved in the domain having said activity) may not be essential for activity and thus are likely to be amenable to alteration without altering said activity.

Further, a person skilled in the art knows that the codon usage between organisms can differ. Therefore, he may adapt the codon usage in the nucleic acid molecule of the present invention to the usage of the organism or the cell compartment for example of the plastid or mitochondria in which the polynucleotide or polypeptide is expressed. In a particular preferred embodiment, codon-adapted nucleic acid molecules of the present invention comprise the sequence of SEQ ID NO: 6, or 7, which represent codon-adapted nucleic acid molecules corresponding to SEQ ID NO: 1, or 3.

Accordingly, the invention relates to nucleic acid molecules encoding a polypeptide having above-mentioned activity, in an organism or parts thereof by for example expression either in the cytosol or in an organelle such as a plastid or mitochondria or both, preferably in plastids that contain changes in amino acid residues that are not essential for said activity. Such polypeptides differ in amino acid sequence from a sequence contained in the sequences shown in SEQ ID NO: 2 or 4, or a homolog thereof yet retain said activity described herein. The nucleic acid molecule can comprise a nucleotide sequence encoding a polypeptide, wherein the polypeptide comprises an amino acid sequence at least about 50% identical to an amino acid sequence shown SEQ ID NO: 2 or 4, or a homolog thereof and is capable of participation in increasing herbicide tolerance or resistance, as compared to a corresponding, e.g. non-transformed, wild type plant cell, plant or part thereof after increasing its activity, e.g. its expression by for example expression either in the cytosol or in an organelle such as a plastid or mitochondria or both, preferably in plastids. Preferably, the protein encoded by the nucleic acid molecule is at least about 60% identical to the sequence shown in SEQ ID NO: 2 or 4, or a homolog thereof, more preferably at least about 70% identical to one of the sequences shown in SEQ ID NO: 2 or 4, or a homolog thereof, even more preferably at least about 80%, 90%, 95% homologous to the sequence shown in SEQ ID NO: 2 or 4, or a homolog thereof, and most preferably at least about 96%, 97%, 98%, or 99% identical to the sequence shown in SEQ ID NO: 2 or 4, or a homolog thereof.

To determine the percentage homology (=identity, herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage homology between the two sequences is a function of the number of identical positions shared by the sequences (i.e. % homology=number of identical positions/total number of positions×100). The terms "homology" and "identity" are thus to be considered as synonyms.

For the determination of the percentage homology (=identity) of two or more amino acids or of two or more nucleotide sequences several computer software programs have been developed. The homology of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R.

Pearson and D. J. Lipman, PNAS 85, 2444 (1988); W. R. Pearson, Enzymology 183, 63 (1990)). Another useful program for the calculation of homologies of different sequences is the standard BLAST® program, which is included in the Biomax pedant software (Biomax, Munich, Federal Republic of Germany). This leads unfortunately sometimes to suboptimal results since BLAST® does not always include complete sequences of the subject and the querry. Nevertheless as this program is very efficient it can be used for the comparison of a huge number of sequences. The following settings are typically used for such a comparisons of sequences: -p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST® report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [TIF]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast[nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence homology are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which has 80% homology with sequence SEQ ID NO: 1 at the nucleic acid level is understood as meaning a sequence which, upon comparison with the sequence SEQ ID NO: 1 by the above program "Needle" with the above parameter set, has a 80% homology.

Homology between two polypeptides is understood as meaning the identity of the amino acid sequence over in each case the entire sequence length which is calculated by comparison with the aid of the above program "Needle" using Matrix: EBLOSUM62, Gap_penalty: 8.0, Extend_penalty: 2.0.

For example a sequence which has a 80% homology with sequence SEQ ID NO: 2 at the protein level is understood as meaning a sequence which, upon comparison with the sequence SEQ ID NO: 2 by the above program "Needle" with the above parameter set, has a 80% homology.

Functional equivalents derived from the nucleic acid sequence as shown in SEQ ID NO: 1 or 3, or a homolog thereof according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 2 or 4, or a homolog thereof according to the invention and encode polypeptides having essentially the same properties as the polypeptide as shown in SEQ ID NO: 2 or 4, or a homolog thereof.

Functional equivalents derived from one of the polypeptides as shown in SEQ ID NO: 2 or 4, or a homolog thereof according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 2 or 4, or a homolog thereof according to the invention and having essentially the same properties as the polypeptide as shown in SEQ ID NO: 2 or 4, or a homolog thereof.

"Essentially the same properties" of a functional equivalent is above all understood as meaning that the functional equivalent has above mentioned activity, by for example expression either in the cytosol or in an organelle such as a plastid or mitochondria or both, preferably in plastids while increasing the amount of protein, activity or function of said functional equivalent in an organism, e.g. a microorganism, a plant or plant tissue or animal tissue, plant or animal cells or a part of the same.

A nucleic acid molecule encoding an homologous to a protein sequence of SEQ ID NO: 2 or 4, or a homolog thereof can be created by introducing one or more nucleotide substitutions, additions or deletions into a nucleotide sequence of the nucleic acid molecule of the present invention, in particular of SEQ ID NO: 1 or 3, or a homolog thereof such that one or more amino acid substitutions, additions or deletions are introduced into the encoded protein. Mutations can be introduced into the encoding sequences of SEQ ID NO: 1 or 3, or a homolog thereof by standard techniques, such as site-directed mutagenesis and PCR-mediated mutagenesis.

Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophane), beta-branched side chains (e.g., threonine, valine, isoleucine) and aromatic side chains (e.g., tyrosine, phenylalanine, tryptophane, histidine).

Thus, a predicted nonessential amino acid residue in a polypeptide of the invention or a polypeptide used in the process of the invention is preferably replaced with another amino acid residue from the same family. Alternatively, in another embodiment, mutations can be introduced randomly along all or part of a coding sequence of a nucleic acid molecule of the invention or used in the process of the invention, such as by saturation mutagenesis, and the resultant mutants can be screened for activity described herein to identify mutants that retain or even have increased above mentioned activity, e.g. conferring increased herbicide tolerance or resistance, as compared to a corresponding, e.g. non-transformed, wild type plant cell, plant or part thereof.

The inventors of the present invention have surprisingly found that by expressing in a plant a nucleic acid comprising a nucleotide sequence which comprises the sequence of SEQ ID NO: 1, or 3, or a variant or derivative thereof, the tolerance or resistance of said plant to particular PPO inhibiting herbicides could be remarkably increased as compared to a control or wildtype plant, that lacks the herbicide-resistance characteristics and/or particular PPO polynucleotide of the invention that are disclosed herein.

Furthermore, the inventors of the present invention have found that by substituting one or more of the key amino acid residues, employing e.g. one of the above described methods to mutate the encoding nucleic acids, the tolerance or resistance to particular PPO-inhibiting herbicides could be increased even more as compared to the activity of the wild type PPO enzymes with SEQ ID NO: 2, or 4. Preferred substitutions of such a mutated PPO are those that increase the herbicide tolerance of the plant, but leave the biological activity of the oxidase activity substantially unaffected.

The term "mutated PPO nucleic acid" refers to a PPO nucleic acid having a sequence that is mutated from a wild-type PPO nucleic acid of SEQ ID NO: 1 or 3, and that confers increased PPO-inhibiting herbicide tolerance to a plant in which it is expressed. Furthermore, the term "mutated protoporphyrinogen oxidase (mutated PPO)" refers to the replacement of an amino acid of the wild-type primary sequences SEQ ID NO: 2, or 4, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

Accordingly, in another object of the present invention the key amino acid residues of a PPO enzyme, a variant, derivative, orthologue, paralogue or homologue thereof, is substituted by any other amino acid.

In one embodiment, the key amino acid residues of a PPO enzyme, a variant, derivative, orthologue, paralogue or homologue thereof, is substituted by a conserved amino acid as depicted in Table 2.

TABLE 2

Examples of conserved amino acid substitutions

| Residue | Conservative Substitutions | Residue | Conservative Substitutions |
|---------|---------------------------|---------|---------------------------|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

It will be understood by the person skilled in the art that amino acids located in a close proximity to the positions of amino acids mentioned below may also be substituted. Thus, in another embodiment the variant of SEQ ID NO: 2, or 4, a variant, derivative, orthologue, paralogue or homologue thereof comprises a mutated PPO, wherein an amino acid±3, ±2 or ±1 amino acid positions from a key amino acid is substituted by any other amino acid.

Based on techniques well-known in the art, a highly characteristic sequence pattern can be developed, by means of which further of mutated PPO candidates with the desired activity may be searched.

Searching for further mutated PPO candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

Furthermore, by applying the method of site directed mutagenesis, in particular saturation mutagenes (see e.g. Schenk et al., Biospektrum 03/2006, pages 277-279), the inventors of the present invention have identified and generated specific amino acid substitutions and combinations thereof, which—when introduced into a plant by transforming and expressing the respective mutated PPO encoding nucleic acid—confer increased herbicide resistance or tolerance to a PPO inhibiting herbicide to said plant.

It is to be understood that any amino acid besides the ones mentioned hereinafter could be used as a substitutent. Assays to test for the functionality of such mutants are readily available in the art, and respectively, described in the Example section of the present invention.

In a preferred embodiment, the mutated PPO refers to a polypeptide comprising the sequence of SEQ ID NO: 2 or 4, wherein the amino acid sequence differs from an amino acid sequence of SEQ ID NO: 2 or 4 at or corresponding to position 137, 415, and/or position 438 of SEQ ID NO: 2.

Examples of differences at these amino acid positions include, but are not limited to, one or more of the following:
the amino acid at or corresponding to position 137 is other than Arginine;
the amino acid at or corresponding to position 415 is other than Leucine
the amino acid at or corresponding to position 438 is other than Phenylalanine.

In some embodiments, the mutated PPO enzyme of SEQ ID NO: 2 comprises one or more of the following:
the amino acid at or corresponding to position 137 is Leu, Ala, Val, Ile, Met, Tyr, Gly, Asn, Cys, Phe, Ser, Thr, Gln, or His;
the amino acid at or corresponding to position 415 is Ala, Arg, Val, Ile, Met, His, Lys, Asp, Glu, Ser, Thr, Asn, Gln, Cys, Gly, Pro, Phe, Tyr, or Trp
the amino acid at or corresponding to position 438 is Ala, Leu, Val, Ile, Met, His, Lys, Asp, Glu, Ser, Thr, Asn, Gln, Cys, Gly, Pro, Arg, Tyr, or Trp.

In another preferred embodiment, the mutated PPO comprises a sequence of SEQ ID NO: 2 a variant, derivative, orthologue, paralogue or homologue thereof, in which:
the amino acid at or corresponding to position 137 is Ala, Leu, Val, Ile, Met, His, Lys, Asp, Glu, Ser, Thr, Asn, Gln, Cys, Gly, Pro, Phe, Tyr, or Trp, and the amino acid at or corresponding to position 438 is Ala, Leu, Val, Ile, Met, His, Lys, Asp, Glu, Ser, Thr, Asn, Gln, Cys, Gly, Pro, Arg, Tyr, or Trp.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 137 is Leu, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is His.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Lys.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Asp.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Glu.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Ser.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Thr.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Asn.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Gln.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Pro.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Arg.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 137 is Val, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 137 is Ile, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 137 is Ile, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 137 is Ile, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Asp.

In another preferred embodiment, the mutated PPO comprises a sequence of SEQ ID NO: 2 a variant, derivative, orthologue, paralogue or homologue thereof, in which:

the amino acid at or corresponding to position 137 is Met, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 438 is Leu.

In another preferred embodiment, the mutated PPO comprises a sequence of SEQ ID NO: 2 a variant, derivative, orthologue, paralogue or homologue thereof, in which:

the amino acid at or corresponding to position 137 is Ser, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is His.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Lys.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Asp.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Glu.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Ser.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Thr.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Asn.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Gln.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Pro.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Arg.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 137 is Ser, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 137 is Thr, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 137 is Thr, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 137 is Thr, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 137 is Thr, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 137 is Thr, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 137 is Thr, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Gin.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Asn.

In another preferred embodiment, the mutated PPO comprises a sequence of SEQ ID NO: 2 a variant, derivative, orthologue, paralogue or homologue thereof, in which:

the amino acid at or corresponding to position 137 is Gln, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Gly.

In another preferred embodiment, the mutated PPO comprises a sequence of SEQ ID NO: 2 a variant, derivative, orthologue, paralogue or homologue thereof, in which:

the amino acid at or corresponding to position 137 is Cys, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:

the amino acid at or corresponding to position 137 is Gly, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is His.

In another preferred embodiment, the mutated PPO comprises a sequence of SEQ ID NO: 2 a variant, derivative, orthologue, paralogue or homologue thereof, in which:

the amino acid at or corresponding to position 137 is Tyr, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Ala, Leu, Val, Ile, Met, His, Lys, Asp, Glu, Ser, Thr, Asn, Gln, Cys, Gly, Pro, Phe, Tyr, or Trp, and the amino acid at or corresponding to position 415 is Ala, Arg, Val, Ile, Met, His, Lys, Asp, Glu, Ser, Thr, Asn, Gln, Cys, Gly, Pro, Phe, Tyr, or Trp.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Ala, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Leu, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Val, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Ile, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Met, and the amino acid at or corresponding to position 415 is Met.

In another preferred embodiment, the mutated PPO comprises a sequence of SEQ ID NO: 2 a variant, derivative, orthologue, paralogue or homologue thereof, in which:

the amino acid at or corresponding to position 137 is Met, and the amino acid at or corresponding to position 415 is His.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Lys.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Asp.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Glu.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Ser.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Thr.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Asn.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Gln.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Cys.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Gly.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Pro.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Phe.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Tyr.

In another preferred embodiment, the mutated PPO comprises a sequence of SEQ ID NO: 2 a variant, derivative, orthologue, paralogue or homologue thereof, in which: the amino acid at or corresponding to position 137 is Met, and the amino acid at or corresponding to position 415 is Trp.

In another preferred embodiment, the mutated PPO comprises a sequence of SEQ ID NO: 2 a variant, derivative, orthologue, paralogue or homologue thereof, in which: the amino acid at or corresponding to position 137 is His, and the amino acid at or corresponding to position 415 is Ala.

In another preferred embodiment, the mutated PPO comprises a sequence of SEQ ID NO: 2 a variant, derivative, orthologue, paralogue or homologue thereof, in which: the amino acid at or corresponding to position 137 is His, and the amino acid at or corresponding to position 415 is Arg.

In another preferred embodiment, the mutated PPO comprises a sequence of SEQ ID NO: 2 a variant, derivative, orthologue, paralogue or homologue thereof, in which: the amino acid at or corresponding to position 137 is His, and the amino acid at or corresponding to position 415 is Val.

In another preferred embodiment, the mutated PPO comprises a sequence of SEQ ID NO: 2 a variant, derivative, orthologue, paralogue or homologue thereof, in which: the amino acid at or corresponding to position 137 is His, and the amino acid at or corresponding to position 415 is Ile.

In another preferred embodiment, the mutated PPO comprises a sequence of SEQ ID NO: 2 a variant, derivative, orthologue, paralogue or homologue thereof, in which: the amino acid at or corresponding to position 137 is His, and the amino acid at or corresponding to position 415 is Met.

In another preferred embodiment, the mutated PPO comprises a sequence of SEQ ID NO: 2 a variant, derivative, orthologue, paralogue or homologue thereof, in which: the amino acid at or corresponding to position 137 is His, and the amino acid at or corresponding to position 415 is His.

In another preferred embodiment, the mutated PPO comprises a sequence of SEQ ID NO: 2 a variant, derivative, orthologue, paralogue or homologue thereof, in which: the amino acid at or corresponding to position 137 is His, and the amino acid at or corresponding to position 415 is Lys.

In another preferred embodiment, the mutated PPO comprises a sequence of SEQ ID NO: 2 a variant, derivative, orthologue, paralogue or homologue thereof, in which: the amino acid at or corresponding to position 137 is His, and the amino acid at or corresponding to position 415 is Asp.

In another preferred embodiment, the mutated PPO comprises a sequence of SEQ ID NO: 2 a variant, derivative, orthologue, paralogue or homologue thereof, in which:

the amino acid at or corresponding to position 137 is His, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is His, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Lys, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Asp, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Gin.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Glu, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Ser, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Arg.

In another preferred embodiment, the mutated PPO comprises a sequence of SEQ ID NO: 2 a variant, derivative, orthologue, paralogue or homologue thereof, in which:

the amino acid at or corresponding to position 137 is Thr, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Thr, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Asn, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Gin, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Gin, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Gln, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Asn.

In another preferred embodiment, the mutated PPO comprises a sequence of SEQ ID NO: 2 a variant, derivative, orthologue, paralogue or homologue thereof, in which:

the amino acid at or corresponding to position 137 is Cys, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Cys, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Gly.

In another preferred embodiment, the mutated PPO comprises a sequence of SEQ ID NO: 2 a variant, derivative, orthologue, paralogue or homologue thereof, in which:

the amino acid at or corresponding to position 137 is Gly, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Gly, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Lys.

In another preferred embodiment, the mutated PPO comprises a sequence of SEQ ID NO: 2 a variant, derivative, orthologue, paralogue or homologue thereof, in which:

the amino acid at or corresponding to position 137 is Pro, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Pro, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:

the amino acid at or corresponding to position 137 is Pro, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Phe, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is His.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Lys.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Asp.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Glu.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Ser.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Thr.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Asn.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Gln.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Cys.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Gly.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Pro.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Phe.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Tyr.

In another preferred embodiment, the mutated PPO comprises a sequence of SEQ ID NO: 2 a variant, derivative, orthologue, paralogue or homologue thereof, in which:
the amino acid at or corresponding to position 137 is Tyr, and the amino acid at or corresponding to position 415 is Trp.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 415 is Ala.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 415 is Arg.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 415 is Val.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 415 is Ile.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 415 is Met.

In another preferred embodiment, the mutated PPO comprises a sequence of SEQ ID NO: 2 a variant, derivative, orthologue, paralogue or homologue thereof, in which:
the amino acid at or corresponding to position 137 is Trp, and the amino acid at or corresponding to position 415 is His.

In another preferred embodiment, the mutated PPO comprises a sequence of SEQ ID NO: 2 a variant, derivative, orthologue, paralogue or homologue thereof, in which:

the amino acid at or corresponding to position 137 is Trp, and the amino acid at or corresponding to position 415 is Lys.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Asp.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Glu.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Ser.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Thr.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Asn.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Gln.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Cys.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Gly.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Pro.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Phe.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Tyr.

In another preferred embodiment, the mutated PPO comprises a sequence of SEQ ID NO: 2 a variant, derivative, orthologue, paralogue or homologue thereof, in which: the amino acid at or corresponding to position 137 is Trp, and the amino acid at or corresponding to position 415 is Trp.

In another preferred embodiment, the mutated PPO comprises a sequence of SEQ ID NO: 2 a variant, derivative, orthologue, paralogue or homologue thereof, in which: the amino acid at or corresponding to position 415 is Ala, Arg, Val, Ile, Met, His, Lys, Asp, Glu, Ser, Thr, Asn, Gln, Cys, Gly, Pro, Phe, Tyr, or Trp, and the amino acid at or corresponding to position 438 is Ala, Leu, Val, Ile, Met, His, Lys, Asp, Glu, Ser, Thr, Asn, Gln, Cys, Gly, Pro, Arg, Tyr, or Trp.

In another preferred embodiment, the mutated PPO comprises a sequence of SEQ ID NO: 2 a variant, derivative, orthologue, paralogue or homologue thereof, in which: the amino acid at or corresponding to position 415 is Ala, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 415 is Ala, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 415 is Ala, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 415 is Ala, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 415 is Ala, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 415 is Ala, and the amino acid at or corresponding to position 438 is His.

In another preferred embodiment, the mutated PPO comprises a sequence of SEQ ID NO: 2 a variant, derivative, orthologue, paralogue or homologue thereof, in which: the amino acid at or corresponding to position 415 is Ala, and the amino acid at or corresponding to position 438 is Lys.

In another preferred embodiment, the mutated PPO comprises a sequence of SEQ ID NO: 2 a variant, derivative, orthologue, paralogue or homologue thereof, in which: the amino acid at or corresponding to position 415 is Ala, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Ala, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Thr.

In another preferred embodiment, the mutated PPO comprises a sequence of SEQ ID NO: 2 a variant, derivative, orthologue, paralogue or homologue thereof, in which:

the amino acid at or corresponding to position 415 is Arg, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Arg, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Val, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 415 is Val, and the amino acid at or corresponding to position 438 is Pro.

In another preferred embodiment, the mutated PPO comprises a sequence of SEQ ID NO: 2 a variant, derivative, orthologue, paralogue or homologue thereof, in which: the amino acid at or corresponding to position 415 is Val, and the amino acid at or corresponding to position 438 is Arg.

In another preferred embodiment, the mutated PPO comprises a sequence of SEQ ID NO: 2 a variant, derivative, orthologue, paralogue or homologue thereof, in which: the amino acid at or corresponding to position 415 is Val, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 415 is Val, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is His.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Lys.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Asp.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Glu.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Ser.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Thr.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Asn.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Gln.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Pro.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Arg.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 415 is Ile, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Leu.

In another preferred embodiment, the mutated PPO comprises a sequence of SEQ ID NO: 2 a variant, derivative, orthologue, paralogue or homologue thereof, in which:

the amino acid at or corresponding to position 415 is Met, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is His.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Lys.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Asp.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Glu.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Ser.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Thr.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Asn.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Gln.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Pro.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Arg.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 415 is Met, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 415 is His, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 415 is His, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 415 is His, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 415 is His, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 415 is His, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 415 is His, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is His, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Lys, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Asp, and the amino acid at or corresponding to position 438 is Asn.

In another preferred embodiment, the mutated PPO comprises a sequence of SEQ ID NO: 2 a variant, derivative, orthologue, paralogue or homologue thereof, in which:

the amino acid at or corresponding to position 415 is Asp, and the amino acid at or corresponding to position 438 is Gln.

In another preferred embodiment, the mutated PPO comprises a sequence of SEQ ID NO: 2 a variant, derivative, orthologue, paralogue or homologue thereof, in which: the amino acid at or corresponding to position 415 is Asp, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 415 is Asp, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 415 is Asp, and the amino acid at or corresponding to position 438 is Pro.

In another preferred embodiment, the mutated PPO comprises a sequence of SEQ ID NO: 2 a variant, derivative, orthologue, paralogue or homologue thereof, in which: the amino acid at or corresponding to position 415 is Asp, and the amino acid at or corresponding to position 438 is Arg.

In another preferred embodiment, the mutated PPO comprises a sequence of SEQ ID NO: 2 a variant, derivative, orthologue, paralogue or homologue thereof, in which: the amino acid at or corresponding to position 415 is Asp, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 415 is Asp, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Ile.

In another preferred embodiment, the mutated PPO comprises a sequence of SEQ ID NO: 2 a variant, derivative, orthologue, paralogue or homologue thereof, in which:

the amino acid at or corresponding to position 415 is Glu, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is His.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Lys.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Asp.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Glu.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Ser.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Thr.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Asn.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Gln.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 415 is Glu, and the amino acid at or corresponding to position 438 is Gly.

In another preferred embodiment, the mutated PPO comprises a sequence of SEQ ID NO: 2 a variant, derivative, orthologue, paralogue or homologue thereof, in which:

the amino acid at or corresponding to position 415 is Glu, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Glu, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Glu, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Glu, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Ser, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:

the amino acid at or corresponding to position 415 is Ser, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Thr, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Asn, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is His.

In another preferred embodiment, the mutated PPO comprises a sequence of SEQ ID NO: 2 a variant, derivative, orthologue, paralogue or homologue thereof, in which:

the amino acid at or corresponding to position 415 is Gln, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Gln, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Cys, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Gly, and the amino acid at or corresponding to position 438 is Gln.

In another preferred embodiment, the mutated PPO comprises a sequence of SEQ ID NO: 2 a variant, derivative, orthologue, paralogue or homologue thereof, in which:

the amino acid at or corresponding to position 415 is Gly, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 415 is Gly, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 415 is Gly, and the amino acid at or corresponding to position 438 is Pro.

In another preferred embodiment, the mutated PPO comprises a sequence of SEQ ID NO: 2 a variant, derivative, orthologue, paralogue or homologue thereof, in which: the amino acid at or corresponding to position 415 is Gly, and the amino acid at or corresponding to position 438 is Arg.

In another preferred embodiment, the mutated PPO comprises a sequence of SEQ ID NO: 2 a variant, derivative, orthologue, paralogue or homologue thereof, in which: the amino acid at or corresponding to position 415 is Gly, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 415 is Gly, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is His.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Lys.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Asp.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Glu.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Ser.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Thr.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Asn.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Gln.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 415 is Pro, and the amino acid at or corresponding to position 438 is Pro.

In another preferred embodiment, the mutated PPO comprises a sequence of SEQ ID NO: 2 a variant, derivative, orthologue, paralogue or homologue thereof, in which:

the amino acid at or corresponding to position 415 is Pro, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Pro, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Pro, and the amino acid at or corresponding to position 438 is Trp.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Ala.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Leu.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Val.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Phe, and the amino acid at or corresponding to position 438 is Trp.

In another preferred embodiment, the mutated PPO comprises a sequence of SEQ ID NO: 2 a variant, derivative, orthologue, paralogue or homologue thereof, in which:

the amino acid at or corresponding to position 415 is Tyr, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Ile.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Met.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is His.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Lys.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Asp.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Glu.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Ser.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Thr.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Asn.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Gln.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Cys.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Gly.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Pro.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Arg.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Tyr.

In another preferred embodiment, the mutated PPO comprises a sequence of SEQ ID NO: 2 a variant, derivative, orthologue, paralogue or homologue thereof, in which: the amino acid at or corresponding to position 415 is Tyr, and the amino acid at or corresponding to position 438 is Trp.

In another preferred embodiment, the mutated PPO comprises a sequence of SEQ ID NO: 2 a variant, derivative, orthologue, paralogue or homologue thereof, in which: the amino acid at or corresponding to position 415 is Trp, and the amino acid at or corresponding to position 438 is Ala.

In another preferred embodiment, the mutated PPO comprises a sequence of SEQ ID NO: 2 a variant, derivative, orthologue, paralogue or homologue thereof, in which: the amino acid at or corresponding to position 415 is Trp, and the amino acid at or corresponding to position 438 is Leu.

In another preferred embodiment, the mutated PPO comprises a sequence of SEQ ID NO: 2 a variant, derivative, orthologue, paralogue or homologue thereof, in which: the amino acid at or corresponding to position 415 is Trp, and the amino acid at or corresponding to position 438 is Val.

In another preferred embodiment, the mutated PPO comprises a sequence of SEQ ID NO: 2 a variant, derivative, orthologue, paralogue or homologue thereof, in which: the amino acid at or corresponding to position 415 is Trp, and the amino acid at or corresponding to position 438 is Ile.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Met.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is His.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Lys.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Asp.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Glu.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Ser.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Thr.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Asn.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Gln.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Cys.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Gly.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Pro.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Arg.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Tyr.

In another preferred embodiment, the mutated PPO comprises a sequence of SEQ ID NO: 2 a variant, derivative, orthologue, paralogue or homologue thereof, in which:
the amino acid at or corresponding to position 415 is Trp, and the amino acid at or corresponding to position 438 is Trp.

In other embodiments, the mutated PPO comprises a sequence of SEQ ID NO: 4, a variant, derivative, orthologue, paralogue or homologue thereof, in which:
the amino acid at or corresponding to position 299 is other than Thr, and is preferably Leu, Ala, Pro, Lys, Arg, Val, Ile, Met, Tyr, Trp, Gly, Asn, Asp, Cys, Phe, Ser, Gln, Glu, or His; and/or
the amino acid at or corresponding to position 300 is other than Ser, and is preferably Leu, Ala, Arg, Val, Ile, Met, His, Lys, Asp, Glu, Thr, Asn, Gln, Cys, Gly, Pro, Phe, Tyr, or Trp and/or
the amino acid at or corresponding to position 420 is other than Tyr and is preferably Ala, Leu, Val, Ile, Met, His, Lys, Asp, Glu, Ser, Thr, Asn, Gln, Cys, Gly, Pro, Arg, Phe, or Trp.

In a preferred, the mutated PPO comprises a sequence of SEQ ID NO: 4, a variant, derivative, orthologue, paralogue or homologue thereof, in which:
the amino acid at or corresponding to position 299 is Leu, and the amino acid at or corresponding to position 420 is Met.

In another preferred, the mutated PPO comprises a sequence of SEQ ID NO: 4, a variant, derivative, orthologue, paralogue or homologue thereof, in which:
the amino acid at or corresponding to position 299 is Leu, and the amino acid at or corresponding to position 300 is Gly, and the amino acid at or corresponding to position 420 is Val.

It will be within the knowledge of the skilled artisan to identify conserved regions and motifs shared between the homologues, orthologues and paralogues encoded by SEQ ID NO: 1, or 3, such as those depicted in Table 1. Having identified such conserved regions that may represent suitable binding motifs, amino acids corresponding to amino acids at the preferred positions listed above, can be chosen to be substituted by any other amino acid, for example by conserved amino acids as shown in table 2, preferably by the amino acids listed above.

Furthermore, such conserved regions and motifs can be identified by employing so-called amino acid substitution matrices which are well known in the art. See, e.g., the PAM matrices (Dayhoff et al., 1978) and the BLOSUM matrices (Henikoff and Henikoff, 1992.) Both substitution matrix families are parameterized by sequence divergence. The PAM matrices are based on a formal Markov model of sequence evolution. The BLOSUM matrices use an ad hoc approach. Both families were derived according to the following general approach, although the details of each step differ between the two methods. 1. Use a set of "trusted" multiple sequence alignments (ungapped) to infer model parameters; 2. Count observed amino acid pairs in the trusted alignments, correcting for sample bias; 3. Estimate substitution frequencies from amino acid pair counts; 4. Construct a log odds scoring matrix from substitution frequencies.

In a preferred embodiment, the so-called Position Weight Matrix (PWM) is used (Stormo, et al. (1982) Nucleic Acids Research 10 (9): 2997-3011). When the PWM elements are calculated using log likelihoods, the score of a sequence given a particular PWM can be calculated be adding (rather than multiplying) the relevant values at each position in the PWM. The sequence score gives an indication of how different the sequence is from a random sequence. The score is 0 if the sequence has the same probability of being a functional site and of being a random site. The score is greater than 0 if it is more likely to be a functional site than a random site, and less than 0 if it is more likely to be a random site than a functional site. (Guigo, Roderic. "An Introduction to Position Specific Scoring Matrices". bioinformatica.upf.edu). The sequence score can also be interpreted in a physical framework as the binding energy for that sequence.

The values contributing to the matching score are calculated as the natural logarithm of the likelihood of the amino acid to occur at this position in the motif divided by the background probability of occurrence assuming a uniform distribution. Hence, the value of 0.42 for the occurrence of A at position 126 is calculated as ln(0.076/0.05), showing that the likelihood of an A at this position is with 7.6% more frequent than the expected random occurrence with 5%.

As an example, log odd values for positions 128, 397, and 420 of SEQ ID NO: 27 (*Amaranthus* PPO2), which is used as reference sequence, are shown below.

| R128: | | | | | |
|---|---|---|---|---|---|
| Amino acid | N126 | K127 | R128 | Y129 | I130 |
| A | 0.42 | 0.22 | 0.72 | 0.05 | -0.03 |
| C | -1.45 | -0.75 | -1.50 | -1.53 | -1.13 |
| D | 0.42 | 0.03 | -0.27 | -1.69 | -0.90 |
| E | -0.03 | -0.05 | -0.85 | -1.53 | -0.79 |
| F | -0.65 | 0.09 | -0.38 | 0.94 | 0.66 |
| G | 0.69 | 0.43 | -0.01 | -0.49 | -1.18 |
| H | -0.65 | -0.58 | -0.64 | -0.23 | -0.76 |
| I | -0.97 | -0.58 | -0.24 | 0.08 | 1.29 |
| K | 0.35 | 0.41 | -0.20 | -0.73 | -1.92 |
| L | 0.30 | -0.05 | -0.12 | 0.89 | 1.05 |
| M | -0.62 | -0.86 | -0.93 | -0.92 | -0.79 |
| N | 0.17 | 0.20 | -0.33 | -1.00 | -1.23 |
| P | 0.17 | -0.42 | -0.43 | -1.45 | -0.46 |
| Q | -0.31 | -0.34 | -0.54 | -0.80 | -1.13 |
| R | 0.73 | 0.34 | 1.32 | -0.04 | -0.63 |
| S | 0.36 | 0.39 | 0.79 | -0.36 | -0.54 |
| T | 0.28 | 0.06 | 0.38 | -0.27 | -0.66 |
| V | -0.44 | 0.11 | 0.32 | 0.81 | 1.17 |
| W | -1.31 | -1.08 | -2.27 | -0.34 | -0.86 |
| Y | -1.62 | 0.52 | -0.54 | 1.26 | 0.40 | worstScore: 1.69444132814779

Thus, in another embodiment, the invention refers to a nucleic acid encoding a polypeptide comprising a motif corresponding to position 126, 127, 128, 129, and 130 of SEQ ID: 27 with a matching score greater than 0, or 0.5, or 1.0, or 1.5, or 2.0, or 2.5, or 3.0, or 3.5, or 4, or 4.5, or 5; calculated as the sum of the amino acids corresponding to position 126, and the amino acid corresponding to position 127, and the amino acid corresponding to position 128, and the amino acid corresponding to position 129, and the amino acid corresponding to position 130. Preferably, the score is between 1.69 and 4.61

| L397: | | | | | |
|---|---|---|---|---|---|
| Amino acid | K395 | T396 | L397 | G398 | T399 |
| A | 0.49 | 0.44 | 0.16 | 1.03 | 0.36 |
| C | -1.47 | -1.01 | -1.46 | -1.78 | -0.06 |
| D | 0.14 | 0.28 | 0.48 | -0.16 | -1.07 |
| E | -0.53 | -0.02 | -0.55 | -0.43 | -0.38 |
| F | -1.10 | 0.52 | -0.08 | -1.16 | 0.07 |
| G | 0.39 | -0.76 | -0.47 | 1.92 | -0.44 |
| H | -0.30 | -1.70 | -1.06 | -0.92 | -0.95 |
| I | -1.36 | 0.96 | 0.46 | -1.66 | 0.35 |
| K | -0.24 | -0.76 | -0.06 | -0.69 | -1.64 |
| L | -0.96 | 0.62 | 1.42 | -0.82 | 0.38 |
| M | -1.58 | -0.88 | -0.51 | -1.66 | -0.38 |
| N | -0.34 | -0.66 | -0.03 | 0.26 | -0.47 |
| P | 1.29 | -0.43 | 0.14 | 0.27 | 0.07 |
| Q | -0.03 | -1.08 | -1.20 | -0.37 | 0.05 |
| R | 0.60 | -0.82 | -0.24 | -0.13 | -0.10 |
| S | 1.14 | -0.04 | -0.13 | 0.04 | 0.42 |
| T | 0.14 | 0.32 | 0.42 | -0.57 | 0.64 |
| V | -0.67 | 0.62 | -0.01 | -1.03 | 0.94 |
| W | -2.54 | 0.37 | -2.36 | -1.78 | -0.41 |
| Y | -1.47 | -0.66 | -0.55 | -0.98 | -0.80 | worstScore: 2.31021955717484

Thus, in another embodiment, the invention refers to a nucleic acid encoding a polypeptide comprising a motif corresponding to position 395, 396, 397, 398, and 399 of SEQ ID: 27 with a matching score greater than 0, or 0.5, or 1.0, or 1.5, or 2.0, or 2.5, or 3.0, or 4.5, or 5, or 5.5, or 6; calculated as the sum of the amino acids corresponding to position 395, and the amino acid corresponding to position 396, and the amino acid corresponding to position 397, and the amino acid corresponding to position 398, and the amino acid corresponding to position 399. Preferably, the score is between 2.31 and 5.56

| F420: | | | | | |
|---|---|---|---|---|---|
| Amino acid | T418 | T419 | F420 | V421 | G422 |
| A | 0.42 | 1.26 | -1.01 | 0.82 | 0.52 |
| C | -0.57 | 0.32 | -0.85 | -2.03 | -2.36 |
| D | -2.20 | -2.07 | -1.60 | -2.03 | -0.99 |
| E | -0.51 | -1.62 | -0.64 | -1.68 | -0.94 |
| F | -0.29 | -0.26 | 1.51 | 0.36 | -0.46 |
| G | -0.71 | 1.11 | -3.27 | -0.94 | 1.58 |
| H | -0.71 | -2.90 | 0.10 | -2.03 | -0.55 |
| I | -0.13 | 0.40 | -0.42 | 1.10 | -0.85 |
| K | -2.04 | -2.62 | -6.31 | -1.68 | -1.42 |
| L | 0.40 | 0.72 | 0.59 | 0.78 | -0.23 |
| M | 0.25 | -0.66 | 0.35 | 0.27 | -1.42 |
| N | -1.69 | -2.07 | -0.92 | -0.77 | -0.10 |
| P | -1.91 | -1.71 | -2.20 | -1.58 | 0.43 |
| Q | -0.67 | -2.62 | -0.32 | -1.34 | -0.99 |
| R | 0.29 | -2.62 | -2.38 | -2.18 | -0.77 |
| S | 0.57 | 0.25 | 0.25 | 0.12 | 0.92 |
| T | 1.39 | -0.15 | -0.04 | 0.65 | 0.47 |
| V | 1.15 | 1.30 | -0.12 | 1.26 | -0.07 |
| W | -2.04 | -2.07 | 0.38 | -2.86 | -0.73 |
| Y | -0.86 | -0.98 | 1.20 | -0.43 | -0.12 | worstScore: 3.68475507992571

Thus, in another embodiment, the invention refers to a nucleic acid encoding a polypeptide comprising a motif corresponding to position 418, 419, 420, 421, 422, and 423 of SEQ ID: 27 with a matching score greater than 0, or 0.5, or 1.0, or 1.5, or 2.0, or 2.5, or 3.0, or 4.5, or 5, or 5.5, or 6; or 6.5, or 7; calculated as the sum of the amino acids corresponding to position 418, and the amino acid corresponding to position 419, and the amino acid corresponding to position 420, and the amino acid corresponding to position 421, and the amino acid corresponding to position 422. Preferably, the score is between 3.68 and 6.73

Table 2b shows an overview of preferred mutation sites that are shared between homologues, orthologues and paralogues listed in Table 1.

deletion, insertion or substitution of nucleotides from the sequences shown, preferably from SEQ ID NO: 1 or 3, or a homolog thereof, or from the derived nucleic acid sequences, the intention being, however, that the enzyme activity or the biological activity of the resulting proteins synthesized is advantageously retained or increased.

In one embodiment of the present invention, the nucleic acid molecule of the invention or used in the process of the invention comprises the sequences shown in any of the SEQ ID NO: 1 or 3, or a homolog thereof. It is preferred that the nucleic acid molecule comprises as little as possible other nucleotides not shown in any one of SEQ ID NO: 1 or 3, or TABLE 2b

| SEQ | Pos 1 | Pos 2 | Pos 3 | Pos 4 | Pos 5 | Pos 6 | Pos 7 | Pos 8 | Pos 9 | Pos 10 | Pos 11 | Pos 12 | Pos 13 | Pos 14 | Pos 15 |
|---|---|---|---|---|---|---|---|---|---|---|---|---|---|---|---|
| 2 | H135 | K136 | R137 | Y138 | T139 | V140 | S158 | L160 | T163 | P173 | K178 | E194 | S195 | E201 | V208 |
| 4 | A136 | P137 | R138 | F139 | V140 | L141 | F159 | L161 | I164 | A174 | P179 | E186 | S187 | R193 | V200 |
| 27 | N126 | K127 | R128 | Y129 | I130 | A131 | S149 | I151 | A154 | P164 | K169 | E182 | S183 | E189 | F196 |
| 28 | N126 | K127 | R128 | Y129 | I130 | A131 | S149 | I151 | A154 | P164 | K169 | E182 | S183 | E189 | F196 |
| 29 | N126 | K127 | R128 | Y129 | I130 | A131 | S149 | I151 | A154 | P164 | K169 | E182 | S183 | E189 | F196 |
| 30 | N126 | K127 | R128 | Y129 | I130 | A131 | S149 | I151 | A154 | P164 | K169 | E182 | S183 | E189 | F196 |
| 31 | A155 | P156 | R157 | F158 | V159 | L160 | F178 | L180 | F183 | A193 | P198 | E205 | S206 | R212 | V219 |

| SEQ | Pos 16 | Pos 17 | Pos 18 | Pos 19 | Pos 20 | Pos 21 | Pos 22 | Pos 23 | Pos 24 | Pos 25 | Pos 26 | Pos 27 | Pos 28 | Pos 29 | Pos 30 |
|---|---|---|---|---|---|---|---|---|---|---|---|---|---|---|---|
| 2 | D214 | S221 | A222 | G223 | L228 | I230 | R231 | H232 | N239 | S246 | A258 | G271 | R272 | N273 | L307 |
| 4 | E206 | Y213 | A214 | G215 | L220 | M222 | R223 | A224 | R231 | S238 | K250 | A264 | P265 | K266 | T299 |
| 27 | D202 | C209 | G210 | G211 | L216 | M218 | H219 | H220 | N227 | S234 | S246 | K259 | P260 | R261 | L295 |
| 28 | D202 | C209 | G210 | G211 | L216 | M218 | H219 | H220 | N227 | S234 | S246 | K259 | P260 | R261 | L295 |
| 29 | D202 | C209 | G210 | — | L215 | M217 | Y218 | H219 | N226 | S233 | S245 | K258 | P259 | R260 | L294 |
| 30 | D202 | C209 | G210 | — | L215 | M217 | H218 | H219 | N226 | S233 | S245 | K258 | P259 | R260 | L294 |
| 31 | E225 | Y232 | A233 | G234 | L239 | M241 | K242 | A243 | T250 | S257 | R269 | K283 | P284 | K285 | S318 |

| SEQ | Pos 31 | Pos 32 | Pos 33 | Pos 34 | Pos 35 | Pos 36 | Pos 37 | Pos 38 | Pos 39 | Pos 40 | Pos 41 | Pos 42 | Pos 43 | Pos 44 | Pos 45 |
|---|---|---|---|---|---|---|---|---|---|---|---|---|---|---|---|
| 2 | S308 | C313 | D320 | S341 | S352 | G363 | F366 | L368 | D369 | D375 | L401 | L415 | F435 | T436 | T437 |
| 4 | S300 | E305 | Q307 | S321 | P332 | L343 | D346 | A348 | D349 | Y355 | L381 | L397 | L417 | L418 | N419 |
| 27 | S296 | Q301 | G308 | S324 | R335 | G346 | F349 | L351 | D352 | T358 | L384 | L397 | F417 | T418 | T419 |
| 28 | S296 | Q301 | G308 | S324 | R335 | G346 | F349 | L351 | D352 | T358 | L384 | L397 | F417 | T418 | T419 |
| 29 | S295 | Q300 | G307 | S323 | R334 | G345 | F348 | L350 | D351 | T357 | L383 | L396 | F416 | T417 | T418 |
| 30 | S295 | Q300 | G307 | S323 | R334 | G345 | F348 | L350 | D351 | T357 | L383 | L396 | F416 | T417 | T418 |
| 31 | N319 | L324 | G326 | S340 | P351 | L362 | V365 | A367 | D368 | Y374 | L400 | L416 | I436 | L437 | S438 |

| SEQ | Pos 46 | Pos 47 | Pos 48 | Pos 49 | Pos 50 | Pos 51 | Pos 52 | Pos 53 | Pos 54 | Pos 55 | Pos 56 | Pos 57 | Pos 58 | Pos 59 | Pos 60 |
|---|---|---|---|---|---|---|---|---|---|---|---|---|---|---|---|
| 2 | F438 | A450 | T452 | K456 | L467 | V469 | H480 | Y488 | S494 | A495 | G500 | Y511 | K516 | D533 | K544 |
| 4 | Y420 | K432 | E434 | V438 | L449 | R453 | V464 | F472 | D478 | R479 | K484 | L497 | V502 | S519 | — |
| 27 | F420 | A432 | T434 | K438 | L449 | T451 | F462 | Y470 | S476 | V477 | D482 | Y493 | K498 | E515 | K528 |
| 28 | F420 | A432 | T434 | K438 | L449 | T451 | F462 | Y470 | S476 | V477 | D482 | Y493 | K498 | E515 | K528 |
| 29 | F419 | A431 | T433 | K437 | L448 | T450 | F461 | Y469 | S475 | V476 | D481 | Y492 | K497 | E514 | K527 |
| 30 | F419 | A431 | T433 | K437 | L448 | T450 | F461 | Y469 | C475 | V476 | D481 | Y492 | K497 | E514 | K527 |
| 31 | Y439 | K451 | E453 | A457 | L468 | N472 | V483 | F491 | D497 | V498 | K503 | L516 | V521 | S538 | — |

Following mutagenesis of one of the sequences as shown herein, the encoded protein can be expressed recombinantly and the activity of the protein can be determined using, for example, assays described herein.

The highest homology of the nucleic acid molecule used in the process according to the invention was found for the following database entries by Gap search.

Homologues of the nucleic acid sequences used, with the sequence shown in SEQ ID NO: 1 or 3, or a homolog thereof, comprise also allelic variants with at least approximately 30%, 35%, 40% or 45% homology, by preference at least approximately 50%, 60% or 70%, more preferably at least approximately 90%, 91%, 92%, 93%, 94% or 95% and even more preferably at least approximately 96%, 97%, 98%, 99% or more homology with one of the nucleotide sequences shown or the abovementioned derived nucleic acid sequences or their homologues, derivatives or analogues or parts of these. Allelic variants encompass in particular functional variants which can be obtained by a homolog thereof. In one embodiment, the nucleic acid molecule comprises less than 500, 400, 300, 200, 100, 90, 80, 70, 60, 50 or 40 further nucleotides. In a further embodiment, the nucleic acid molecule comprises less than 30, 20 or 10 further nucleotides. In one embodiment, the nucleic acid molecule use in the process of the invention is identical to the sequences shown in SEQ ID NO: 1 or 3, or a homolog thereof.

Also preferred is that the nucleic acid molecule used in the process of the invention encodes a polypeptide comprising the sequence shown in SEQ ID NO: 2 or 4, or a homolog thereof. In one embodiment, the nucleic acid molecule encodes less than 150, 130, 100, 80, 60, 50, 40 or 30 further amino acids. In a further embodiment, the encoded polypeptide comprises less than 20, 15, 10, 9, 8, 7, 6 or 5 further amino acids. In one embodiment used in the inventive process, the encoded polypeptide is identical to the sequences shown in SEQ ID NO: 2 or 4, or a homolog thereof.

In one embodiment, the nucleic acid molecule of the invention or used in the process encodes a polypeptide comprising the sequence shown in SEQ ID NO: 2 or 4, or a homolog thereof comprises less than 100 further nucleotides. In a further embodiment, said nucleic acid molecule comprises less than 30 further nucleotides. In one embodiment, the nucleic acid molecule used in the process is identical to a coding sequence of the sequences shown in SEQ ID NO: 1 or 3, or a homolog thereof.

Polypeptides (=proteins), which still have the essential biological or enzymatic activity of the polypeptide of the present invention conferring increased herbicide tolerance or resistance, as compared to a corresponding, e.g. non-transformed, wild type plant cell, plant or part thereof i.e. whose activity is essentially not reduced, are polypeptides with at least 10% or 20%, by preference 30% or 40%, especially preferably 50% or 60%, very especially preferably 80% or 90 or more of the wild type biological activity or enzyme activity, advantageously, the activity is essentially not reduced in comparison with the activity of a polypeptide shown in SEQ ID NO: 2 or 4, or a homolog thereof expressed under identical conditions.

Homologues of SEQ ID NO: 1 or 3, or of the derived sequences of SEQ ID NO: 2 or 4, or a homolog thereof also mean truncated sequences, cDNA, single-stranded DNA or RNA of the coding and noncoding DNA sequence. Homologues of said sequences are also understood as meaning derivatives, which comprise noncoding regions such as, for example, UTRs, terminators, enhancers or promoter variants. The promoters upstream of the nucleotide sequences stated can be modified by one or more nucleotide substitution(s), insertion(s) and/or deletion(s) without, however, interfering with the functionality or activity either of the promoters, the open reading frame (=ORF) or with the 3'-regulatory region such as terminators or other 3'-regulatory regions, which are far away from the ORF. It is furthermore possible that the activity of the promoters is increased by modification of their sequence, or that they are replaced completely by more active promoters, even promoters from heterologous organisms. Appropriate promoters are known to the person skilled in the art and are mentioned herein below.

Further, an embodiment of the invention is an expression vector comprising a nucleic acid molecule comprising a nucleic acid molecule selected from the group consisting of:
(a) a nucleic acid molecule encoding the polypeptide comprising the sequence of SEQ ID NO: 2 or 4, or a homolog thereof;
(b) a nucleic acid molecule comprising the sequence of SEQ ID NO: 1 or 3, or a homolog thereof,
(c) a nucleic acid molecule, which, as a result of the degeneracy of the genetic code, can be derived from a polypeptide sequence of SEQ ID NO: 2 or 4, or a homolog thereof, and confers increased herbicide tolerance or resistance, as compared to a corresponding, e.g. non-transformed, wild type plant cell, a plant or a part thereof;
(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of SEQ ID NO: 1 or 3, or a homolog thereof, and confers increased herbicide tolerance or resistance, as compared to a corresponding, e.g. non-transformed, wild type plant cell, a plant or a part thereof;
(e) a nucleic acid molecule encoding a polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the polypeptide encoded by the nucleic acid molecule of (a), (b), (c) or (d) and having the activity represented by a nucleic acid molecule comprising a polynucleotide of SEQ ID NO: 1 or 3, or a homolog thereof, and confers increased herbicide tolerance or resistance as compared to a corresponding, e.g. non-transformed, wild type plant cell, a plant or a part thereof;
(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;
(g) a nucleic acid molecule encoding a polypeptide which can be isolated with the aid of monoclonal or polyclonal antibodies made against a polypeptide encoded by one of the nucleic acid molecules of (a), (b), (c), (d), (e) or (f) and having the activity represented by the nucleic acid molecule comprising a polynucleotide as depicted in SEQ ID NO: 1 or 3, or a homolog thereof;
(h) a nucleic acid molecule which is obtainable by screening a suitable nucleic acid library, especially a cDNA library and/or a genomic library, under stringent hybridization conditions with a probe comprising a complementary sequence of a nucleic acid molecule of (a) or (b) or with a fragment thereof, having 15 nt, preferably 20 nt, 30 nt, 50 nt, 100 nt, 200 nt, 500 nt, 750 nt or 1000 nt or more of a nucleic acid molecule complementary to a nucleic acid molecule sequence characterized in (a) to (e) and encoding a polypeptide having the activity represented by a protein comprising a polypeptide as depicted SEQ ID NO: 2 or 4, or a homolog thereof.

The invention further provides an isolated recombinant expression vector comprising the nucleic acid molecule of the invention, wherein expression of the vector or nucleic acid molecule, respectively in a host cell results in an increased herbicide tolerance or resistance, as compared to the corresponding, e.g. non-transformed, wild type of the host cell.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* T-DNA such as the gene 3 known as octopine synthase of the Ti-plasmid pTiACH5 (Gielen et al., EMBO J. 3, 835 1(984)) or functional equivalents thereof but also all other terminators functionally active in plants are suitable. As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., Nucl. Acids Research 15, 8693 (1987)).

Plant gene expression has to be operably linked to an appropriate promoter conferring gene expression in a timely, cell or tissue specific manner. Preferred are promoters driving constitutive expression (Benfey et al., EMBO J. 8, 2195 (1989)) like those derived from plant viruses like the 35S CaMV (Franck et al., Cell 21, 285 (1980)), the 19S CaMV (see also U.S. Pat. No. 5,352,605 and PCT Application No. WO 84/02913) or plant promoters like those from Rubisco small subunit described in U.S. Pat. No. 4,962,028. Other promoters, e.g. super-promoter (Ni et al., Plant Journal 7, 661 (1995)), Ubiquitin promoter (Callis et al., J. Biol. Chem., 265, 12486 (1990); U.S. Pat. Nos. 5,510,474; 6,020,190; Kawalleck et al., Plant. Molecular Biology, 21, 673 (1993)) or 34S promoter (GenBank Accession numbers M59930 and X16673) were similar useful for the present invention and are known to a person skilled in the art. Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., BioEssays 10, 108 (1989). Examples of seed preferred promoters include, but are not limited to, cellulose synthase (celA), Cim1, gamma-zein, globulin-1, maize 19 kD zein (cZ19B1), and the like.

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional advantageous regulatory sequences are, for example, included in the plant promoters such as CaMV/35S (Franck et al., Cell 21 285 (1980)), PRP1 (Ward et al., Plant. Mol. Biol. 22, 361 (1993)), SSU, OCS, lib4, usp, STLS1, B33, LEB4, nos, ubiquitin, napin or phaseolin promoter. Also advantageous in this connection are inducible promoters such as the promoters described in EP 388 186 (benzyl sulfonamide inducible), Gatz et al., Plant J. 2, 397 (1992) (tetracyclin inducible), EP-A-0 335 528 (abscisic acid inducible) or WO 93/21334 (ethanol or cyclohexenol inducible). Additional useful plant promoters are the cytoplasmic FBPase promoter or ST-LSI promoter of potato (Stockhaus et al., EMBO J. 8, 2445 (1989)), the phosphorybosyl phyrophoshate amido transferase promoter of *Glycine max* (gene bank accession No. U87999) or the noden specific promoter described in EP-A-0 249 676. Additional particularly advantageous promoters are seed specific promoters which can be used for monocotyledones or dicotyledones and are described in U.S. Pat. No. 5,608,152 (napin promoter from rapeseed), WO 98/45461 (phaseolin promoter from *Arabidopsis*), U.S. Pat. No. 5,504,200 (phaseolin promoter from *Phaseolus vulgaris*), WO 91/13980 (Bce4 promoter from *Brassica*) and Baeumlein et al., Plant J., 2 (2), 233 (1992) (LEB4 promoter from leguminosa). Said promoters are useful in dicotyledones. The following promoters are useful for example in monocotyledones Ipt-2- or Ipt-1-promoter from barley (WO 95/15389 and WO 95/23230) or hordein promoter from barley. Other useful promoters are described in WO 99/16890. It is possible in principle to use all natural promoters with their regulatory sequences like those mentioned above for the novel process. It is also possible and advantageous in addition to use synthetic promoters.

The gene construct may also comprise further genes which are to be inserted into the organisms and which are for example involved in herbicide tolerance or resistance increase. It is possible and advantageous to insert and express in host organisms regulatory genes such as genes for inducers, repressors or enzymes which intervene by their enzymatic activity in the regulation, or one or more or all genes of a biosynthetic pathway. These genes can be heterologous or homologous in origin. The inserted genes may have their own promoter or else be under the control of same promoter as the sequences of the nucleic acid of SEQ ID NO: 1 or 3, or their homologs.

The gene construct advantageously comprises, for expression of the other genes present, additionally 3' and/or 5' terminal regulatory sequences to enhance expression, which are selected for optimal expression depending on the selected host organism and gene or genes.

These regulatory sequences are intended to make specific expression of the genes and protein expression possible as mentioned above. This may mean, depending on the host organism, for example that the gene is expressed or over-expressed only after induction, or that it is immediately expressed and/or over-expressed.

The regulatory sequences or factors may moreover preferably have a beneficial effect on expression of the introduced genes, and thus increase it. It is possible in this way for the regulatory elements to be enhanced advantageously at the transcription level by using strong transcription signals such as promoters and/or enhancers. However, in addition, it is also possible to enhance translation by, for example, improving the stability of the mRNA.

Other preferred sequences for use in plant gene expression cassettes are targeting-sequences necessary to direct the gene product in its appropriate cell compartment (for review see Kermode, Crit. Rev. Plant Sci. 15 (4), 285 (1996) and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, Annu. Rev. Plant Physiol. Plant Mol. Biol. 48, 89 (1997)). Chemically inducible promoters are especially suitable if gene expression is wanted to occur in a time specific manner.

Table xx lists several examples of promoters that may be used to regulate transcription of the nucleic acid coding sequences of the present invention.

TABLE xx

Examples of tissue-specific and inducible promoters in plants

| Expression | Reference |
|---|---|
| Cor78 - Cold, drought, salt, ABA, wounding-inducible | Ishitani, et al., Plant Cell 9, 1935 (1997), Yamaguchi-Shinozaki and Shinozaki, Plant Cell 6, 251 (1994) |
| Rci2A - Cold, dehydration-inducible | Capel et al., Plant Physiol 115, 569 (1997) |
| Rd22 - Drought, salt | Yamaguchi-Shinozaki and Shinozaki, Mol. Gen. Genet. 238, 17 (1993) |
| Cor15A - Cold, dehydration, ABA | Baker et al., Plant Mol. Biol. 24, 701 (1994) |
| GH3- Auxin inducible | Liu et al., Plant Cell 6, 645 (1994) |
| ARSK1-Root, salt inducible | Hwang and Goodman, Plant J. 8, 37 (1995) |
| PtxA - Root, salt inducible | GenBank accession X67427 |
| SbHRGP3 - Root specific | Ahn et al., Plant Cell 8, 1477 (1998). |
| KST1 - Guard cell specific | Plesch et al., Plant Journal. 28(4), 455- (2001) |
| KAT1 - Guard cell specific | Plesch et al., Gene 249, 83 (2000), Nakamura et al., Plant Physiol. 109, 371 (1995) |
| salicylic acid inducible | PCT Application No. WO 95/19443 |
| tetracycline inducible | Gatz et al., Plant J. 2, 397 (1992) |
| Ethanol inducible | PCT Application No. WO 93/21334 |
| Pathogen inducible PRP1 | Ward et al., Plant. Mol. Biol. 22, 361 -(1993) |
| Heat inducible hsp80 | U.S. Pat. No. 5,187,267 |
| Cold inducible alpha-amylase | PCT Application No. WO 96/12814 |
| Wound-inducible pinII | European Patent No. 375 091 |
| RD29A - salt-inducible | Yamaguchi-Shinozalei et al. Mol. Gen. Genet. 236, 331 (1993) |
| Plastid-specific viral RNA-polymerase | PCT Application No. WO 95/16783, PCT Application WO 97/06250 |

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, Cell 43, 729 (1985)).

In one embodiment, the language "substantially free of cellular material" includes preparations of a protein having less than about 30% (by dry weight) of contaminating material (also referred to herein as a "contaminating polypeptide"), more preferably less than about 20% of contaminating material, still more preferably less than about 10% of contaminating material, and most preferably less than about 5% contaminating material.

The nucleic acid molecules, polypeptides, polypeptide homologs, fusion polypeptides, primers, vectors, and host cells described herein can be used in one or more of the following methods: identification of S. cerevisiae, E. coli or Brassica napus, Glycine max, Zea mays or Oryza sativa and related organisms; mapping of genomes of organisms related to S. cerevisiae, E. coli; identification and localization of S. cerevisiae, E. coli or Brassica napus, Glycine max, Zea mays or Oryza sativa sequences of interest; evolutionary studies; determination of polypeptide regions required for function; modulation of a polypeptide activity; modulation of the metabolism of one or more cell functions; modulation of the transmembrane transport of one or more compounds; modulation of herbicide tolerance or resistance, and modulation of expression of polypeptide nucleic acids.

The nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

There are a number of mechanisms by which the alteration of the polypeptide of the invention may directly affect herbicide tolerance or resistance.

The effect of the genetic modification in plants regarding herbicide tolerance or resistance can be assessed by treating the modified plant with respective herbicides as, e.g., described in the EXAMPLES, and then analyzing the growth characteristics and/or metabolism of the plant in comparison to non-modified plants. Such analysis techniques are well known to one skilled in the art, and include evaluation of the plant phenotype, dry weight, fresh weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, Vol. 17; Rehm et al., 1993 Biotechnology, Vol. 3, Chapter III: Product recovery and purification, page 469-714, VCH: Weinheim; Belter P. A. et al., 1988, Bioseparations: downstream processing for biotechnology, John Wiley and Sons; Kennedy J. F., and Cabral J. M. S., 1992, Recovery processes for biological materials, John Wiley and Sons; Shaeiwitz J. A. and Henry J. D., 1988, Biochemical separations, in Ulmann's Encyclopedia of Industrial Chemistry, Vol. B3, Chapter 11, page 1-27, VCH: Weinheim; and Dechow F. J., 1989, Separation and purification techniques in biotechnology, Noyes Publications).

For example, plant expression vectors comprising the nucleic acids disclosed herein, or fragments thereof, can be constructed and transformed into an appropriate plant cell such as rape, maize, cotton, rice, wheat, sugar cane, sugar beet, soy bean, *Arabidopsis thaliana*, potato, *Medicago truncatula*, etc., using standard protocols. The resulting transgenic cells and/or plants derived therefrom can then be assayed for generation or alteration of their herbicide tolerance or resistance.

The present invention also provides antibodies that specifically bind to the polypeptide according to the invention, or a portion thereof, as encoded by a nucleic acid described herein. Antibodies can be made by many well-known methods (see, e.g. Harlow and Lane, "Antibodies; A Laboratory Manual", Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. See, for example, Kelly et al., Bio/Technology 10, 163 (1992); Bebbington et al., Bio/Technology 10, 169 (1992).

Gene expression in plants is regulated by the interaction of protein transcription factors with specific nucleotide sequences within the regulatory region of a gene. One example of transcription factors are polypeptides that contain zinc finger (ZF) motifs. Each ZF module is approximately 30 amino acids long folded around a zinc ion. The DNA recognition domain of a ZF protein is a α-helical structure that inserts into the major grove of the DNA double helix. The module contains three amino acids that bind to the DNA with each amino acid contacting a single base pair in the target DNA sequence. ZF motifs are arranged in a modular repeating fashion to form a set of fingers that recognize a contiguous DNA sequence. For example, a three-fingered ZF motif will recognize 9 bp of DNA. Hundreds of proteins have been shown to contain ZF motifs with between 2 and 37 ZF modules in each protein (Isalan M. et al., Biochemistry 37 (35), 12026 (1998); Moore M. et al., Proc. Natl. Acad. Sci. USA 98 (4), 1432 (2001) and Moore M. et al., Proc. Natl. Acad. Sci. USA 98 (4), 1437 (2001); U.S. Pat. Nos. 6,007,988 and 6,013,453).

The regulatory region of a plant gene contains many short DNA sequences (cis-acting elements) that serve as recognition domains for transcription factors, including ZF proteins. Similar recognition domains in different genes allow the coordinate expression of several genes encoding enzymes in a metabolic pathway by common transcription factors. Variation in the recognition domains among members of a gene family facilitates differences in gene expression within the same gene family, for example, among tissues and stages of development and in response to environmental conditions.

Typical ZF proteins contain not only a DNA recognition domain but also a functional domain that enables the ZF protein to activate or repress transcription of a specific gene. Experimentally, an activation domain has been used to activate transcription of the target gene (U.S. Pat. No. 5,789,538 and patent application WO 95/19431), but it is also possible to link a transcription repressor domain to the ZF and thereby inhibit transcription (patent applications WO 00/47754 and WO 01/002019). It has been reported that an enzymatic function such as nucleic acid cleavage can be linked to the ZF (patent application WO 00/20622).

The invention provides a method that allows one skilled in the art to isolate the regulatory region of one or more polypeptide according to the invention-encoding genes from the genome of a plant cell and to design zinc finger transcription factors linked to a functional domain that will interact with the regulatory region of the gene. The interaction of the zinc finger protein with the plant gene can be designed in such a manner as to alter expression of the gene and preferably thereby to confer increasing herbicide tolerance or resistance.

In particular, the invention provides a method of producing a transgenic plant with a coding nucleic acid, wherein expression of the nucleic acid(s) in the plant results in increasing herbicide tolerance or resistance, as compared to a wild type plant comprising: (a) transforming a plant cell with an expression vector comprising a encoding nucleic acid, and (b) generating from the plant cell a transgenic plant with enhanced increased herbicide tolerance or resistance as compared to a wild type plant. For such plant transformation, binary vectors such as pBinAR can be used (Hofgen and Willmitzer, Plant Science 66, 221 (1990)). Moreover suitable binary vectors are for example pBIN19, pBI101, pGPTV or pPZP (Hajukiewicz P. et al., Plant Mol. Biol., 25, 989 (1994)).

Alternate methods of transfection include the direct transfer of DNA into developing flowers via electroporation or *Agrobacterium* mediated gene transfer. *Agrobacterium* mediated plant transformation can be performed using for example the GV3101 (pM P90) (Koncz and Schell, Mol. Gen. Genet. 204, 383 (1986)) or LBA4404 (Ooms et al., Plasmid, 7, 15 (1982); Hoekema et al., Nature, 303, 179 (1983)) *Agrobacterium tumefaciens* strain. Transformation can be performed by standard transformation and regeneration techniques (Deblaere et al., Nucl. Acids. Res. 13, 4777 (1994); Gelvin and Schilperoort, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick B. R. and Thompson J. E., Methods in Plant Molecular Biology and Biotechnology, Boca Raton: CRC Press, 1993.-360 S., ISBN 0-8493-5164-2). For example, rapeseed can be transformed via cotyledon or hypocotyl transformation (Moloney et al., Plant Cell Reports 8, 238 (1989); De Block et al., Plant Physiol. 91, 694 (1989)). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., Plant Cell Report 13, 282 (1994)). Additionally, transformation of soybean can be performed using for example a technique described in European Patent No. 424 047, U.S. Pat. No. 5,322,783, European Patent No. 397 687, U.S. Pat. No. 5,376,543 or 5,169,770. Transformation of maize can be achieved by particle bombardment, polyethylene glycol mediated DNA uptake or via the silicon carbide fiber technique (see, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

In one embodiment, the present invention relates to a method for the identification of a gene product conferring in increasing herbicide tolerance or resistance, as compared to a corresponding, e.g. non-transformed, wild type cell in a cell of an organism for example plant, comprising the following steps:
(a) contacting, e.g. hybridizing, some or all nucleic acid molecules of a sample, e.g. cells, tissues, plants or microorganisms or a nucleic acid library, which can contain a candidate gene encoding a gene product conferring increased herbicide tolerance or resistance with a nucleic acid molecule as shown in SEQ ID NO: 1 or 3, or a functional homologue thereof;
(b) identifying the nucleic acid molecules, which hybridize under relaxed or stringent conditions with said nucleic acid molecule, in particular to the nucleic acid molecule sequence shown in SEQ ID NO: 1 or 3, or a homolog thereof, and, optionally, isolating the full length cDNA clone or complete genomic clone;
(c) identifying the candidate nucleic acid molecules or a fragment thereof in host cells, preferably in a plant cell;
(d) increasing the expression of the identified nucleic acid molecules in the host cells for which increased herbicide tolerance or resistance are desired;
(e) assaying the level of increased herbicide tolerance or resistance of the host cells; and
(f) identifying the nucleic acid molecule and its gene product which confers increased herbicide tolerance or resistance, in the host cell compared to the wild type.

Relaxed hybridization conditions are: After standard hybridization procedures washing steps can be performed at low to medium stringency conditions usually with washing conditions of 40°–55° C. and salt conditions between 2×SSC and 0.2×SSC with 0.1% SDS in comparison to stringent washing conditions as e.g. 60° to 68° C. with 0.1% SDS. Further examples can be found in the references listed above for the string end hybridization conditions. Usually washing steps are repeated with increasing stringency and length until a useful signal to noise ratio is detected and depend on many factors as the target, e.g. its purity, GC-content, size etc, the probe, e.g. its length, is it a RNA or a DNA probe, salt conditions, washing or hybridization temperature, washing or hybridization time etc.

In another embodiment, the present invention relates to a method for the identification of a gene product the expression of which confers increased herbicide tolerance or resistance, in a cell, comprising the following steps:
(a) identifying a nucleic acid molecule in an organism, which is at least 20%, preferably 25%, more preferably 30%, even more preferred are 35%. 40% or 50%, even more preferred are 60%, 70% or 80%, most preferred are 90% or 95% or more homolog to the nucleic acid molecule encoding a protein comprising the polypeptide molecule as shown in SEQ ID NO: 2 or 4, or a homolog therefor being encoded by a nucleic acid molecule comprising a polynucleotide as shown in SEQ ID NO: 1 or 3, or a homologue thereof as described herein, for example via homology search in a data bank;
(b) enhancing the expression of the identified nucleic acid molecules in the host cells;
(c) assaying the level of enhancement in increasing herbicide tolerance or resistance, in the host cells; and
(d) identifying the host cell, in which the enhanced expression confers the increasing herbicide tolerance or resistance in the host cell compared to a wild type.

Further, the nucleic acid molecule disclosed herein, in particular the nucleic acid molecule shown in SEQ ID NO: 1 or 3, may be sufficiently homologous to the sequences of related species such that these nucleic acid molecules may serve as markers for the construction of a genomic map in related organism or for association mapping. Furthermore natural variation in the genomic regions corresponding to nucleic acids disclosed herein, in particular the nucleic acid molecule shown in SEQ ID NO: 1 or 3, or homologous thereof may lead to variation in the activity of the proteins disclosed herein, in particular the proteins comprising polypeptides as shown in SEQ ID NO: 2 or 4, and their homolgous and in consequence in a natural variation of an increased herbicide tolerance or resistance.

In consequence natural variation eventually also exists in form of more active allelic variants leading already to a relative increase in herbicide tolerance or resistance. Different variants of the nucleic acids molecule disclosed herein, in particular the nucleic acid comprising the nucleic acid molecule as shown SEQ ID NO: 1 or 3, or a homolog thereof, which corresponds to different levels of increased herbicide tolerance or resistance can be identified and used for marker assisted breeding for an increased herbicide tolerance or resistance, Accordingly, the present invention relates to a method for breeding plants with an increased herbicide tolerance or resistance comprising
(a) selecting a first plant variety with an increased herbicide tolerance or resistance, based on increased expression of a nucleic acid of the invention as disclosed herein, in particular of a nucleic acid molecule comprising a nucleic acid molecule as shown in SEQ ID NO: 1 or 3, or a homolog thereof, or a polypeptide comprising a polypeptide as shown in SEQ ID NO: 2 or 4, or a homolog thereof, or a homologue thereof as described herein;
(b) associating the level of increased herbicide tolerance or resistance with the expression level or the genomic structure of a gene encoding said polypeptide or said nucleic acid molecule;
(c) crossing the first plant variety with a second plant variety, which significantly differs in its level of increased herbicide tolerance or resistance; and
(d) identifying, which of the offspring varieties has got increased levels of herbicide tolerance or resistance, As described SUPRA, the present invention provides plants, plant tissues, plant cells, and host cells that are resistant or tolerant of at least one PPO-inhibiting herbicide. In some embodiments, the plants, plant tissues, plant cells, and host cells demonstrate enhanced resistance or enhanced tolerance to at least one PPO-inhibiting herbicide. The term 'enhanced' refers to an increase in the amount of resistance or tolerance above that which is expected. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, microspore, or host cell, but that said amount does not kill or inhibit as severely the growth of the herbicide-resistant plants, plant tissues, plant cells, microspores, and host cells of the present invention. Typically, the effective amount of an herbicide is an amount that is routinely used in agricultural production systems to kill weeds of interest. Such an amount is known to those of ordinary skill in the art, or can be easily determined using methods known in the art. Furthermore, it is recognized that the effective amount of an herbicide in an agricultural production system might be substantially different than an effective amount of an herbicide for a plant culture system such as, for example, the microspore culture system.

The PPO enzymes of the present invention and PPO-inhibiting herbicide resistant plants of the invention find use in methods for controlling weeds.

Thus, the present invention further provides a method for controlling undesired vegetation at a plant cultivation site in the vicinity of an herbicide-resistant plant, such as a plant comprising a PPO nucleic acid molecule of the invention, i.e. a nucleotide sequence encoding a polypeptide comprising the sequence of SEQ ID NO: 2 or 4, or a homolog thereof. The method comprises applying an effective amount of a PPO-inhibiting herbicide to the weeds and to the herbicide-resistant plant, wherein the plant has resistance to at least one PPO-inhibiting herbicide, when compared to a wild-type plant.

Furthermore, the present invention provides method for growing the plant according to the present invention while controlling weeds in the vicinity of said plant, said method comprising the steps of:

c) growing said plant; and
applying a herbicide composition comprising a PPO-inhibiting herbicide to the plant and weeds, wherein the herbicide normally inhibits protoporphyrinogen oxidase, at a level of the herbicide that would inhibit the growth of a corresponding wild-type plant.

In another embodiment, the invention relates to a combination useful for weed control, comprising (a) a polynucleotide encoding a wildtype or mutated PPO polypeptide according to the present invention, which polynucleotide is capable of being expressed in a plant to thereby provide to that plant tolerance to a PPO inhibiting herbicide; and (b) a PPO inhibiting herbicide.

In another embodiment, the invention relates to a process for preparing a combination useful for weed control comprising (a) providing a polynucleotide encoding a wildtype or mutated PPO polypeptide according to the present invention, which polynucleotide is capable of being expressed in a plant to thereby provide to that plant tolerance to a PPO inhibiting herbicide; and (b) providing a PPO inhibiting herbicide.

In a preferred embodiment, said step of providing a polynucleotide comprises providing a plant containing the polynucleotide.

In another preferred embodiment, said step of providing a polynucleotide comprises providing a seed containing the polynucleotide.

In another preferred embodiment, said process further comprises a step of applying the PPO inhibiting herbicide to the seed.

In another embodiment, the invention relates to the use of a combination useful for weed control, comprising (a) a polynucleotide encoding a wildtype or mutated PPO polypeptide according to the present invention, which polynucleotide is capable of being expressed in a plant to thereby provide to that plant tolerance to a PPO inhibiting herbicide; and (b) a PPO inhibiting herbicide, to control weeds at a plant cultivation site.

The term "control of undesired vegetation" is to be understood as meaning the controlling, particularly killing of weeds and/or otherwise retarding or inhibiting the normal growth of the weeds. Weeds, in the broadest sense, are understood as meaning all those plants which grow in locations where they are undesired, e.g. at a plant cultivation site. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide post emergence to relatively immature undesirable vegetation to achieve the maximum control of weeds.

The herbicides useful for the present invention are those that interfere with the activity of the PPO enzyme such that PPO activity is reduced in the presence of the herbicide. Such herbicides may also be referred to herein as "PPO-inhibiting herbicides" or simply "PPO inhibitors." As used herein, an "PPO-inhibiting herbicide" or an "PPO inhibitor" is not meant to be limited to single herbicide that interferes with the activity of the PPO enzyme. Thus, unless otherwise stated or evident from the context, an "PPO-inhibiting herbicide" or an "PPO inhibitor" can be a one herbicide or a mixture of two, three, four, or more herbicides, each of which interferes with the activity of the PPO enzyme. The PPO-inhibiting herbicide for use in the methods provided herein can be applied by any method known in the art including, but not limited to, seed treatment, soil treatment, and foliar treatment.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant wildtype or mutated PPO protein" or "herbicide-resistant wildtype or mutated PPO protein", it is intended that such a PPO protein displays higher PPO activity, relative to the PPO activity of a wild-type PPO protein, when in the presence of at least one herbicide that is known to interfere with PPO activity and at a concentration or level of the herbicide that is known to inhibit the PPO activity of the wild-type mutated PPO protein. Furthermore, the PPO activity of such a herbicide-tolerant or herbicide-resistant mutated PPO protein may be referred to herein as "herbicide-tolerant" or "herbicide-resistant" PPO activity.

Generally, if the PPO-inhibiting herbicides (also referred to as compounds A) and/or the herbicidal compounds B as described herein, which can be employed in the context of the present invention, are capable of forming geometrical isomers, for example E/Z isomers, it is possible to use both, the pure isomers and mixtures thereof, in the compositions useful for the present the invention. If the PPO-inhibiting herbicides A and/or the herbicidal compounds B as described herein have one or more centers of chirality and, as a consequence, are present as enantiomers or diastereomers, it is possible to use both, the pure enantiomers and diastereomers and their mixtures, in the compositions according to the invention. If the PPO-inhibiting herbicides A and/or the herbicidal compounds B as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds. Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl) ammonium (diolamine salt), tris(2-hydroxyethyl)ammonium (trolamine salt), tris(2-hydroxypropyl)ammonium, benzyltrimethylammonium, benzyltriethylammonium, N,N, N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine. Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

The PPO-inhibiting herbicides A and/or the herbicidal compounds B as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

Examples of PPO inhibiting herbicides which can be used according to the present invention are acifluorfen, acifluorfen-sodium, aclonifen, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, chlornitrofen, flumipropyn, fluoronitrofen, flupropacil, furyloxyfen, nitrofluorfen, ethyl [3-[2-chloro-4-fluoro-5-(1-methyl-6-trifluoromethyl-2,4-dioxo-1, 2,3,4-tetrahydropyrimidin-3-yl)phenoxy]-2-pyridyloxy] acetate (CAS 353292-31-6; S-3100), N-ethyl-3-2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2, 4-dione (CAS 451484-50-7), 1,5-dimethyl-6-thioxo-3-(2,2, 7-trifluoro-3-oxo-4-(prop-2-ynyl)-3,4-dihydro-2H-benzo[b] [1,4]oxazin-6-yl)-1,3,5-triazinane-2,4-dione (CAS 1258-836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4), and uracils of formula III

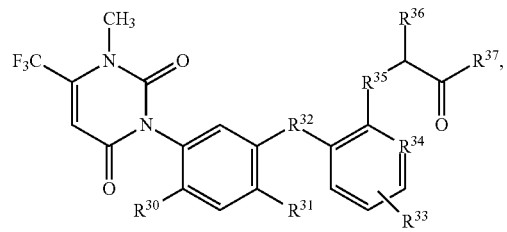

wherein
$R^{30}$ and $R^{31}$ independently of one another are F, Cl or CN;
$R^{32}$ is O or S;
$R^{33}$ is H, F, Cl, $CH_3$ or $OCH_3$;

$R^{34}$ is CH or N;
$R^{35}$ is O or S;
$R^{36}$ is H, CN, CH$_3$, CF$_3$, OCH$_3$, OC$_2$H$_5$, SCH$_3$, SC$_2$H$_5$, (CO)OC$_2$H$_5$ or CH$_2$R$^{38}$,
  wherein $R^{38}$ is F, Cl, OCH$_3$, SCH$_3$, SC$_2$H$_5$, CH$_2$F, CH$_2$Br or CH$_2$OH;
and
$R^{37}$ is (C$_1$-C$_6$-alkyl)amino, (C$_1$-C$_6$-dialkyl)amino, (NH) OR$^{39}$, OH, OR$^{40}$ or SR$^{40}$
  wherein $R^{39}$ is CH$_3$, C$_2$H$_5$ or phenyl; and
    $R^{40}$ is independently of one another C$_1$-C$_6$-alkyl, C$_2$-C$_6$-alkenyl, C$_3$-C$_6$-alkynyl, C$_1$-C$_6$-haloalkyl, C$_1$-C$_6$-alkoxy-C$_1$-C$_6$-alkyl, C$_1$-C$_6$-alkoxy-C1-C6-alkoxy-C$_1$-C$_6$-alkyl, C$_2$-C$_6$-cyanoalkyl, C$_1$-C$_4$-alkoxy-carbonyl-C$_1$-C$_4$-alkyl, C$_1$-C$_4$-alkyl-carbonyl-amino, C$_1$-C$_6$-alkylsulfinyl-C$_1$-C$_6$-alkyl, C$_1$-C6-alkyl-sulfonyl-C$_1$-C$_6$-alkyl, C$_1$-C$_6$-dialkoxy-C$_1$-C$_6$-alkyl, C$_1$-C$_6$-alkyl-carbonyloxy-C$_1$-C$_6$-alkyl, phenyl-carbonyl-C$_1$-C$_6$-alkyl, tri(C$_1$-C$_3$-alkyl)-silyl-C$_1$-C$_6$-alkyl, tri(C$_1$-C$_3$-alkyl)-silyl-C$_1$-C$_6$-alkenyl, tri(C$_1$-C$_3$-alkyl)-silyl-C$_1$-C$_6$-alkynyl, tri(C$_1$-C$_3$-alkyl)-silyl-C$_1$-C$_6$-alkoxy-C$_1$-C$_6$-alkyl, dimethylamino, tetrahydropyranyl, tetrahydrofuranyl-C$_1$-C$_3$-alkyl, phenyl-C$_1$-C$_6$-alkoxy-C$_1$-C$_6$-alkyl, phenyl-C$_1$-C$_3$-alkyl, pyridyl-C$_1$-C$_3$-alkyl, pyridyl, phenyl,
      which pyridyls and phenyls independently of one another are substituted by one to five substituents selected from the group consisting of halogen, C$_1$-C$_3$-alkyl or C$_1$-C$_2$-haloalkyl;
    C$_3$-C$_6$-cycloalkyl or C$_3$-C$_6$-cycloalkyl-C$_1$-C$_4$-alkyl,
      which cycloalkyls independently of one another are unsubstituted or substituted by one to five substituents selected from the group consisting of halogen, C$_1$-C$_3$-alkyl and C$_1$-C$_2$-haloalkyl;
including their agriculturally acceptable alkali metal salts or ammonium salts.

Preferred PPO-inhibiting herbicides that can be used according to the present invention are:
Acifluorfen, acifluorfen-sodium, azafenidin, bencarbazone, benzfendizone, butafenacil, carfentrazone-ethyl, cinidon-ethyl, flufenpyr-ethyl, flumiclorac-pentyl, flumioxazin, fluoroglycofen-ethyl, fluthiacet-methyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]-acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258-836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4)
uracils of formula III.1 (corresponding to uracils of formula III, wherein $R^{30}$ is F, $R^{31}$ is Cl, $R^{32}$ is O; $R^{33}$ is H; $R^{34}$ is CH; $R^{35}$ is O and $R^{37}$ is OR$^{40}$)

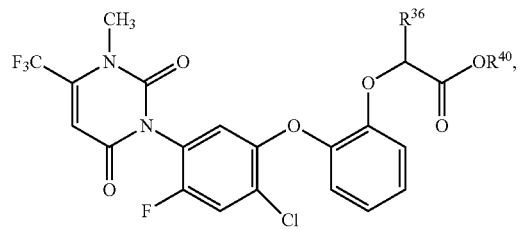

III.1 wherein
$R^{36}$ is OCH$_3$, OC$_2$H$_5$, SCH$_3$ or SC$_2$H$_5$;
and
$R^{40}$ is C$_1$-C$_6$-alkyl, C$_2$-C$_6$-alkenyl, C$_3$-C$_6$-alkynyl, C$_1$-C$_6$-haloalkyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, C$_1$-C$_3$-cyanoalkyl, phenyl-C$_1$-C$_3$-alkyl, pyridyl-C$_1$-C$_3$-alkyl, C$_3$-C$_6$-cycloalkyl or C$_3$-C$_6$-cycloalkyl-C$_1$-C$_4$-alkyl,
  which cycloalkyls are unsubstituted or substituted by one to five substituents selected from the group consisting of halogen, C$_1$-C$_3$-alkyl and C$_1$-C$_2$-haloalkyl;
and
uracils of formula III.2 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is OR$^{40}$ with $R^{40}$ is C$_1$-C$_6$-alkyl)

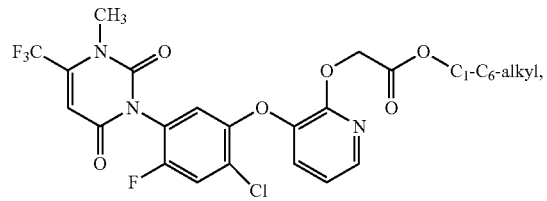

III.2

Particularly preferred PPO-inhibiting herbicides that can be used according to the present invention are:
acifluorfen, acifluorfen-sodium, butafenacil, carfentrazone-ethyl, cinidon-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)-phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 12588-36-72-4), and 2-(2,2,7-Trifluoro-3-oxo-4-prop-2-ynyl-3,4-dihydro-2H-benzo[1,4]oxazin-6-yl)-4,5,6,7-tetrahydroisoindole-1,3-dione (CAS 1300118-96-0), 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), uracils of formula III.1.1 (corresponding to uracils of formula III, wherein $R^{30}$ is F, $R^{31}$ is Cl, $R^{32}$ is O; $R^{33}$ is H; $R^{34}$ is CH; $R^{35}$ is O, $R^{36}$ is OCH$_3$ and $R^{37}$ is OR$^{40}$)

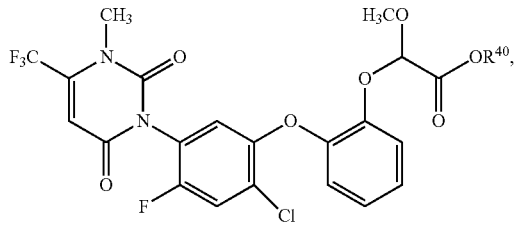

III.1.1 wherein $R^{40}$ is C$_1$-C$_6$-alkyl, C$_2$-C$_6$-alkenyl, C$_3$-C$_6$-alkynyl, C$_1$-C$_6$-haloalkyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, C$_1$-C$_3$-cyanoalkyl, phenyl-C$_1$-C$_3$-alkyl, pyridyl-C$_1$-C$_3$-alkyl, C$_3$-C$_6$-cycloalkyl or C$_3$-C$_6$-cycloalkyl-C$_1$-C$_4$-alkyl, which cycloalkyls are unsubstituted or substituted by one to five substituents selected from the group consisting of halogen, C$_1$-C$_3$-alkyl and C$_1$-C$_2$-haloalkyl;

is preferably CH$_3$, CH$_2$CH$_2$OC$_2$H$_5$, CH$_2$CHF$_2$, cyclohexyl, (1-methylcyclopropyl)methyl or CH$_2$(pyridine-4-yl);

uracils of formula III.2.1 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is OR$^{40}$ with $R^{40}$ is CH$_3$)

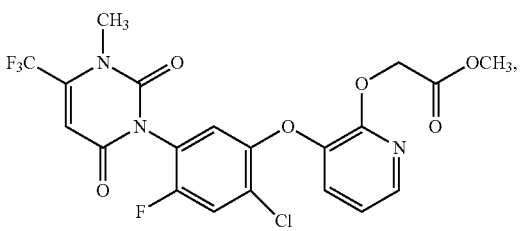

III.2.1 and uracils of formula III.2.2 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is OR$^{40}$ with $R^{40}$ is C$_2$H$_5$)

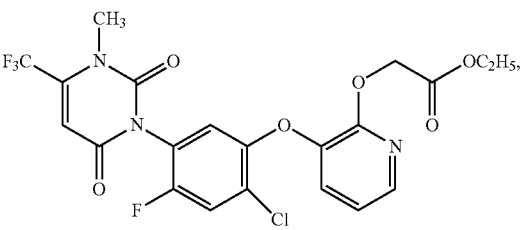

III.2.2

Especially preferred PPO-inhibiting herbicides are the PPO-inhibiting herbicides.1 to A.14 listed below in table A:

TABLE A

| | |
|---|---|
| A.1 | acifluorfen |
| A.2 | butafenacil |
| A.3 | carfentrazone-ethyl |
| A.4 | cinidon-ethyl |
| A.5 | flumioxazin |
| A.6 | fluthiacet-methyl |
| A.7 | fomesafen |
| A.8 | lactofen |
| A.9 | oxadiargyl |
| A.10 | oxyfluorfen |
| A.11 | saflufenacil |
| A.12 | sulfentrazone |
| A.13 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) |
| A.14 | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) |

The PPO-inhibiting herbicides described above that are useful to carry out the present invention are often best applied in conjunction with one or more other herbicides to obtain control of a wider variety of undesirable vegetation. For example, PPO-inhibiting herbicides may further be used in conjunction with additional herbicides to which the crop plant is naturally tolerant, or to which it is resistant via expression of one or more additional transgenes, e.g. those as mentioned hereinafter in greater detail, or to which it is resistant via mutagenesis and breeding methods as described hereinafter.

When used in conjunction with other targeting herbicides, the PPO-inhibiting herbicides, to which the plant of the present invention had been made resistant or tolerant, can be formulated with the other herbicide or herbicides, tank mixed with the other herbicide or herbicides, or applied sequentially with the other herbicide or herbicides.

Suitable components for mixtures are, for example, selected from the herbicides of class b1) to b15)

B) herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chloroflurenol, chloroflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, fluorenol, fluorenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters; including their agriculturally acceptable salts or derivatives.

Examples of herbicides B which can be used in combination with the PPO-inhibiting herbicides according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim,
4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312-337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam,
pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8),
sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, clomazone, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:

glyphosate, glyphosate-isopropylammonium, glyphosate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napronamide and napropamide, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

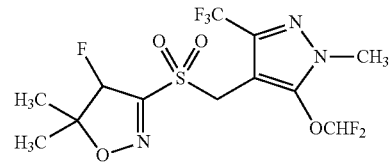

II.1

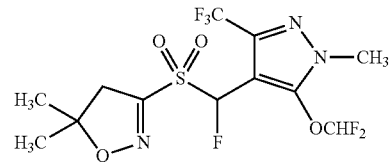

II.2

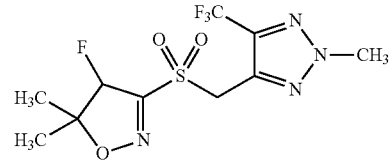

II.3

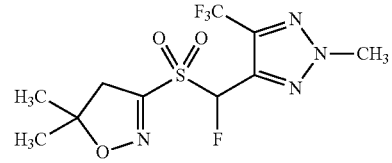

II.4

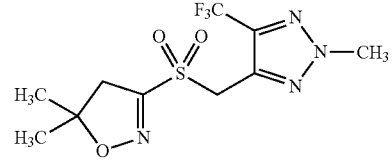

II.5

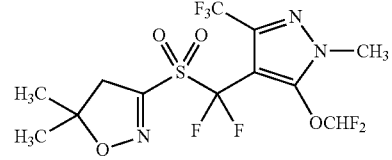

II.6

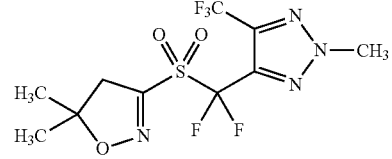

II.7

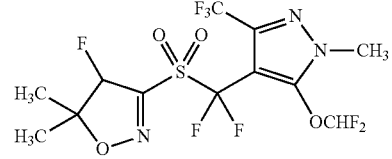

II.8

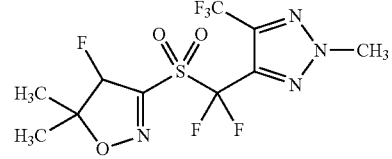

II.9 the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, indaziflam, triaziflam, isoxaben and 1-Cyclohexyl-5-pentafluorphenyloxy-1⁴-[1,2,4,6]thiatriazin-3-ylamine;

b12) from the group of the decoupler herbicides: dinoseb, dinoterb and DNOC and its salts;

b13) from the group of the auxinic herbicides: 2,4-D and its salts and esters such as clacyfos, 2,4-DB and its salts and esters, aminocyclopyrachlor and its salts and esters, aminopyralid and its salts such as aminopyralid-tris (2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors: diflufenzopyr, diflufenzopyr-sodium, naptalam and naptalam-sodium;

b15) from the group of the other herbicides: bromobutide, chloroflurenol, chloroflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, fluorenol, fluorenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Preferred herbicides B that can be used in combination with the PPO-inhibiting herbicides according to the present invention are:

b1) from the group of the lipid biosynthesis inhibitors: clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors: amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazone-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors: ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors: acifluorfen, acifluorfen-sodium, azafenidin, bencarbazone, benzfendizone, butafenacil, carfentrazone-ethyl, cinidon-ethyl, flufenpyr-ethyl, flumiclorac-pentyl, flumioxazin, fluoroglycofen-ethyl, fluthiacet-methyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]-acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-

(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione; 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, and 3-[7-Chloro-5-fluoro-2-(trifluoromethyl)-1H-benzimidazol-4-yl]-1-methyl-6-(trifluoro- methyl)-1H-pyrimidine-2,4-dione (CAS 212754-02-4);

b5) from the group of the bleacher herbicides: aclonifen, beflubutamid, benzobicyclon, clomazone, diflufenican, flurochloridone, flurtamone, isoxaflutole, mesotrione, norflurazon, picolinafen, pyrasulfotole, pyrazolynate, sulcotrione, tefuryltrione, tembotrione, topramezone, bicyclopyrone, 4-(3-trifluoromethylphenoxy)-2-(4-trifluoromethylphenyl)pyrimidine (CAS 180608-33-7), amitrole and flumeturon;

b6) from the group of the EPSP synthase inhibitors: glyphosate, glyphosate-isopropylammonium, glyphosate-potassium and glyphosate-trimesium (sulfosate);

b7) from the group of the glutamine synthase inhibitors: glufosinate, glufosinate-P, glufosinate-ammonium;

b8) from the group of the DHP synthase inhibitors: asulam;

b9) from the group of the mitosis inhibitors: benfluralin, dithiopyr, ethalfluralin, oryzalin, pendimethalin, thiazopyr and trifluralin;

b10) from the group of the VLCFA inhibitors: acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, isoxaben and 1-Cyclohexyl-5-pentafluorphenyloxy-1$^4$-[1,2,4,6]thiatriazin-3-ylamine;

b13) from the group of the auxinic herbicides: 2,4-D and its salts and esters, aminocyclopyrachlor and its salts and esters, aminopyralid and its salts such as aminopyralid-tris(2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac and triclopyr and its salts and esters;

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methylbromide, MSMA, oxaziclomefone, pyributicarb, triaziflam and tridiphane.

Particularly preferred herbicides B that can be used in combination with the PPO-inhibiting herbicides according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazone-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258-836-72-4), and 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides: clomazone, diflufenican, flurochloridone, isoxaflutole, mesotrione, picolinafen, sulcotrione, tefuryltrione, tembotrione, topramezone, bicyclopyrone, amitrole and flumeturon;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;
b9) from the group of the mitosis inhibitors: pendimethalin and trifluralin;
b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;
b11) from the group of the cellulose biosynthesis inhibitors: isoxaben;
b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, quinclorac and quinmerac;
b14) from the group of the auxin transport inhibitors: diflufenzopyr and diflufenzopyr-sodium,
b15) from the group of the other herbicides: dymron (=daimuron), indanofan, indaziflam, oxaziclomefone and triaziflam.

Moreover, it may be useful to apply the PPO-inhibiting herbicides, when used in combination with a compound B described SUPRA, in combination with safeners. Safeners are chemical compounds which prevent or reduce damage on useful plants without having a major impact on the herbicidal action of herbicides towards unwanted plants. They can be applied either before sowings (e.g. on seed treatments, shoots or seedlings) or in the pre-emergence application or post-emergence application of the useful plant.

Furthermore, the safeners C, the PPO-inhibiting herbicides and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON46-60, CAS 71526-07-3), and 2,2,5-trimethyl-3-(dichloroacetyl)-1,3-oxazolidine (R-29148, CAS 52836-31-4).

Also preferred safeners C are benoxacor, cloquintocet, cyprosulfamide, dichlormid, fenchlorazole, fenclorim, furilazole, isoxadifen, mefenpyr, 4-(dichloroacetyl)-1-oxa-4-azaspiro-[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C, which, as component C, are constituent of the composition according to the invention are the safeners C as defined above; in particular the safeners C.1-C.12 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenchlorazole |
| C.6 | fenclorim |
| C.7 | furilazole |
| C.8 | isoxadifen |
| C.9 | mefenpyr |
| C.10 | naphtalic acid anhydride |
| C.11 | 4-(dichloroacetyl)-1-oxa-4-azaspiro[4.5]decane (MON4660, CAS 71526-07-3) |
| C.12 | 2,2,5-trimethyl-3-(dichloro-acetyl)-1,3-oxazolidine (R-29148, CAS 52836-31-4) |

The PPO-inhibiting herbicides (compounds A) and the active compounds B of groups b1) to b15) and the active compounds C are known herbicides and safeners, see, for example, Alan Wood's The Compendium of Pesticide Common Names (www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl) methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium and aminopyralid-tris(2-hydroxypropyl) ammonium.

Suitable salts of glyphosate are for example glyphosate-ammonium, glyphosate-diammonium, glyphosate-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

The preferred embodiments of the invention mentioned herein below have to be understood as being preferred either independently from each other or in combination with one another.

According to a preferred embodiment of the invention, the composition comprises as component B at least one, preferably exactly one herbicide B.

According to another preferred embodiment of the invention, the composition comprises at least two, preferably exactly two, herbicides B different from each other.

According to another preferred embodiment of the invention, the composition comprises at least three, preferably exactly three, herbicides B different from each other.

According to another preferred embodiment of the invention, the composition comprises as component A at least one, preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)-phenoxy]-2-pyridyloxy]acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]

oxazin-6-yl)-1,3,5-triazinane-2,4-dione (CAS 1258836-72-4), and as component B at least one, preferably exactly one, herbicide B.

According to another preferred embodiment of the invention, the composition comprises as component A at least one, preferably exactly preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and at least two, preferably exactly two, herbicides B different from each other.

According to another preferred embodiment of the invention, the composition comprises as component A at least one, preferably exactly preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) and at least three, preferably exactly three, herbicides B different from each other.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b1), in particular selected from the group consisting of clethodim, clodinafop-propargyl, cycloxydim, cyhalofop-butyl, fenoxaprop-P-ethyl, fluazifop, pinoxaden, profoxydim, quizalofop, sethoxydim, tepraloxydim, tralkoxydim, esprocarb, prosulfocarb, thiobencarb and triallate.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b2), in particular selected from the group consisting of bensulfuron-methyl, bispyribac-sodium, cloransulam-methyl, cyclosulfamuron, diclosulam, flumetsulam, flupyrsulfuron-methyl-sodium, foramsulfuron, halosulfuron-methyl, imazamox, imazapic, imazapyr, imazaquin, imazethapyr, imazosulfuron, iodosulfuron, iodosulfuron-methyl-sodium, mesosulfuron-methyl, metazosulfuron, nicosulfuron, penoxsulam, propoxycarbazone-sodium, pyrazosulfuron-ethyl, pyrithiobac-sodium, pyroxsulam, rimsulfuron, sulfosulfuron, thiencarbazon-methyl, thifensulfuron-methyl, trifloxysulfuron and tritosulfuron.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b3), in particular selected from the group consisting of ametryn, atrazine, bentazon, bromoxynil, diuron, fluometuron, hexazinone, isoproturon, linuron, metribuzin, paraquat, paraquat-dichloride, prometryne, propanil, terbutryn and terbuthylazine.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b4), in particular selected from the group consisting of acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-

31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4).

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b5), in particular selected from the group consisting of clomazone, diflufenican, flurochloridone, isoxaflutole, mesotrione, picolinafen, sulcotrione, tefuryltrione, tembotrione, topramezone, bicyclopyrone, amitrole and flumeturon.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b6), in particular selected from the group consisting of glyphosate, glyphosate-isopropylammonium and glyphosate-trimesium (sulfosate).

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b7), in particular selected from the group consisting of glufosinate, glufosinate-P and glufosinate-ammonium.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b9), in particular selected from the group consisting of pendimethalin and trifluralin.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4)), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b13), in particular selected from the group consisting of 2,4-D and its salts and esters, aminocyclopyrachlor and its salts and esters, aminopyralid and its salts such as aminopyralid-tris (2-hydroxypropyl)ammonium and its esters, clopyralid and its salts and esters, dicamba and its salts and esters, fluroxypyr-meptyl, quinclorac and quinmerac.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b14), in particular selected from the group consisting of diflufenzopyr and diflufenzopyr-sodium.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b15), in particular selected from the group consisting of dymron (=daimuron), indanofan, indaziflam, oxaziclomefone and triaziflam.

Here and below, the term "binary compositions" includes compositions comprising one or more, for example 1, 2 or 3, active compounds of the PPO-inhibiting herbicide and either one or more, for example 1, 2 or 3, herbicides B.

In binary compositions comprising at least one PPO-inhibiting herbicide as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

Particularly preferred herbicides B are the herbicides B as defined above; in particular the herbicides B.1-B.229 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | fluazifop |
| B.8 | metamifop |
| B.9 | pinoxaden |
| B.10 | profoxydim |
| B.11 | quizalofop |
| B.12 | sethoxydim |
| B.13 | tepraloxydim |
| B.14 | tralkoxydim |
| B.15 | esprocarb |
| B.16 | ethofumesate |
| B.17 | molinate |
| B.18 | prosulfocarb |
| B.19 | thiobencarb |
| B.20 | triallate |
| B.21 | bensulfuron-methyl |
| B.22 | bispyribac-sodium |
| B.23 | cloransulam-methyl |
| B.24 | chlorsulfuron |
| B.25 | clorimuron |
| B.26 | cyclosulfamuron |
| B.27 | diclosulam |
| B.28 | florasulam |
| B.29 | flumetsulam |
| B.30 | flupyrsulfuron-methyl-sodium |
| B.31 | foramsulfuron |
| B.32 | halosulfuron-methyl |
| B.33 | imazamox |
| B.34 | imazamox-ammonium |
| B.35 | imazapic |
| B.36 | imazapic-ammonium |
| B.37 | imazapic-isopropylammonium |
| B.38 | imazapyr |
| B.39 | imazapyr-ammonium |
| B.40 | imazapyr-isopropylammonium |
| B.41 | imazaquin |
| B.42 | imazaquin-ammonium |
| B.43 | imazethapyr |
| B.44 | imazethapyr-ammonium |
| B.45 | imazethapyr-isopropylammonium |
| B.46 | imazosulfuron |
| B.47 | iodosulfuron-methyl-sodium |
| B.48 | iofensulfuron |
| B.49 | iofensulfuron-sodium |
| B.50 | mesosulfuron-methyl |
| B.51 | metazosulfuron |
| B.52 | metsulfuron-methyl |
| B.53 | metosulam |
| B.54 | nicosulfuron |
| B.55 | penoxsulam |
| B.56 | propoxycarbazon-sodium |
| B.57 | pyrazosulfuron-ethyl |
| B.58 | pyribenzoxim |
| B.59 | pyriftalid |
| B.60 | pyrithiobac-sodium |
| B.61 | pyroxsulam |
| B.62 | propyrisulfuron |
| B.63 | rimsulfuron |

TABLE B-continued

Herbicide B

| | |
|---|---|
| B.64 | sulfosulfuron |
| B.65 | thiencarbazone-methyl |
| B.66 | thifensulfuron-methyl |
| B.67 | tribenuron-methyl |
| B.68 | trifloxysulfuron |
| B.69 | tritosulfuron |
| B.70 | triafamone |
| B.71 | ametryne |
| B.72 | atrazine |
| B.73 | bentazon |
| B.74 | bromoxynil |
| B.75 | bromoxynil-octanoate |
| B.76 | bromoxynil-heptanoate |
| B.77 | bromoxynil-potassium |
| B.78 | diuron |
| B.79 | fluometuron |
| B.80 | hexazinone |
| B.81 | isoproturon |
| B.82 | linuron |
| B.83 | metamitron |
| B.84 | metribuzin |
| B.85 | prometryne |
| B.86 | propanil |
| B.87 | simazin |
| B.88 | terbuthylazine |
| B.89 | terbutryn |
| B.90 | paraquat-dichloride |
| B.91 | acifluorfen |
| B.92 | acifluorfen-sodium |
| B.93 | azafenidin |
| B.94 | bencarbazone |
| B.95 | benzfendizone |
| B.96 | bifenox |
| B.97 | butafenacil |
| B.98 | carfentrazone |
| B.99 | carfentrazone-ethyl |
| B.100 | chlomethoxyfen |
| B.101 | cinidon-ethyl |
| B.102 | fluazolate |
| B.103 | flufenpyr |
| B.104 | flufenpyr-ethyl |
| B.105 | flumiclorac |
| B.106 | flumiclorac-pentyl |
| B.107 | flumioxazin |
| B.108 | fluoroglycofen |
| B.109 | fluoroglycofen-ethyl |
| B.110 | fluthiacet |
| B.111 | fluthiacet-methyl |
| B.112 | fomesafen |
| B.113 | halosafen |
| B.114 | lactofen |
| B.115 | oxadiargyl |
| B.116 | oxadiazon |
| B.117 | oxyfluorfen |
| B.118 | pentoxazone |
| B.119 | profluazol |
| B.120 | pyraclonil |
| B.121 | pyraflufen |
| B.122 | pyraflufen-ethyl |
| B.123 | saflufenacil |
| B.124 | sulfentrazone |
| B.125 | thidiazimin |
| B.126 | tiafenacil |
| B.127 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate (CAS 353292-31-6) |
| B.128 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.129 | N-ethyl-3-(2,6-dichloro-4-trifluoromethylphenoxy)-5-methyl-1H-pyrazole-1-carboxamide (CAS 452098-92-9) |
| B.130 | N-tetrahydrofurfuryl-3-(2,6-dichloro-4-trifluoromethylphenoxy)-5-methyl-1H-pyrazole-1-carboxamide (CAS 915396-43-9) |
| B.131 | N-ethyl-3-(2-chloro-6-fluoro-4-trifluoromethylphenoxy)-5-methyl-1H-pyrazole-1-carboxamide (CAS 452099-05-7) |
| B.132 | N-tetrahydrofurfuryl-3-(2-chloro-6-fluoro-4-trifluoro-methylphenoxy)-5-methyl-1H-pyrazole-1-carboxamide (CAS 452100-03-7) |
| B.133 | 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione |
| B.134 | 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione |
| B.135 | 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione |
| B.136 | methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3] |
| B.137 | 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4) |
| B.138 | benzobicyclon |
| B.139 | clomazone |
| B.140 | diflufenican |
| B.141 | flurochloridone |
| B.142 | isoxaflutole |
| B.143 | mesotrione |
| B.144 | norflurazone |
| B.145 | picolinafen |
| B.146 | sulcotrione |
| B.147 | tefuryltrione |
| B.148 | tembotrione |
| B.149 | topramezone |
| B.150 | topramezone-sodium |
| B.151 | bicyclopyrone |
| B.152 | amitrole |
| B.153 | fluometuron |
| B.154 | glyphosate |
| B.155 | glyphosate-ammonium |
| B.156 | glyphosate-dimethylammonium |
| B.157 | glyphosate-isopropylammonium |
| B.158 | glyphosate-trimesium (sulfosate) |
| B.159 | glyphosate-potassium |
| B.160 | glufosinate |
| B.161 | glufosinate-ammonium |
| B.162 | glufosinate-P |
| B.163 | glufosinate-P-ammonium |
| B.164 | pendimethalin |
| B.165 | trifluralin |
| B.166 | acetochlor |
| B.167 | butachlor |
| B.168 | cafenstrole |
| B.169 | dimethenamid-P |
| B.170 | fentrazamide |
| B.171 | flufenacet |
| B.172 | mefenacet |
| B.173 | metazachlor |
| B.174 | metolachlor |

TABLE B-continued

| | Herbicide B |
|---|---|
| B.175 | S-metolachlor |
| B.176 | pretilachlor |
| B.177 | fenoxasulfone |
| B.178 | isoxaben |
| B.179 | ipfencarbazone |
| B.180 | pyroxasulfone |
| B.181 | 2,4-D |
| B.182 | 2,4-D-isobutyl |
| B.183 | 2,4-D-dimethylammonium |
| B.184 | 2,4-D-N,N,N-trimethylethanolammonium |
| B.185 | aminopyralid |
| B.186 | aminopyralid-methyl |
| B.187 | aminopyralid-tris(2-hydroxypropyl)ammonium |
| B.188 | clopyralid |
| B.189 | clopyralid-methyl |
| B.190 | clopyralid-olamine |
| B.191 | dicamba |
| B.192 | dicamba-butotyl |
| B.193 | dicamba-diglycolamine |
| B.194 | dicamba-dimethylammonium |
| B.195 | dicamba-diolamine |
| B.196 | dicamba-isopropylammonium |
| B.197 | dicamba-potassium |
| B.198 | dicamba-sodium |
| B.199 | dicamba-trolamine |
| B.200 | dicamba-N,N-bis-(3-aminopropyl)methylamine |
| B.201 | dicamba-diethylenetriamine |
| B.202 | fluroxypyr |
| B.203 | fluroxypyr-meptyl |
| B.204 | MCPA |
| B.205 | MCPA-2-ethylhexyl |
| B.206 | MCPA-dimethylammonium |
| B.207 | quinclorac |
| B.208 | quinclorac-dimethylammonium |
| B.209 | quinmerac |
| B.210 | quinmerac-dimethylammonium |
| B.211 | aminocyclopyrachlor |
| B.212 | aminocyclopyrachlor-potassium |
| B.213 | aminocyclopyrachlor-methyl |
| B.214 | diflufenzopyr |
| B.215 | diflufenzopyr-sodium |
| B.216 | dymron |
| B.217 | indanofan |
| B.218 | indaziflam |
| B.219 | oxaziclomefone |
| B.220 | triaziflam |
| B.221 | II.1 |
| B.222 | II.2 |
| B.223 | II.3 |
| B.224 | II.4 |
| B.225 | II.5 |
| B.226 | II.6 |
| B.227 | II.7 |
| B.228 | II.8 |
| B.229 | II.9 |

Particularly preferred are compositions 1.1 to 1.229, comprising acifluorfen and the substance(s) as defined in the respective row of table B-1:

TABLE B-1

(compositions 1.1 to 1.229):

| comp. no. | herbicide B |
|---|---|
| 1.1 | B.1 |
| 1.2 | B.2 |
| 1.3 | B.3 |
| 1.4 | B.4 |
| 1.5 | B.5 |
| 1.6 | B.6 |
| 1.7 | B.7 |
| 1.8 | B.8 |
| 1.9 | B.9 |
| 1.10 | B.10 |
| 1.11 | B.11 |
| 1.12 | B.12 |
| 1.13 | B.13 |
| 1.14 | B.14 |
| 1.15 | B.15 |
| 1.16 | B.16 |
| 1.17 | B.17 |
| 1.18 | B.18 |
| 1.19 | B.19 |
| 1.20 | B.20 |
| 1.21 | B.21 |
| 1.22 | B.22 |
| 1.23 | B.23 |
| 1.24 | B.24 |
| 1.25 | B.25 |
| 1.26 | B.26 |
| 1.27 | B.27 |
| 1.28 | B.28 |
| 1.29 | B.29 |
| 1.30 | B.30 |
| 1.31 | B.31 |
| 1.32 | B.32 |
| 1.33 | B.33 |
| 1.34 | B.34 |
| 1.35 | B.35 |
| 1.36 | B.36 |
| 1.37 | B.37 |
| 1.38 | B.38 |
| 1.39 | B.39 |
| 1.40 | B.40 |
| 1.41 | B.41 |
| 1.42 | B.42 |
| 1.43 | B.43 |
| 1.44 | B.44 |
| 1.45 | B.45 |
| 1.46 | B.46 |
| 1.47 | B.47 |
| 1.48 | B.48 |
| 1.49 | B.49 |
| 1.50 | B.50 |
| 1.51 | B.51 |
| 1.52 | B.52 |
| 1.53 | B.53 |
| 1.54 | B.54 |
| 1.55 | B.55 |
| 1.56 | B.56 |
| 1.57 | B.57 |
| 1.58 | B.58. |
| 1.59 | B.59 |
| 1.60 | B.60 |
| 1.61 | B.61 |
| 1.62 | B.62 |
| 1.63 | B.63 |
| 1.64 | B.64 |
| 1.65 | B.65 |
| 1.66 | B.66 |
| 1.67 | B.67 |
| 1.68 | B.68 |
| 1.69 | B.69 |
| 1.70 | B.70 |
| 1.71 | B.71 |
| 1.72 | B.72 |
| 1.73 | B.73 |
| 1.74 | B.74 |
| 1.75 | B.75 |
| 1.76 | B.76 |
| 1.77 | B.77 |
| 1.78 | B.78 |
| 1.79 | B.79 |
| 1.80 | B.80 |
| 1.81 | B.81 |

TABLE B-1-continued (compositions 1.1 to 1.229):

| comp. no. | herbicide B |
|---|---|
| 1.82 | B.82 |
| 1.83 | B.83 |
| 1.84 | B.84 |
| 1.85 | B.85 |
| 1.86 | B.86 |
| 1.87 | B.87 |
| 1.88 | B.88 |
| 1.89 | B.89 |
| 1.90 | B.90 |
| 1.91 | B.91 |
| 1.92 | B.92 |
| 1.93 | B.93 |
| 1.94 | B.94 |
| 1.95 | B.95 |
| 1.96 | B.96 |
| 1.97 | B.97 |
| 1.98 | B.98 |
| 1.99 | B.99 |
| 1.100 | B.100 |
| 1.101 | B.101 |
| 1.102 | B.102 |
| 1.103 | B.103 |
| 1.104 | B.104 |
| 1.105 | B.105 |
| 1.106 | B.106 |
| 1.107 | B.107 |
| 1.108 | B.108 |
| 1.109 | B.109 |
| 1.110 | B.110 |
| 1.111 | B.111 |
| 1.112 | B.112 |
| 1.113 | B.113 |
| 1.114 | B.114 |
| 1.115 | B.115 |
| 1.116 | B.116 |
| 1.117 | B.117 |
| 1.118 | B.118 |
| 1.119 | B.119 |
| 1.120 | B.120 |
| 1.121 | B.121 |
| 1.122 | B.122 |
| 1.123 | B.123 |
| 1.124 | B.124 |
| 1.125 | B.125 |
| 1.126 | B.126 |
| 1.127 | B.127 |
| 1.128 | B.128 |
| 1.129 | B.129 |
| 1.130 | B.130 |
| 1.131 | B.131 |
| 1.132 | B.132 |
| 1.133 | B.133 |
| 1.134 | B.134 |
| 1.135 | B.135 |
| 1.136 | B.136 |
| 1.137 | B.137 |
| 1.138 | B.138 |
| 1.139 | B.139 |
| 1.140 | B.140 |
| 1.141 | B.141 |
| 1.142 | B.142 |
| 1.143 | B.143 |
| 1.144 | B.144 |
| 1.145 | B.145 |
| 1.146 | B.146 |
| 1.147 | B.147 |
| 1.148 | B.148 |
| 1.149 | B.149 |
| 1.150 | B.150 |
| 1.151 | B.151 |
| 1.152 | B.152 |
| 1.153 | B.153 |
| 1.154 | B.154 |
| 1.155 | B.155 |
| 1.156 | B.156 |
| 1.157 | B.157 |
| 1.158 | B.158 |
| 1.159 | B.159 |
| 1.160 | B.160 |
| 1.161 | B.161 |
| 1.162 | B.162 |
| 1.163 | B.163 |
| 1.164 | B.164 |
| 1.165 | B.165 |
| 1.166 | B.166 |
| 1.167 | B.167 |
| 1.168 | B.168 |
| 1.169 | B.169 |
| 1.170 | B.170 |
| 1.171 | B.171 |
| 1.172 | B.172 |
| 1.173 | B.173 |
| 1.174 | B.174 |
| 1.175 | B.175 |
| 1.176 | B.176 |
| 1.177 | B.177 |
| 1.178 | B.178 |
| 1.179 | B.179 |
| 1.180 | B.180 |
| 1.181 | B.181 |
| 1.182 | B.182 |
| 1.183 | B.183 |
| 1.184 | B.184 |
| 1.185 | B.185 |
| 1.186 | B.186 |
| 1.187 | B.187 |
| 1.188 | B.188 |
| 1.189 | B.189 |
| 1.190 | B.190 |
| 1.191 | B.191 |
| 1.192 | B.192 |
| 1.193 | B.193 |
| 1.194 | B.194 |
| 1.195 | B.195 |
| 1.196 | B.196 |
| 1.197 | B.197 |
| 1.198 | B.198 |
| 1.199 | B.199 |
| 1.200 | B.200 |
| 1.201 | B.201 |
| 1.202 | B.202 |
| 1.203 | B.203 |
| 1.204 | B.204 |
| 1.205 | B.205 |
| 1.206 | B.206 |
| 1.207 | B.207 |
| 1.208 | B.208 |
| 1.209 | B.209 |
| 1.210 | B.210 |
| 1.211 | B.211 |
| 1.212 | B.212 |
| 1.213 | B.213 |
| 1.214 | B.214 |
| 1.215 | B.215 |
| 1.216 | B.216 |
| 1.217 | B.217 |
| 1.218 | B.218 |
| 1.219 | B.219 |
| 1.220 | B.220 |
| 1.221 | B.221 |
| 1.222 | B.222 |
| 1.223 | B.223 |
| 1.224 | B.224 |
| 1.225 | B.225 |
| 1.226 | B.226 |
| 1.227 | B.227 |
| 1.228 | B.228 |
| 1.229 | B.229 |

Also especially preferred are compositions 2.1. to 2.229 which differ from the corresponding compositions 1.1 to 1.229 only in that they comprise as component A acifluorfen-sodium.

Also especially preferred are compositions 3.1. to 3.229 which differ from the corresponding compositions 1.1 to 1.229 only in that they comprise as component A azafenidin.

Also especially preferred are compositions 4.1. to 4.229 which differ from the corresponding compositions 1.1 to 1.229 only in that they comprise as component A bencarbazone.

Also especially preferred are compositions 5.1. to 5.229 which differ from the corresponding compositions 1.1 to 1.229 only in that they comprise as component A benzfendizone.

Also especially preferred are compositions 6.1. to 6.229 which differ from the corresponding compositions 1.1 to 1.229 only in that they comprise as component A bifenox.

Also especially preferred are compositions 7.1. to 7.229 which differ from the corresponding compositions 1.1 to 1.227 only in that they comprise as component A butafenacil.

Also especially preferred are compositions 8.1. to 8.229 which differ from the corresponding compositions 1.1 to 1.229 only in that they comprise as component A carfentrazone.

Also especially preferred are compositions 9.1. to 9.229 which differ from the corresponding compositions 1.1 to 1.229 only in that they comprise as component A carfentrazone-ethyl.

Also especially preferred are compositions 10.1. to 10.229 which differ from the corresponding compositions 1.1 to 1.229 only in that they comprise as component A chlomethoxyfen.

Also especially preferred are compositions 11.1. to 11.229 which differ from the corresponding compositions 1.1 to 1.229 only in that they comprise as component A cinidon-ethyl.

Also especially preferred are compositions 12.1. to 12.229 which differ from the corresponding compositions 1.1 to 1.229 only in that they comprise as component A fluazolate.

Also especially preferred are compositions 13.1. to 13.229 which differ from the corresponding compositions 1.1 to 1.229 only in that they comprise as component A flufenpyr.

Also especially preferred are compositions 14.1. to 14.229 which differ from the corresponding compositions 1.1 to 1.229 only in that they comprise as component A flufenpyr-ethyl.

Also especially preferred are compositions 15.1. to 15.229 which differ from the corresponding compositions 1.1 to 1.229 only in that they comprise as component A flumiclorac.

Also especially preferred are compositions 16.1. to 16.229 which differ from the corresponding compositions 1.1 to 1.229 only in that they comprise as component A flumiclorac-pentyl.

Also especially preferred are compositions 17.1. to 17.229 which differ from the corresponding compositions 1.1 to 1.229 only in that they comprise as component A flumioxazin.

Also especially preferred are compositions 18.1. to 18.229 which differ from the corresponding compositions 1.1 to 1.229 only in that they comprise as component A fluoroglycofen.

Also especially preferred are compositions 19.1. to 19.229 which differ from the corresponding compositions 1.1 to 1.229 only in that they comprise as component A fluoroglycofen-ethyl.

Also especially preferred are compositions 20.1. to 20.229 which differ from the corresponding compositions 1.1 to 1.229 only in that they comprise as component A fluthiacet.

Also especially preferred are compositions 21.1. to 21.229 which differ from the corresponding compositions 1.1 to 1.229 only in that they comprise as component A fluthiacet-methyl.

Also especially preferred are compositions 22.1. to 22.229 which differ from the corresponding compositions 1.1 to 1.229 only in that they comprise as component A fomesafen.

Also especially preferred are compositions 23.1. to 23.229 which differ from the corresponding compositions 1.1 to 1.229 only in that they comprise as component A halosafen.

Also especially preferred are compositions 24.1. to 24.229 which differ from the corresponding compositions 1.1 to 1.229 only in that they comprise as component A lactofen.

Also especially preferred are compositions 25.1. to 25.229 which differ from the corresponding compositions 1.1 to 1.229 only in that they comprise as component A oxadiargyl.

Also especially preferred are compositions 26.1. to 26.229 which differ from the corresponding compositions 1.1 to 1.229 only in that they comprise as component A oxadiazon.

Also especially preferred are compositions 27.1. to 27.229 which differ from the corresponding compositions 1.1 to 1.229 only in that they comprise as component A oxyfluorfen.

Also especially preferred are compositions 28.1. to 28.229 which differ from the corresponding compositions 1.1 to 1.229 only in that they comprise as component A pentoxazone.

Also especially preferred are compositions 29.1. to 29.229 which differ from the corresponding compositions 1.1 to 1.229 only in that they comprise as component A profluazol.

Also especially preferred are compositions 30.1. to 30.229 which differ from the corresponding compositions 1.1 to 1.229 only in that they comprise as component A pyraclonil.

Also especially preferred are compositions 31.1. to 31.229 which differ from the corresponding compositions 1.1 to 1.229 only in that they comprise as component A pyraflufen.

Also especially preferred are compositions 32.1. to 32.229 which differ from the corresponding compositions 1.1 to 1.229 only in that they comprise as component A pyraflufen-ethyl.

Also especially preferred are compositions 33.1. to 33.229 which differ from the corresponding compositions 1.1 to 1.229 only in that they comprise as component A saflufenacil.

Also especially preferred are compositions 34.1. to 34.229 which differ from the corresponding compositions 1.1 to 1.229 only in that they comprise as component A sulfentrazone.

Also especially preferred are compositions 35.1. to 35.229 which differ from the corresponding compositions 1.1 to 1.229 only in that they comprise as component A thidiazimin.

Also especially preferred are compositions 36.1. to 36.229 which differ from the corresponding compositions 1.1 to 1.229 only in that they comprise as component A tiafenacil.

Also especially preferred are compositions 37.1. to 37.229 which differ from the corresponding compositions 1.1 to 1.229 only in that they comprise as component A ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100).

Also especially preferred are compositions 38.1. to 38.229 which differ from the corresponding compositions 1.1 to 1.229 only in that they comprise as component A 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4)

Also especially preferred are compositions 39.1. to 39.229 which differ from the corresponding compositions 1.1 to 1.229 only in that they comprise as component A N-ethyl-3-(2,6-dichloro-4-trifluoromethylphenoxy)-5-methyl-1H-pyrazole-1-carboxamide (CAS 452098-92-9).

Also especially preferred are compositions 40.1. to 40.229 which differ from the corresponding compositions 1.1 to 1.229 only in that they comprise as component A N-tetrahydrofurfuryl-3-(2,6-dichloro-4-trifluoromethylphenoxy)-5-methyl-1H-pyrazole-1-carboxamide (CAS 915396-43-9).

Also especially preferred are compositions 41.1. to 41.229 which differ from the corresponding compositions 1.1 to 1.229 only in that they comprise as component A N-ethyl-3-(2-chloro-6-fluoro-4-trifluoromethylphenoxy)-5-methyl-1H-pyrazole-1-carboxamide (CAS 452099-05-7).

Also especially preferred are compositions 42.1. to 42.229 which differ from the corresponding compositions 1.1 to 1.229 only in that they comprise as component A N-tetrahydrofurfuryl-3-(2-chloro-6-fluoro-4-trifluoromethylphenoxy)-5-methyl-1H-pyrazole-1-carboxamide (CAS 452100-03-7).

Also especially preferred are compositions 43.1. to 43.229 which differ from the corresponding compositions 1.1 to 1.229 only in that they comprise as component A 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione.

Also especially preferred are compositions 44.1. to 44.229 which differ from the corresponding compositions 1.1 to 1.229 only in that they comprise as component A methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3).

Also especially preferred are compositions 45.1. to 45.229 which differ from the corresponding compositions 1.1 to 1.229 only in that they comprise as component A 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4).

Also especially preferred are compositions 46.1. to 46.229 which differ from the corresponding compositions 1.1 to 1.229 only in that they comprise as component A 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione.

Also especially preferred are compositions 47.1. to 47.229 which differ from the corresponding compositions 1.1 to 1.229 only in that they comprise as component A 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione Also especially preferred are compositions 48.1. to 48.229 which differ from the corresponding compositions 1.1 to 1.229 only in that they additionally comprise benoxacor as safener C.

Also especially preferred are compositions 49.1. to 49.229 which differ from the corresponding compositions 1.1 to 1.229 only in that they additionally comprise cloquintocet as safener C.

Also especially preferred are compositions 50.1. to 50.229 which differ from the corresponding compositions 1.1 to 1.229 only in that they additionally comprise cyprosulfamide as safener C.

Also especially preferred are compositions 51.1. to 51.229 which differ from the corresponding compositions 1.1 to 1.229 only in that they additionally comprise dichlormid as safener C.

Also especially preferred are compositions 52.1. to 52.229 which differ from the corresponding compositions 1.1 to 1.229 only in that they additionally comprise fenchlorazole as safener C.

Also especially preferred are compositions 53.1. to 53.229 which differ from the corresponding compositions 1.1 to 1.229 only in that they additionally comprise fenclorim as safener C.

Also especially preferred are compositions 54.1. to 54.229 which differ from the corresponding compositions 1.1 to 1.229 only in that they additionally comprise furilazole as safener C.

Also especially preferred are compositions 55.1. to 55.229 which differ from the corresponding compositions 1.1 to 1.229 only in that they additionally comprise isoxadifen as safener C.

Also especially preferred are compositions 56.1. to 56.229 which differ from the corresponding compositions 1.1 to 1.229 only in that they additionally comprise mefenpyr as safener C.

Also especially preferred are compositions 57.1. to 57.229 which differ from the corresponding compositions 1.1 to 1.229 only in that they additionally comprise 4-(dichloroacetyl)-1-oxa-4-azaspiro[4.5]decane (MON4660, CAS 71526-07-3) as safener C.

Also especially preferred are compositions 58.1. to 58.229 which differ from the corresponding compositions 1.1 to 1.229 only in that they additionally comprise 2,2,5-trimethyl-3-(dichloroacetyl)-1,3-oxazolidine (R-29148, CAS 52836-31-4) as safener C.

As mentioned before, PPO inhibiting herbicides are often best applied in conjunction with one or more other herbicides to obtain control of a wider variety of undesirable vegetation. It is generally preferred to use the compounds, in particular the PPO-inhibiting herbicides and compositions described SUPRA, which are useful for the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

Consequently, in certain embodiments, the PPO nucleic acids of the present invention can be stacked with any combination of polynucleotide sequences of interest in order to create plants with a desired phenotype. For example, the PPO nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723, 756; 5,593,881; and Geiser et al (1986) Gene 48: 109). The combinations generated can also include multiple copies of any one of the polynucleotides of interest.

By way of example, polynucleotides that may be stacked with the nucleic acids of the present invention include nucleic acids encoding polypeptides conferring resistance to pests/pathogens such as viruses, nematodes, insects or fungi, and the like. Exemplary polynucleotides that may be stacked with nucleic acids of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737, 514; 5,723,756; 5,593,881; and Geiser et al., (1986) Gene 48:109), lectins (Van Damme et al. (1994) Plant Mol. Biol. 24:825, pentin (described in U.S. Pat. No. 5,981,722), and the like; traits desirable for disease or herbicide resistance (e.g., fumonisin detoxification genes (U.S. Pat. No. 5,792, 931); avirulence and disease resistance genes (Jones et al. (1994) Science 266:789; Martin et al., (1993) Science 262: 1432; Mindrinos et al. (1994) Cell 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) Science, 304:1151-1154; and in U.S. Patent App. Pub. Nos. 20070004912, 20050246798, and 20050060767)); glufosinate resistance (e.g, phosphinothricin acetyl transferase genes PAT and BAR, described in U.S. Pat. Nos. 5,561,236 and 5,276,268); resistance to herbicides including sulfonyl urea, DHT (2,4D), and PPO herbicides (e.g., glyphosate acetyl transferase, aryloxy alkanoate dioxygenase, acetolactate synthase, 4-Hydroxyphenylpyruvate dioxygenase (HPPD), and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference.

In a particularly preferred embodiment, the plant comprises at least one additional heterologous nucleic acid comprising a nucleotide sequence encoding a herbicide tolerance enzyme selected, for example, from the group consisting of 5-enolpyruvylshikimate-3-phosphate synthase (EPSPS), Glyphosate acetyl transferase (GAT), Cytochrome P450, phosphinothricin acetyltransferase (PAT), Acetohydroxyacid synthase (AHAS; EC 4.1.3.18, also known as acetolactate synthase or ALS), 4-Hydroxyphenylpyruvate dioxygenase (HPPD), Phytoene desaturase (PD) and dicamba degrading enzymes as disclosed in WO 02/068607.

In other aspects, plants of the invention include those plants which, in addition to being tolerant to PPO-inhibiting herbicides, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, PPO-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, PPO-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, PPO-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype PPO proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity.

PPO-inhibiting herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, PPO-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA(b), CryIIIA, CryIIIB(bI) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the PPO-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles {*Lyctus* spp., the pollen beetle *Meligethes aeneus*; the common cockshafer *Melolontha melolontha*; the American spider beetle *Mezium americanum*; the golden spider beetle *Niptus hololeucs*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*; the greenhouse millipede *Oxidus gracilis*; the beet fly *Pegomyia betae*; the frit fly *Oscinella frit*; fruit flies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear psylla *Cacopsylla pyricola*; the currant aphid *Cryptomyzus ribis*; the grape phylloxera *Daktulosphaira vitifoliae*; the citrus psylla *Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit tortrix moth); *Archips podana* (fruit tree tortrix moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis virescens* (tobacco budworm), *Homeosoma electellum* (sunflower moth); *Homona magnanima* (oriental tea tree tortrix moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armywonn); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differ entialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus*

*abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculata*; Thysanoptera such as the tobacco thrips *Frankliniella fusca*, the flower thrips *Frankliniella intonsa*, the western flower thrips *Frankliniella occidentalism* the cotton bud thrips *Frankliniella schultzei*, the banded greenhouse thrips *Hercinothrips femoralis*, the soybean thrips *Neohydatothrips variabilis*, Kelly's citrus thrips *Pezothrips kellyanus*, the avocado thrips *Scirtothrips perseae*, the melon thrips *Thrips palmi*, and the onion thrips *Thrips tabaci*; and the like, and combinations comprising one or more of the foregoing organisms.

In some embodiments, expression of one or more protein toxins (e.g., insecticidal proteins) in the PPO-inhibiting herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the PPO-inhibiting herbicides-tolerant plants is effective for controlling cabbage seedpod weevil, the Bertha armyworm, *Lygus* bugs, or the diamondback moth.

Furthermore, in one embodiment, PPO-inhibiting herbicides-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, PPO-inhibiting herbicides-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, PPO-inhibiting herbicides-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera® rape, Dow Agro Sciences, Canada).

Furthermore, in some embodiments, PPO-inhibiting herbicides-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, PPO-inhibiting herbicides-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), I-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, I,2'-disinapoyl-2-feruloylgentiobiose, 3-0-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, PPO-inhibiting herbicides-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla. In other embodiments, PPO-inhibiting herbicides-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

As described above, the present invention teaches compositions and methods for increasing the PPO-inhibiting tolerance of a crop plant or seed as compared to a wild-type variety of the plant or seed. In a preferred embodiment, the PPO-inhibiting tolerance of a crop plant or seed is increased such that the plant or seed can withstand a PPO-inhibiting herbicide application of preferably approximately 1-1000 g ai ha$^{-1}$, more preferably 1-200 g ai ha$^{-1}$, even more preferably 5-150 g ai ha$^{-1}$, and most preferably 10-100 g ai ha$^{-1}$. As used herein, to "withstand" a PPO-inhibiting herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Furthermore, the present invention provides methods that involve the use of at least one PPO-inhibiting herbicide, optionally in combination with one or more herbicidal compounds B, and, optionally, a safener C, as described in detail supra.

In these methods, the PPO-inhibiting herbicide can be applied by any method known in the art including, but not limited to, seed treatment, soil treatment, and foliar treatment. Prior to application, the PPO-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

Prior to application, the PPO-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to PPO-inhibiting herbicide, a wide variety of formulations can be employed for protecting plants from weeds, so as to enhance plant growth and reduce competition for nutrients. A PPO-inhibiting herbicide can be used by itself for pre-emergence, post-emergence, pre-planting, and at-planting control of weeds in areas surrounding the crop plants described herein, or a PPO-inhibiting herbicide formulation can be used that contains other additives. The PPO-inhibiting herbicide can also be used as a seed treatment. Additives found in a PPO-inhibiting herbicide formulation include other herbicides, detergents, adjuvants, spreading agents, sticking agents, stabilizing agents, or the like. The PPO-inhibiting herbicide formulation can be a wet or dry preparation and can include, but is not limited to, flowable powders, emulsifiable concentrates, and liquid concentrates. The PPO-inhibiting herbicide and herbicide formulations can be applied in accordance with conventional methods, for example, by spraying, irrigation, dusting, or the like.

The formulations can be prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

In general, the formulations comprise from 0.01 to 95% by weight, preferably from 0.1 to 90% by weight, of the PPO-inhibiting herbicide. In this case, the PPO-inhibiting herbicides are employed in a purity of from 90% to 100% by weight, preferably 95% to 100% by weight (according to NMR spectrum). For seed treatment purposes, respective formulations can be diluted 2-10 fold leading to concentrations in the ready to use preparations of 0.01 to 60% by weight active compound by weight, preferably 0.1 to 40% by weight. The PPO-inhibiting herbicide can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the PPO-inhibiting herbicide according to the invention. Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water. The active compound concentrations in the ready-to-use preparations can be varied within relatively wide ranges. In general, they are from 0.0001 to 10%, preferably from 0.01 to 1% per weight. The PPO-inhibiting herbicide may also be used successfully in the ultra-low-volume process (ULV), it being possible to apply formulations comprising over 95% by weight of active compound, or even to apply the active compound without additives.

Suitable formulations are described in detail in PCT/EP2009/063387 and PCT/EP2009/063386, which are incorporated herein by reference.

In other aspects, a method for treating a plant of the present invention is provided.

In some embodiments, the method comprises contacting the plant with an agronomically acceptable composition as defined above.

In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a PPO-inhibiting herbicides herbicidal composition to the descendent plant.

In another embodiment, the invention refers to harvestable parts of the transgenic plant according to the present invention. Preferably, the harvestable parts comprise the PPO nucleic acid or PPO protein of the present invention. The harvestable parts may be seeds, roots, leaves and/or flowers comprising the PPO nucleic acid or PPO protein or parts thereof. Preferred parts of soy plants are soy beans comprising the PPO nucleic acid or PPO protein.

In another embodiment, the invention refers to products derived from a transgenic plant according to the present invention, parts thereof or harvestable parts thereof. A preferred product is meal or oil, preferably, soybean meal or soybean oil. Preferably, the soybean meal and/or oil comprises the PPO nucleic acid or PPO protein.

In another embodiment, the invention refers to a method for the production of a product, which method comprises
a) growing the plants of the invention or obtainable by the methods of invention and
b) producing said product from or by the plants of the invention and/or parts, e.g. seeds, of these plants.

In a further embodiment the method comprises the steps
a) growing the plants of the invention,
b) removing the harvestable parts as defined above from the plants and
c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Site-Directed Mutagenesis of *Alopecurus* PPO

All nucleic acid coding sequence and all single and double mutants based on SEQ ID NO: 1, or 3, were synthesized and cloned by Geneart (Geneart AG, Regensburg, Germany). Rational design mutants were synthesized by Geneart. Random PPO gene libraries were synthesized by Geneart. Plasmids were isolated from *E. coli* TOP10 by performing a plasmid minpreparation and confirmed by DNA sequencing.

Example 2

Expression and Purification of Recombinant Wildtype and Mutant *Alopecurus* PPO (Taken from: Franck E. Dayan, Pankaj R. Daga, Stephen O. Duke, Ryan M. Lee, Patrick J. Tranel, Robert J. Doerksen. Biochemical and structural consequences of a glycine deletion in the α-8 helix of protoporphyrinogen oxidase. Biochimica et Biophysica Acta 1804 (2010), 1548-56) Clones in pRSET vector were transformed into BL21(DE3)-pLysS strain of E. coll. Cells were grown in 250 mL of LB with 100 µgmL-1 of carbenicillin, shaking overnight at 37° C. Cultures were diluted in 1 L of LB with antibiotic and grown at 37° C. shaking for 2 h, induced with 1 mM IPTG and grown at 25° C. shaking for 5 more hours. The cells were harvested by centrifugation at 1600×g, washed with 0.09% NaCl, and stored at −80° C. Cells were lysed using a French press at 140 M Pa in 50 mM sodium phosphate pH 7.5, 1 M NaCl, 5 mM imidazole, 5% glycerol, and 1 µg mL-1 leupeptin. Following lysis, 0.5 U of benzonase (Novagen, EMD Chemicals, Inc., Gibbstown, N.J.) and PMSF (final concentration of 1 mM) were added. Cell debris was removed by centrifugation at 3000×g. His-tagged PPO proteins were purified on a nickel activated Hitrap Chelating HP column (GE Healthcare Bio-Sciences Corp., Piscataway, N.J.) equilibrated with 20 mM sodium phosphate pH 8.0, 50 mM NaCl, 5 mM imidazole, 5 mM MgCl2, 0.1 mM EDTA, and 17% glycerol. PPO is eluted with 250 mM imidazole. The active protein was desalted on a PD-10 column (GE Healthcare Bio-Sciences Corp., Piscataway, N.J.) equilibrated with a 20 mM sodium phosphate buffer, pH 7.5, 5 mM MgCl2, 1 mM EDTA and 17% glycerol. Each liter of culture provided approximately 10 mg of pure PPO, which was stored at −20° C. until being used in assays.

Example 3

PPO Enzyme Assay (Non-Recombinant)

PPO protein (EC 1.3.3.4) was extracted from coleoptiles or shoots (150 g fresh weight) of dark-grown corn, black nightshade, morning glory, and velvetleaf seedlings as described previously (Grossmann et al. 2010). Before harvesting, the seedlings were allowed to green for 2 hours in the light in order to achieve the highest specific enzyme activities in the thylakoid fractions at low chlorophyll concentrations. At high chlorophyll concentrations significant quenching of fluorescence occurs, which limits the amount of green thylakoids that can be used in the test. Plant materials were homogenized in the cold with a Braun blender using a fresh-weight-to-volume ratio of 1:4. Homogenization buffer consisted of tris(hydroxymethyl) aminomethane (Tris)-HCl (50 mM; pH 7.3), sucrose (0.5 M), magnesium chloride (1 mM), ethylenediaminetetraacetic acid (EDTA) (1 mM) and bovine serum albumin (2 g $L^{-1}$). After filtration through four layers of Miracloth, crude plastid preparations were obtained after centrifugation at 10 000× g for 5 min and resuspension in homogenization buffer before centrifugation at 150×g for 2 min to remove crude cell debris. The supernatant was centrifuged at 4000×g for 15 min and the pellet fraction was resuspended in 1 ml of a buffer containing Tris-HCl (50 mM; pH 7.3), EDTA (2 mM), leupeptin (2 µM), pepstatin (2 µM) and glycerol (200 ml $L^{-1}$) and stored at −80° C. until use. Protein was determined in the enzyme extract with bovine serum albumin as a standard. PPO activity was assayed fluorometrically by monitoring the rate of Proto formation from chemically reduced protoporphyrinogen IX under initial velocity conditions. The assay mixture consisted of Tris-HCl (100 mM; pH 7.3), EDTA (1 mM), dithiothreitol (5 mM), Tween 80 (0.085%), protoporphyrinogen IX (2 µM), and 40 µg extracted protein in a total volume of 200 µl. The reaction was initiated by addition of substrate protoporphyrinogen IX at 22° C. saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control were prepared in dimethyl sulfoxide (DMSO) solution (0.1 mM concentration of DMSO in the assay) and added to the assay mixture in concentrations of 0.005 µM to 5 µM before incubation. Fluorescence was monitored directly from the assay mixture using a POLARstar Optima/Galaxy (BMG) with excitation at 405 nm and emission monitored at 630 nm. Non-enzymatic activity in the presence of heat-inactivated extract was negligible. Inhibition of enzyme activity induced by the herbicide was expressed as percentage inhibition relative to untreated controls. Molar concentrations of compound required for 50% enzyme inhibition (1050 values) were calculated by fitting the values to the dose-response equation using non-linear regression analysis.

Example 4

PPO Enzyme Assay (Recombinant)

Proto was purchased from Sigma-Aldrich (Milwaukee, Wis.). Protogen was prepared according to Jacobs and Jacobs (N. J. Jacobs, J. M. Jacobs, Assay for enzymatic protoporphyrinogen oxidation, a late step in heme synthesis, Enzyme 28 (1982) 206-219). Assays were conducted in 100 mM sodium phosphate pH 7.4 with 0.1 mM EDTA, 0.1% Tween 20, 5 µM FAD, and 500 mM imidazole. Dose-response curves with the PPO inhibitors saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control, and MC-15608 were obtained in the presence of 150 µM Protogen. Dose response was measured between the inhibitor concentration range of 1.00E-05 M to 1.00E-12 M. The excitation and emission bandwidths were set at 1.5 and 30 nm, respectively. All assays were made in duplicates or triplicates and measured using a POLARstar Optima/Galaxy (BMG) with excitation at 405 nm and emission monitored at 630 nm. Molar concentrations of compound required for 50% enzyme inhibition ($IC_{50}$ values) were calculated by fitting the values to the dose-response equation using non-linear regression analysis. Values were measured for *Alopecurus* wildtype and mutant PPO (ALOMY) in comparison with *Amaranthus* wildtype and mutant PPO (AMARE): Results are shown in the following Tables 3:

TABLE 3a

| Amino Acid Substitution | SEQ. ID NO. | Species | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|---|
| PPO herbicide sensitive PPO2 | 2 | ALOMY | 530 | 2.11E−07 | 3.64E−11 |
| PPO herbicide sensitive PPO2 WC | | AMARE | 1000 | 1.86E−09 | 5.17E−10 |
| PPO herbicide sensitive PPO2 AC | | AMARE | 800 | 1.78E−10 | 5.96E−11 |
| dG210 | | AMARE | 80 | 1.60E−06 | 2.12E−09 |
| R137I | 2 | ALOMY | 780 | 1.81E−06 | 1.30E−09 |
| R128I | | AMARE | 250 | 3.65E−07 | |
| R137V | 2 | ALOMY | 1060 | 1.93E−06 | 5.99E−10 |
| R128V | | AMARE | 600 | 2.49E−07 | |
| R137A | 2 | ALOMY | 700 | 2.08E−06 | 4.01E−11 |
| R128A | | AMARE | 730 | 1.29E−07 | 1.40E−10 |
| R137L | 2 | ALOMY | 420 | 6.73E−06 | 3.56E−09 |
| R128L | | AMARE | 700 | 2.22E−07 | 7.73E−10 |
| R137M | 2 | ALOMY | 1200 | >>0.00001 | 8.25E−10 |
| R128M | | AMARE | 200 | 6.97E−07 | |
| F438L | 2 | ALOMY | 905 | >0.00001 | 8.71E−08 |
| F420L | | AMARE | 200 | 7.20E−06 | 9.93E−10 |
| F438V | 2 | ALOMY | 1300 | >0.00001 | 3.64E−08 |
| F420V | | AMARE | 200 | 1.59E−06 | 1.61E−09 |
| F438M | 2 | ALOMY | 460 | >0.00001 | 2.23E−09 |
| F420M | | AMARE | 350 | 6.77E−07 | 2.75E−10 |
| R137A, F438M | 2 | ALOMY | 405 | >>0.00001 | 9.44E−08 |
| R128A, F420M | | AMARE | 400 | >0.00001 | 6.24E−09 |
| R137A, F438V | 2 | ALOMY | 220 | >>0.00001 | 5.37E−07 |
| R128A, F420V | | AMARE | 510 | >0.00001 | 2.50E−08 |
| F438I | 2 | ALOMY | 910 | >>0.00001 | 6.01E−08 |
| F420I | | AMARE | 200 | 9.19E−07 | 4.95E−10 |
| F438A | 2 | ALOMY | ND | ND | ND |
| F420A | | AMARE | ND | ND | ND |
| R137A, F438A | 2 | ALOMY | ND | ND | ND |
| R128A, F420A | | AMARE | ND | ND | ND |
| R137L, F438A | 2 | ALOMY | ND | ND | ND |
| R128L, F420A | | AMARE | ND | ND | ND |
| R137L, F438L | 2 | ALOMY | ND | ND | ND |
| R128L, F420L | | AMARE | 300 | >0.00001 | 1.71E−06 |
| R137L, F438V | 2 | ALOMY | ND | ND | ND |
| R128L, F420V | | AMARE | 300 | >0.00001 | 1.51E−06 |
| R137L, F438M | 2 | ALOMY | 230 | ND | 2.83E−06 |
| R128L, F420M | | AMARE | 400 | >0.00001 | 2.46E−07 |

TABLE 3a-continued

| Amino Acid Substitution | SEQ. ID NO. | Species | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|---|
| R137I, F438L | 2 | ALOMY | ND | ND | ND |
| R128I, F420L |  | AMARE | 200 | >0.00001 | 4.66E−07 |
| R137I, F438V | 2 | ALOMY | ND | ND | ND |
| R128I, F420V |  | AMARE | 470 | >0.00001 | 4.24E−07 |
| R137I, F438M | 2 | ALOMY | 322 | ND | 3.42E−06 |
| R128I, F420M |  | AMARE | 500 | >0.00001 | 2.46E−07 |
| R137V, F438A | 2 | ALOMY | ND | ND | ND |
| R128V, F420A |  | AMARE | ND | ND | ND |
| R137V, F438L | 2 | ALOMY | ND | ND | ND |
| R128V, F420L |  | AMARE | 370 | >0.00001 | 4.41E−07 |
| R137V, F438V | 2 | ALOMY | ND | ND | ND |
| R128V, F420V |  | AMARE | 300 | >0.00001 | 4.47E−07 |
| R137M, F438L | 2 | ALOMY | ND | ND | ND |
| R128M, F420L |  | AMARE | 300 | >0.00001 | 6.95E−07 |
| R137M, F438M | 2 | ALOMY | 220 | ND | 1.09E−06 |
| R128M, F420M |  | AMARE | 480 | >0.00001 | 7.05E−08 |
| R137A, F438L | 2 | ALOMY | ND | ND | ND |
| R128A, F420L |  | AMARE | 300 | >0.00001 | 1.62E−08 |
| R137M, F438I | 2 | ALOMY | ND | ND | ND |
| R128M, F420I |  | AMARE | 350 | >0.00001 | 4.45E−07 |
| R137L, F438I | 2 | ALOMY | ND | ND | ND |
| R128L, F420I |  | AMARE | 450 | >0.00001 | 1.23E−06 |
| R137M, F438A | 2 | ALOMY | ND | ND | ND |
| R128M, F420A |  | AMARE | ND | ND | ND |
| R137V, F438I | 2 | ALOMY | ND | ND | ND |
| R128V, F420I |  | AMARE | 300 | >0.00001 | 2.23E−07 |
| R137A, F438I | 2 | ALOMY | ND | ND | ND |
| R128A, F420I |  | AMARE | 330 | >0.00001 | 2,46E−08 |
| R137V, F438M | 2 | ALOMY | 582 | ND | 1.62E−06 |
| R128V, F420M |  | AMARE | 460 | >0.00001 | 4.27E−08 |
| R137I, F438I | 2 | ALOMY | ND | ND | ND |
| R128I, F420I |  | AMARE | 100 | >0.00001 | 4.33E−07 |
| R137M, F438V | 2 | ALOMY | ND | ND | ND |
| R128M, F420V |  | AMARE | 270 | >0.00001 | 7.04E−07 |
| R137I, F438A | 2 | ALOMY | ND | ND | ND |
| R128I, F420A |  | AMARE | ND | ND | ND |

TABLE 3b

| Common Name | Name | SEQ. ID NO. | Mutation | FU/min (rate) | IC50 (M) | inhibition (%) at 1 × 10−5M |
|---|---|---|---|---|---|---|
| FOMESAFEN |  | 2 | WT | 830 | 9.03E−08 |  |
| FOMESAFEN |  | 2 | R137V, F438M | 634 | ≥1.00E−05 | 18 |
| FOMESAFEN |  | 2 | R137C | 103 | 1.03E−05 |  |
| FOMESAFEN |  | 2 | R137N | 78 | ≥1.00E−05 | 11 |
| FOMESAFEN |  | 2 | R137Y, F438M | 129 | ≥1.00E−05 | −5 |
| FOMESAFEN |  | 2 | L415M, F438M | 105 | 3.54E−06 |  |
| LACTOFEN | (2-ethoxy-1-methyl-2-oxo-ethyl) 5-[2-chloro-4-(trifluoromethyl)phenoxy]-2-nitro-benzoate | 2 | WT | 830 | 1.87E−08 |  |
| LACTOFEN | (2-ethoxy-1-methyl-2-oxo-ethyl) 5-[2-chloro-4-(trifluoromethyl)phenoxy]-2-nitro-benzoate | 2 | R137V, F438M | 634 | ≥1.00E−05 | 46 |
| LACTOFEN | (2-ethoxy-1-methyl-2-oxo-ethyl) 5-[2-chloro-4-(trifluoromethyl)phenoxy]-2-nitro-benzoate | 2 | R137C | 103 | 4.22E−07 |  |
| LACTOFEN | (2-ethoxy-1-methyl-2-oxo-ethyl) 5-[2-chloro-4-(trifluoromethyl)phenoxy]-2-nitro-benzoate | 2 | R137N | 78 | 8.54E−08 |  |
| LACTOFEN | (2-ethoxy-1-methyl-2-oxo-ethyl) 5-[2-chloro-4-(trifluoromethyl)phenoxy]-2-nitro-benzoate | 2 | R137Y, F438M | 129 | ≥1.00E−05 | 39 |
| LACTOFEN | (2-ethoxy-1-methyl-2-oxo-ethyl) 5-[2-chloro-4-(trifluoromethyl)phenoxy]-2-nitro-benzoate | 2 | L415M, F438M | 105 | 5.62E−07 |  |
| BUTAFENACIL |  | 2 | WT | 830 | 1.31E−11 |  |
| BUTAFENACIL |  | 2 | R137V, F438M | 634 | 3.00E−07 |  |

TABLE 3b-continued

| Common Name | Name | SEQ. ID NO. | Mutation | FU/min (rate) | IC50 (M) | inhibition (%) at 1 × 10−5M |
|---|---|---|---|---|---|---|
| BUTAFENACIL | | 2 | R137C | 103 | 4.19E−10 | |
| BUTAFENACIL | | 2 | R137N | 78 | 8.32E−10 | |
| BUTAFENACIL | | 2 | R137Y, F438M | 129 | 1.25E−06 | |
| BUTAFENACIL | | 2 | L415M, F438M | 105 | 1.58E−09 | |
| CARFENTRAZONE-ETHYL | | 2 | WT | 830 | 1.47E−09 | |
| CARFENTRAZONE-ETHYL | | 2 | R137V, F438M | 634 | 5.27E−08 | |
| CARFENTRAZONE-ETHYL | | 2 | R137C | 103 | 2.38E−10 | |
| CARFENTRAZONE-ETHYL | | 2 | R137N | 78 | 5.62E−10 | |
| CARFENTRAZONE-ETHYL | | 2 | R137Y, F438M | 129 | 5.63E−07 | |
| CARFENTRAZONE-ETHYL | | 2 | L415M, F438M | 105 | 2.80E−07 | |
| ACIFLUORFEN | 5-(2-CHLORO-4-TRIFLUOROMETHYL-PHENOXY)-2-NITRO-BENZOIC ACID | 2 | WT | 830 | 1.14E−06 | |
| ACIFLUORFEN | 5-(2-CHLORO-4-TRIFLUOROMETHYL-PHENOXY)-2-NITRO-BENZOIC ACID | 2 | R137V, F438M | 634 | ≥1.00E−05 | 6 |
| ACIFLUORFEN | 5-(2-CHLORO-4-TRIFLUOROMETHYL-PHENOXY)-2-NITRO-BENZOIC ACID | 2 | R137C | 103 | ≥1.00E−05 | 29 |
| ACIFLUORFEN | 5-(2-CHLORO-4-TRIFLUOROMETHYL-PHENOXY)-2-NITRO-BENZOIC ACID | 2 | R137N | 78 | ≥1.00E−05 | 24 |
| ACIFLUORFEN | 5-(2-CHLORO-4-TRIFLUOROMETHYL-PHENOXY)-2-NITRO-BENZOIC ACID | 2 | R137Y, F438M | 129 | ≥1.00E−05 | 7 |
| ACIFLUORFEN | 5-(2-CHLORO-4-TRIFLUOROMETHYL-PHENOXY)-2-NITRO-BENZOIC ACID | 2 | L415M, F438M | 105 | ≥1.00E−05 | 43 |
| FLUMIOXAZIN | 2-(7-fluoro-3-oxo-4-prop-2-ynyl-1,4-benzoxazin-6-yl)-4,5,6,7-tetrahydroisoindole-1,3-dione | 2 | WT | 830 | 1.44E−10 | |
| FLUMIOXAZIN | 2-(7-fluoro-3-oxo-4-prop-2-ynyl-1,4-benzoxazin-6-yl)-4,5,6,7-tetrahydroisoindole-1,3-dione | 2 | R137V, F438M | 634 | ≥1.00E−05 | 13 |
| FLUMIOXAZIN | 2-(7-fluoro-3-oxo-4-prop-2-ynyl-1,4-benzoxazin-6-yl)-4,5,6,7-tetrahydroisoindole-1,3-dione | 2 | R137C | 103 | 3.09E−08 | |
| FLUMIOXAZIN | 2-(7-fluoro-3-oxo-4-prop-2-ynyl-1,4-benzoxazin-6-yl)-4,5,6,7-tetrahydroisoindole-1,3-dione | 2 | R137N | 78 | 5.11E−10 | |
| FLUMIOXAZIN | 2-(7-fluoro-3-oxo-4-prop-2-ynyl-1,4-benzoxazin-6-yl)-4,5,6,7-tetrahydroisoindole-1,3-dione | 2 | R137Y, F438M | 129 | ≥1.00E−05 | 0 |
| FLUMIOXAZIN | 2-(7-fluoro-3-oxo-4-prop-2-ynyl-1,4-benzoxazin-6-yl)-4,5,6,7-tetrahydroisoindole-1,3-dione | 2 | L415M, F438M | 105 | 2.29E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 2 | WT | 830 | 8.12E−08 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 2 | R137V, F438M | 634 | 9.48E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 2 | R137C | 103 | 7.84E−08 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 2 | R137N | 78 | 2.88E−07 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 2 | R137Y, F438M | 129 | ≥1.00E−05 | 11 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 2 | L415M, F438M | 105 | ≥1.00E−05 | 28 |
| OXIFLUORFEN | 2-CHLORO-1-(3-ETHOXY-4-NITROPHENOXY)-4-(TRIFLUOROMETHYL)BENZENE | 2 | WT | 830 | 8.24E−09 | |
| OXIFLUORFEN | 2-CHLORO-1-(3-ETHOXY-4-NITROPHENOXY)-4-(TRIFLUOROMETHYL)BENZENE | 2 | R137V, F438M | 635 | ≥1.00E−05 | 24 |
| OXIFLUORFEN | 2-CHLORO-1-(3-ETHOXY-4-NITROPHENOXY)-4-(TRIFLUOROMETHYL)BENZENE | 2 | R137C | 94 | 2.79E−07 | |
| OXIFLUORFEN | 2-CHLORO-1-(3-ETHOXY-4-NITROPHENOXY)-4-(TRIFLUOROMETHYL)BENZENE | 2 | R137N | 68 | 2.57E−06 | |

TABLE 3b-continued

| Common Name | Name | SEQ. ID NO. | Mutation | FU/min (rate) | IC50 (M) | inhibition (%) at 1 × 10−5M |
|---|---|---|---|---|---|---|
| OXIFLUORFEN | 2-CHLORO-1-(3-ETHOXY-4-NITROPHENOXY)-4-(TRIFLUOROMETHYL)BENZENE | 2 | R137Y, F438M | 132 | ≥1.00E−05 | 29 |
| OXIFLUORFEN | 2-CHLORO-1-(3-ETHOXY-4-NITROPHENOXY)-4-(TRIFLUOROMETHYL)BENZENE | 2 | L415M, F438M | 67 | 7.03E−08 | |
| OXADIARGYL | | 2 | WT | 830 | 1.17E−09 | |
| OXADIARGYL | | 2 | R137V, F438M | 635 | 1.78E−08 | |
| OXADIARGYL | | 2 | R137C | 94 | 7.11E−10 | |
| OXADIARGYL | | 2 | R137N | 68 | 3.48E−09 | |
| OXADIARGYL | | 2 | R137Y, F438M | 132 | 1.46E−08 | |
| OXADIARGYL | | 2 | L415M, F438M | 67 | 1.02E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 2 | WT | 830 | 6.45E−11 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 2 | R137V, F438M | 635 | 9.50E−07 | |
| S-3101 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 2 | R137C | 94 | 5.52E−10 | |
| S-3102 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 2 | R137N | 68 | 2.37E−09 | |
| S-3103 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 2 | R137Y, F438M | 132 | 9.92E−07 | |
| S-3104 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 2 | L415M, F438M | 67 | 1.21E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | 2 | WT | 830 | 3.64E−11 | |
| BAS 850H | See above | 2 | R137I, F438M | 286 | 6.43E−07 | |
| BAS 850H | See above | 2 | R137V, F438M | 634 | 7.77E−07 | |
| BAS 850H | See above | 2 | R137V, F438M | 635 | 8.30E−07 | |
| BAS 850H | See above | 2 | R137V, F438M | 467 | 5.96E−07 | |
| BAS 850H | See above | 2 | R137C | 103 | 6.93E−11 | |
| BAS 850H | See above | 2 | R137C | 94 | 1.18E−10 | |
| BAS 850H | See above | 2 | R137C | 92 | 1.07E−10 | |
| BAS 850H | See above | 2 | R137G | 409 | 2.90E−10 | |
| BAS 850H | See above | 2 | R137N | 78 | 9.37E−11 | |
| BAS 850H | See above | 2 | R137N | 68 | 9.42E−11 | |
| BAS 850H | See above | 2 | R137F | 489 | 1.46E−09 | |
| BAS 850H | See above | 2 | R137S | 481 | 9.24E−11 | |
| BAS 850H | See above | 2 | R137T | 683 | 5.78E−10 | |
| BAS 850H | See above | 2 | R137H | 240 | 1.17E−10 | |
| BAS 850H | See above | 2 | R137Q | 1145 | 6.10E−10 | |
| BAS 850H | See above | 2 | R137Y, F438M | 129 | 1.34E−06 | |
| BAS 850H | See above | 2 | R137Y, F438M | 132 | 6.05E−07 | |
| BAS 850H | See above | 2 | R137Y, F438M | 107 | 5.12E−07 | |
| BAS 850H | See above | 2 | R137F, F438M | 123 | 2.22E−06 | |
| BAS 850H | See above | 2 | L415M, F438M | 105 | 2.79E−09 | |
| BAS 850H | See above | 2 | L415M, F438M | 67 | 4.44E−09 | |
| BAS 850H | See above | 2 | L415M, F438M | 98 | 4.08E−09 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 2 | WT | 830 | 2.43E−10 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 2 | R137V, F438M | 635 | ≥1.00E−05 | 27 |
| 850 analogon | 2-(2,2,7-trifluoro-3-oxo-4-prop-2-ynyl-1,4-benzoxazin-6-yl)-4,5,6,7-tetrahydroisoindole-1,3-dione | 2 | R137C | 94 | 9.29E−10 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 2 | R137N | 68 | 7.45E−09 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 2 | R137Y, F438M | 132 | ≥1.00E−05 | 20 |
| 850 analogon | 2-(2,2,7-trifluoro-3-oxo-4-prop-2-ynyl-1,4-benzoxazin-6-yl)-4,5,6,7-tetrahydroisoindole-1,3-dione | 2 | L415M, F438M | 67 | 9.11E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 2 | WT | 830 | 1.89E−10 | |

TABLE 3b-continued

| Common Name | Name | SEQ. ID NO. | Mutation | FU/min (rate) | IC50 (M) | inhibition (%) at 1 × 10-5M |
|---|---|---|---|---|---|---|
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 2 | R137V, F438M | 635 | 3.12E-06 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 2 | R137C | 94 | 4.79E-10 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 2 | R137N | 68 | 1.60E-09 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 2 | R137Y, F438M | 132 | 3.12E-06 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 2 | L415M, F438M | 67 | 1.12E-09 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | WT | 830 | 1.94E-10 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137I, F438M | 286 | 1.43E-07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137V, F438M | 467 | 1.51E-07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137G | 409 | 5.00E-10 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137F | 489 | 6.94E-10 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137S | 481 | 3.30E-10 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137T | 683 | 3.36E-10 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137H | 240 | 2.83E-10 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137Q | 1145 | 6.78E-10 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137Y, F438M | 107 | 8.26E-07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137F, F438M | 123 | 3.78E-07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | L415M, F438M | 98 | 2.62E-07 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | WT | 830 | 8.16E-10 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137I, F438M | 286 | 1.60E-07 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137V, F438M | 467 | 2.36E-07 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137C | 92 | 8.47E-10 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137G | 409 | 8.78E-10 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137Y, F438M | 107 | 2.44E-06 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | L415M, F438M | 98 | 1.09E-07 | |

TABLE 3b-continued

| Common Name | Name | SEQ. ID NO. | Mutation | FU/min (rate) | IC50 (M) | inhibition (%) at 1 × 10−5M |
|---|---|---|---|---|---|---|
| | (trifluoromethyl)pyrimidin-1-yl]phenoxy]phenoxy]-2-methoxy-acetate | | | | | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | WT | 830 | 2.99E−09 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137I, F438M | 286 | 3.00E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137V, F438M | 467 | 3.42E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137G | 409 | 9.84E−10 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137F | 489 | 8.93E−09 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137S | 481 | 7.90E−10 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137T | 683 | 6.62E−09 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137H | 240 | 9.90E−09 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137Q | 1145 | 3.31E−09 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137Y, F438M | 107 | 5.57E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137F, F438M | 123 | 5.58E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | L415M, F438M | 98 | 1.14E−06 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | WT | 830 | 6.71E−10 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137I, F438M | 286 | 1.82E−07 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137V, F438M | 467 | 2.03E−07 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137C | 92 | 3.86E−09 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137G | 409 | 1.25E−09 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137Y, F438M | 107 | 5.38E−06 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | L415M, F438M | 98 | 2.54E−07 | |

TABLE 3b-continued

| Common Name | Name | SEQ. ID NO. | Mutation | FU/min (rate) | IC50 (M) | inhibition (%) at 1 × 10−5M |
|---|---|---|---|---|---|---|
| | (trifluoromethyl)pyrimidin-1-yl]phenoxy]phenoxy]-2-methoxy-acetate | | | | | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | WT | 830 | 7.51E−10 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137I, F438M | 286 | 2.04E−07 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137V, F438M | 467 | 2.00E−07 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137C | 92 | 9.25E−10 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137G | 409 | 1.93E−09 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137Y, F438M | 107 | 2.66E−06 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | L415M, F438M | 98 | 8.04E−07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | WT | 830 | 3.35E−10 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137I, F438M | 286 | 3.36E−07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137V, F438M | 467 | 7.50E−07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137C | 92 | 1.95E−10 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137G | 409 | 1.23E−09 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | R137Y, F438M | 107 | 1.45E−06 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 | L415M, F438M | 98 | 1.51E−07 | |

IC50 (M): Concentration of inhibitor required for 50% inhibition of enzyme activity; ≥1.00E−5: indicates a very high IC50 over the measurement boundaries, which reflects very high in vitro tolerance.

Example 5

Engineering PPO-Derivative Herbicide Tolerant Plants Having Wildtype or Mutated PPO Sequences PPO-derivative herbicide tolerant soybean (*Glyceine max*), corn (*Zea mays*), and Canola (*Brassica napus* or *Brassica Rapa* var. or *Brassica campestris* L.) plants are produced by a method as described by Olhoft et al. (US patent 2009/0049567). For transformation of soybean or *Arabidopsis thaliana*, Wildtype or Mutated PPO sequences based on one of the following sequences SEQ ID NO: 1, or 3, are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOD in between ubiquitin promoter (PcUbi) and nopaline synthase terminator (NOS) sequence. For corn transformation, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOD in between corn ubiquitin promoter (ZmUbi) and nopaline synthase terminator (NOS) sequence. Binary plasmids are introduced to Agrobacterium tumefaciens for plant transformation. Plasmid constructs are introduced into soybean's axillary meristem cells at the primary node of seedling explants via Agrobacterium-mediated transformation. After inoculation and co-cultivation with Agrobacteria, the explants are transferred to shoot introduction media without selection for one week. The explants were subsequently transferred to a shoot induction medium with 1-3 µM imazapyr (Arsenal) for 3 weeks to select for transformed cells. Explants with healthy callus/shoot pads at the primary node are then transferred to shoot elongation medium containing 1-3 µM imazapyr until a shoot elongated or the explant died. Transgenic plantlets are rooted, subjected to TaqMan analysis for the presence of the transgene, transferred to soil and grown to maturity in greenhouse. Transformation of corn plants are done by a method described by McElver and Singh (WO 2008/124495). Plant transformation vector constructs containing mutated PPO sequences are introduced into maize immature embryos via Agrobacterium-mediated transformation.

Transformed cells were selected in selection media supplemented with 0.5-1.5 µM imazethapyr for 3-4 weeks. Transgenic plantlets were regenerated on plant regeneration media and rooted afterwards. Transgenic plantlets are subjected to TaqMan analysis for the presence of the transgene before being transplanted to potting mixture and grown to maturity in greenhouse. Arabidopsis thaliana are transformed with wildtype or mutated PPO sequences by floral dip method as described by McElver and Singh (WO 2008/124495). Transgenic Arabidopsis plants were subjected to TaqMan analysis for analysis of the number of integration loci. Transformation of Oryza sativa (rice) are done by protoplast transformation as described by Peng et al. (U.S. Pat. No. 6,653,529) T0 or T1 transgenic plant of soybean, corn, and rice containing mutated PPO sequences are tested for improved tolerance to PPO-derived herbicides in greenhouse studies and mini-plot studies with the following PPO-inhibiting herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control.

Example 6

Tissue Culture Conditions

An in vitro tissue culture mutagenesis assay has been developed to isolate and characterize plant tissue (e.g., maize, rice tissue) that is tolerant to protoporphyrinogen oxidase inhibiting herbicides, (saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control). The assay utilizes the somaclonal variation that is found in in vitro tissue culture. Spontaneous mutations derived from somaclonal variation can be enhanced by chemical mutagenesis and subsequent selection in a stepwise manner, on increasing concentrations of herbicide.

The present invention provides tissue culture conditions for encouraging growth of friable, embryogenic maize or rice callus that is regenerable. Calli were initiated from 4 different maize or rice cultivars encompassing Zea mays and Japonica (Taipei 309, Nipponbare, Koshihikari) and Indica (Indica 1) varieties, respectively. Seeds were surface sterilized in 70% ethanol for approximately 1 min followed by 20% commercial Clorox bleach for 20 minutes. Seeds were rinsed with sterile water and plated on callus induction media. Various callus induction media were tested. The ingredient lists for the media tested are presented in Table 4.

TABLE 4

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | | 30 g/L | | |
| Sucrose | VWR | | | | | 10 g/L | 30 g/L |
| NAA | Duchefa | | | | | 50 µg/L | |
| 2,4-D | Sigma | 2.0 mg/L | | | | | 1.0 mg/L |
| MgCl₂•6H₂O | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001 M callus induction media was selected after testing numerous variations. Cultures were kept in the dark at 30° C. Embryogenic callus was subcultured to fresh media after 10-14 days.

Example 7

Selection of Herbicide-Tolerant Calli

Once tissue culture conditions were determined, further establishment of selection conditions were established through the analysis of tissue survival in kill curves with saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Careful consideration of accumulation of the herbicide in the tissue, as well as its persistence and stability in the cells and the culture media was performed. Through these experiments, a sub-lethal dose has been established for the initial selection of mutated material. After the establishment of the starting dose of saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control in selection media, the tissues were selected in a step-wise fashion by increasing the concentration of the PPO inhibitor with each transfer until cells are recovered that grew vigorously in the presence of toxic doses. The resulting calli were further subcultured every 3-4 weeks to R001 M with selective agent. Over 26,000 calli were subjected to selection for 4-5 subcultures until the selective pressure was above toxic levels as determined by kill curves and observations of continued culture. Alternatively, liquid cultures initiated from calli in MS711R with slow shaking and weekly subcultures. Once liquid cultures were established, selection agent was added directly to the flask at each subculture. Following 2-4 rounds of liquid selection, cultures were transferred to filters on solid R001 M media for further growth.

Example 8

Regeneration of Plants

Tolerant tissue was regenerated and characterized molecularly for PPO gene sequence mutations and/or biochemically for altered PPO activity in the presence of the selective agent. In addition, genes involved directly and/or indirectly in tetrapyrrole biosynthesis and/or metabolism pathways were also sequenced to characterize mutations. Finally, enzymes that change the fate (e.g. metabolism, translocation, transportation) were also sequence to characterized mutations. Following herbicide selection, calli were regenerated using a media regime of R025M for 10-14 days, R026M for ca. 2 weeks, R327M until well formed shoots were developed, and R008S until shoots were well rooted for transfer to the greenhouse. Regeneration was carried out in the light. No selection agent was included during regeneration. Once strong roots were established, MO regenerants were transplant to the greenhouse in square or round pots. Transplants were maintained under a clear plastic cup until they were adapted to greenhouse conditions. The greenhouse was set to a day/night cycle of 27° C./21° C. (80° F./70° F.) with 600 W high pressure sodium lights supplementing light to maintain a 14 hour day length. Plants were watered according to need, depending in the weather and fertilized daily.

Example 9

Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using the appropriate forward and reverse primer.

PCR amplification was performed using Hotstar Taq DNA Polymerase (Qiagen) using touchdown thermocycling program as follows: 96° C. for 15 min, followed by 35 cycles (96° C., 30 sec; 58° C.—0.2° C. per cycle, 30 sec; 72° C., 3 min and 30 sec), 10 min at 72° C. PCR products were verified for concentration and fragment size via agarose gel electrophoresis. Dephosphorylated PCR products were analyzed by direct sequence using the PCR primers (DNA Landmarks, or Entelechon). Chromatogram trace files (.scf) were analyzed for mutation relative to the wild-type gene using Vector NTI Advance 10™ (Invitrogen). Based on sequence information, mutations were identified in several individuals. Sequence analysis was performed on the representative chromatograms and corresponding AlignX alignment with default settings and edited to call secondary peaks.

Example 10

Demonstration of Herbicide-Tolerance

T0 or T1 transgenic plant of soybean, corn, Canola varieties and rice containing PPO1 and or PPO2 sequences are tested for improved tolerance to herbicides in greenhouse studies and mini-plot studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly, and grown in the same containers or they are first grown separately and transplanted into the test containers a few days prior to treatment.

For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated. Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0% to 100%, 0% being no injury and 100% being complete death.

Transgenic *Arabidopsis thaliana* plants were assayed for improved tolerance to saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control, in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) *Physiologia Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 μmol Phot*m$^{-2}$*s$^{-1}$ with 14:10 h light:dark photoperiod. Growth inhibition is evaluated seven to ten days after seeding in comparison to wild type plants. The results are shown in Table 5 and FIG. 2.

Figure 3:
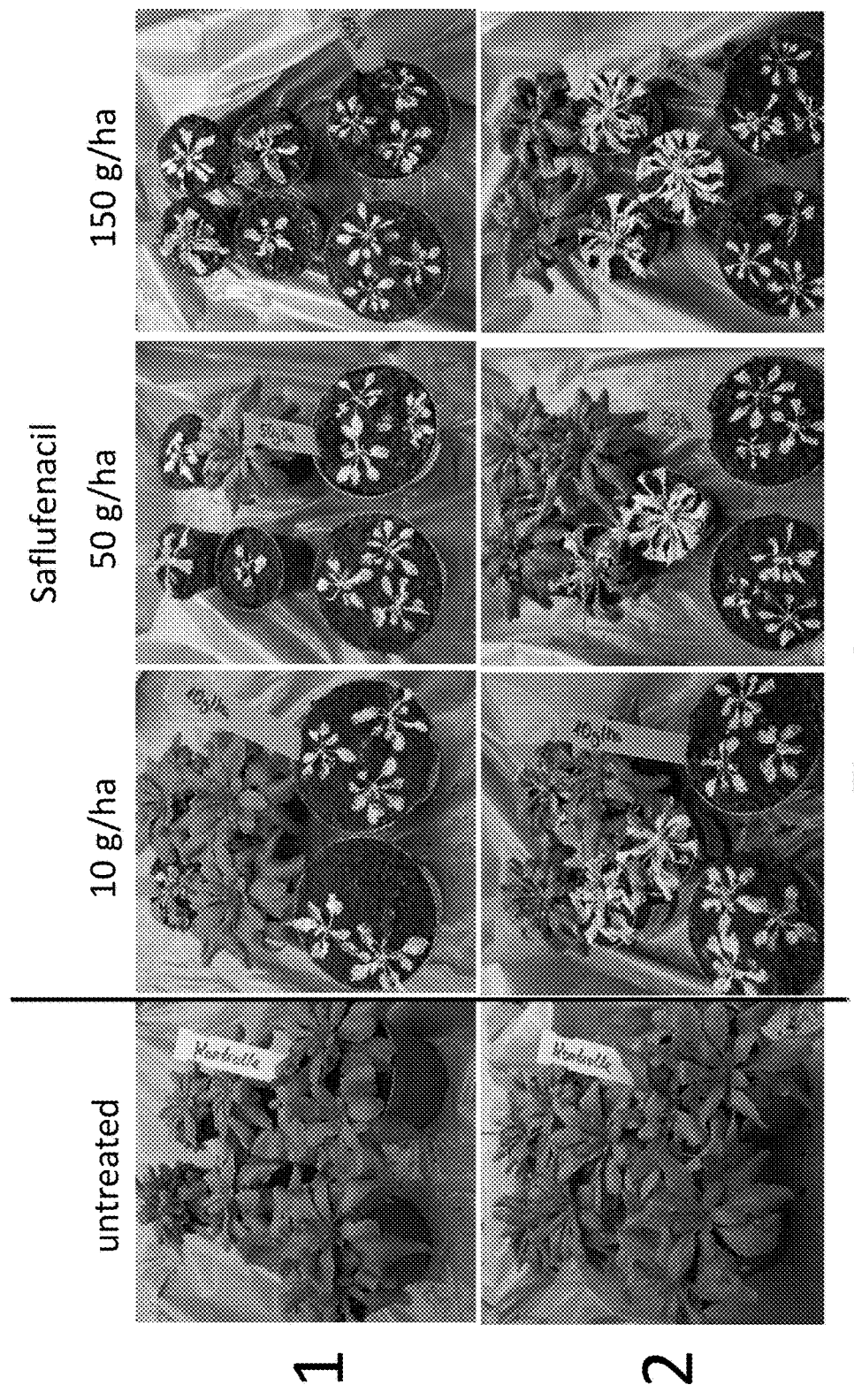
FIG. 3 shows T1 *Arabidopsis* plants (1 per pot) transformed with nucleic acids encoding mutated *Alopecurus* (ALOMY) PPO1 comprising (1) Am_PPO1_T299L_Y420M; or (2) Am_PPO1_T299L_S300G_Y420V. For comparison, wildtype plants (3 per pot) always placed at the bottom of each picture.

Additionally, transgenic T1 *Arabidopsis* plants were tested for improved tolerance to herbicides in greenhouse studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (BAS 850H; CAS 1258836-72-4), flumioxazin, butafenacil, acifluorfen, lactofen, bifenox, sulfentrazone, and photosynthesis inhibitor diuron as negative control. The results are shown FIG. 3

TABLE 5

Relative tolerance rates (TF = Tolerance Factor) of transgenic *Arabidopsis* plants as compared to a non-transgenic *Arabidopsis* plant (non-transgenic = 1.0), treated with various PPO inhibitors. Growth inhibition is evaluated seven to ten days after seeding in comparison to wild type plants.

| mutation | TF Saflufenacil | BAS 850H |
|---|---|---|
| Am_PPO2_R137A | 1500 | >50 |
| Am_PPO2_R137V | 1500 | >50 |
| Am_PPO2_R137I | 2140 | >50 |
| Am_PPO2_R137L | 3300 | >50 |
| Am_PPO2_R137M | 3300 | >50 |
| Am_PPO2_F438V | 1560 | >50 |
| Am_PPO2_F438I | 3300 | >50 |
| Am_PPO2_F438L | 1700 | >50 |
| Am_PPO2_F438M | 2500 | >50 |
| Am_PPO2_R137A_F438V | 2500 | >50 |
| Am_PPO2_R137A_F438I | 950 | >50 |
| Am_PPO2_R137A_F438L | 2300 | >50 |
| Am_PPO2_R137A_F438M | 2500 | >50 |
| Am_PPO2_R137L_F438I | 2700 | >50 |
| Am_PPO2_R137L_F438L | 2700 | >50 |

TABLE 5-continued

Relative tolerance rates (TF = Tolerance Factor) of transgenic *Arabidopsis* plants as compared to a non-transgenic *Arabidopsis* plant (non-transgenic = 1.0), treated with various PPO inhibitors. Growth inhibition is evaluated seven to ten days after seeding in comparison to wild type plants.

| mutation | TF Saflufenacil | BAS 850H |
|---|---|---|
| Am_PPO2_R137L_F438M | 3100 | >50 |
| Am_PPO2_R137M_F438V | 1900 | >50 |
| Am_PPO2_R137M_F438I | 1740 | >50 |
| Am_PPO2_R137M_F438L | 1340 | >50 |
| Am_PPO2_R137M_F438M | 1700 | >50 |

Example 11

Herbicide Selection Using Tissue Culture

Media was selected for use and kill curves developed as specified above. For selection, different techniques were utilized. Either a step wise selection was applied, or an immediate lethal level of herbicide was applied. In either case, all of the calli were transferred for each new round of selection. Selection was 4-5 cycles of culture with 3-5 weeks for each cycle. Cali were placed onto nylon membranes to facilitate transfer (200 micron pore sheets, Biodesign, Saco, Me.). Membranes were cut to fit 100×20 mm Petri dishes and were autoclaved prior to use 25-35 calli (average weight/calli being 22 mg) were utilized in every plate. In addition, one set of calli were subjected to selection in liquid culture media with weekly subcultures followed by further selection on semi-solid media. Mutant lines were selected using saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Efficiencies of obtaining mutants was high either based on a percentage of calli that gave rise to a regenerable, mutant line or the number of lines as determined by the gram of tissue utilized.

Example 12

Maize Whole Plant Transformation and PPO Inhibitor Tolerance Testing

Figure 5:
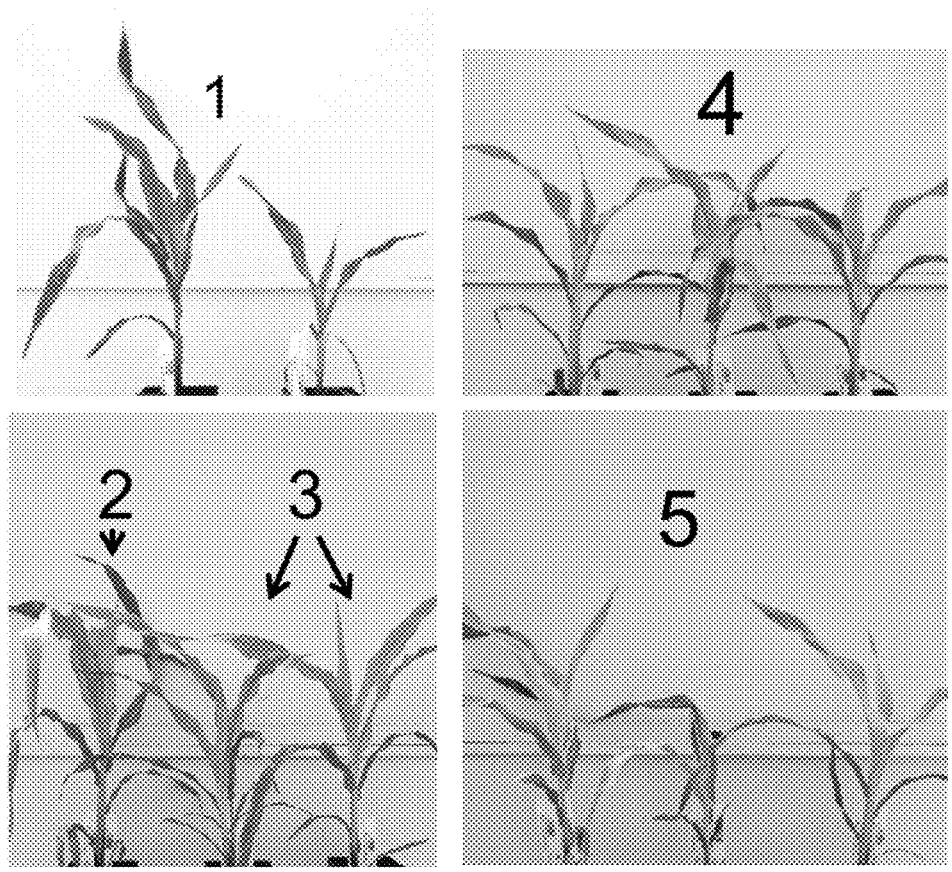
FIG. 5 shows T0 Transformed corn 3 days after treatment. Plants were sprayed at the V2-V3 stage.
1=Wild type;
2=tp-SorbiPPO2_AlomyPPO2_R130L_F431M (SEQ ID NO: 22);
3=tp-ZeamaPPO2_AlomyPPO2_R130L (SEQ ID NO: 14);
4=tp-ZeamaPPO2_AlomyPPO2_R130L_F431M (SEQ ID NO: 17);
5=tp-ZeamaPPO2_AlomyPPO2_R130M_F431M (SEQ ID NO: 19)

Immature embryos were transformed according to the procedure outlined in Peng et al. (WO2006/136596). Plants were tested for the presence of the T-DNA by Taqman analysis with the target being the nos terminator which is present in all constructs. Healthy looking plants were sent to the greenhouse for hardening and subsequent spray testing. The plants were individually transplanted into MetroMix 360 soil in 4' pots. Once in the greenhouse (day/night cycle of 27° C./21° C. with 14 hour day length supported by 600 W high pressure sodium lights), they were allowed to grow for 14 days. They were then sprayed with a treatment of 25 to 200 g ai/ha saflufenacil+1.0% v/v methylated seed oil (MSO) and/or 25-200 g ai/ha 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (BAS 850H; CAS 1258836-72-4) plus 1% MSO. Other PPO inhibiting herbicides were also tested in a similar fashion for confirming cross resistance: flumioxazin, butafenacil, acifluorfen, lactofen, bifenox, sulfentrazone, and photosynthesis inhibitor diuron as negative control. Herbicide injury evaluations were taken at 7, 14 and 21 days after treatment. Herbicide injury evaluations were taken 2, 7, 14 and 21 days post-spray to look for injury to new growth points and overall plant health. The top survivors were transplanted into gallon pots filled with MetroMix 360 for seed production. The results are shown in Table 6 and FIG. 5. It will be acknowledged by the person skilled in the art that by replacing the natural transit peptide of an *Alopecurus* PPO2 comprising the sequence of SEQ ID NO: 2, against a heterologous transit peptide from *Zea mays* (SEQ ID NO: 8) or *Sorghum bicolor* (SEQ ID NO: 9), the native N-terminal end of SEQ ID NO: 2 is shortened by 7 amino acids. Therefore, preferred mutational sites at or corresponding to, for example, positions R137 or F438 on SEQ ID NO: 2, as described above in the description in greater detail, are identical to positions R130 or F431 in said fusion proteins. See e.g. construct named tp-ZeamaPPO2::AlomyPPO2_R130A_F431V in Table 6.

TABLE 6a

Transgenic T0 corn events were sprayed in the greenhouse with the indicated amount of compound + 1% (v/v) MSO at V2 stage. Herbicide injury was evaluated 7 days after treatment with a 0 to 9 rating scale where 0 is no injury relative to an unsprayed wild type check and 9 is completely dead; BAS 800H refers to Saflufenacil/Kixor; BAS 850H refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4);

| SEQ ID | Event | Unsprayed | BAS 800H g ai/ha | | | BAS 850H g ai/ha | | |
|---|---|---|---|---|---|---|---|---|
| | | | 50 | 75 | 100 | 50 | 75 | 100 |
| untransformed | wild type | 0 | 7 | 8 | 8 | 6 | 6 | 6 |
| AlomyPPO1_R138A | 1 | 0 | | | 6 | | | |
| | 2 | 0 | | | 6 | | | |
| | 3 | 0 | | | 6 | | | |
| AlomyPPO1_Y420V | 1 | 0 | | | 5 | | | |
| | 2 | 0 | | | 4 | | | |
| | 3 | 0 | | | 6 | | | |
| | 4 | 0 | | | 6 | | | |
| | 5 | | | | | 6 | | |
| | 6 | 0 | | | 6 | | | |
| AlomyPPO1_Y420M | 1 | 0 | | | 5 | | | |
| | 2 | 0 | | | 6 | | | |
| | 3 | 0 | | | 6 | | | |
| | 4 | | | | | 6 | | |
| | 5 | 0 | | | 5 | | | |
| AlomyPPO1_R138A_Y420V | 1 | 0 | | | | | | |
| | 2 | | | | 6 | | | |
| | 3 | 0 | | | | | | |
| | 4 | | | | 5 | | | |
| | 5 | | | | | 5 | | |
| | 6 | 0 | | | | | | |
| | 7 | | | | 5 | | | |
| | 8 | 0 | | | | | | |
| | 9 | 0 | | | | | | |
| | 10 | 0 | | | | | | |
| | 11 | | | | | 5 | | |
| AlomyPPO1_R138A_Y420M | 1 | 0 | | | | | | |
| | 2 | | | | 5 | | | |
| | 3 | 2 | | | | | | |
| | 4 | | | | 6 | | | |
| | 5 | 0 | | | | | | |
| | 6 | | | | 5 | | | |
| | 7 | 0 | | | | | | |
| | 8 | 2 | | | | | | |
| | 9 | 0 | | | | | | |

TABLE 6a-continued

Transgenic T0 corn events were sprayed in the greenhouse with the indicated amount of compound + 1% (v/v) MSO at V2 stage. Herbicide injury was evaluated 7 days after treatment with a 0 to 9 rating scale where 0 is no injury relative to an unsprayed wild type check and 9 is completely dead; BAS 800H refers to Saflufenacil/Kixor; BAS 850H refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4);

| SEQ ID | Event | Unsprayed | BAS 800H g ai/ha | | | BAS 850H g ai/ha | | |
|---|---|---|---|---|---|---|---|---|
| | | | 50 | 75 | 100 | 50 | 75 | 100 |
| tp-ZeamaPPO2::AlomyPPO2 | 1 | 0 | | | | 5 | | |
| | 2 | 0 | | | | 5 | | |
| | 3 | 0 | | | | 6 | | |
| | 4 | 0 | | | | 6 | | |
| tp-ZeamaPPO2::AlomyPPO2_R130A | 1 | 0 | | | | 7 | | |
| | 2 | 0 | | | | 4 | | |
| | 3 | 0 | | | | 5 | | |
| | 4 | 0 | | | | 5 | | |
| | 5 | 0 | | | | 6 | | |
| | 6 | 0 | | | | 5 | | |
| | 7 | 0 | | 0 | | 6 | | 5 |
| | 8 | 0 | | | | 5 | | |
| | 9 | 0 | | 0 | | 6 | | 5 |
| | 10 | | | | | 6 | | |
| | 11 | | | | | 5 | | |
| | 12 | | | | | 5 | | |
| | 13 | | | | | 6 | | |
| | 14 | | | | | 6 | | |
| | 15 | | | | | 6 | | |
| tp-ZeamaPPO2::AlomyPPO2_F431V | 1 | 0 | | | | 3 | | 4 |
| | 2 | 0 | | | | 4 | | |
| | 3 | 0 | | | | 4 | | |
| | 4 | 0 | | 0 | | 4 | | 4 |
| | 5 | 0 | | 0 | | 4 | | 4 |
| | 6 | | | | | 4 | | |
| | 7 | | | | | 5 | | |
| | 8 | 0 | | | | 4 | | |
| | 9 | 0 | | | | 4 | | |
| | 10 | 0 | | 0 | | 4 | | 4 |
| | 11 | 0 | | 0 | | 4 | | 4 |
| | 12 | | | | | 4 | | |
| | 13 | | | | | 5 | | |
| | 14 | 0 | | | | 4 | | |
| | 15 | 0 | | | | 5 | | |
| | 16 | 0 | | | | 4 | | 4 |
| | 17 | | | | | 5 | | |
| | 18 | | | | | 4 | | |
| | 19 | | | | | 4 | | |
| | 20 | | | | | 4 | | |
| tp-ZeamaPPO2::AlomyPPO2_R130A_F431V | 1 | 0 | | | | 4 | | |
| | 2 | 1 | | | | 5 | | |
| | 3 | 0 | | | | 5 | | |
| | 4 | 0 | | | | 4 | | |
| | 5 | 0 | | | | 4 | | |
| | 6 | 0 | | | | 4 | | |
| | 7 | 0 | | | | 4 | | |
| tp-SorbiPPO2::AlomyPPO2 | 1 | 0 | | | | 5 | | |
| | 2 | 0 | | | | 5 | | |
| | 3 | 0 | | | | 5 | | |
| | 4 | 0 | | | | 5 | | |
| | 5 | 0 | | | | 5 | | |
| | 6 | 0 | | | | 6 | | |
| | 7 | 0 | | | | 5 | | |
| | 8 | 0 | | | | 6 | | |
| | 9 | 0 | | | | 5 | | 5 |
| tp-SorbiPPO2::AlomyPPO2_R130A | 1 | 0 | | | | 4 | | |
| | 2 | 0 | | | | 5 | | |
| | 3 | 0 | | | | 5 | | |
| | 4 | 0 | | | | 5 | | |
| tp-SorbiPPO2::AlomyPPO2_F431V | 1 | 1 | | | | | | |
| | 2 | | | | | 4 | | |
| | 3 | | | | | | | 5 |
| | 4 | 0 | | | | | | |

TABLE 6a-continued

Transgenic T0 corn events were sprayed in the greenhouse with the indicated amount of compound + 1% (v/v) MSO at V2 stage. Herbicide injury was evaluated 7 days after treatment with a 0 to 9 rating scale where 0 is no injury relative to an unsprayed wild type check and 9 is completely dead; BAS 800H refers to Saflufenacil/Kixor; BAS 850H refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4);

| SEQ ID | Event | Unsprayed | BAS 800H g ai/ha 50 | 75 | 100 | BAS 850H g ai/ha 50 | 75 | 100 |
|---|---|---|---|---|---|---|---|---|
| | 5 | | | | | 5 | | |
| | 6 | 0 | | | | | | |
| | 7 | | | | | 5 | | |
| | 8 | | | | | | | 6 |
| | 9 | | 3 | | | | | |
| tp-SorbiPPO2::AlomyPPO2_R130A_F431V | 1 | 0 | | | | 6 | | |
| | 2 | 0 | | | | 5 | | |
| | 3 | 0 | | | | 5 | | |
| | 4 | 0 | | | | 4 | | |
| | 5 | 0 | 7 | | | 2 | 7 | |
| | 6 | 0 | 7 | | | 3 | 6 | |
| | 7 | 0 | | | | 3 | 6 | |
| | 8 | 0 | | | | 2 | 6 | |
| | 9 | 1 | | | | 2 | 6 | |
| tp-ZeamaPPO2::c-AlomyPPO2_R130L | 1 | | | | | 4 | | |
| | 2 | | | | | 3 | | |
| | 3 | | | | | 0 | | |
| | 4 | | | | | 2 | | |
| | 5 | | | | | 2 | | |
| | 6 | | | | | 1 | | |
| tp-ZeamaPPO2::c-AlomyPPO2_R130A_F431M | 1 | 0 | | | | 5 | | |
| | 2 | 0 | | | | 4 | | |
| | 3 | 0 | | | | 4 | | |
| | 4 | 0 | | | | 5 | | |
| | 5 | | | | | 4 | | |
| | 6 | | | | | 4 | | |
| | 7 | | | | | 6 | | |
| | 8 | | | | | 6 | | |
| | 9 | | | | | 7 | | |
| | 10 | | | | | 3 | | |
| | 11 | | | | | 6 | | |
| | 12 | | | | | 6 | | |
| | 13 | | | | | 6 | | |
| | 14 | | | | | 4 | | |
| | 15 | | | | | 3 | | |
| tp-ZeamaPPO2::c-AlomyPPO2_R130L_F431V | 1 | 1 | | | | 3 | | |
| | 2 | 2 | | | | 4 | | |
| | 3 | | | | | 3 | | |
| | 4 | | | | | 3 | | |
| | 5 | | | | | 4 | | |
| | 6 | | | | | 4 | | |
| | 7 | | | | | 4 | | |
| | 8 | | | | | 4 | | |
| | 9 | | | | | 4 | | |
| | 10 | | | | | 4 | | |
| | 11 | | | | | 5 | | |
| | 12 | | | | | 6 | | |
| tp-ZeamaPPO2::c-AlomyPPO2_R130L_F431M | 1 | | | | | 3 | | |
| | 2 | | | | | 3 | | |
| | 3 | | | | | 1 | | |
| | 4 | | | | | 1 | | |
| | 5 | | | | | 0 | | |
| | 6 | | | | | 1 | | |
| | 7 | | | | | 2 | | |
| tp-ZeamaPPO2::c-AlomyPPO2_R130M_F431V | 1 | 1 | | | | 3 | | |
| | 2 | 0 | | | | 4 | | |
| | 3 | | | | | 2 | | |
| | 4 | 0 | | | | 4 | | |
| | 5 | | | | | 4 | | |
| | 6 | | | | | 4 | | |
| | 7 | | | | | 4 | | |
| tp-ZeamaPPO2::c-AlomyPPO2_R130M_F431M | 1 | 0 | | | | 2 | | |
| | 2 | 0 | | | | 0 | | |
| | 3 | | | | | 2 | | |
| | 4 | | | | | 2 | | |
| | 5 | | | | | 3 | | |
| | 6 | | | | | 0 | | |
| | 7 | | | | | 2 | | |
| | 8 | | | | | 0 | | |
| | 9 | | | | | 2 | | |
| | 10 | | | | | 0 | | |
| | 11 | | | | | 2 | | |
| | 12 | | | | | 2 | | |
| | 13 | | | | | 1 | | |
| | 14 | | | | | 3 | | |
| | 15 | | | | | 3 | | |
| | 16 | | | | | 3 | | |
| | 17 | | | | | 3 | | |
| | 18 | | | | | 4 | | |
| tp-SorbiPPO2::c-AlomyPPO2_R130A_F431M | 1 | 0 | | | | 4 | | |
| | 2 | | | | | 5 | | |
| | 3 | | | | | 4 | | |
| | 4 | | | | | 4 | | |
| | 5 | | | | | 4 | | |
| | 6 | | | | | 5 | | |
| | 7 | 0 | | | | 5 | | |
| | 8 | | | | | 5 | | |
| | 9 | | | | | 4 | | |
| | 10 | | | | | 5 | | |
| | 11 | | | | | 4 | | |
| | 12 | | | | | 5 | | |
| | 13 | | | | | 5 | | |
| | 14 | | | | | 4 | | |
| | 15 | | | | | 4 | | |
| | 16 | | | | | 5 | | |
| | 17 | | | | | 5 | | |
| tp-SorbiPPO2::c-AlomyPPO2_R130L_F431V | 1 | | | | | 4 | | |
| | 2 | | | | | 4 | | |
| | 3 | | | | | 4 | | |
| | 4 | | | | | 3 | | |
| | 5 | | | | | 5 | | |
| | 6 | | | | | 4 | | |
| tp-SorbiPPO2::c-AlomyPPO2_R130L_F431M | 1 | | | | | 3 | | |
| | 2 | | | | | 4 | | |
| | 3 | | | | | 3 | | |
| | 4 | | | | | 3 | | |
| | 5 | | | | | 2 | | |
| | 6 | | | | | 0 | | |
| | 7 | | | | | 3 | | |
| | 8 | | | | | 6 | | |
| | 9 | | | | | 1 | | |
| | 10 | | | | | 1 | | |
| AlomyPPO2 | 1 | | | | | 6 | 6 | |
| | 2 | | | | | | | |
| | 3 | | | | | 6 | | |
| | 4 | | | | | 6 | | |
| AlomyPPO2_R137A | 1 | | | | | 5 | | |
| | 2 | | | | | 5 | | |
| | 3 | | 1 | | | 4 | 5 | |
| | 4 | | 0 | | | 5 | | |
| | 5 | | 0 | | | 4 | | |
| | 6 | | 0 | | | 5 | | |
| | 7 | | | | | 6 | | |
| | 8 | | | | | 6 | | |

TABLE 6a-continued

Transgenic T0 corn events were sprayed in the greenhouse with the indicated amount of compound + 1% (v/v) MSO at V2 stage. Herbicide injury was evaluated 7 days after treatment with a 0 to 9 rating scale where 0 is no injury relative to an unsprayed wild type check and 9 is completely dead; BAS 800H refers to Saflufenacil/Kixor; BAS 850H refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4);

| SEQ ID | Event | Un-sprayed | BAS 800H g ai/ha | | | BAS 850H g ai/ha | | |
|---|---|---|---|---|---|---|---|---|
| | | | 50 | 75 | 100 | 50 | 75 | 100 |
| | 9 | | | | | 5 | | |
| | 10 | | | | | 5 | | |
| AlomyPPO2_R137L | 1 | 0 | | | | 4 | 5 | |
| | 2 | | | | | 4 | | |
| | 3 | | | | | 3 | | |
| | 4 | | | | | 4 | | |
| | 5 | | | | | 4 | | |
| | 6 | | | | | 5 | | |
| | 7 | 0 | | | | 3 | | |
| | 8 | 0 | | | | 4 | | |
| | 9 | 0 | | | | 4 | | |
| | 10 | 0 | | | | 5 | | |
| | 11 | | | | | 4 | | |
| | 12 | | | | | 5 | | |
| | 13 | 0 | | | | 4 | | |
| | 14 | 0 | | | | 4 | | |
| | 15 | 0 | | | | 5 | | |
| | 16 | 1 | | | | 4 | | |
| | 17 | 0 | | | | 5 | | |
| | 18 | | | | | 4 | | |
| | 19 | | | | | 5 | | |
| | 20 | | | | | 5 | | |
| | 21 | | | | | 5 | | |
| | 22 | | | | | 5 | | |
| | 23 | | | | | 5 | | |
| | 24 | | | | | 5 | | |
| | 25 | | | | | 4 | | |
| | 26 | | | | | 6 | | |
| | 27 | | | | | 6 | | |
| | 28 | | | | | 4 | | |
| | 29 | 0 | | | | 4 | | |
| | 30 | 0 | | | | 4 | | |
| | 31 | 0 | | | | 5 | | |
| | 32 | 1 | | | | 4 | | |
| | 33 | 0 | | | | 5 | | |
| | 34 | 4 | | | | 4 | | |
| | 35 | | | | | 5 | | |
| | 36 | | | | | 5 | | |
| | 37 | | | | | 5 | | |
| | 38 | | | | | 5 | | |
| | 39 | | | | | 5 | | |
| | 40 | | | | | 5 | | |
| | 41 | | | | | 4 | | |
| | 42 | | | | | 6 | | |
| | 43 | | | | | 6 | | |
| | 44 | | | | | 4 | | |
| | 45 | 0 | | | | 4 | | |
| | 46 | | | | | 4 | | |
| | 47 | | | | | 3 | | |
| | 48 | | | | | 3 | | |
| | 49 | | | | | 4 | | |
| | 50 | | | | | 5 | | |
| | 51 | | | | | 5 | | |
| | 52 | | | | | 4 | | |
| | 53 | | | | | 5 | | |
| | 54 | | | | | 5 | | |
| | 55 | | | | | 5 | | |
| | 56 | | | | | 5 | | |
| AlomyPPO2_R137I | 1 | 0 | | | | 4 | | |
| | 2 | 0 | | | | 3 | | |
| | 3 | 1 | | | | 6 | 4 | |
| | 4 | 0 | | | | 4 | 4 | |
| | 5 | | | | | 4 | | |
| | 6 | | | | | 7 | | |
| | 7 | | | | | 4 | | |
| | 8 | 0 | | | | 4 | | |
| | 9 | 0 | | | | 3 | | |
| | 10 | 1 | | | | 6 | 4 | |
| | 11 | 0 | | | | 4 | 4 | |
| | 12 | | | | | 4 | | |
| | 13 | | | | | 7 | | |
| | 14 | | | | | 4 | | |
| | 15 | 0 | | | | 4 | | |
| | 16 | | | | | 3 | | |
| | 17 | | | | | 4 | | |
| | 18 | | | | | 4 | | |
| | 19 | | | | | 5 | | |
| | 20 | | | | | 4 | | |
| | 21 | | | | | 4 | | |
| | 22 | | | | | 6 | | |
| | 23 | | | | | 6 | | |
| | 24 | | | | | 5 | | |
| AlomyPPO2_R137M | 1 | 0 | | | | 5 | | |
| | 2 | 0 | | | | 5 | | 5 |
| | 3 | 0 | | 0 | | 5 | | 6 |
| | 4 | | | | | 6 | | |
| | 5 | | | | | 5 | | |
| | 6 | | | | | 5 | | |
| | 7 | | | | | 4 | | |
| | 8 | | | | | 5 | | |
| | 9 | | | | | 6 | | |
| | 10 | 0 | | | | 5 | | |
| | 11 | 0 | | | | 5 | | 5 |
| | 12 | 0 | | 0 | | 5 | | 6 |
| | 13 | | | | | 6 | | |
| | 14 | | | | | 5 | | |
| | 15 | | | | | 5 | | |
| | 16 | | | | | 4 | | |
| | 17 | | | | | 5 | | |
| | 18 | | | | | 6 | | |
| | 19 | 0 | | | | 4 | | |
| | 20 | | | | | 5 | | |
| | 21 | | | | | 5 | | |
| | 22 | | | | | 5 | | |
| | 23 | | | | | 6 | | |
| | 24 | | | | | 4 | | |
| | 25 | | | | | 4 | | |
| | 26 | | | | | 4 | | |
| AlomyPPO2_F438V | 1 | | | | | 4 | | |
| | 2 | | | | | 4 | | |
| | 3 | 0 | | | | 4 | | |
| | 4 | 2 | | | | 4 | | 5 |
| | 5 | | | | | 4 | | |
| | 6 | | | | | 4 | | |
| | 7 | | | | | 1 | | |
| | 8 | 0 | | | | 1 | | |
| | 9 | | | | | 0 | | |
| | 10 | | | | | 2 | | |
| | 11 | | | | | 2 | | |
| | 12 | 0 | | | | 4 | | 4 |
| | 13 | 0 | | | | 3 | | |
| | 14 | 0 | | | | 4 | | |
| | 15 | 0 | | | | 6 | | |
| | 16 | 0 | | | | 6 | | |
| | 17 | 1 | | | | 2 | | |
| | 18 | 3 | | | | 4 | | |

TABLE 6a-continued

Transgenic T0 corn events were sprayed in the greenhouse with the indicated amount of compound + 1% (v/v) MSO at V2 stage. Herbicide injury was evaluated 7 days after treatment with a 0 to 9 rating scale where 0 is no injury relative to an unsprayed wild type check and 9 is completely dead; BAS 800H refers to Saflufenacil/Kixor; BAS 850H refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4);

| SEQ ID | Event | Unsprayed | BAS 800H g ai/ha 50 | 75 | 100 | BAS 850H g ai/ha 50 | 75 | 100 |
|---|---|---|---|---|---|---|---|---|
| | 19 | | | | | 4 | | |
| | 20 | | | | | 3 | | |
| | 21 | | | | | 4 | | |
| | 22 | | | | | 4 | | |
| AlomyPPO2_F438L | 1 | 0 | | | | 4 | | |
| | 2 | 1 | | | | 3 | | |
| | 3 | 0 | | | | 3 | | |
| | 4 | 1 | | | | 4 | | |
| | 5 | 0 | | | | 4 | 4 | |
| | 6 | | | | | 4 | | |
| | 7 | 0 | | | | 4 | | |
| | 8 | 1 | | | | 3 | | |
| | 9 | 0 | | | | 3 | | |
| | 10 | 1 | | | | 4 | | |
| | 11 | 0 | | | | 4 | 4 | |
| | 12 | | | | | 4 | | |
| | 13 | | | | | 4 | | |
| | 14 | | | | | 5 | | |
| | 15 | | | | | 4 | | |
| | 16 | | | | | 4 | | |
| | 17 | | | | | 4 | | |
| | 18 | | | | | 5 | | |
| | 19 | | | | | 3 | | |
| | 20 | | | | | 4 | | |
| | 21 | | | | | 1 | | |
| | 22 | 0 | | | | 3 | 4 | |
| | 23 | | | | | 6 | | |
| | 24 | | | | | 4 | | |
| AlomyPPO2_F438I | 1 | 0 | | | | 1 | | |
| | 2 | 0 | | | | 6 | | |
| | 3 | 0 | | | | 1 | | |
| | 4 | 0 | | | | 0 | | |
| | 5 | | | | | 7 | | |
| | 6 | | | | | 6 | | |
| | 7 | | | | | 0 | | |
| | 8 | | | | | 1 | | |
| | 9 | | | | | 2 | | |
| | 10 | | | | | 1 | | |
| | 11 | | | | | 7 | | |
| | 12 | | | | | 1 | | |
| | 13 | | | | | 2 | | |
| | 14 | | | | | 7 | | |
| | 15 | | | | | 4 | | |
| | 16 | | | | | 3 | | |
| | 17 | | | | | 1 | | |
| | 18 | | | | | 0 | | |
| | 19 | | | | | 3 | | |
| AlomyPPO2_F438M | 1 | 5 | | | | 6 | | |
| | 2 | | | | | 0 | | |
| | 3 | | | | | 6 | | |
| | 4 | | | | | 0 | | |
| | 5 | | | | | 1 | | |
| | 6 | | | | | 3 | | |
| | 7 | | | | | 1 | | |
| | 8 | | | | | 6 | | |
| | 9 | | | | | 5 | | |
| | 10 | | | | | 4 | | |
| | 11 | | | | | 3 | | |
| | 12 | | | | | 4 | | |
| | 13 | | | | | | | |
| | 14 | | | | | | | |
| AlomyPPO2_R137A_F438V | 1 | 0 | | | | 5 | | 6 |
| | 2 | 0 | | | | 2 | | |
| | 3 | 0 | | | | 4 | | |
| | 4 | 0 | | | | 4 | | |
| | 5 | 0 | | | | 5 | | |
| AlomyPPO2_R137A_F438I | 1 | 0 | | | | 4 | | 4 |
| | 2 | 0 | | | | 4 | | |
| | 3 | 0 | | | | 4 | | 5 |
| AlomyPPO2_R137A_F438M | 1 | 1 | | | | 1 | | |
| | 2 | 0 | | | | 3 | | |
| | 3 | 0 | | | | 4 | | |
| | 4 | 0 | | | | 4 | | |
| | 5 | 0 | | | | 3 | | 5 |
| AlomyPPO2_R137M_F438I | 1 | | | | | 2 | | |
| | 2 | | | | | 3 | | |
| | 3 | | | | | 4 | | |
| | 4 | | | | | 3 | | |
| | 5 | | | | | 4 | | |
| | 6 | | | | | 4 | | |
| | 7 | | | | | 4 | | |
| | 8 | | | | | 4 | | |
| | 9 | | | | | 3 | | |
| | 10 | 0 | | | | 3 | 3 | |
| | 11 | 0 | | | | 3 | 4 | |
| | 12 | 1 | | | | 3 | | |
| | 13 | | | | | 4 | | |
| | 14 | | | | | 3 | | |
| | 15 | | | | | 4 | | |
| | 16 | | | | | 6 | | |
| | 17 | | | | | 6 | | |

TABLE 6b

Transgenic T1 corn events were sprayed with 100 g ai BAS800H and 50 g ai BAS850H + 1% (v/v) MSO at V2-V3 developmental stage in the field. Herbicide injury was evaluated at 3, 7, 14, and 21 days after treatment (DAT) with a 0 to 100 rating scale where 0 is no injury relative to an unsprayed wild type check and 100 is completely dead.

| Construct | SED ID | Event | 3 DAT | 7 DAT | 14 DAT | 21 DAT |
|---|---|---|---|---|---|---|
| RTP11168-1 | AlomyPPO1 | 1 | 70 | 70 | | |
| RTP11168-1 | | 2 | 50 | 60 | | |
| RTP11168-1 | | 3 | 70 | 70 | 30 | 20 |

TABLE 6b-continued

Transgenic T1 corn events were sprayed with 100 g ai BAS800H and 50 g ai BAS850H + 1% (v/v) MSO at V2-V3 developmental stage in the field. Herbicide injury was evaluated at 3, 7, 14, and 21 days after treatment (DAT) with a 0 to 100 rating scale where 0 is no injury relative to an unsprayed wild type check and 100 is completely dead.

| Construct | SED ID | Event | 3 DAT | 7 DAT | 14 DAT | 21 DAT |
|---|---|---|---|---|---|---|
| RTP11170-1 | AlomyPPO1_Y420V | 4 | 10 | 60 | 40 | 30 |
| RTP11170-1 | | 5 | 30 | 60 | 20 | 10 |
| RTP11170-1 | | 6 | 20 | 60 | 30 | 30 |
| RTP11170-1 | | 7 | 10 | 70 | 20 | 10 |
| RTP11170-1 | | 8 | 80 | 80 | | |
| RTP11170-1 | | 9 | 10 | 30 | 30 | 30 |
| RTP11170-1 | | 10 | 70 | 80 | | |
| RTP11170-1 | | 11 | 30 | 60 | 10 | 10 |
| RTP11170-1 | | 12 | 40 | 60 | 10 | 10 |
| RTP11170-1 | | 13 | 30 | 40 | 20 | 10 |
| RTP11170-1 | | 14 | 20 | 40 | 20 | 20 |
| RTP11170-1 | | 15 | 30 | 70 | | |
| RTP11170-1 | | 16 | 20 | 40 | 30 | 20 |
| RTP11170-1 | | 17 | 30 | 60 | 40 | 20 |
| RTP11171-1 | AlomyPPO1_Y420M | 18 | 20 | 50 | 30 | 20 |
| RTP11171-1 | | 19 | 50 | 60 | 30 | 30 |
| RTP11171-1 | | 20 | 60 | 70 | 30 | 30 |
| RTP11171-1 | | 21 | 70 | 70 | 50 | 50 |
| RTP11171-1 | | 22 | 50 | 60 | 30 | 20 |
| RTP11171-1 | | 23 | 20 | 60 | 30 | 20 |
| RTP11171-1 | | 24 | 50 | 50 | 40 | 30 |
| RTP11171-1 | | 25 | 30 | 60 | 30 | 30 |
| RTP11171-1 | | 26 | 50 | 60 | 10 | 0 |
| RTP11171-1 | | 27 | 60 | 40 | 20 | 10 |
| RTP11171-1 | | 28 | 60 | 50 | 30 | 30 |
| RTP11171-1 | | 29 | 30 | 40 | 40 | 40 |
| RTP11171-1 | | 30 | 50 | 60 | | |
| RTP11171-1 | | 31 | 60 | 30 | 30 | 20 |
| RTP11171-1 | | 32 | 30 | 50 | 40 | 40 |
| RTP11172-3 | AlomyPPO1_R138A_Y420V | 33 | 50 | 50 | 40 | 30 |
| RTP11172-3 | | 34 | 70 | 80 | | |
| RTP11172-3 | | 35 | 70 | 70 | 40 | 30 |
| RTP11172-3 | | 36 | 90 | 90 | | |
| RTP11172-3 | | 37 | 40 | 50 | 30 | 30 |
| RTP11172-3 | | 38 | 80 | 60 | | |
| RTP11172-3 | | 39 | 60 | 60 | 40 | 30 |
| RTP11172-3 | | 40 | 70 | 50 | 40 | 30 |
| RTP11173-1 | AlomyPPO1_R138A_Y420M | 41 | 70 | 70 | 70 | 80 |
| RTP11173-1 | | 42 | 50 | 60 | | |
| RTP11173-1 | | 43 | 70 | 60 | | |
| RTP11173-1 | | 44 | 70 | 80 | | |
| RTP11173-1 | | 45 | 70 | 80 | | |
| RTP11173-1 | | 46 | 70 | 50 | | |
| RTP11173-1 | | 47 | 40 | 50 | 40 | 30 |
| RTP11173-1 | | 48 | 60 | 70 | 70 | 70 |
| RTP11173-1 | | 49 | 60 | 50 | 50 | 40 |
| RTP11173-1 | | 50 | 50 | 40 | 40 | 40 |
| RTP11180-1 | tp-SorbiPPO2::AlomyPPO2_F431V | 51 | 20 | 30 | 30 | 10 |
| RTP11180-1 | | 52 | 10 | 40 | 30 | 30 |
| RTP11180-1 | | 53 | 10 | 40 | 30 | 10 |
| RTP11180-1 | | 54 | 20 | 40 | 20 | 10 |
| RTP11180-1 | | 55 | 40 | 50 | 40 | 20 |
| RTP11180-1 | | 56 | 30 | 40 | 30 | 20 |
| RTP11180-1 | | 57 | 10 | 30 | 40 | 20 |
| RTP11180-1 | | 58 | 10 | 30 | 30 | 20 |
| RTP11180-1 | | 59 | 20 | 30 | 20 | 20 |
| RTP11180-1 | | 60 | 40 | 30 | 30 | 20 |
| RTP11180-1 | | 61 | 20 | 40 | 30 | 20 |
| RTP11180-1 | | 62 | 20 | 50 | 40 | 20 |
| RTP11180-1 | | 63 | 30 | 40 | 40 | 20 |
| RTP11180-1 | | 64 | 60 | 40 | 40 | 30 |
| RTP11180-1 | | 65 | 20 | 40 | 10 | 10 |
| RTP11181-1 | tp-SorbiPPO2::AlomyPPO2_R130A_F431V | 66 | 30 | 60 | 30 | 30 |
| RTP11181-1 | | 67 | 50 | 50 | 60 | 60 |
| RTP11181-1 | | 68 | 50 | 50 | 50 | 60 |
| RTP11181-1 | | 69 | 60 | 50 | 40 | 50 |
| RTP11181-1 | | 70 | 60 | 60 | 50 | 80 |
| RTP11181-1 | | 71 | 40 | 50 | 60 | 80 |
| RTP11181-1 | | 72 | 80 | 70 | 70 | 80 |
| RTP11181-1 | | 73 | 70 | 80 | 60 | 80 |
| RTP11181-1 | | 74 | 40 | 70 | 60 | 80 |
| RTP11181-1 | | 75 | 70 | 60 | 60 | 70 |

TABLE 6b-continued

Transgenic T1 corn events were sprayed with 100 g ai BAS800H and 50 g ai BAS850H + 1% (v/v) MSO at V2-V3 developmental stage in the field. Herbicide injury was evaluated at 3, 7, 14, and 21 days after treatment (DAT) with a 0 to 100 rating scale where 0 is no injury relative to an unsprayed wild type check and 100 is completely dead.

| Construct | SED ID | Event | 3 DAT | 7 DAT | 14 DAT | 21 DAT |
|---|---|---|---|---|---|---|
| RTP11181-1 | | 76 | 70 | 70 | 60 | 70 |
| RTP11181-1 | | 77 | 70 | 80 | 60 | 70 |
| RTP11181-1 | | 78 | 60 | 60 | 50 | 70 |
| RTP11181-1 | | 79 | 50 | 60 | 50 | 70 |

Example 13

Soybean Transformation and PPO Inhibitor Tolerance Testing

Figure 4:
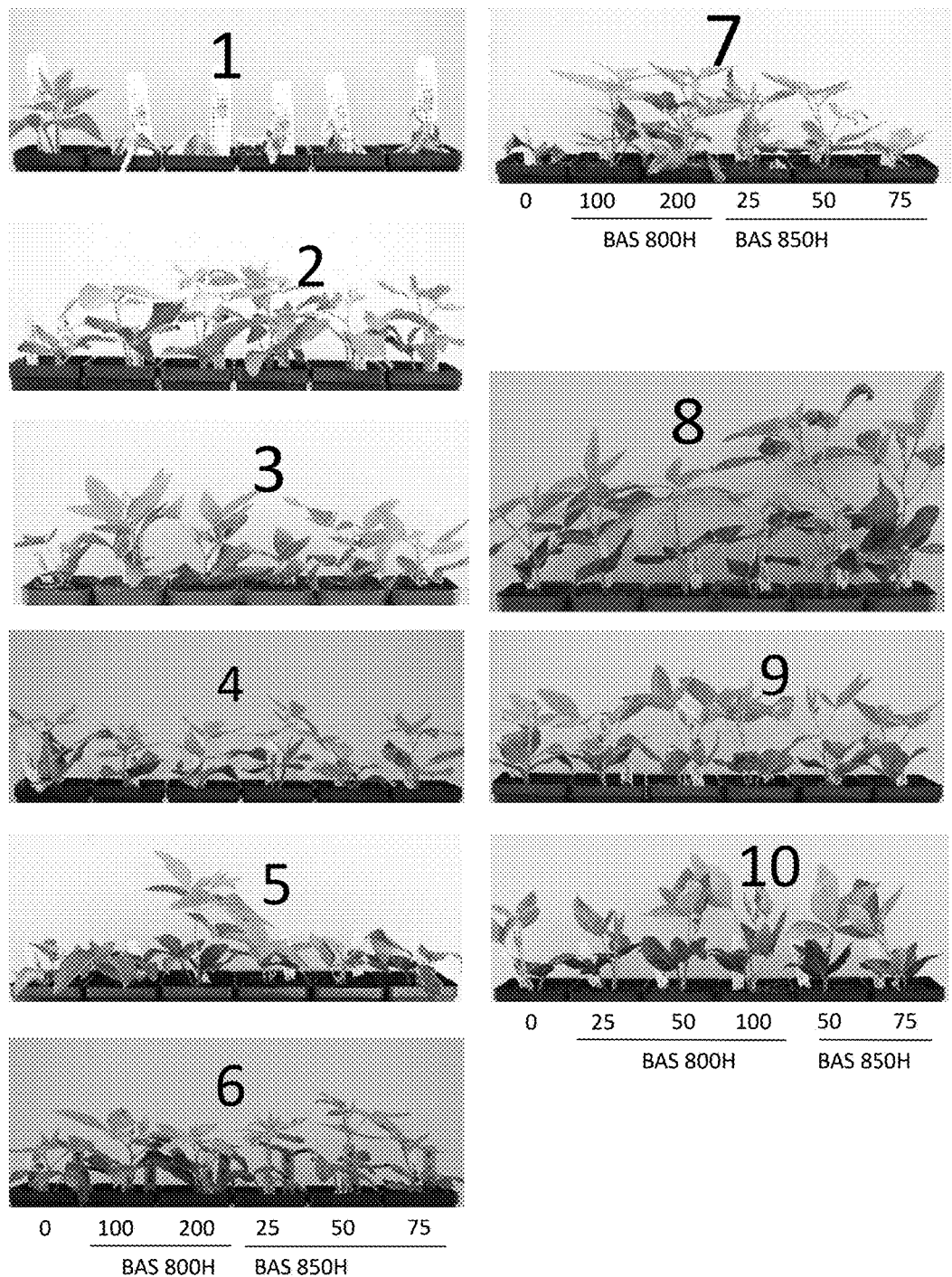
FIG. 4 shows clones of T0 transformed soybean plants 7 days after treatment with the indicated herbicide+1% (v/v) MSO. Plants were sprayed at the V2 stage; 1=Wild type; 2=AlomyPPO2_R137L_F438M; 3=AlomyPPO2_F438M; 4=AlomyPPO2_R137L_F438V; 5=AlomyPPO2_R137L_F438L; 6=AlomyPPO2_R137M_F438M; 7=AlomyPPO2_R137A_F438M; 8=AlomyPPO1_R138A_Y420V; 9=Alomy- PPO1_R138L_Y420V; 10=AlomyPPO1_R138L_Y420M; concentrations of BAS800H (Saflufenacil) and BAS 850H (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione) are given in g a.i./ha. The concentrations for constructs 1, 2, 3, 4, 5, and 6 are 0, 100, 200, (BAS800H; Saflufenacil); and 25, 50, 75 BAS 850H (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione) g a.i./ha, The concentrations for constructs 8, 9, and 10 are 0, 25, 50, 100 (BAS800H; Saflufenacil); and 50, 75 BAS 850H (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione) g a.i./ha

Soybean cv Jake was transformed as previously described by Siminszky et al., Phytochem Rev. 5:445-458 (2006). After regeneration, transformants were transplanted to soil in small pots, placed in growth chambers (16 hr day/8 hr night; 25° C. day/23° C. night; 65% relative humidity; 130-150 microE m-2 s-1) and subsequently tested for the presence of the T-DNA via Taqman analysis. After a few weeks, healthy, transgenic positive, single copy events were transplanted to larger pots and allowed to grow in the growth chamber. An optimal shoot for cutting was about 3-4 inches tall, with at least two nodes present. Each cutting was taken from the original transformant (mother plant) and dipped into rooting hormone powder (indole-3-butyric acid, IBA). The cutting was then placed in oasis wedges inside a bio-dome. The mother plant was taken to maturity in the greenhouse and harvested for seed. Wild type cuttings were also taken simultaneously to serve as negative controls. The cuttings were kept in the bio-dome for 5-7 days and then transplanted to 3 inch pots and then acclimated in the growth chamber for two more days. Subsequently, the cuttings were transferred to the greenhouse, acclimated for approximately 4 days, and then sprayed with a treatment of 0-200 g ai/ha saflufenacil (BAS 800H) plus 1% MSO and/or 25-200 g ai/ha 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (BAS 850H; CAS 1258836-72-4) plus 1% MSO. Other PPO inhibiting herbicides were also tested in a similar fashion for confirming cross resistance: flumioxazin, butafenacil, acifluorfen, lactofen, bifenox, sulfentrazone, and photosynthesis inhibitor diuron as negative control. Herbicide injury evaluations were taken at 2, 7, 14 and 21 days after treatment. Results are shown in Table 7 and FIG. 4.

TABLE 7

Herbicide injury of transgenic cuttings taken from T0 plants. Spray was at V2 stage and herbicide injury evaluation was taken 1 week after treatment.

| SEQ ID | Event number | BAS 800H g ai/ha | | | | | BAS 850H g ai/ha | | |
|---|---|---|---|---|---|---|---|---|---|
| | | 0 | 25 | 50 | 100 | 200 | 25 | 50 | 75 |
| Wild type | | 0 | 9 | 9 | 9 | 9 | 8 | 9 | 9 |
| AlomyPPO2 | 1 | 1 | 9 | 9 | 9 | * | 8 | 9 | * |
| | 2 | 2 | 4 | 6 | 6 | * | 7 | 7 | * |
| | 3 | 2 | 5 | 6 | 7 | * | 7 | 9 | * |
| | 4 | 2 | 9 | 9 | 9 | * | 8 | 8 | * |
| | 5 | 1 | 2 | 2 | 3 | * | 7 | 8 | * |
| | 6 | 3 | 4 | 4 | 6 | * | 9 | 9 | * |
| AlomyPPO2_R137A | 1 | 0 | 3 | 0 | 2 | * | 7 | 7 | * |
| AlomyPPO2_R137V | 1 | 2 | 1 | 0 | 2 | * | 7 | 9 | * |
| | 2 | 2 | 5 | 6 | 9 | * | 8 | 8 | * |
| AlomyPPO2_R137I | 1 | 4 | 3 | 4 | 4 | * | 6 | 6 | * |
| | 2 | 2 | 1 | 0 | 2 | * | 4 | 5 | * |
| | 3 | 2 | 7 | 6 | 8 | * | 8 | 7 | * |
| | 4 | 2 | 9 | 9 | 9 | * | 9 | 9 | * |
| | 5 | 1 | 9 | 9 | 9 | * | 8 | 9 | * |
| AlomyPPO2_R137L | 1 | 3 | 3 | 3 | 4 | * | 3 | 3 | * |
| | 2 | 8 | * | * | 3 | * | * | 3 | * |
| | 3 | 2 | 5 | 5 | 5 | * | 8 | 9 | * |
| | 4 | 0 | 0 | 0 | 5 | * | 1 | 2 | * |
| | 5 | * | 2 | 3 | 4 | * | 3 | 4 | * |
| AlomyPPO2_R137M | 1 | 0 | 1 | 3 | 2 | * | 4 | 6 | * |
| | 2 | 1 | 9 | 9 | 9 | * | 8 | 9 | * |
| | 3 | 2 | 1 | 4 | 5 | * | 6 | 7 | * |
| | 4 | 3 | 3 | 6 | 7 | * | 5 | 6 | * |
| | 5 | 2 | 4 | 6 | 6 | * | 6 | 6 | * |
| | 6 | * | 3 | 1 | 4 | * | 7 | 8 | * |
| | 7 | 2 | 9 | 9 | 9 | * | 9 | 9 | * |
| | 8 | 4 | 9 | 9 | 9 | * | 9 | 9 | * |
| | 9 | 4 | 3 | 4 | 4 | * | 9 | 9 | * |
| | 10 | 3 | 3 | 4 | 5 | * | 9 | 8 | * |

TABLE 7-continued

Herbicide injury of transgenic cuttings taken from T0 plants. Spray was at V2 stage and herbicide injury evaluation was taken 1 week after treatment.

| SEQ ID | Event number | 0 | BAS 800H g ai/ha 25 | 50 | 100 | 200 | BAS 850H g ai/ha 25 | 50 | 75 |
|---|---|---|---|---|---|---|---|---|---|
|  | 11 | 0 | 0 | 2 | 2 | * | 9 | 7 | * |
|  | 12 | 4 | 6 | 6 | 6 | * | 7 | 9 | * |
| AlomyPPO2_F438V | 1 | 3 |  | 1 | 6 | 0 | * | 1 | 5 |
| AlomyPPO2_F438l | 1 | 0 | * | 4 | 4 | 5 | * | 7 | 6 |
|  | 2 | 1 | * | 1 | 2 | 1 | * | 0 | 4 |
|  | 3 | 1 | * | 9 | 9 | 9 | * | 9 | 9 |
|  | 4 | 2 | * | 9 | 9 | 9 | * | 9 | 8 |
|  | 5 | 6 | * | 3 | 2 | 1 | * | 3 | 6 |
| AlomyPPO2_F438L | 1 | 0 | * | 2 | 3 | 3 | * | 4 | 4 |
|  | 2 | 0 | * | 1 | 3 | 1 | * | 6 | 6 |
|  | 3 | 1 | * | 9 | 9 | 9 | * | 8 | 9 |
|  | 4 | 3 | * | 9 | 9 | 9 | * | 9 | 9 |
|  | 5 | 1 | * | 0 | 6 | 0 | * | 6 | 4 |
| AlomyPPO2_F438M | 1 | 4 | * | 0 | 4 | 2 | * | 3 | 4 |
|  | 2 | * | * | 5 | 4 | 5 | * | 5 | 4 |
|  | 3 | 0 | * | * | 0 | 0 | 3 | 2 | 1 |
|  | 4 | 0 | 9 | 9 | 9 | 9 | 8 | * | * |
| AlomyPPO2_R137A_F438V | 1 | 3 | * | * | 4 | 4 | 1 | 4 | 5 |
|  | 2 | 5 | * | * | 2 | 3 | 6 | 5 | 5 |
|  | 3 | 0 | * | * | 4 | 6 | 7 | 5 | 7 |
|  | 4 | 0 | * | * | 1 | * | 6 | 5 | 5 |
|  | 5 | 7 | * | * | 4 | 4 | 4 | 6 | 6 |
| AlomyPPO2_R137A_F438I | 1 | 1 | * | * | 3 | 3 | 4 | 5 | 5 |
|  | 2 | 2 | * | * | 9 | 9 | 5 | 6 | 8 |
|  | 3 | 1 | * | * | 4 | 6 | 5 | 6 | 7 |
|  | 4 | 3 | * | * | 6 | 8 | 7 | 7 | 8 |
|  | 5 | 3 | * | * | 9 | 9 | 8 | 8 | 8 |
|  | 6 | 3 | * | * | 5 | 5 | 6 | 6 | 8 |
|  | 7 | 3 | * | * | 4 | 4 | 7 | 7 | 9 |
|  | 8 | 2 | * | * | 4 | 4 | 5 | 7 | 7 |
|  | 9 | 0 | * | * | 5 | 7 | 7 | 7 | 7 |
|  | 10 | 0 | * | * | 4 | 6 | 5 | 7 | 6 |
|  | 11 | 4 | * | * | 5 | 4 | 6 | 6 | 5 |
| AlomyPPO2_R137A_F438L | 1 | 0 | * | * | 5 | 6 | 6 | 7 | 7 |
|  | 2 | 0 | * | * | 9 | 9 | 9 | 9 | 9 |
|  | 3 | 0 | * | * | 9 | 9 | 8 | 9 | 9 |
|  | 4 | * | * | * | 4 | 6 | * | 5 | 5 |
|  | 5 | 0 | * | * | 9 | 9 | 8 | 9 | 9 |
|  | 6 | 0 | * | * | 9 | 9 | 9 | 9 | 9 |
| AlomyPPO2_R137A_F438M | 1 | 0 | * | * | 9 | 9 | 8 | 8 | 9 |
|  | 2 | 4 | * | * | 0 | 0 | 5 | 5 | 5 |
|  | 3 | 0 | * | * | 0 | 4 | 6 | 6 | 7 |
|  | 4 | 0 | * | * | 9 | 9 | 8 | 8 | 9 |
|  | 5 | 1 | * | * | 6 | 6 | 6 | 6 | 8 |
|  | 6 | 2 | * | * | 0 | 1 | 5 | 5 | 5 |
|  | 7 | 5 | * | * | 9 | 6 | 5 | 4 | 5 |
|  | 8 | 0 | * | * | 9 | 9 | 9 | 9 | 9 |
|  | 9 | 3 | * | * | 9 | 9 | 9 | 9 | 9 |
|  | 10 | 4 | * | * | 1 | 1 | 3 | 4 | 4 |
| AlomyPPO2_R137L_F438V | 1 | 1 | * | * | 0 | 1 | 3 | 4 | 3 |
|  | 2 | 1 | * | * | 9 | 9 | 9 | 9 | 9 |
|  | 3 | 2 | * | * | 6 | 6 | 6 | 6 | 6 |
|  | 4 | 2 | * | * | 2 | 3 | 3 | 3 | 3 |
|  | 5 | * | * | * | 5 | 5 | 5 | 6 | 6 |
|  | 6 | 4 | * | * | 4 | 4 | 5 | 5 | 7 |
|  | 7 | 2 | * | * | 3 | 3 | 3 | 4 | 6 |
|  | 8 | 0 | * | * | 9 | 9 | 9 | 9 | 8 |
|  | 9 | 2 | * | * | 9 | 9 | 8 | 9 | 9 |
|  | 10 | 2 | * | * | 3 | 3 | 4 | 5 | 7 |
|  | 11 | 1 | * | * | 9 | 9 | 9 | 9 | 8 |
| AlomyPPO2_R137L_F438I | 1 | 1 | * | * | 9 | 9 | 8 | 8 | 9 |
|  | 2 | 1 | * | * | 9 | 9 | 9 | 8 | 8 |
|  | 3 | 0 | * | * | 9 | 9 | 8 | 9 | 9 |
|  | 4 | 2 | * | * | 9 | 9 | 8 | 9 | 9 |
| AlomyPPO2_R137L_F438L | 1 | 0 | * | * | 3 | 3 | 3 | 4 | 3 |
|  | 2 | 0 | * | * | 0 | 0 | 2 | 2 | 3 |
|  | 3 | 0 | * | * | 2 | 2 | 2 | 1 | 5 |
|  | 4 | 0 | * | * | 9 | 9 | 8 | 8 | 9 |
|  | 5 | 1 | * | * | 1 | 2 | 3 | 5 | 6 |
|  | 6 | 2 | * | * | 3 | 4 | 5 | 5 | 5 |
| AlomyPPO2_R137L_F438M | 1 | 0 | * | * | 1 | 3 | 1 | 3 | 4 |
|  | 2 | * | * | * | 6 | 5 | 6 | 6 | 6 |
|  | 3 | 1 | * | * | 0 | 0 | 1 | 2 | 3 |

TABLE 7-continued

Herbicide injury of transgenic cuttings taken from T0 plants. Spray was at V2 stage and herbicide injury evaluation was taken 1 week after treatment.

| SEQ ID | Event number | 0 | BAS 800H g ai/ha 25 | 50 | 100 | 200 | BAS 850H g ai/ha 25 | 50 | 75 |
|---|---|---|---|---|---|---|---|---|---|
| | 4 | 2 | * | * | 2 | 3 | 2 | 7 | 1 |
| | 5 | * | * | * | 3 | 3 | 2 | 2 | 4 |
| | 6 | 1 | * | * | 4 | 6 | 6 | 7 | 7 |
| | 7 | * | * | * | 6 | 7 | * | 6 | 7 |
| | 8 | 0 | * | * | 2 | 3 | 3 | 7 | 7 |
| | 9 | 0 | * | * | 9 | 9 | 9 | 9 | 9 |
| | 10 | 0 | * | * | 9 | 9 | 8 | 8 | 9 |
| AlomyPPO2_R137M_F438V | 1 | 2 | * | * | 1 | 2 | 3 | 3 | 4 |
| | 2 | 1 | * | * | 1 | 1 | 3 | 4 | 4 |
| | 3 | 0 | * | * | 6 | 6 | 6 | 7 | 7 |
| | 4 | 1 | * | * | 9 | 9 | 9 | 8 | 9 |
| | 5 | 3 | * | * | * | 1 | * | * | 6 |
| AlomyPPO2_R137M_F438I | 1 | 2 | * | * | 3 | 2 | 4 | 4 | 4 |
| | 2 | 4 | * | * | 9 | 9 | 9 | 9 | 9 |
| | 3 | 3 | * | * | 2 | 0 | 6 | 6 | 5 |
| | 4 | 0 | * | * | 9 | 9 | 9 | 8 | 9 |
| AlomyPPO2_R137M_F438L | 1 | 1 | * | * | 6 | 7 | 7 | 7 | 7 |
| | 2 | 4 | * | * | 3 | 5 | 3 | 4 | 6 |
| | 3 | 5 | * | * | 3 | 3 | 4 | 5 | 5 |
| | 4 | 4 | * | 4 | 6 | 6 | * | 5 | 5 |
| AlomyPPO2_R137M_F438M | 1 | 0 | * | * | 0 | 2 | 3 | 3 | 5 |
| | 2 | 0 | * | * | 4 | 5 | 4 | 4 | 6 |
| | 3 | 0 | * | * | 1 | 2 | 3 | 2 | 3 |
| | 4 | 1 | * | * | 9 | 7 | 5 | 6 | 4 |
| | 5 | 1 | * | * | 0 | 1 | 1 | 3 | 4 |
| | 6 | 3 | * | * | 6 | 6 | 6 | 7 | 7 |
| | 7 | * | * | * | 9 | 9 | * | 8 | 8 |
| | 8 | * | * | * | 7 | 4 | 4 | 7 | 7 |
| | 9 | 1 | * | * | 5 | 6 | 5 | 5 | 7 |
| | 10 | 1 | * | * | 9 | 9 | 8 | 9 | 9 |
| | 11 | * | * | * | 4 | 4 | 7 | 5 | 6 |
| | 12 | 4 | * | * | 3 | 2 | 4 | 6 | 7 |
| | 13 | 1 | * | * | 5 | 6 | 6 | 6 | 7 |
| | 14 | 3 | * | * | 9 | 9 | 9 | 9 | 9 |
| | 15 | 1 | * | * | 9 | 9 | 9 | 9 | 9 |
| | 16 | 1 | * | 9 | 9 | 9 | * | 9 | 9 |
| AlomyPPO1_R138A | 1 | 1 | 6 | 4 | 4 | * | 5 | 8 | * |
| | 2 | 3 | 9 | 9 | 9 | * | 9 | 9 | * |
| AlomyPPO1_R138L | 1 | 1 | 8 | 8 | 8 | * | 8 | 8 | * |
| | 2 | 1 | 8 | 9 | 9 | * | 9 | 8 | * |
| | 3 | 1 | 7 | 8 | 8 | * | 8 | 7 | * |
| | 4 | 0 | 6 | 6 | 9 | * | 9 | 9 | * |
| | 5 | 1 | 6 | 7 | 9 | * | 6 | 7 | * |
| | 6 | 0 | 6 | 8 | 8 | * | 8 | 9 | * |
| AlomyPPO1_Y420V | 1 | 1 | 9 | 9 | 9 | * | 9 | 9 | * |
| | 2 | 0 | 4 | 5 | 4 | * | 9 | 7 | * |
| | 3 | 0 | 9 | 9 | 9 | * | 9 | 8 | * |
| | 4 | * | 0 | 2 | 0 | * | 3 | 5 | * |
| | 5 | 0 | 8 | 9 | 9 | * | 9 | 9 | * |
| AlomyPPO1_Y420M | 1 | 1 | 3 | 5 | 5 | * | 6 | 8 | * |
| | 2 | 0 | 4 | 4 | 4 | * | 5 | 6 | * |
| | 3 | 3 | 9 | 8 | 8 | * | 9 | 9 | * |
| AlomyPPO1_R138A_Y420V | 1 | 1 | 0 | 4 | 2 | * | 7 | 9 | * |
| | 2 | 1 | 2 | 1 | 1 | * | 4 | 5 | * |
| | 3 | 1 | 1 | 1 | 2 | * | 5 | 5 | * |
| | 4 | 0 | 2 | 2 | 4 | * | 8 | 7 | * |
| | 5 | 0 | 0 | 0 | 0 | * | 3 | 4 | * |
| | 6 | 0 | 1 | 1 | 1 | * | 7 | 7 | * |
| | 7 | 0 | 1 | 4 | 2 | * | 7 | 7 | * |
| | 8 | 0 | 9 | 9 | 9 | * | 9 | 9 | * |
| AlomyPPO1_R138A_Y420M | 1 | 2 | 0 | 3 | 3 | * | 7 | 9 | * |
| | 2 | 0 | 7 | 7 | 7 | * | 8 | 8 | * |
| | 3 | * | 2 | 3 | 3 | * | 5 | 9 | * |
| | 4 | 0 | 9 | 9 | 9 | * | 9 | 9 | * |
| | 5 | 2 | 9 | 9 | 9 | * | 9 | 9 | * |
| | 6 | * | * | 3 | 4 | * | 7 | 7 | * |
| AlomyPPO1_R138L_Y420V | 1 | 0 | 9 | 9 | 9 | * | 9 | 9 | * |
| | 2 | 1 | 1 | 1 | 0 | * | 1 | 0 | * |
| | 3 | 1 | 0 | 1 | 2 | * | 4 | 4 | * |
| | 4 | 2 | 2 | 3 | 3 | * | 4 | 4 | * |
| | 5 | * | * | 6 | 4 | * | 6 | 6 | * |
| | 6 | 3 | 9 | 9 | 9 | * | 9 | 9 | * |

TABLE 7-continued

Herbicide injury of transgenic cuttings taken from T0 plants. Spray was at V2 stage and herbicide injury evaluation was taken 1 week after treatment.

| SEQ ID | Event number | BAS 800H g ai/ha | | | | | BAS 850H g ai/ha | | |
|---|---|---|---|---|---|---|---|---|---|
| | | 0 | 25 | 50 | 100 | 200 | 25 | 50 | 75 |
| | 7 | 0 | 0 | 0 | 0 | * | 0 | 3 | * |
| | 8 | 0 | 3 | 4 | 6 | * | 5 | 6 | * |
| AlomyPPO1_R138L_Y420M | 1 | 0 | 5 | 6 | 6 | * | 6 | 6 | * |
| | 2 | 0 | 2 | 1 | 3 | * | 3 | 5 | * |
| | 3 | 2 | 3 | 5 | 5 | * | 5 | 5 | * |
| | 4 | 0 | 3 | 1 | 1 | * | 3 | 4 | * |
| | 5 | 2 | 3 | 2 | 2 | * | 3 | 2 | * |
| | 6 | * | 3 | 3 | 4 | * | 5 | 5 | * |
| | 7 | 0 | 9 | 9 | 9 | * | 9 | 9 | * |
| | 8 | 2 | 4 | 5 | 5 | * | 4 | 4 | * |
| | 9 | 0 | 4 | 4 | 4 | * | 4 | 5 | * |
| | 10 | 3 | 9 | 9 | 9 | * | 9 | 9 | * |
| | 11 | 0 | 4 | 5 | 6 | * | 6 | 6 | * |

The following gives a definition of the injury scores measured above:

| Score | Description of injury |
|---|---|
| 0 | No Injury |
| 1 | Minimal injury, only a few patches of leaf injury or chlorosis. |
| 2 | Minimal injury with slightly stronger chlorosis. Overall growth points remain undamaged. |
| 3 | Slightly stronger injury on secondary leaf tissue, but primary leaf and growth points are still undamaged. |
| 4 | Overall plant morphology is slightly different, some chlorosis and necrosis in secondary growth points and leaf tissue. Stems are intact. Regrowth is highly probable within 1 week. |
| 5 | Overall plant morphology is clearly different, some chlorosis and necrosis on a few leaves and growth points, but primary growth point is intact. Stem tissue is still green. Regrowth is highly probably within 1 week. |
| 6 | Strong injury can be seen on the new leaflet growth. Plant has a high probability to survive only through regrowth at different growth points. Most of the leaves are chlorotic/necrotic but stem tissue is still green. May have regrowth but with noticeable injured appearance. |
| 7 | Most of the active growth points are necrotic. There may be a single growth point that could survive and may be partially chlorotic or green and partially necrotic. Two leaves may still be chlorotic with some green; the rest of the plant including stem is necrotic. |
| 8 | Plant will likely die, and all growth points are necrotic. One leaf may still be chlorotic with some green. The remainder of the plant is necrotic. |
| 9 | Plant is dead. |
| * | Not tested |

Example 14

Sequencing and Full Length Assembly of *Alopecurus myosuroides* PPO Genes

Isolation of RNA and cDNA Synthesis

Leaf tissue of *Alopecurus myosuroides* were harvested, frozen and grounded in liquid nitrogen and total RNA was extracted using an Ambion RNAqueous-Midi kit (AM1911, Ambion) with the Plant RNA Isolation Aid (AM9690, Ambion) as per manufacturer's recommendation. The last elution was done with 10 ul of elution solution. To validate the quality of the extracted RNA 1 uL of the final product was run on a Bioanalyzer 2100 using the RNA 6000 Nano kit with the Plant RNA Nano method. The final solution, containing purified RNA, was stored at −80° C. until library preparation.

For assembly of *Alopecurus myosuroides* PPO genes, an RNA sequencing experiment was performed. RNA sequencing libraries were produced using TruSeq RNA Sample preparation kits V2 (RS-122-2001) from Illumina according to the instructions of the manufacturer. Briefly, 1 μg of total RNA was first purified twice on a poly-dT column. During the second elution step, RNA was fragmented and primed for cDNA synthesis. The material was reverse transcribed, RNA was removed and the second strand was produced. After rendering the ends of the fragment blunt, 3' ends were adenylated and Illumina sequencing-specific bar-coded adaptors were ligated at both ends of the fragments. The DNA fragments bearing adaptors at both ends were enriched by a 15 cycle PCR amplification. Libraries are pooled prior to sequencing. The pooled libraries were first put on a flowcell using a TruSeq PE Cluster kit V3 (PE-401-3001) on the cBot and clusters are amplified on the device. Afterwards, the flowcell is transferred onto the Illumina Hiseq machine and the material on the flowcell is then sequenced using Illumina TruSeq SBS Kit V3 (FC-401-3001) as per manufacturer's recommendation.

The data produced by the Illumina Hiseq sequencer was first trimmed at both ends using a quality threshold of 15 using the FASTQC Quality Trimmer (www.bioinformatics.babraham.ac.uk/projects/fastqc/). These sequences were further analyzed to remove any Illumina adaptor sequences using CutAdapt (code.google.com/p/cutadapt/). Sequence reads were assembled using CLC bio algorithm (version 4.01). The PPO full length gene sequences (SEQUENCE ID 1, 3) were identified by performing a BLAST® search with *Arabidopsis thaliana* PPO sequences as query and the *Alopecurus myosuroides* CLC bio assembly as database.

Example 15

Demonstration of Herbicide Tolerance in a Transient Tobacco Expression System

Transient expression of *Alopecurus myosuroides* PPO genes (SEQUENCE ID 1 or 3) are done as described previously (Voinnet O., et al., 2003, The Plant Journal 33, 949-956). In brief, binary vector cloning with *Alopecurus myosuroides* PPO genes are done as described in EXAMPLE 5 and transformed in *Agrobacterium tumefaciens* (strain: pGV 2260). Young leaves of *Nicotiana benthamiana* are infiltrated with transgenic *Agrobacterium* suspension ($OD^{600}$ of 1.0) harbouring binary vector constructs with a *Alopecurus myosuroides* PPO gene. Two to three days after infiltration punches of leaf discs (0.75 cm in diameter) are transferred to 6-well plates with medium containing herbicide of interest in different concentrations. Multi well plates are incubated in a growth chamber at 22° C., 75% relative humidity and 110 μmol Phot*$m^{-2}$*$s^{-1}$ with 14:10 h light:dark photoperiod. Herbicide effect are monitored by visual inspection and analysis of photosynthetic yield by imaging PAM (Walz, Effeltrich, Germany) 24 h, 48 h and 96 h after treatment. Tolerance factors are calculated based on IC50 values of PSII yield inhibition of transformed versus non-transformed leave discs.

The invention claimed is:

1. A nucleic acid construct comprising, in operable linkage:
   (1) a nucleic acid molecule encoding a protoporphyrinogen oxidase (PPO) polypeptide selected from the group consisting of:
      (a) a nucleic acid molecule encoding the PPO polypeptide comprising the sequence of SEQ ID NO: 2;
      (b) a nucleic acid molecule comprising the sequence of SEQ ID NO: 1; and
      (c) a nucleic acid molecule encoding a PPO polypeptide having 95% or more identity with the amino acid sequence of SEQ ID NO: 2, wherein transgenic expression of said nucleic acid molecule in a plant cell, a plant, or a plant part confers increased herbicide tolerance or resistance, as compared to a corresponding, non-transformed, wild type plant cell, a wild type plant or a part thereof; and
   (2) a heterologous promoter.

2. A nucleic acid construct comprising, in operable linkage:
   (1) a nucleic acid molecule encoding a protoporphyrinogen oxidase (PPO) polypeptide having 95% or more identity with the amino acid sequence of SEQ ID NO: 2, wherein transgenic expression of said nucleic acid molecule in a plant cell, a plant, or a plant part confers increased herbicide tolerance or resistance, as compared to a corresponding, non-transformed, wild type plant cell, a wild type plant or a part thereof; and
   (2) a heterologous promoter,
   wherein the nucleic acid molecule encodes a mutated PPO polypeptide in which the amino acid at or corresponding to position 137 of SEQ ID NO: 2 and/or the amino acid at or corresponding to position 415 of SEQ ID NO: 2, and/or the amino acid at or corresponding to position 438 of SEQ ID NO: 2 is substituted by another amino acid.

3. A vector comprising the nucleic acid construct of claim 2.

4. A plant nucleus, plant cell, plant tissue, propagation material, pollen, progeny, harvested material or a plant comprising the nucleic acid construct of claim 2.

5. The transgenic plant cell nucleus, transgenic plant cell, transgenic plant or part thereof of claim 4 derived from a monocotyledonous plant.

6. The transgenic plant cell nucleus, transgenic plant cell, transgenic plant or part thereof of claim 4 derived from a dicotyledonous plant.

7. The transgenic plant cell nucleus, transgenic plant cell, transgenic plant or part thereof of claim 4, wherein the corresponding plant is selected from the group consisting of corn (maize), wheat, rye, oat, triticale, rice, barley, soybean, peanut, cotton, oil seed rape, including canola and winter oil seed rape, *manihot*, pepper, sunflower, sugar cane, sugar beet, flax, borage, safflower, linseed, primrose, rapeseed, turnip rape, *tagetes*, solanaceous plants comprising potato, tobacco, eggplant, tomato; *Vicia* species, pea, alfalfa, coffee, cacao, tea, *Salix* species, oil palm, coconut, perennial grass, forage crops and *Arabidopsis thaliana*.

* * * * *

UNITED STATES PATENT AND TRADEMARK OFFICE
CERTIFICATE OF CORRECTION

| | | |
|---|---|---|
| PATENT NO. | : 10,392,630 B2 | Page 1 of 1 |
| APPLICATION NO. | : 14/911814 | |
| DATED | : August 27, 2019 | |
| INVENTOR(S) | : Raphael Aponte et al. | |

It is certified that error appears in the above-identified patent and that said Letters Patent is hereby corrected as shown below:

In the Claims

At Column 330, Line 22, "plant nucleus," should be -- plant cell nucleus, --.

Signed and Sealed this
Twenty-third Day of April, 2024

Katherine Kelly Vidal
*Director of the United States Patent and Trademark Office*